United States Patent
Matsumura et al.

(10) Patent No.: US 11,633,499 B2
(45) Date of Patent: *Apr. 25, 2023

(54) ANTI-TMEM-180 ANTIBODY, ANTICANCER DRUG AND CANCER TESTING METHOD

(71) Applicants: NATIONAL CANCER CENTER JAPAN, Tokyo (JP); RIN INSTITUTE INC., Tokyo (JP)

(72) Inventors: Yasuhiro Matsumura, Chiba (JP); Masahiro Yasunaga, Chiba (JP); Shinji Saijou, Chiba (JP); Shingo Hanaoka, Chiba (JP); Takahiro Anzai, Chiba (JP); Shino Manabe, Chiba (JP)

(73) Assignees: NATIONAL CANCER CENTER JAPAN, Tokyo (JP); RIN INSTITUTE INC., Tokyo (JP)

( * ) Notice: Subject to any disclaimer, the term of this patent is extended or adjusted under 35 U.S.C. 154(b) by 510 days.

This patent is subject to a terminal disclaimer.

(21) Appl. No.: 16/083,077

(22) PCT Filed: Mar. 7, 2017

(86) PCT No.: PCT/JP2017/008900
§ 371 (c)(1),
(2) Date: Sep. 7, 2018

(87) PCT Pub. No.: WO2017/154868
PCT Pub. Date: Sep. 14, 2017

(65) Prior Publication Data
US 2019/0060480 A1    Feb. 28, 2019

(30) Foreign Application Priority Data

Mar. 8, 2016 (JP) .............................. JP2016-044946
Aug. 22, 2016 (JP) .............................. JP2016-161697

(51) Int. Cl.
| | |
|---|---|
| *G01N 33/574* | (2006.01) |
| *C07K 16/30* | (2006.01) |
| *A61K 47/68* | (2017.01) |
| *C12N 15/09* | (2006.01) |
| *C12N 5/10* | (2006.01) |
| *A61K 39/395* | (2006.01) |
| *A61K 49/00* | (2006.01) |
| *A61P 35/00* | (2006.01) |
| *C12N 15/62* | (2006.01) |

(52) U.S. Cl.
CPC ........ *A61K 47/6851* (2017.08); *A61K 39/395* (2013.01); *A61K 49/00* (2013.01); *A61P 35/00* (2018.01); *C07K 16/30* (2013.01); *C12N 5/10* (2013.01); *C12N 15/09* (2013.01); *C12N 15/62* (2013.01); *G01N 33/574* (2013.01); *G01N 33/57419* (2013.01)

(58) Field of Classification Search
CPC ................................................ G01N 33/57484
See application file for complete search history.

(56) References Cited

U.S. PATENT DOCUMENTS

| | | | |
|---|---|---|---|
| 2003/0148321 A1* | 8/2003 | Pecker | G01N 33/57426 435/6.16 |
| 2006/0275844 A1* | 12/2006 | Linke | G16H 70/60 702/19 |
| 2011/0244501 A1* | 10/2011 | Chu | C12N 5/068 435/29 |
| 2014/0038901 A1* | 2/2014 | Lyden | G01N 33/6893 435/7.1 |
| 2014/0357660 A1* | 12/2014 | Mock | C12Q 1/6886 514/291 |
| 2015/0017660 A1* | 1/2015 | Ochiya | G01N 33/57434 435/7.23 |
| 2016/0354403 A1* | 12/2016 | von Andrian | C07K 14/47 |
| 2017/0260284 A1 | 9/2017 | Matsumura et al. | |

FOREIGN PATENT DOCUMENTS

| | | |
|---|---|---|
| EP | 3192527 A1 | 7/2017 |
| WO | WO-2013/094307 A1 | 6/2013 |
| WO | WO-2014/041185 A2 | 3/2014 |
| WO | WO-2016/039321 A1 | 3/2016 |

OTHER PUBLICATIONS

Baxevanis (Expert Opinion: Drug Discovery, vol. 3, No. 4, p. 441-452, 2008) (Year: 2008).*
Ludwig et al. (Nature Reviews: Cancer, vol. 5, p. 845-856, 2005) (Year: 2005).*
Pepe et al. (Journal of the National Cancer Institute, vol. 93, No. 14, p. 1054-1061, 2001) (Year: 2001).*
Mantovani (European Journal of Cancer, vol. 30A, No. 3, p. 363-369, 1994) (Year: 1994).*
Paul (Fundamental Immunology, 3rd Edition, 1993, pp. 292-295) (Year: 1993).*
Bendig M. M. (Methods: A Companion to Methods in Enzymology, 1995; 8:83-93) (Year: 1995).*

(Continued)

*Primary Examiner* — Michael Allen
(74) *Attorney, Agent, or Firm* — Clark & Elbing LLP; Susan M. Michaud

(57) ABSTRACT

An object of the present invention is to provide an anticancer drug capable of treating cancer by finding a target molecule specifically expressed in cancer cells and by specifically acting on the target molecule, and to provide a cancer testing method including a step of measuring the target molecule in a sample. The present invention provides an anticancer drug containing, as an active ingredient thereof, an anti-transmembrane protein 180 (TMEM-180) antibody or an antigen-binding fragment thereof. In addition, the present invention provides a cancer testing method including a step of measuring the amount of TMEM-180 in a sample collected from a subject.

2 Claims, 26 Drawing Sheets

Specification includes a Sequence Listing.

(56) References Cited

OTHER PUBLICATIONS

Rudikoff et al. (Proceedings of the National Academy of Sciences USA, vol. 79, p. 1979-1983, 1982) (Year: 1982).*
Peterson (Methods, vol. 87, p. 31-45, 2015) (Year: 2015).*
Ogata-Kawata (Pios One, vol. 9, No. 4, e92921, p. 1-9, 2014) (Year: 2014).*
Welton (Molecular and Cellular Proteomics, vol. 9, p. 1324-1338, 2010) (Year: 2010).*
Henderson (Frontiers in Oncology, vol. 2, Article 38, p. 1-9, 2012) (Year: 2012).*
Cunningham et al., "Cetuximab monotherapy and cetuximab plus irinotecan in irinotecan-refractory metastatic colorectal cancer," N Engl J Med. 351(4):337-45 (2004).
Goldstein et al., "Biological efficacy of a chimeric antibody to the epidermal growth factor receptor in a human tumor xenograft model," Clin Cancer Res. 1(11):1311-8 (1995).
International Search Report dated May 30, 2017 for International Patent Application No. PCT/JP2017/008900, Matsumura et al., "Anti-Tmem-180 antibody, anticancer agent, and test method for cancer," filed Mar. 7, 2017 (7 pages).
Karapetis et al., "K-ras mutations and benefit from cetuximab in advanced colorectal cancer," N Engl J Med. 359(17):1757-65 (2008).
Extended European Search Report dated Oct. 21, 2019 for European Patent Application No. 17763208.0, Matsumura et al., "Anti-Tmem-180 Antibody, Anticancer Agent, and Test Method for Cancer," filed Mar. 7, 2017 (13 pages).
Homem de Mello et al., "Genomic profile in gestational and non-gestational choriocarcinomas," Placenta. 50:8-15(2017).
Isacke et al., "p180, a novel recycling transmembrane glycoprotein with restricted cell type expression," Mol Cell Biol. 10(6):2606-18 (1990).
Perez De La Lastra et al., "Epitope mapping of 10 monoclonal antibodies against the pig analogue of human membrane cofactor protein (MCP)," Immunology. 96(4):663-70 (1999).
UniProtKB/Swiss-Prot Accession No. Q14CX5, "Transmembrane protein 180," <https://www.ncbi.nlm.nih.gov/protein/122012175?sat=34&satkey=12202116>, created Oct. 31, 2006, sequence updated Aug. 22, 2006; annotation updated (pub date): Jan. 9, 2007, retrieved Feb. 18, 2020 (4 pages).
Hunter et al., "Detection of microRNA Expression in Human Peripheral Blood Microvesicles," PLoS One. 3(11):e3694 (2008) (11 pages).
Koga et al., "Exosome can prevent RNase from degrading microRNA in feces," J. Gastrointest. Oncol. 2(4):215-222 (2011).
Kosaka et al., "Secretory Mechanisms and Intercellular Transfer of MicroRNAs in Living Cells," J. Biol. Chem. 285(23):17442-17452 (2010) (17 pages).
Panfoli, "Cancer exosomes in urine: a promising biomarker source," Transl. Cancer Res. 6(8):S1389-1393 (2017).
Van Niel et al., "Exosomes: A Common Pathway for a Specialized Function," J. Biochem. 140(1):13-21 (2006).

* cited by examiner 1361-5 antibody
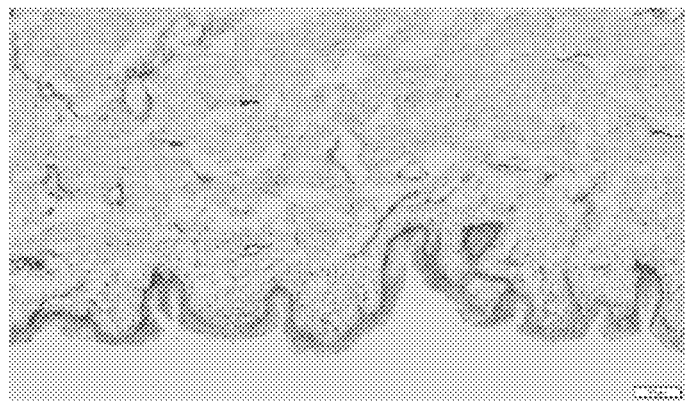
Cetuximab
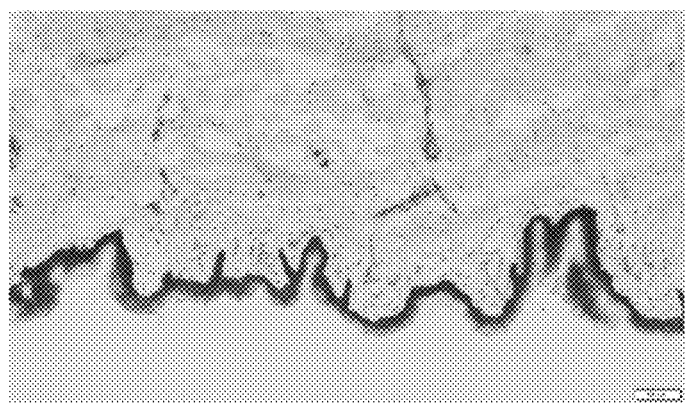
Fig. 13

Brain
Heart
Small intestine
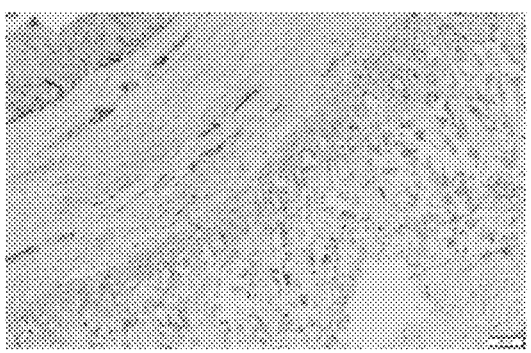
Lung
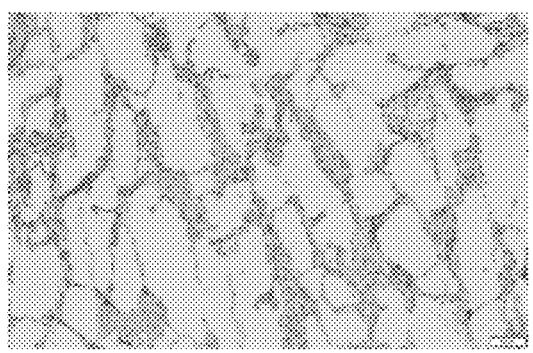
Liver
Kidney
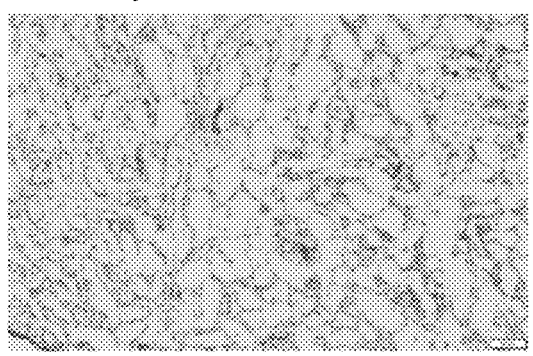
Fig. 14

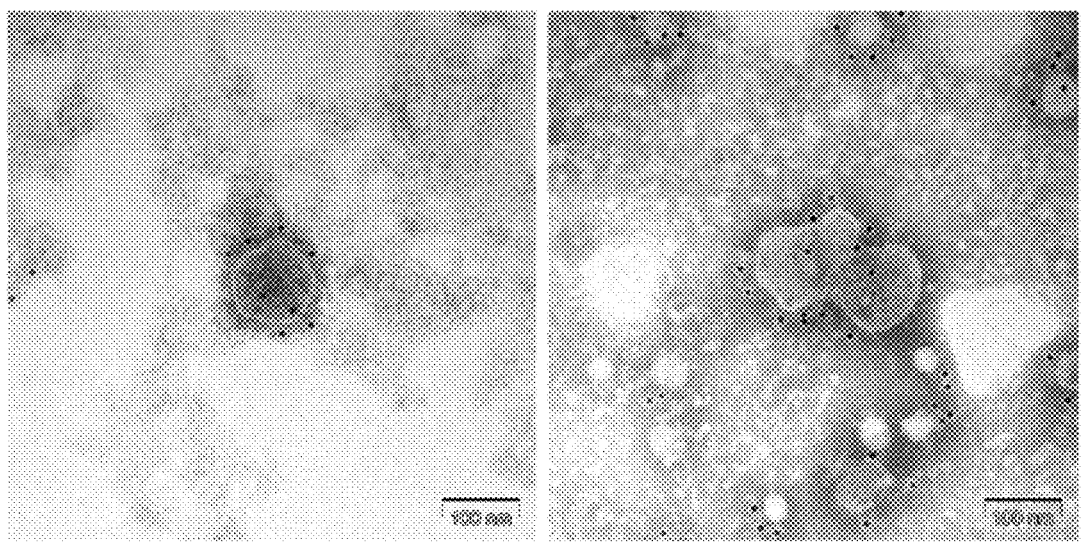
1842-2: DLD-1(B)OE (anti CD9)   Secondary antibody: 10 nm gold colloid labelled
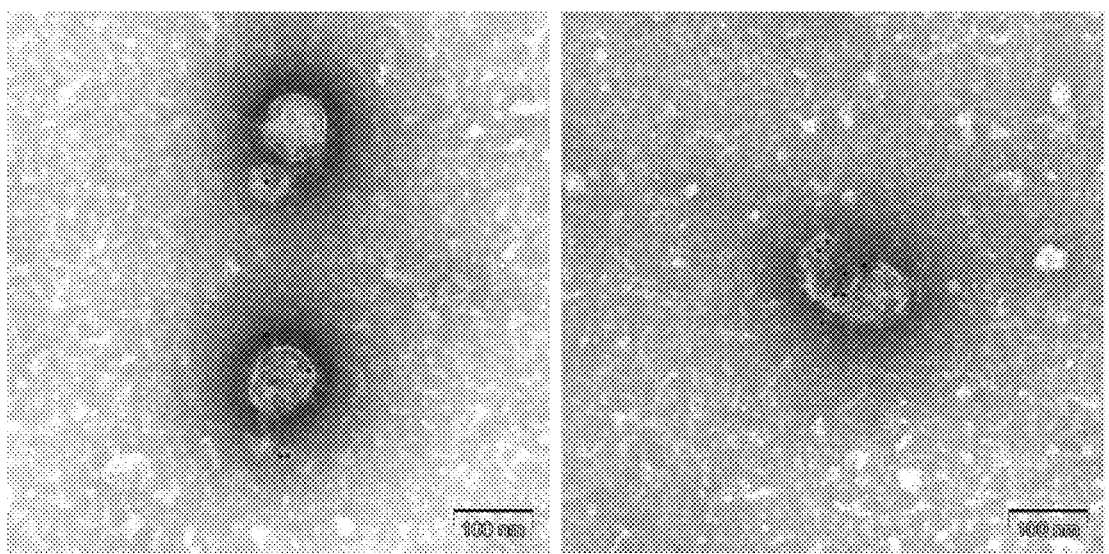
1842-1: DLD-1(B)OE   Primary antibody (669 rat IgM)
Fig. 23

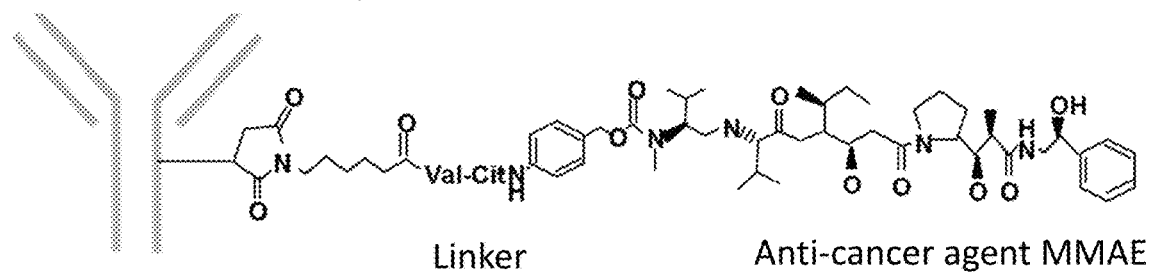
Fig. 24
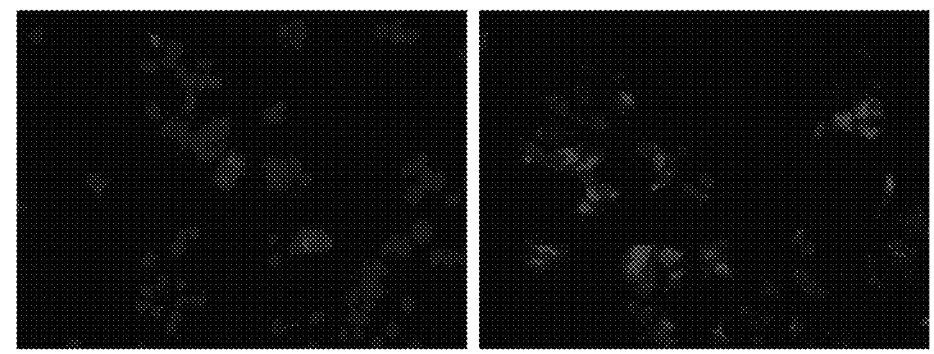
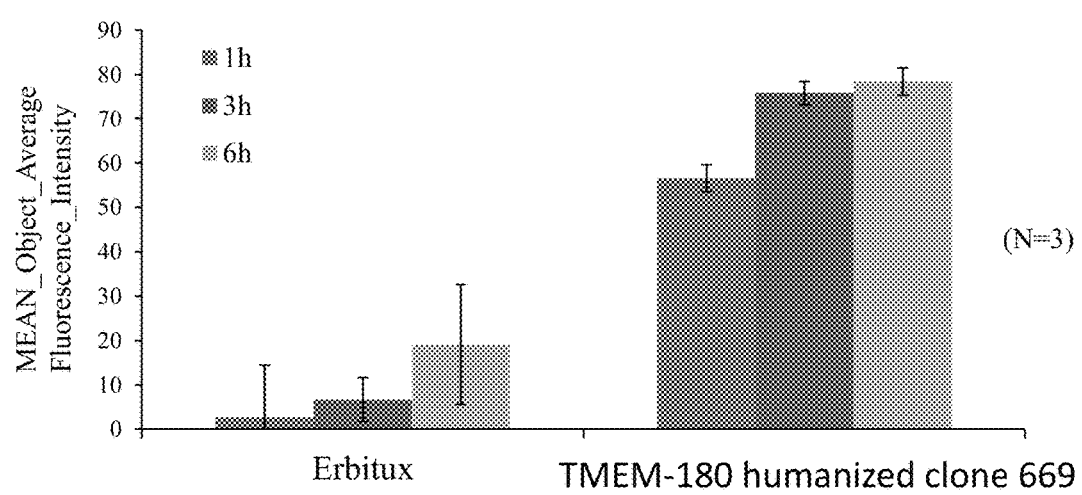
Fig. 25

```
gRNA-3           gRNA-3              PAM
WT     ----ATGTGTTCCTGCTGTACTACGTGGACACCT----
                                  →

#3-3   ----ATGTGTTCCTGCTGTACTTACGTGGACACCT----
       ----ATGTGTTCCTGCTGTA---ACCTGGACACCT----
            +1/m1,d2(-/-)

#3-4   ----ATGTGTTCCTG-GACACCACGTGGACACCT----
            d1,m6(mosaic)

#3-5   ----ATGTGTTCCTGCTGTACTAC----GACACCT----
            d3/d3(-/-)

#3-6   ----ATGTGTTCCTGCTGTACTTACGTGGACACCT----
#3-9,#3-10  +1/+1(-/-)

#3-11  ----ATGTGTTCCTGCTGTACTTACGTGGACACCT----
       ----ATGTGTTCCTGCTGTACT-CGTGGACACCT----
            +1/d1(mosaic)

#3-12  ----ATGTGTTCCTGCTGTACCTACGTGGACACCT----
       ----ATGTGTTCCTGCTGTAC-ACTGGACACCT----
            +1/d1(-/-)
```

```
gRNA-1           gRNA-1              PAM
WT     ----ATAGCTGTGGTGTACGGCTCGTGGCCCTC----
                                 →

#1-1   ----ATAGCTGTGGTGTACGGCTCG---GCCCTC----
       ----ATAGCTGTGGTGTACGGCTTCGTTGGTCC----
            d3/insertion(mosaic)

#1-2   ----ATAGCTGTGGTGTACGGC--------CCTC----
            d8/d8(-/-)
```

Fig. 27

SEQUENCE LISTING

```
<160> NUMBER OF SEQ ID NOS: 206

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

Gly Phe Ser Leu Thr Arg Tyr Asn Val His
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic Construct

<400> SEQUENCE: 2

Val Ile Trp Thr Gly Gly Ser Thr Asp
1               5

<210> SEQ ID NO 3
<211> LENGTH: 4
```

```
<212> TYPE: PRT
<213> ORGANISM: Artificial Sequence
<220> FEATURE:
<223> OTHER INFORMATION: Synthetic Construct

<400> SEQUENCE: 3

Asp Leu Gly Tyr
1

<210> SEQ ID NO 4
<211> LENGTH: 16
<212> TYPE: PRT
<213> ORGANISM: Artificial Sequence
<220> FEATURE:
<223> OTHER INFORMATION: Synthetic Construct

<400> SEQUENCE: 4

Lys Ser Ser Gln Ser Leu Lys Tyr Arg Asp Gly Lys Thr Tyr Leu Asn
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Gln Val Ser Lys Leu Asp Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Cys Gln Gly Ser Tyr Ser Pro His Thr
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic Construct

<400> SEQUENCE: 7

Gly Phe Ser Leu Thr Ser Tyr Tyr Met Gln
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

Phe Ile Arg Ser Gly Gly Ser Thr Glu
1               5

<210> SEQ ID NO 9
<211> LENGTH: 10
<212> TYPE: PRT
```

```
<213> ORGANISM: Artificial Sequence
<220> FEATURE:
<223> OTHER INFORMATION: Synthetic Construct

<400> SEQUENCE: 9

Ala Phe Tyr Gly Gly Tyr Tyr Phe Asp Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic Construct

<400> SEQUENCE: 10

Lys Ala Ser Gln Asn Val Gly Ser Asn Val Asp
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct

<400> SEQUENCE: 11

Lys Ala Ser Asn Arg Tyr Thr
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Construct

<400> SEQUENCE: 12

Met Gln Ser Asn Thr Lys Tyr Thr
1               5

<210> SEQ ID NO 13
<211> LENGTH: 131
<212> TYPE: PRT
<213> ORGANISM: Artificial Sequence
<220> FEATURE:
<223> OTHER INFORMATION: Synthetic Construct

<400> SEQUENCE: 13

Met Ala Val Leu Val Leu Leu Leu Cys Leu Val Thr Phe Pro Thr Cys
1               5                   10                  15

Val Leu Ser Gln Val Gln Leu Lys Glu Ser Gly Pro Gly Leu Val Gln
            20                  25                  30

Pro Ser Gln Thr Leu Ser Leu Thr Cys Thr Val Ser Gly Phe Ser Leu
        35                  40                  45

Thr Arg Tyr Asn Val His Trp Val Arg Gln Pro Gly Lys Gly Leu
    50                  55                  60

Glu Trp Met Gly Val Ile Trp Thr Gly Gly Ser Thr Asp Tyr Asn Ser
65                  70                  75                  80

Ala Leu Lys Ser Arg Leu Ser Ile Ser Arg Asp Thr Ser Lys Ser Gln
                85                  90                  95

Val Phe Leu Lys Met Asn Ser Leu Gln Thr Glu Asp Ile Ala Thr Tyr
            100                 105                 110
```

Tyr Cys Ala Arg Asp Leu Gly Tyr Trp Gly Gln Gly Val Met Val Thr
            115                 120                 125

Val Ser Ser
    130

<210> SEQ ID NO 14
<211> LENGTH: 132
<212> TYPE: PRT
<213> ORGANISM: Artificial Sequence
<220> FEATURE:
<223> OTHER INFORMATION: Synthetic Construct

<400> SEQUENCE: 14

Met Met Ser Pro Ala Gln Phe Leu Phe Leu Leu Met Leu Trp Ile Gln
1               5                   10                  15

Glu Thr His Ser Asp Ile Val Met Thr Gln Thr Pro Leu Ser Leu Ser
                20                  25                  30

Val Ala Ile Gly Gln Ser Ala Ser Ile Ser Cys Lys Ser Ser Gln Ser
            35                  40                  45

Leu Lys Tyr Arg Asp Gly Lys Thr Tyr Leu Asn Trp Val Phe Gln Ser
    50                  55                  60

Pro Gly Gln Ser Pro Lys Arg Leu Ile Tyr Gln Val Ser Lys Leu Asp
65                  70                  75                  80

Ser Gly Val Pro Asp Arg Phe Ser Gly Thr Gly Ser Glu Thr Asp Phe
                85                  90                  95

Thr Leu Lys Ile Ser Arg Val Glu Ala Glu Asp Leu Gly Val Tyr Tyr
            100                 105                 110

Cys Cys Gln Gly Ser Tyr Ser Pro His Thr Phe Gly Ala Gly Thr Lys
            115                 120                 125

Leu Glu Leu Lys
    130

<210> SEQ ID NO 15
<211> LENGTH: 137
<212> TYPE: PRT
<213> ORGANISM: Artificial Sequence
<220> FEATURE:
<223> OTHER INFORMATION: Synthetic Construct

<400> SEQUENCE: 15

Met Ala Ile Leu Val Leu Leu Leu Cys Leu Val Thr Ile Pro His Ser
1               5                   10                  15

Val Leu Ser Gln Val Gln Leu Lys Glu Thr Gly Pro Gly Leu Val Gln
                20                  25                  30

Pro Thr Gln Thr Leu Ser Ile Thr Cys Thr Val Ser Gly Phe Ser Leu
            35                  40                  45

Thr Ser Tyr Tyr Met Gln Trp Val Arg Gln Thr Pro Gly Lys Gly Leu
    50                  55                  60

Glu Trp Met Gly Phe Ile Arg Ser Gly Gly Ser Thr Glu Tyr Asn Ser
65                  70                  75                  80

Glu Phe Lys Ser Arg Leu Ser Ile Ser Arg Asp Thr Ser Lys Asn Gln
                85                  90                  95

Val Phe Leu Lys Met Asn Ser Leu Lys Thr Glu Asp Thr Gly Val Tyr
            100                 105                 110

Tyr Cys Ala Arg Ala Phe Tyr Gly Gly Tyr Tyr Phe Asp Tyr Trp Gly
            115                 120                 125

Gln Gly Val Met Val Thr Val Ser Ser
    130                 135

```
<210> SEQ ID NO 16
<211> LENGTH: 130
<212> TYPE: PRT
<213> ORGANISM: Artificial Sequence
<220> FEATURE:
<223> OTHER INFORMATION: Synthetic Construct

<400> SEQUENCE: 16

Met Gly Ile Arg Met Glu Ser His Thr Arg Val Phe Ile Phe Leu Leu
1               5                   10                  15

Leu Trp Leu Ser Gly Ala Asp Gly Asp Ile Val Met Thr Gln Ser Pro
            20                  25                  30

Thr Ser Ile Ser Ile Ser Val Gly Glu Arg Val Thr Met Asn Cys Lys
        35                  40                  45

Ala Ser Gln Asn Val Gly Ser Asn Val Asp Trp Tyr Gln Gln Lys Thr
    50                  55                  60

Gly Gln Ser Pro Lys Leu Leu Ile Tyr Lys Ala Ser Asn Arg Tyr Thr
65                  70                  75                  80

Gly Val Pro Asp Arg Phe Thr Gly Ser Gly Ser Gly Thr Asp Phe Thr
                85                  90                  95

Phe Thr Ile Ser Asn Met Gln Ala Glu Asp Leu Ala Val Tyr Tyr Cys
            100                 105                 110

Met Gln Ser Asn Thr Lys Tyr Thr Phe Gly Ala Gly Thr Lys Leu Glu
        115                 120                 125

Leu Lys
    130

<210> SEQ ID NO 17
<211> LENGTH: 517
<212> TYPE: PRT
<213> ORGANISM: Homo sapiens
<220> FEATURE:
<221> NAME/KEY: MISC_FEATURE
<223> OTHER INFORMATION: TMEM-180 protein.

<400> SEQUENCE: 17

Met Gly Leu Gly Gln Pro Gln Ala Trp Leu Gly Leu Pro Thr Ala
1               5                   10                  15

Val Val Tyr Gly Ser Leu Ala Leu Phe Thr Thr Ile Leu His Asn Val
            20                  25                  30

Phe Leu Leu Tyr Tyr Val Asp Thr Phe Val Ser Val Tyr Lys Ile Asn
        35                  40                  45

Lys Met Ala Phe Trp Val Gly Glu Thr Val Phe Leu Leu Trp Asn Ser
    50                  55                  60

Leu Asn Asp Pro Leu Phe Gly Trp Leu Ser Arg Gln Phe Leu Ser
65                  70                  75                  80

Ser Gln Pro Arg Ser Gly Ala Gly Leu Ser Ser Arg Ala Val Val Leu
                85                  90                  95

Ala Arg Val Gln Ala Leu Gly Trp His Gly Pro Leu Leu Ala Leu Ser
            100                 105                 110

Phe Leu Ala Phe Trp Val Pro Trp Ala Pro Gly Leu Gln Phe Leu
        115                 120                 125

Leu Cys Leu Cys Leu Tyr Asp Gly Phe Leu Thr Leu Val Asp Leu His
    130                 135                 140

His His Ala Leu Leu Ala Asp Leu Ala Leu Ser Ala His Asp Arg Thr
145                 150                 155                 160
```

His Leu Asn Phe Tyr Cys Ser Leu Phe Ser Ala Ala Gly Ser Leu Ser
            165                 170                 175

Val Phe Ala Ser Tyr Ala Phe Trp Asn Lys Glu Asp Phe Ser Ser Phe
        180                 185                 190

Arg Ala Phe Cys Val Thr Leu Ala Val Ser Ser Gly Leu Gly Phe Leu
            195                 200                 205

Gly Ala Thr Gln Leu Leu Arg Arg Val Glu Ala Ala Arg Lys Asp
        210                 215                 220

Pro Gly Cys Ser Gly Leu Val Val Asp Ser Gly Leu Cys Gly Glu Glu
225                 230                 235                 240

Leu Leu Val Gly Ser Glu Glu Ala Asp Ser Ile Thr Leu Gly Arg Tyr
                245                 250                 255

Leu Arg Gln Leu Ala Arg His Arg Asn Phe Leu Trp Phe Val Ser Met
            260                 265                 270

Asp Leu Val Gln Val Phe His Cys His Phe Asn Ser Asn Phe Phe Pro
            275                 280                 285

Leu Phe Leu Glu His Leu Leu Ser Asp His Ile Ser Leu Ser Thr Gly
        290                 295                 300

Ser Ile Leu Leu Gly Leu Ser Tyr Val Ala Pro His Leu Asn Asn Leu
305                 310                 315                 320

Tyr Phe Leu Ser Leu Cys Arg Arg Trp Gly Val Tyr Ala Val Val Arg
                325                 330                 335

Gly Leu Phe Leu Leu Lys Leu Gly Leu Ser Leu Leu Met Leu Leu Ala
            340                 345                 350

Gly Pro Asp His Leu Ser Leu Leu Cys Leu Phe Ile Ala Ser Asn Arg
        355                 360                 365

Val Phe Thr Glu Gly Thr Cys Lys Leu Leu Thr Leu Val Val Thr Asp
    370                 375                 380

Leu Val Asp Glu Asp Leu Val Leu Asn His Arg Lys Gln Ala Ala Ser
385                 390                 395                 400

Ala Leu Leu Phe Gly Met Val Ala Leu Val Thr Lys Pro Gly Gln Thr
                405                 410                 415

Phe Ala Pro Leu Leu Gly Thr Trp Leu Leu Cys Phe Tyr Thr Gly His
            420                 425                 430

Asp Leu Phe Gln Gln Ser Leu Ile Thr Pro Val Gly Ser Ala His Pro
        435                 440                 445

Trp Pro Glu Pro Pro Ala Pro Ala Pro Ala Gln Ala Pro Thr Leu Arg
    450                 455                 460

Gln Gly Cys Phe Tyr Leu Leu Val Leu Val Pro Ile Thr Cys Ala Leu
465                 470                 475                 480

Leu Gln Leu Phe Thr Trp Ser Gln Phe Thr Leu His Gly Arg Arg Leu
                485                 490                 495

His Met Val Lys Ala Gln Arg Gln Asn Leu Ser Gln Ala Gln Thr Leu
            500                 505                 510

Asp Val Lys Met Val
        515

<210> SEQ ID NO 18
<211> LENGTH: 73
<212> TYPE: DNA
<213> ORGANISM: Artificial Sequence
<220> FEATURE:
<223> OTHER INFORMATION: Synthetic Construct

<400> SEQUENCE: 18

```
cagacctgca cctgaacgtg gttgagagct gaggaattga cggtcactga gggactgtaa    60
tgctgcactt cgc                                                       73
```

<210> SEQ ID NO 19
<211> LENGTH: 78
<212> TYPE: DNA
<213> ORGANISM: Artificial Sequence
<220> FEATURE:
<223> OTHER INFORMATION: Synthetic Construct

<400> SEQUENCE: 19

```
caaccacgtt caggtgcagg tctgtcttca cgtgctgttg tactggctcg tgttcaagag    60
ttcaaactgg aggacctg                                                  78
```

<210> SEQ ID NO 20
<211> LENGTH: 33
<212> TYPE: DNA
<213> ORGANISM: Artificial Sequence
<220> FEATURE:
<223> OTHER INFORMATION: Synthetic Construct

<400> SEQUENCE: 20

```
gagatataca tatgtcggag gtgactcgta gtc                                 33
```

<210> SEQ ID NO 21
<211> LENGTH: 31
<212> TYPE: DNA
<213> ORGANISM: Artificial Sequence
<220> FEATURE:
<223> OTHER INFORMATION: Synthetic Construct

<400> SEQUENCE: 21

```
tggtgctcga aataggctg aacatcaaat g                                    31
```

<210> SEQ ID NO 22
<211> LENGTH: 54
<212> TYPE: DNA
<213> ORGANISM: Artificial Sequence
<220> FEATURE:
<223> OTHER INFORMATION: Synthetic Construct

<400> SEQUENCE: 22

```
gcgaagtgca gcattacagt ccgatcatct gagtctgctg tgcctcttca ttgc          54
```

<210> SEQ ID NO 23
<211> LENGTH: 66
<212> TYPE: DNA
<213> ORGANISM: Artificial Sequence
<220> FEATURE:
<223> OTHER INFORMATION: Synthetic Construct

<400> SEQUENCE: 23

```
caggtcctcc agtttgaact cagaagctgc ttgcttacga tgattcagca ccaggtcctc    60
gtctac                                                               66
```

<210> SEQ ID NO 24
<211> LENGTH: 33
<212> TYPE: DNA
<213> ORGANISM: Artificial Sequence
<220> FEATURE:
<223> OTHER INFORMATION: Synthetic Construct

<400> SEQUENCE: 24

```
gagatataca tatgtcggag gtgactcgta gtc                                 33
```

<210> SEQ ID NO 25
<211> LENGTH: 31
<212> TYPE: DNA
<213> ORGANISM: Artificial Sequence
<220> FEATURE:
<223> OTHER INFORMATION: Synthetic Construct

<400> SEQUENCE: 25
tggtgctcga gaataggctg aacatcaaat g                                31

<210> SEQ ID NO 26
<211> LENGTH: 45
<212> TYPE: DNA
<213> ORGANISM: Artificial Sequence
<220> FEATURE:
<223> OTHER INFORMATION: Synthetic Construct

<400> SEQUENCE: 26
ctaatacgac tcactatagg gcaagcagtg gtatcaacgc agagt                 45

<210> SEQ ID NO 27
<211> LENGTH: 22
<212> TYPE: DNA
<213> ORGANISM: Artificial Sequence
<220> FEATURE:
<223> OTHER INFORMATION: Synthetic Construct

<400> SEQUENCE: 27
ctaatacgac tcactatagg gc                                          22

<210> SEQ ID NO 28
<211> LENGTH: 29
<212> TYPE: DNA
<213> ORGANISM: Artificial Sequence
<220> FEATURE:
<223> OTHER INFORMATION: Synthetic Construct

<400> SEQUENCE: 28
cccatggcca ccarattcty atcagacag                                   29

<210> SEQ ID NO 29
<211> LENGTH: 45
<212> TYPE: DNA
<213> ORGANISM: Artificial Sequence
<220> FEATURE:
<223> OTHER INFORMATION: Synthetic Construct

<400> SEQUENCE: 29
ctaatacgac tcactatagg gcaagcagtg gtatcaacgc agagt                 45

<210> SEQ ID NO 30
<211> LENGTH: 22
<212> TYPE: DNA
<213> ORGANISM: Artificial Sequence
<220> FEATURE:
<223> OTHER INFORMATION: Synthetic Construct

<400> SEQUENCE: 30
ctaatacgac tcactatagg gc                                          22

<210> SEQ ID NO 31
<211> LENGTH: 28
<212> TYPE: DNA
<213> ORGANISM: Artificial Sequence
<220> FEATURE:

<223> OTHER INFORMATION: Synthetic Construct

<400> SEQUENCE: 31
gttgttcawg argcacacga ctgaggca                                              28

<210> SEQ ID NO 32
<211> LENGTH: 10
<212> TYPE: PRT
<213> ORGANISM: Artificial Sequence
<220> FEATURE:
<223> OTHER INFORMATION: Synthetic Construct

<400> SEQUENCE: 32

Gly Phe Thr Phe Ser Asp Tyr Ala Met Ala
1               5                   10

<210> SEQ ID NO 33
<211> LENGTH: 9
<212> TYPE: PRT
<213> ORGANISM: Artificial Sequence
<220> FEATURE:
<223> OTHER INFORMATION: Synthetic Construct

<400> SEQUENCE: 33

Thr Ile Ile Tyr Asp Gly Ser Ser Thr
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic Construct

<400> SEQUENCE: 34

His Trp Tyr Trp Tyr Phe Asp Phe
1               5

<210> SEQ ID NO 35
<211> LENGTH: 11
<212> TYPE: PRT
<213> ORGANISM: Artificial Sequence
<220> FEATURE:
<223> OTHER INFORMATION: Synthetic Construct

<400> SEQUENCE: 35

Leu Ala Ser Glu Gly Ile Ser Asn Asp Leu Ala
1               5                   10

<210> SEQ ID NO 36
<211> LENGTH: 7
<212> TYPE: PRT
<213> ORGANISM: Artificial Sequence
<220> FEATURE:
<223> OTHER INFORMATION: Synthetic Construct

<400> SEQUENCE: 36

Ala Ala Ser Arg Leu Gln Asp
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic Construct

<400> SEQUENCE: 37

Gln Gln Ser Tyr Lys Tyr Pro Leu Thr
1               5

<210> SEQ ID NO 38
<211> LENGTH: 136
<212> TYPE: PRT
<213> ORGANISM: Artificial Sequence
<220> FEATURE:
<223> OTHER INFORMATION: Synthetic Construct

<400> SEQUENCE: 38

Met Asp Ile Arg Leu Ser Leu Ala Phe Leu Val Leu Phe Ile Lys Gly
1               5                   10                  15

Val Gln Cys Glu Val Gln Leu Val Glu Ser Gly Gly Gly Leu Val Gln
                20                  25                  30

Pro Gly Asn Ser Leu Lys Leu Ser Cys Ala Ala Ser Gly Phe Thr Phe
            35                  40                  45

Ser Asp Tyr Ala Met Ala Trp Val Arg Gln Ser Pro Lys Lys Gly Leu
    50                  55                  60

Glu Trp Val Ala Thr Ile Ile Tyr Asp Gly Ser Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Ala Thr His Trp Tyr Trp Tyr Phe Asp Phe Trp Gly Pro
        115                 120                 125

Gly Thr Met Val Thr Val Ser Ser
    130                 135

<210> SEQ ID NO 39
<211> LENGTH: 127
<212> TYPE: PRT
<213> ORGANISM: Artificial Sequence
<220> FEATURE:
<223> OTHER INFORMATION: Synthetic Construct

<400> SEQUENCE: 39

Met Gly Val Pro Thr Gln Leu Leu Gly Leu Leu Leu Leu Trp Ile Thr
1               5                   10                  15

Asp Ala Ile Cys Asp Ile Gln Met Thr Gln Ser Pro Ala Ser Leu Ser
                20                  25                  30

Ala Ser Leu Gly Glu Thr Val Ser Ile Glu Cys Leu Ala Ser Glu Gly
            35                  40                  45

Ile Ser Asn Asp Leu Ala Trp Tyr Gln Gln Lys Ser Gly Lys Ser Pro
    50                  55                  60

Gln Leu Leu Ile Tyr Ala Ala Ser Arg Leu Gln Asp Gly Val Pro Ser
65                  70                  75                  80

Arg Phe Ser Gly Ser Gly Ser Gly Thr Arg Tyr Ser Leu Lys Ile Ser
                85                  90                  95

Gly Met Gln Pro Glu Asp Glu Ala Asp Tyr Phe Cys Gln Gln Ser Tyr
            100                 105                 110

Lys Tyr Pro Leu Thr Phe Gly Ser Gly Thr Lys Leu Glu Ile Lys
        115                 120                 125

<210> SEQ ID NO 40
<211> LENGTH: 10

```
<212> TYPE: PRT
<213> ORGANISM: Artificial Sequence
<220> FEATURE:
<223> OTHER INFORMATION: Synthetic Construct

<400> SEQUENCE: 40

Gly Phe Thr Phe Ser Asp Tyr Ala Met Ala
1               5                   10

<210> SEQ ID NO 41
<211> LENGTH: 9
<212> TYPE: PRT
<213> ORGANISM: Artificial Sequence
<220> FEATURE:
<223> OTHER INFORMATION: Synthetic Construct

<400> SEQUENCE: 41

Thr Ile Ile Tyr Asp Gly Ser Ser Thr
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic Construct

<400> SEQUENCE: 42

His Trp Tyr Trp Tyr Phe Asp Phe
1               5

<210> SEQ ID NO 43
<211> LENGTH: 11
<212> TYPE: PRT
<213> ORGANISM: Artificial Sequence
<220> FEATURE:
<223> OTHER INFORMATION: Synthetic Construct

<400> SEQUENCE: 43

Leu Ala Ser Glu Gly Ile Ser Asn Asp Leu Ala
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Synthetic Construct

<400> SEQUENCE: 44

Ala Ala Ser Arg Leu Gln Asp
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Construct

<400> SEQUENCE: 45

Gln Gln Ser Tyr Lys Tyr Pro Leu Thr
1               5

<210> SEQ ID NO 46
<211> LENGTH: 136
<212> TYPE: PRT
```

```
<213> ORGANISM: Artificial Sequence
<220> FEATURE:
<223> OTHER INFORMATION: Synthetic Construct

<400> SEQUENCE: 46

Met Asp Ile Arg Leu Ser Leu Ala Phe Leu Val Leu Phe Ile Lys Gly
1               5                   10                  15

Val Gln Cys Glu Val Gln Leu Val Glu Ser Gly Gly Gly Leu Val Gln
            20                  25                  30

Pro Gly Asn Ser Leu Lys Leu Ser Cys Ala Ala Ser Gly Phe Thr Phe
        35                  40                  45

Ser Asp Tyr Ala Met Ala Trp Val Arg Gln Ser Pro Lys Lys Gly Leu
    50                  55                  60

Glu Trp Val Ala Thr Ile Ile Tyr Asp Gly Ser Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Ala Thr His Trp Tyr Trp Tyr Phe Asp Phe Trp Gly Pro
        115                 120                 125

Gly Thr Met Val Thr Val Ser Ser
        130                 135

<210> SEQ ID NO 47
<211> LENGTH: 127
<212> TYPE: PRT
<213> ORGANISM: Artificial Sequence
<220> FEATURE:
<223> OTHER INFORMATION: Synthetic Construct

<400> SEQUENCE: 47

Met Gly Val Pro Thr Gln Leu Leu Gly Leu Leu Leu Leu Trp Ile Thr
1               5                   10                  15

Asp Ala Ile Cys Asp Ile Gln Met Thr Gln Ser Pro Ala Ser Leu Ser
            20                  25                  30

Ala Ser Leu Gly Glu Thr Val Ser Ile Glu Cys Leu Ala Ser Glu Gly
        35                  40                  45

Ile Ser Asn Asp Leu Ala Trp Tyr Gln Gln Lys Ser Gly Lys Ser Pro
    50                  55                  60

Gln Leu Leu Ile Tyr Ala Ala Ser Arg Leu Gln Asp Gly Val Pro Ser
65                  70                  75                  80

Arg Phe Ser Gly Ser Gly Ser Gly Thr Arg Tyr Ser Leu Lys Ile Ser
                85                  90                  95

Gly Met Gln Pro Glu Asp Glu Ala Asp Tyr Phe Cys Gln Gln Ser Tyr
            100                 105                 110

Lys Tyr Pro Leu Thr Phe Gly Ser Gly Thr Lys Leu Glu Ile Lys
        115                 120                 125

<210> SEQ ID NO 48
<211> LENGTH: 5
<212> TYPE: PRT
<213> ORGANISM: Artificial Sequence
<220> FEATURE:
<223> OTHER INFORMATION: Synthetic Construct

<400> SEQUENCE: 48

Asp Cys Ala Leu Asn
1               5
```

<210> SEQ ID NO 49
<211> LENGTH: 15
<212> TYPE: PRT
<213> ORGANISM: Artificial Sequence
<220> FEATURE:
<223> OTHER INFORMATION: Synthetic Construct

<400> SEQUENCE: 49

Trp Ile Asn Thr Gln Thr Gly Lys Pro Thr Tyr Ala Asp Asp Phe
1               5                   10                  15

<210> SEQ ID NO 50
<211> LENGTH: 8
<212> TYPE: PRT
<213> ORGANISM: Artificial Sequence
<220> FEATURE:
<223> OTHER INFORMATION: Synthetic Construct

<400> SEQUENCE: 50

Glu Asp Tyr Gly Tyr Phe Asp Tyr
1               5

<210> SEQ ID NO 51
<211> LENGTH: 11
<212> TYPE: PRT
<213> ORGANISM: Artificial Sequence
<220> FEATURE:
<223> OTHER INFORMATION: Synthetic Construct

<400> SEQUENCE: 51

Gln Ala Ser Gln Asn Ile Asn Lys Phe Ile Ala
1               5                   10

<210> SEQ ID NO 52
<211> LENGTH: 7
<212> TYPE: PRT
<213> ORGANISM: Artificial Sequence
<220> FEATURE:
<223> OTHER INFORMATION: Synthetic Construct

<400> SEQUENCE: 52

Tyr Thr Ser Thr Leu Val Ser
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic Construct

<400> SEQUENCE: 53

Leu Gln Tyr Asp Asn Leu Arg Thr
1               5

<210> SEQ ID NO 54
<211> LENGTH: 136
<212> TYPE: PRT
<213> ORGANISM: Artificial Sequence
<220> FEATURE:
<223> OTHER INFORMATION: Synthetic Construct

<400> SEQUENCE: 54

Met Asp Trp Leu Trp Asn Leu Leu Phe Leu Met Val Val Ala Gln Ser
1               5                   10                  15

```
Ala Gln Ala Gln Ile Gln Leu Val Gln Ser Gly Pro Glu Leu Lys Lys
            20                  25                  30

Pro Gly Glu Ser Val Lys Ile Ser Cys Lys Ala Ser Gly Tyr Thr Phe
        35                  40                  45

Thr Asp Cys Ala Leu Asn Trp Val Lys Gln Ala Pro Gly Asn Gly Leu
 50                  55                  60

Lys Trp Met Gly Trp Ile Asn Thr Gln Thr Gly Lys Pro Thr Tyr Ala
65                  70                  75                  80

Asp Asp Phe Lys Gln Arg Phe Val Phe Ser Leu Glu Thr Ser Ala Ser
                85                  90                  95

Thr Ala Tyr Leu Gln Ile Asn Asn Leu Asn Ile Glu Asp Thr Ala Thr
            100                 105                 110

Tyr Phe Cys Thr Arg Glu Asp Tyr Gly Tyr Phe Asp Tyr Trp Gly Gln
        115                 120                 125

Gly Val Met Val Thr Val Ser Ser
        130                 135

<210> SEQ ID NO 55
<211> LENGTH: 126
<212> TYPE: PRT
<213> ORGANISM: Artificial Sequence
<220> FEATURE:
<223> OTHER INFORMATION: Synthetic Construct

<400> SEQUENCE: 55

Met Arg Thr Ser Ile Gln Leu Leu Gly Leu Leu Leu Trp Leu His
1               5                   10                  15

Asp Ala Gln Cys Asp Ile Gln Met Thr Gln Ser Pro Pro Ser Leu Ser
            20                  25                  30

Ala Ser Leu Gly Asp Lys Val Thr Ile Thr Cys Gln Ala Ser Gln Asn
        35                  40                  45

Ile Asn Lys Phe Ile Ala Trp Tyr Gln Gln Lys Pro Gly Lys Ala Pro
 50                  55                  60

Arg His Leu Val His Tyr Thr Ser Thr Leu Val Ser Gly Thr Pro Ser
65                  70                  75                  80

Arg Phe Ser Gly Ser Gly Ser Gly Arg Asp Tyr Ser Phe Ser Ile Ser
                85                  90                  95

Asn Val Glu Ser Glu Asp Ile Ala Ser Tyr Tyr Cys Leu Gln Tyr Asp
            100                 105                 110

Asn Leu Arg Thr Phe Gly Gly Gly Thr Lys Leu Glu Leu Lys
        115                 120                 125

<210> SEQ ID NO 56
<211> LENGTH: 5
<212> TYPE: PRT
<213> ORGANISM: Artificial Sequence
<220> FEATURE:
<223> OTHER INFORMATION: Synthetic Construct

<400> SEQUENCE: 56

Asn Tyr Gly Met His
1               5

<210> SEQ ID NO 57
<211> LENGTH: 15
<212> TYPE: PRT
<213> ORGANISM: Artificial Sequence
<220> FEATURE:
<223> OTHER INFORMATION: Synthetic Construct
```

<400> SEQUENCE: 57

Ser Ile Ser Pro Ser Gly Gly Ser Thr Tyr Tyr Arg Asp Ser Val
1               5                   10                  15

<210> SEQ ID NO 58
<211> LENGTH: 13
<212> TYPE: PRT
<213> ORGANISM: Artificial Sequence
<220> FEATURE:
<223> OTHER INFORMATION: Synthetic Construct

<400> SEQUENCE: 58

Ser Ala Ser Ile Thr Ala Tyr Tyr Tyr Val Met Asp Ala
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Synthetic Construct

<400> SEQUENCE: 59

Lys Ala Ser Gln Asn Val Gly Ser Asn Val Asp
1               5                   10

<210> SEQ ID NO 60
<211> LENGTH: 7
<212> TYPE: PRT
<213> ORGANISM: Artificial Sequence
<220> FEATURE:
<223> OTHER INFORMATION: Synthetic Construct

<400> SEQUENCE: 60

Lys Ala Ser Asn Arg Tyr Thr
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic Construct

<400> SEQUENCE: 61

Met Gln Ser Asn Ser Tyr Pro Pro Thr
1               5

<210> SEQ ID NO 62
<211> LENGTH: 141
<212> TYPE: PRT
<213> ORGANISM: Artificial Sequence
<220> FEATURE:
<223> OTHER INFORMATION: Synthetic Construct

<400> SEQUENCE: 62

Met Asp Ile Arg Leu Ser Leu Gly Phe Leu Val Leu Phe Ile Lys Gly
1               5                   10                  15

Val Gln Cys Glu Val Gln Leu Val Glu Ser Gly Gly Gly Leu Val Gln
            20                  25                  30

Pro Gly Arg Ser Leu Lys Leu Ser Cys Ala Ala Ser Gly Phe Thr Phe
        35                  40                  45

Ser Asn Tyr Gly Met His Trp Ile Arg Gln Ala Pro Thr Lys Gly Leu
    50                  55                  60

```
Glu Trp Val Ala Ser Ile Ser Pro Ser Gly Gly Ser Thr Tyr Tyr Arg
 65                  70                  75                  80

Asp Ser Val Lys Gly Arg Phe Thr Ile Ser Arg Asp Asn Ala Lys Ser
                 85                  90                  95

Thr Leu Tyr Leu Gln Met Asp Ser Leu Arg Ser Glu Asp Thr Ala Thr
            100                 105                 110

Tyr Tyr Cys Ala Thr Ser Ala Ser Ile Thr Ala Tyr Tyr Tyr Val Met
        115                 120                 125

Asp Ala Trp Gly Gln Gly Ala Ser Val Thr Val Ser Ser
    130                 135                 140
```

```
<210> SEQ ID NO 63
<211> LENGTH: 127
<212> TYPE: PRT
<213> ORGANISM: Artificial Sequence
<220> FEATURE:
<223> OTHER INFORMATION: Synthetic Construct

<400> SEQUENCE: 63

Met Glu Ser His Thr Arg Val Phe Ile Phe Leu Leu Leu Trp Leu Ser
 1               5                  10                  15

Gly Ala Asp Gly Asp Ile Val Met Thr Gln Ser Pro Thr Ser Met Ser
                 20                  25                  30

Ile Ser Val Gly Asp Arg Val Thr Met Asn Cys Lys Ala Ser Gln Asn
            35                  40                  45

Val Gly Ser Asn Val Asp Trp Tyr Gln Gln Lys Thr Gly Gln Ser Pro
        50                  55                  60

Lys Leu Leu Ile Tyr Lys Ala Ser Asn Arg Tyr Thr Gly Val Pro Asp
 65                  70                  75                  80

Arg Phe Thr Gly Ser Gly Ser Gly Thr Asp Phe Thr Phe Thr Ile Ser
                 85                  90                  95

Asn Met Gln Ala Glu Asp Leu Ala Val Tyr Tyr Cys Met Gln Ser Asn
            100                 105                 110

Ser Tyr Pro Pro Thr Phe Gly Gly Gly Thr Lys Leu Glu Leu Arg
        115                 120                 125
```

```
<210> SEQ ID NO 64
<211> LENGTH: 5
<212> TYPE: PRT
<213> ORGANISM: Artificial Sequence
<220> FEATURE:
<223> OTHER INFORMATION: Synthetic Construct

<400> SEQUENCE: 64

Asn Tyr Trp Met Thr
 1               5
```

```
<210> SEQ ID NO 65
<211> LENGTH: 15
<212> TYPE: PRT
<213> ORGANISM: Artificial Sequence
<220> FEATURE:
<223> OTHER INFORMATION: Synthetic Construct

<400> SEQUENCE: 65

Ser Ile Thr Asn Thr Gly Gly Ser Thr Tyr Tyr Pro Asp Ser Val
 1               5                  10                  15
```

```
<210> SEQ ID NO 66
<211> LENGTH: 12
<212> TYPE: PRT
```

```
<213> ORGANISM: Artificial Sequence
<220> FEATURE:
<223> OTHER INFORMATION: Synthetic Construct

<400> SEQUENCE: 66

Ala Gly Tyr Ser Ser Tyr Pro Asp Tyr Phe Asp Tyr
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Synthetic Construct

<400> SEQUENCE: 67

Lys Ala Gly Gln Asn Ile Tyr Asn Tyr Leu Ala
1               5                   10

<210> SEQ ID NO 68
<211> LENGTH: 7
<212> TYPE: PRT
<213> ORGANISM: Artificial Sequence
<220> FEATURE:
<223> OTHER INFORMATION: Synthetic Construct

<400> SEQUENCE: 68

Asn Ala Asn Ser Leu Gln Thr
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic Construct

<400> SEQUENCE: 69

Gln Gln Tyr Ser Ser Gly Trp Thr
1               5

<210> SEQ ID NO 70
<211> LENGTH: 140
<212> TYPE: PRT
<213> ORGANISM: Artificial Sequence
<220> FEATURE:
<223> OTHER INFORMATION: Synthetic Construct

<400> SEQUENCE: 70

Met Asp Ile Arg Leu Ser Leu Val Phe Leu Val Leu Phe Ile Lys Gly
1               5                   10                  15

Val Gln Cys Glu Val Gln Leu Val Glu Ser Gly Gly Gly Leu Val Gln
            20                  25                  30

Pro Gly Arg Ser Leu Lys Leu Ser Cys Val Ala Ser Gly Phe Thr Phe
        35                  40                  45

Asn Asn Tyr Trp Met Thr Trp Ile Arg Gln Ala Pro Gly Lys Gly Leu
    50                  55                  60

Glu Trp Val Ala Ser Ile Thr Asn Thr Gly Gly Ser Thr Tyr Tyr Pro
65                  70                  75                  80

Asp Ser Val Lys Gly Arg Phe Thr Ile Ser Arg Asp Tyr Ala Lys Ser
                85                  90                  95

Thr Leu Tyr Leu Gln Met Asn Ser Leu Arg Ser Glu Asp Thr Ala Thr
            100                 105                 110
```

Tyr Tyr Cys Thr Arg Ala Gly Tyr Ser Ser Tyr Pro Asp Tyr Phe Asp
            115                 120                 125

Tyr Trp Gly Gln Gly Val Met Leu Thr Val Ser Ser
    130                 135                 140

<210> SEQ ID NO 71
<211> LENGTH: 126
<212> TYPE: PRT
<213> ORGANISM: Artificial Sequence
<220> FEATURE:
<223> OTHER INFORMATION: Synthetic Construct

<400> SEQUENCE: 71

Met Met Ala Pro Val Gln Leu Leu Gly Leu Leu Leu Leu Trp Leu Pro
1               5                   10                  15

Ala Met Arg Cys Asn Ile Gln Met Thr Gln Ser Pro Ser Leu Leu Ser
            20                  25                  30

Ala Ser Val Gly Asp Arg Val Thr Leu Ser Cys Lys Ala Gly Gln Asn
        35                  40                  45

Ile Tyr Asn Tyr Leu Ala Trp Tyr Gln Gln Lys Leu Gly Glu Ala Pro
    50                  55                  60

Lys Leu Leu Ile Tyr Asn Ala Asn Ser Leu Gln Thr Gly Ile Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Thr Tyr Phe Cys Gln Gln Tyr Ser
            100                 105                 110

Ser Gly Trp Thr Phe Gly Gly Gly Thr Lys Leu Glu Leu Lys
        115                 120                 125

<210> SEQ ID NO 72
<211> LENGTH: 5
<212> TYPE: PRT
<213> ORGANISM: Artificial Sequence
<220> FEATURE:
<223> OTHER INFORMATION: Synthetic Construct

<400> SEQUENCE: 72

Asp Tyr Trp Val Ser
1               5

<210> SEQ ID NO 73
<211> LENGTH: 16
<212> TYPE: PRT
<213> ORGANISM: Artificial Sequence
<220> FEATURE:
<223> OTHER INFORMATION: Synthetic Construct

<400> SEQUENCE: 73

Glu Ile Tyr Pro Asn Ser Gly Ala Thr Asn Phe Asn Glu Asn Phe Lys
1               5                   10                  15

<210> SEQ ID NO 74
<211> LENGTH: 12
<212> TYPE: PRT
<213> ORGANISM: Artificial Sequence
<220> FEATURE:
<223> OTHER INFORMATION: Synthetic Construct

<400> SEQUENCE: 74

Asp Gly Thr Met Gly Ile Ala Tyr Tyr Phe Asp Tyr
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Synthetic Construct

<400> SEQUENCE: 75

Lys Ala Ser Gln Asn Ile Asn Arg Tyr Leu Asn
1               5                   10

<210> SEQ ID NO 76
<211> LENGTH: 7
<212> TYPE: PRT
<213> ORGANISM: Artificial Sequence
<220> FEATURE:
<223> OTHER INFORMATION: Synthetic Construct

<400> SEQUENCE: 76

Asn Ala Asn Ser Leu Gln Thr
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic Construct

<400> SEQUENCE: 77

Leu Gln His Asn Ser Trp Pro Tyr Thr
1               5

<210> SEQ ID NO 78
<211> LENGTH: 139
<212> TYPE: PRT
<213> ORGANISM: Artificial Sequence
<220> FEATURE:
<223> OTHER INFORMATION: Synthetic Construct

<400> SEQUENCE: 78

Met Gly Trp Ile Cys Ile Ile Phe Leu Val Ala Thr Ala Thr Gly Val
1               5                   10                  15

His Ser Gln Val Lys Leu Leu Gln Ser Gly Ala Ala Leu Val Lys Pro
                20                  25                  30

Gly Ala Ser Val Lys Met Ser Cys Lys Ala Ser Gly Tyr Thr Phe Thr
            35                  40                  45

Asp Tyr Trp Val Ser Trp Val Lys Gln Ser His Gly Lys Ser Leu Glu
        50                  55                  60

Trp Ile Gly Glu Ile Tyr Pro Asn Ser Gly Ala Thr Asn Phe Asn Glu
65                  70                  75                  80

Asn Phe Lys Gly Lys Ala Thr Leu Thr Val Asp Lys Ser Thr Ser Thr
                85                  90                  95

Ala Tyr Met Glu Leu Ser Arg Leu Thr Ser Glu Asp Ser Ala Ile Tyr
                100                 105                 110

Tyr Cys Thr Arg Asp Gly Thr Met Gly Ile Ala Tyr Tyr Phe Asp Tyr
            115                 120                 125

Trp Gly Gln Gly Val Met Val Thr Val Ser Ser
        130                 135

<210> SEQ ID NO 79
<211> LENGTH: 127

```
<212> TYPE: PRT
<213> ORGANISM: Artificial Sequence
<220> FEATURE:
<223> OTHER INFORMATION: Synthetic Construct

<400> SEQUENCE: 79

Met Met Ala Ala Val Gln Leu Leu Gly Leu Leu Leu Leu Trp Val Pro
1               5                   10                  15

Ala Met Arg Cys Asp Ile Gln Met Thr Gln Ser Pro Ser Phe Leu Ser
            20                  25                  30

Ala Ser Val Gly Asp Arg Val Thr Ile Asn Cys Lys Ala Ser Gln Asn
        35                  40                  45

Ile Asn Arg Tyr Leu Asn Trp Tyr Gln Gln Lys Leu Gly Glu Ala Pro
    50                  55                  60

Lys Leu Leu Ile Tyr Asn Ala Asn Ser Leu Gln Thr Gly Ile Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Thr Tyr Phe Cys Leu Gln His Asn
            100                 105                 110

Ser Trp Pro Tyr Thr Phe Gly Ala Gly Thr Lys Leu Glu Leu Lys
        115                 120                 125

<210> SEQ ID NO 80
<211> LENGTH: 5
<212> TYPE: PRT
<213> ORGANISM: Artificial Sequence
<220> FEATURE:
<223> OTHER INFORMATION: Synthetic Construct

<400> SEQUENCE: 80

Ser Tyr Asp Ile Ser
1               5

<210> SEQ ID NO 81
<211> LENGTH: 18
<212> TYPE: PRT
<213> ORGANISM: Artificial Sequence
<220> FEATURE:
<223> OTHER INFORMATION: Synthetic Construct

<400> SEQUENCE: 81

Ala Ile Asn Pro Gly Ser Gly Gly Thr Gly Tyr Asn Glu Lys Phe Lys
1               5                   10                  15

Gly Lys

<210> SEQ ID NO 82
<211> LENGTH: 11
<212> TYPE: PRT
<213> ORGANISM: Artificial Sequence
<220> FEATURE:
<223> OTHER INFORMATION: Synthetic Construct

<400> SEQUENCE: 82

Ile His Gly Gly Tyr Arg Tyr Trp Phe Ala Tyr
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Synthetic Construct
```

-continued

<400> SEQUENCE: 83

Arg Ala Ser Ser Ser Val Ser Tyr Met His
1               5                   10

<210> SEQ ID NO 84
<211> LENGTH: 7
<212> TYPE: PRT
<213> ORGANISM: Artificial Sequence
<220> FEATURE:
<223> OTHER INFORMATION: Synthetic Construct

<400> SEQUENCE: 84

Asp Thr Ser Lys Leu Ala Ser
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic Construct

<400> SEQUENCE: 85

Leu Gln Arg Ser Ser Tyr Pro Pro Thr
1               5

<210> SEQ ID NO 86
<211> LENGTH: 139
<212> TYPE: PRT
<213> ORGANISM: Artificial Sequence
<220> FEATURE:
<223> OTHER INFORMATION: Synthetic Construct

<400> SEQUENCE: 86

Met Glu Trp Asn Trp Val Phe Leu Phe Leu Leu Ser Val Thr Ala Gly
1               5                   10                  15

Val His Ser Gln Val Gln Leu Gln Gln Ser Gly Ala Glu Leu Thr Lys
            20                  25                  30

Pro Gly Ser Ser Val Lys Ile Ser Cys Lys Ala Ser Gly Tyr Thr Phe
        35                  40                  45

Thr Ser Tyr Asp Ile Ser Trp Ile Lys Gln Arg Pro Gly Gln Ala Leu
    50                  55                  60

Glu Trp Ile Gly Ala Ile Asn Pro Gly Ser Gly Gly Thr Gly Tyr Asn
65                  70                  75                  80

Glu Lys Phe Lys Gly Lys Ala Thr Leu Thr Val Asp Lys Ser Ser Ser
                85                  90                  95

Thr Ala Phe Met Gln Leu Ser Ser Leu Thr Pro Glu Asp Thr Ala Val
            100                 105                 110

Tyr Tyr Cys Ala Arg Ile His Gly Gly Tyr Arg Tyr Trp Phe Ala Tyr
        115                 120                 125

Trp Gly Gln Gly Thr Leu Val Thr Val Ser Ser
    130                 135

<210> SEQ ID NO 87
<211> LENGTH: 128
<212> TYPE: PRT
<213> ORGANISM: Artificial Sequence
<220> FEATURE:
<223> OTHER INFORMATION: Synthetic Construct

<400> SEQUENCE: 87

```
Met Asp Phe Gln Val Gln Ser Phe Ser Leu Leu Ile Ser Ile Thr
1               5                   10                  15

Val Ile Val Ser Ser Gly Glu Ile Val Leu Thr Gln Ser Pro Thr Thr
            20                  25                  30

Met Ala Ala Ser Pro Gly Glu Lys Val Thr Ile Thr Cys Arg Ala Ser
        35                  40                  45

Ser Ser Val Ser Tyr Met His Trp Phe Gln Gln Lys Ser Gly Thr Ser
    50                  55                  60

Pro Lys Pro Trp Ile Tyr Asp Thr Ser Lys Leu Ala Ser Gly Val Pro
65                  70                  75                  80

Asp Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Leu Gln Arg
            100                 105                 110

Ser Ser Tyr Pro Pro Thr Phe Gly Ala Gly Thr Lys Leu Glu Leu Lys
            115                 120                 125
```

<210> SEQ ID NO 88
<211> LENGTH: 5
<212> TYPE: PRT
<213> ORGANISM: Artificial Sequence
<220> FEATURE:
<223> OTHER INFORMATION: Synthetic Construct

<400> SEQUENCE: 88

```
Ser Asn Gly Val Gly
1               5
```

<210> SEQ ID NO 89
<211> LENGTH: 16
<212> TYPE: PRT
<213> ORGANISM: Artificial Sequence
<220> FEATURE:
<223> OTHER INFORMATION: Synthetic Construct

<400> SEQUENCE: 89

```
Thr Ile Trp Thr Gly Gly Gly Thr Asn Tyr Asn Ser Gly Val Gln Ser
1               5                   10                  15
```

<210> SEQ ID NO 90
<211> LENGTH: 7
<212> TYPE: PRT
<213> ORGANISM: Artificial Sequence
<220> FEATURE:
<223> OTHER INFORMATION: Synthetic Construct

<400> SEQUENCE: 90

```
Glu Tyr Met Gly Phe Asp Tyr
1               5
```

<210> SEQ ID NO 91
<211> LENGTH: 11
<212> TYPE: PRT
<213> ORGANISM: Artificial Sequence
<220> FEATURE:
<223> OTHER INFORMATION: Synthetic Construct

<400> SEQUENCE: 91

```
Lys Ala Ser Gln Asn Val Gly Ile Asn Val Gly
1               5                   10
```

<210> SEQ ID NO 92
<211> LENGTH: 7

```
<212> TYPE: PRT
<213> ORGANISM: Artificial Sequence
<220> FEATURE:
<223> OTHER INFORMATION: Synthetic Construct

<400> SEQUENCE: 92

Trp Ala Ser Asn Arg Asp Thr
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic Construct

<400> SEQUENCE: 93

Leu Gln His Asn Ser Tyr Pro Arg Thr
1               5

<210> SEQ ID NO 94
<211> LENGTH: 134
<212> TYPE: PRT
<213> ORGANISM: Artificial Sequence
<220> FEATURE:
<223> OTHER INFORMATION: Synthetic Construct

<400> SEQUENCE: 94

Met Ala Val Leu Val Leu Leu Leu Cys Leu Val Thr Phe Pro Ser Cys
1               5                   10                  15

Val Leu Ser Gln Val Gln Leu Lys Glu Ser Gly Pro Gly Leu Met Gln
            20                  25                  30

Pro Ser Glu Thr Leu Ser Leu Thr Cys Thr Val Ser Gly Phe Ser Leu
        35                  40                  45

Thr Ser Asn Gly Val Gly Trp Val Arg Gln Pro Leu Gly Lys Gly Leu
    50                  55                  60

Val Trp Met Gly Thr Ile Trp Thr Gly Gly Thr Asn Tyr Asn Ser
65                  70                  75                  80

Gly Val Gln Ser Arg Leu Ser Ile Ser Arg Asp Thr Ser Lys Ser Gln
                85                  90                  95

Val Phe Leu Lys Met Asn Ser Leu Gln Pro Glu Asp Thr Gly Thr Tyr
            100                 105                 110

Tyr Cys Ala Arg Glu Tyr Met Gly Phe Asp Tyr Trp Gly Gln Gly Val
        115                 120                 125

Met Val Thr Val Ser Ser
    130

<210> SEQ ID NO 95
<211> LENGTH: 127
<212> TYPE: PRT
<213> ORGANISM: Artificial Sequence
<220> FEATURE:
<223> OTHER INFORMATION: Synthetic Construct

<400> SEQUENCE: 95

Met Glu Leu Ile Ser Gln Val Phe Val Phe Leu Leu Trp Leu Ser
1               5                   10                  15

Gly Val Tyr Gly Asn Thr Val Met Thr Gln Ser Pro Thr Ser Met Phe
            20                  25                  30

Thr Ser Val Gly Asp Arg Val Thr Met Ser Cys Lys Ala Ser Gln Asn
        35                  40                  45
```

```
Val Gly Ile Asn Val Gly Trp Tyr Gln Gln Lys Thr Gly Gln Ser Pro
 50                  55                  60
Lys Arg Leu Ile Tyr Trp Ala Ser Asn Arg Asp Thr Gly Val Pro Asp
 65                  70                  75                  80
Arg Phe Thr Gly Ser Gly Ser Gly Thr Asp Phe Thr Leu Thr Ile Ser
                 85                  90                  95
Asn Met Gln Ala Glu Asp Pro Ala Ile Tyr Tyr Cys Leu Gln His Asn
             100                 105                 110
Ser Tyr Pro Arg Thr Phe Gly Gly Thr Lys Leu Glu Leu Lys
         115                 120                 125
```

<210> SEQ ID NO 96
<211> LENGTH: 5
<212> TYPE: PRT
<213> ORGANISM: Artificial Sequence
<220> FEATURE:
<223> OTHER INFORMATION: Synthetic Construct

<400> SEQUENCE: 96

```
Ser Asn Gly Val Gly
1               5
```

<210> SEQ ID NO 97
<211> LENGTH: 16
<212> TYPE: PRT
<213> ORGANISM: Artificial Sequence
<220> FEATURE:
<223> OTHER INFORMATION: Synthetic Construct

<400> SEQUENCE: 97

```
Thr Ile Trp Ser Gly Gly Gly Thr Asn Tyr Asn Ser Ala Val Gln Ser
1               5                   10                  15
```

<210> SEQ ID NO 98
<211> LENGTH: 7
<212> TYPE: PRT
<213> ORGANISM: Artificial Sequence
<220> FEATURE:
<223> OTHER INFORMATION: Synthetic Construct

<400> SEQUENCE: 98

```
Glu Glu Lys Gly Phe Ala Tyr
1               5
```

<210> SEQ ID NO 99
<211> LENGTH: 11
<212> TYPE: PRT
<213> ORGANISM: Artificial Sequence
<220> FEATURE:
<223> OTHER INFORMATION: Synthetic Construct

<400> SEQUENCE: 99

```
Lys Ala Ser Gln Asn Val Gly Ile Asn Val Gly
1               5                   10
```

<210> SEQ ID NO 100
<211> LENGTH: 7
<212> TYPE: PRT
<213> ORGANISM: Artificial Sequence
<220> FEATURE:
<223> OTHER INFORMATION: Synthetic Construct

<400> SEQUENCE: 100

```
Trp Ala Ser Asn Arg Asp Thr
1               5
```

<210> SEQ ID NO 101
<211> LENGTH: 9
<212> TYPE: PRT
<213> ORGANISM: Artificial Sequence
<220> FEATURE:
<223> OTHER INFORMATION: Synthetic Construct

<400> SEQUENCE: 101

Leu Gln His Asn Ser Tyr Pro Arg Ala
1               5

<210> SEQ ID NO 102
<211> LENGTH: 134
<212> TYPE: PRT
<213> ORGANISM: Artificial Sequence
<220> FEATURE:
<223> OTHER INFORMATION: Synthetic Construct

<400> SEQUENCE: 102

Met Ala Val Leu Val Leu Leu Cys Leu Val Thr Phe Pro Ser Cys
1               5                   10                  15

Val Leu Ser Gln Val Gln Leu Lys Glu Ser Gly Pro Gly Leu Met Gln
            20                  25                  30

Pro Ser Glu Thr Leu Ser Leu Thr Cys Thr Val Ser Gly Phe Ser Leu
        35                  40                  45

Thr Ser Asn Gly Val Gly Trp Val Arg Gln Pro Leu Gly Lys Gly Leu
    50                  55                  60

Val Trp Met Gly Thr Ile Trp Ser Gly Gly Thr Asn Tyr Asn Ser
65                  70                  75                  80

Ala Val Gln Ser Arg Leu Ser Ile Thr Arg Asp Thr Ser Lys Ser Gln
                85                  90                  95

Val Phe Leu Lys Met Asn Ser Leu Gln Pro Glu Asp Thr Gly Thr Tyr
            100                 105                 110

Tyr Cys Ala Arg Glu Glu Lys Gly Phe Ala Tyr Trp Gly Gln Gly Thr
        115                 120                 125

Leu Val Thr Val Ser Ser
    130

<210> SEQ ID NO 103
<211> LENGTH: 127
<212> TYPE: PRT
<213> ORGANISM: Artificial Sequence
<220> FEATURE:
<223> OTHER INFORMATION: Synthetic Construct

<400> SEQUENCE: 103

Met Glu Leu Ile Ser Gln Val Phe Val Phe Leu Leu Leu Trp Leu Ser
1               5                   10                  15

Gly Val Tyr Gly Asn Ile Val Met Thr Gln Ser Pro Thr Ser Met Ser
            20                  25                  30

Thr Ser Val Gly Asp Arg Val Thr Met Ser Cys Lys Ala Ser Gln Asn
        35                  40                  45

Val Gly Ile Asn Val Gly Trp Tyr Gln Gln Lys Thr Gly Gln Ser Pro
    50                  55                  60

Lys Arg Leu Ile Tyr Trp Ala Ser Asn Arg Asp Thr Gly Val Pro Asp
65                  70                  75                  80

Arg Phe Thr Gly Ser Gly Ser Gly Thr Asp Phe Thr Leu Thr Ile Ser
                85                  90                  95

```
Asn Met Gln Ala Glu Asp Pro Ala Ile Tyr Tyr Cys Leu Gln His Asn
            100                 105                 110

Ser Tyr Pro Arg Ala Phe Gly Gly Gly Thr Lys Leu Glu Leu Arg
        115                 120                 125

<210> SEQ ID NO 104
<211> LENGTH: 10
<212> TYPE: PRT
<213> ORGANISM: Artificial Sequence
<220> FEATURE:
<223> OTHER INFORMATION: Synthetic Construct

<400> SEQUENCE: 104

Cys Leu Tyr Asp Gly Phe Leu Thr Leu Val
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Synthetic Construct

<400> SEQUENCE: 105

Phe Leu Leu Tyr Tyr Val Asp Thr Phe Val
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Synthetic Construct

<400> SEQUENCE: 106

Phe Leu Trp Phe Val Ser Met Asp Leu Val
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Synthetic Construct

<400> SEQUENCE: 107

Phe Leu Ser Leu Cys Arg Arg Trp Gly Val
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Synthetic Construct

<400> SEQUENCE: 108

Phe Leu Leu Lys Leu Gly Leu Ser Leu Leu
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Synthetic Construct
```

```
<400> SEQUENCE: 109

Lys Leu Leu Thr Leu Val Val Thr Asp Leu
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Synthetic Construct

<400> SEQUENCE: 110

Ala Leu Leu Phe Gly Met Val Ala Leu Val
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Synthetic Construct

<400> SEQUENCE: 111

Ala Leu Phe Thr Thr Ile Leu His Asn Val
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Synthetic Construct

<400> SEQUENCE: 112

Trp Leu Leu Gly Leu Pro Thr Ala Val Val
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Synthetic Construct

<400> SEQUENCE: 113

Gln Leu Phe Thr Trp Ser Gln Phe Thr Leu
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Synthetic Construct

<400> SEQUENCE: 114

Leu Ala Leu Ser Phe Leu Ala Phe Trp Val
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Synthetic Construct

<400> SEQUENCE: 115
```

```
Lys Leu Gly Leu Ser Leu Leu Met Leu Leu
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Synthetic Construct

<400> SEQUENCE: 116

Gly Leu Gly Gln Pro Gln Ala Trp Leu Leu
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Synthetic Construct

<400> SEQUENCE: 117

Thr Leu His Gly Arg Arg Leu His Met Val
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Synthetic Construct

<400> SEQUENCE: 118

Leu Leu Trp Asn Ser Leu Asn Asp Pro Leu
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Synthetic Construct

<400> SEQUENCE: 119

Ser Leu Asn Asp Pro Leu Phe Gly Trp Leu
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Synthetic Construct

<400> SEQUENCE: 120

Thr Leu Val Asp Leu His His His Ala Leu
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Synthetic Construct

<400> SEQUENCE: 121
```

Lys Met Ala Phe Trp Val Gly Glu Thr Val
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Synthetic Construct

<400> SEQUENCE: 122

Tyr Leu Leu Val Leu Val Pro Ile Thr Cys
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Synthetic Construct

<400> SEQUENCE: 123

Asn Leu Ser Gln Ala Gln Thr Leu Asp Val
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Synthetic Construct

<400> SEQUENCE: 124

Leu Leu Thr Leu Val Val Thr Asp Leu Val
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Synthetic Construct

<400> SEQUENCE: 125

Leu Leu Ser Asp His Ile Ser Leu Ser Thr
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Synthetic Construct

<400> SEQUENCE: 126

Leu Met Leu Leu Ala Gly Pro Asp His Leu
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Synthetic Construct

<400> SEQUENCE: 127

Arg Gln Leu Ala Arg His Arg Asn Phe Leu

```
1               5                  10

<210> SEQ ID NO 128
<211> LENGTH: 10
<212> TYPE: PRT
<213> ORGANISM: Artificial Sequence
<220> FEATURE:
<223> OTHER INFORMATION: Synthetic Construct

<400> SEQUENCE: 128

Cys Leu Cys Leu Tyr Asp Gly Phe Leu Thr
1               5                  10

<210> SEQ ID NO 129
<211> LENGTH: 10
<212> TYPE: PRT
<213> ORGANISM: Artificial Sequence
<220> FEATURE:
<223> OTHER INFORMATION: Synthetic Construct

<400> SEQUENCE: 129

Leu Leu Cys Phe Tyr Thr Gly His Asp Leu
1               5                  10

<210> SEQ ID NO 130
<211> LENGTH: 10
<212> TYPE: PRT
<213> ORGANISM: Artificial Sequence
<220> FEATURE:
<223> OTHER INFORMATION: Synthetic Construct

<400> SEQUENCE: 130

Val Leu Val Pro Ile Thr Cys Ala Leu Leu
1               5                  10

<210> SEQ ID NO 131
<211> LENGTH: 10
<212> TYPE: PRT
<213> ORGANISM: Artificial Sequence
<220> FEATURE:
<223> OTHER INFORMATION: Synthetic Construct

<400> SEQUENCE: 131

Leu Leu Ala Gly Pro Asp His Leu Ser Leu
1               5                  10

<210> SEQ ID NO 132
<211> LENGTH: 10
<212> TYPE: PRT
<213> ORGANISM: Artificial Sequence
<220> FEATURE:
<223> OTHER INFORMATION: Synthetic Construct

<400> SEQUENCE: 132

Phe Gly Trp Leu Ser Asp Arg Gln Phe Leu
1               5                  10

<210> SEQ ID NO 133
<211> LENGTH: 10
<212> TYPE: PRT
<213> ORGANISM: Artificial Sequence
<220> FEATURE:
<223> OTHER INFORMATION: Synthetic Construct

<400> SEQUENCE: 133

Ser Leu Cys Arg Arg Trp Gly Val Tyr Ala
1               5                  10
```

```
<210> SEQ ID NO 134
<211> LENGTH: 10
<212> TYPE: PRT
<213> ORGANISM: Artificial Sequence
<220> FEATURE:
<223> OTHER INFORMATION: Synthetic Construct

<400> SEQUENCE: 134

Leu Gln Leu Phe Thr Trp Ser Gln Phe Thr
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Synthetic Construct

<400> SEQUENCE: 135

Phe Leu Ser Ser Gln Pro Arg Ser Gly Ala
1               5                   10

<210> SEQ ID NO 136
<211> LENGTH: 10
<212> TYPE: PRT
<213> ORGANISM: Artificial Sequence
<220> FEATURE:
<223> OTHER INFORMATION: Synthetic Construct

<400> SEQUENCE: 136

Gly Leu Gly Phe Leu Gly Ala Thr Gln Leu
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Synthetic Construct

<400> SEQUENCE: 137

Gly Leu Gln Phe Leu Leu Cys Leu Cys Leu
1               5                   10

<210> SEQ ID NO 138
<211> LENGTH: 10
<212> TYPE: PRT
<213> ORGANISM: Artificial Sequence
<220> FEATURE:
<223> OTHER INFORMATION: Synthetic Construct

<400> SEQUENCE: 138

Ala Leu Ser Ala His Asp Arg Thr His Leu
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Synthetic Construct

<400> SEQUENCE: 139

Gln Leu Leu Arg Arg Arg Val Glu Ala Ala
1               5                   10
```

<210> SEQ ID NO 140
<211> LENGTH: 10
<212> TYPE: PRT
<213> ORGANISM: Artificial Sequence
<220> FEATURE:
<223> OTHER INFORMATION: Synthetic Construct

<400> SEQUENCE: 140

Val Val Tyr Gly Ser Leu Ala Leu Phe Thr
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Synthetic Construct

<400> SEQUENCE: 141

Leu Leu Val Leu Val Pro Ile Thr Cys Ala
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Synthetic Construct

<400> SEQUENCE: 142

Leu Leu Phe Gly Met Val Ala Leu Val Thr
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Synthetic Construct

<400> SEQUENCE: 143

Ser Met Asp Leu Val Gln Val Phe His Cys
1               5                   10

<210> SEQ ID NO 144
<211> LENGTH: 10
<212> TYPE: PRT
<213> ORGANISM: Artificial Sequence
<220> FEATURE:
<223> OTHER INFORMATION: Synthetic Construct

<400> SEQUENCE: 144

Ala Leu Leu Ala Asp Leu Ala Leu Ser Ala
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Synthetic Construct

<400> SEQUENCE: 145

Tyr Ala Val Val Arg Gly Leu Phe Leu Leu
1               5                   10

```
<210> SEQ ID NO 146
<211> LENGTH: 10
<212> TYPE: PRT
<213> ORGANISM: Artificial Sequence
<220> FEATURE:
<223> OTHER INFORMATION: Synthetic Construct

<400> SEQUENCE: 146

Tyr Lys Ile Asn Lys Met Ala Phe Trp Val
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Synthetic Construct

<400> SEQUENCE: 147

Phe Asn Ser Asn Phe Phe Pro Leu Phe Leu
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Synthetic Construct

<400> SEQUENCE: 148

Leu Val Leu Val Pro Ile Thr Cys Ala Leu
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Synthetic Construct

<400> SEQUENCE: 149

Gly Leu Ser Ser Arg Ala Val Val Leu Ala
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Synthetic Construct

<400> SEQUENCE: 150

Phe Ala Pro Leu Leu Gly Thr Trp Leu Leu
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Synthetic Construct

<400> SEQUENCE: 151

Ser Tyr Val Ala Pro His Leu Asn Asn Leu
1               5                   10

<210> SEQ ID NO 152
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 152

Val Tyr Ala Val Val Arg Gly Leu Phe Leu
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Synthetic Construct

<400> SEQUENCE: 153

Ser Tyr Ala Phe Trp Asn Lys Glu Asp Phe
1               5                   10

<210> SEQ ID NO 154
<211> LENGTH: 10
<212> TYPE: PRT
<213> ORGANISM: Artificial Sequence
<220> FEATURE:
<223> OTHER INFORMATION: Synthetic Construct

<400> SEQUENCE: 154

Asn Phe Leu Trp Phe Val Ser Met Asp Leu
1               5                   10

<210> SEQ ID NO 155
<211> LENGTH: 10
<212> TYPE: PRT
<213> ORGANISM: Artificial Sequence
<220> FEATURE:
<223> OTHER INFORMATION: Synthetic Construct

<400> SEQUENCE: 155

Phe Phe Pro Leu Phe Leu Glu His Leu Leu
1               5                   10

<210> SEQ ID NO 156
<211> LENGTH: 10
<212> TYPE: PRT
<213> ORGANISM: Artificial Sequence
<220> FEATURE:
<223> OTHER INFORMATION: Synthetic Construct

<400> SEQUENCE: 156

Leu Phe Leu Leu Lys Leu Gly Leu Ser Leu
1               5                   10

<210> SEQ ID NO 157
<211> LENGTH: 10
<212> TYPE: PRT
<213> ORGANISM: Artificial Sequence
<220> FEATURE:
<223> OTHER INFORMATION: Synthetic Construct

<400> SEQUENCE: 157

Thr Phe Ala Pro Leu Leu Gly Thr Trp Leu
1               5                   10

<210> SEQ ID NO 158
<211> LENGTH: 10
```

```
<212> TYPE: PRT
<213> ORGANISM: Artificial Sequence
<220> FEATURE:
<223> OTHER INFORMATION: Synthetic Construct

<400> SEQUENCE: 158

Val Phe Thr Glu Gly Thr Cys Lys Leu Leu
1               5                   10

<210> SEQ ID NO 159
<211> LENGTH: 10
<212> TYPE: PRT
<213> ORGANISM: Artificial Sequence
<220> FEATURE:
<223> OTHER INFORMATION: Synthetic Construct

<400> SEQUENCE: 159

Asn Phe Phe Pro Leu Phe Leu Glu His Leu
1               5                   10

<210> SEQ ID NO 160
<211> LENGTH: 10
<212> TYPE: PRT
<213> ORGANISM: Artificial Sequence
<220> FEATURE:
<223> OTHER INFORMATION: Synthetic Construct

<400> SEQUENCE: 160

Ala Phe Trp Val Gly Glu Thr Val Phe Leu
1               5                   10

<210> SEQ ID NO 161
<211> LENGTH: 10
<212> TYPE: PRT
<213> ORGANISM: Artificial Sequence
<220> FEATURE:
<223> OTHER INFORMATION: Synthetic Construct

<400> SEQUENCE: 161

His Phe Asn Ser Asn Phe Phe Pro Leu Phe
1               5                   10

<210> SEQ ID NO 162
<211> LENGTH: 10
<212> TYPE: PRT
<213> ORGANISM: Artificial Sequence
<220> FEATURE:
<223> OTHER INFORMATION: Synthetic Construct

<400> SEQUENCE: 162

Lys Leu Leu Thr Leu Val Val Thr Asp Leu
1               5                   10

<210> SEQ ID NO 163
<211> LENGTH: 10
<212> TYPE: PRT
<213> ORGANISM: Artificial Sequence
<220> FEATURE:
<223> OTHER INFORMATION: Synthetic Construct

<400> SEQUENCE: 163

Val Phe Leu Leu Tyr Tyr Val Asp Thr Phe
1               5                   10

<210> SEQ ID NO 164
<211> LENGTH: 10
<212> TYPE: PRT
```

<213> ORGANISM: Artificial Sequence
<220> FEATURE:
<223> OTHER INFORMATION: Synthetic Construct

<400> SEQUENCE: 164

Arg Gln Leu Ala Arg His Arg Asn Phe Leu
1               5                   10

<210> SEQ ID NO 165
<211> LENGTH: 10
<212> TYPE: PRT
<213> ORGANISM: Artificial Sequence
<220> FEATURE:
<223> OTHER INFORMATION: Synthetic Construct

<400> SEQUENCE: 165

Arg Gly Leu Phe Leu Leu Lys Leu Gly Leu
1               5                   10

<210> SEQ ID NO 166
<211> LENGTH: 10
<212> TYPE: PRT
<213> ORGANISM: Artificial Sequence
<220> FEATURE:
<223> OTHER INFORMATION: Synthetic Construct

<400> SEQUENCE: 166

Arg Gln Asn Leu Ser Gln Ala Gln Thr Leu
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Synthetic Construct

<400> SEQUENCE: 167

Leu Phe Thr Thr Ile Leu His Asn Val Phe
1               5                   10

<210> SEQ ID NO 168
<211> LENGTH: 10
<212> TYPE: PRT
<213> ORGANISM: Artificial Sequence
<220> FEATURE:
<223> OTHER INFORMATION: Synthetic Construct

<400> SEQUENCE: 168

Ser Leu Asn Asp Pro Leu Phe Gly Trp Leu
1               5                   10

<210> SEQ ID NO 169
<211> LENGTH: 10
<212> TYPE: PRT
<213> ORGANISM: Artificial Sequence
<220> FEATURE:
<223> OTHER INFORMATION: Synthetic Construct

<400> SEQUENCE: 169

Val Phe His Cys His Phe Asn Ser Asn Phe
1               5                   10

<210> SEQ ID NO 170
<211> LENGTH: 10
<212> TYPE: PRT
<213> ORGANISM: Artificial Sequence

```
<220> FEATURE:
<223> OTHER INFORMATION: Synthetic Construct

<400> SEQUENCE: 170

Leu Phe Gly Trp Leu Ser Asp Arg Gln Phe
1               5                   10

<210> SEQ ID NO 171
<211> LENGTH: 5
<212> TYPE: PRT
<213> ORGANISM: Artificial Sequence
<220> FEATURE:
<223> OTHER INFORMATION: Synthetic Construct

<400> SEQUENCE: 171

Asn Tyr Trp Met Thr
1               5

<210> SEQ ID NO 172
<211> LENGTH: 15
<212> TYPE: PRT
<213> ORGANISM: Artificial Sequence
<220> FEATURE:
<223> OTHER INFORMATION: Synthetic Construct

<400> SEQUENCE: 172

Ser Ile Thr Asn Thr Gly Gly Ser Thr Ala Tyr Pro Asp Ser Val
1               5                   10                  15

<210> SEQ ID NO 173
<211> LENGTH: 12
<212> TYPE: PRT
<213> ORGANISM: Artificial Sequence
<220> FEATURE:
<223> OTHER INFORMATION: Synthetic Construct

<400> SEQUENCE: 173

Ala Gly Tyr Ser Ser Tyr Pro Asp Tyr Phe Asp Tyr
1               5                   10

<210> SEQ ID NO 174
<211> LENGTH: 11
<212> TYPE: PRT
<213> ORGANISM: Artificial Sequence
<220> FEATURE:
<223> OTHER INFORMATION: Synthetic Construct

<400> SEQUENCE: 174

Lys Ala Gly Gln Asn Ile Tyr Asn Tyr Leu Ala
1               5                   10

<210> SEQ ID NO 175
<211> LENGTH: 7
<212> TYPE: PRT
<213> ORGANISM: Artificial Sequence
<220> FEATURE:
<223> OTHER INFORMATION: Synthetic Construct

<400> SEQUENCE: 175

Asn Ala Asn Ser Leu Gln Thr
1               5

<210> SEQ ID NO 176
<211> LENGTH: 8
<212> TYPE: PRT
<213> ORGANISM: Artificial Sequence
<220> FEATURE:
```

<223> OTHER INFORMATION: Synthetic Construct

<400> SEQUENCE: 176

Gln Gln Tyr Ser Ser Gly Trp Thr
1               5

<210> SEQ ID NO 177
<211> LENGTH: 140
<212> TYPE: PRT
<213> ORGANISM: Artificial Sequence
<220> FEATURE:
<223> OTHER INFORMATION: Synthetic Construct

<400> SEQUENCE: 177

Met Asp Ile Arg Leu Ser Leu Val Phe Leu Val Leu Phe Ile Lys Gly
1               5                   10                  15

Val Gln Cys Glu Val Gln Leu Val Glu Ser Gly Gly Gly Leu Val Gln
                20                  25                  30

Pro Gly Arg Ser Leu Lys Leu Ser Cys Val Ala Ser Gly Phe Thr Phe
            35                  40                  45

Asn Asn Tyr Trp Met Thr Trp Ile Arg Gln Ala Pro Gly Lys Gly Leu
        50                  55                  60

Glu Trp Val Ala Ser Ile Thr Asn Thr Gly Gly Ser Thr Ala Tyr Pro
65                  70                  75                  80

Asp Ser Val Lys Gly Arg Phe Thr Ile Ser Arg Asp Tyr Ala Lys Ser
                85                  90                  95

Thr Leu Tyr Leu Gln Met Asn Ser Leu Arg Ser Glu Asp Thr Ala Thr
            100                 105                 110

Tyr Tyr Cys Thr Arg Ala Gly Tyr Ser Ser Tyr Pro Asp Tyr Phe Asp
        115                 120                 125

Tyr Trp Gly Gln Gly Val Met Leu Thr Val Ser Ser
    130                 135                 140

<210> SEQ ID NO 178
<211> LENGTH: 120
<212> TYPE: PRT
<213> ORGANISM: Artificial Sequence
<220> FEATURE:
<223> OTHER INFORMATION: Synthetic Construct

<400> SEQUENCE: 178

Met Met Ala Pro Val Gln Leu Leu Gly Leu Leu Leu Leu Trp Leu Pro
1               5                   10                  15

Ala Met Arg Cys Asn Ile Gln Met Thr Gln Ser Pro Ser Leu Leu Ser
                20                  25                  30

Ala Ser Val Gly Asp Arg Val Thr Leu Ser Cys Lys Ala Gly Gln Asn
            35                  40                  45

Ile Tyr Asn Tyr Leu Ala Trp Tyr Gln Gln Lys Leu Gly Glu Ala Pro
        50                  55                  60

Lys Leu Leu Ile Tyr Asn Ala Asn Ser Leu Gln Thr Gly Ile Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Thr Tyr Phe Cys Gln Gln Tyr Ser
            100                 105                 110

Ser Gly Trp Thr Phe Gly Gly Gly
        115                 120

```
<210> SEQ ID NO 179
<211> LENGTH: 1413
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (1)..(1413)

<400> SEQUENCE: 179
```

| | | | | | | | | | | | | | | | | |
|---|---|---|---|---|---|---|---|---|---|---|---|---|---|---|---|---|
| atg | gac | atc | agg | ctc | agc | ttg | gtt | ttc | ctt | gtc | ctt | ttc | ata | aaa | ggt | 48 |
| Met | Asp | Ile | Arg | Leu | Ser | Leu | Val | Phe | Leu | Val | Leu | Phe | Ile | Lys | Gly | |
| 1 | | | | 5 | | | | | 10 | | | | | 15 | | |
| gtc | cag | tgt | gag | gtg | cag | ctg | gtg | gag | tct | ggg | gga | ggc | cta | gtg | cag | 96 |
| Val | Gln | Cys | Glu | Val | Gln | Leu | Val | Glu | Ser | Gly | Gly | Gly | Leu | Val | Gln | |
| | | 20 | | | | | 25 | | | | | 30 | | | | |
| cct | gga | agg | tct | ctg | aaa | cta | tcc | tgt | gta | gcc | tct | gga | ttc | aca | ttc | 144 |
| Pro | Gly | Arg | Ser | Leu | Lys | Leu | Ser | Cys | Val | Ala | Ser | Gly | Phe | Thr | Phe | |
| | | 35 | | | | 40 | | | | | 45 | | | | | |
| aat | aac | tac | tgg | atg | acc | tgg | atc | cgc | cag | gct | cca | ggg | aag | ggg | ctg | 192 |
| Asn | Asn | Tyr | Trp | Met | Thr | Trp | Ile | Arg | Gln | Ala | Pro | Gly | Lys | Gly | Leu | |
| 50 | | | | | 55 | | | | | 60 | | | | | | |
| gag | tgg | gtt | gca | tcc | att | act | aat | act | ggt | ggt | agc | act | gcc | tat | cca | 240 |
| Glu | Trp | Val | Ala | Ser | Ile | Thr | Asn | Thr | Gly | Gly | Ser | Thr | Ala | Tyr | Pro | |
| 65 | | | | | 70 | | | | | 75 | | | | | 80 | |
| gac | tct | gtg | aag | ggc | cga | ttc | act | atc | tcc | aga | gat | tat | gca | aaa | agc | 288 |
| Asp | Ser | Val | Lys | Gly | Arg | Phe | Thr | Ile | Ser | Arg | Asp | Tyr | Ala | Lys | Ser | |
| | | | | 85 | | | | | 90 | | | | | 95 | | |
| acc | cta | tac | ctg | caa | atg | aac | agt | ctg | agg | tct | gag | gac | acg | gcc | act | 336 |
| Thr | Leu | Tyr | Leu | Gln | Met | Asn | Ser | Leu | Arg | Ser | Glu | Asp | Thr | Ala | Thr | |
| | | | 100 | | | | | 105 | | | | | 110 | | | |
| tat | tac | tgt | aca | aga | gct | ggc | tat | agc | agc | tat | ccc | gac | tac | ttt | gat | 384 |
| Tyr | Tyr | Cys | Thr | Arg | Ala | Gly | Tyr | Ser | Ser | Tyr | Pro | Asp | Tyr | Phe | Asp | |
| | | 115 | | | | | 120 | | | | | 125 | | | | |
| tac | tgg | ggc | caa | gga | gtc | atg | ctc | aca | gtc | tcc | tca | gct | agc | acc | aag | 432 |
| Tyr | Trp | Gly | Gln | Gly | Val | Met | Leu | Thr | Val | Ser | Ser | Ala | Ser | Thr | Lys | |
| | 130 | | | | | 135 | | | | | 140 | | | | | |
| ggc | cca | tcg | gtc | ttc | ccc | ctg | gca | ccc | tcc | tcc | aag | agc | acc | tct | ggg | 480 |
| Gly | Pro | Ser | Val | Phe | Pro | Leu | Ala | Pro | Ser | Ser | Lys | Ser | Thr | Ser | Gly | |
| 145 | | | | | 150 | | | | | 155 | | | | | 160 | |
| ggc | aca | gcg | gcc | ctg | ggc | tgc | ctg | gtc | aag | gac | tac | ttc | ccc | gaa | ccg | 528 |
| Gly | Thr | Ala | Ala | Leu | Gly | Cys | Leu | Val | Lys | Asp | Tyr | Phe | Pro | Glu | Pro | |
| | | | | 165 | | | | | 170 | | | | | 175 | | |
| gtg | acg | gtg | tcg | tgg | aac | tca | ggc | gcc | ctg | acc | agc | ggc | gtg | cac | acc | 576 |
| Val | Thr | Val | Ser | Trp | Asn | Ser | Gly | Ala | Leu | Thr | Ser | Gly | Val | His | Thr | |
| | | | 180 | | | | | 185 | | | | | 190 | | | |
| ttc | ccg | gct | gtc | cta | cag | tcc | tca | gga | ctc | tac | tcc | ctc | agc | agc | gtg | 624 |
| Phe | Pro | Ala | Val | Leu | Gln | Ser | Ser | Gly | Leu | Tyr | Ser | Leu | Ser | Ser | Val | |
| | | 195 | | | | | 200 | | | | | 205 | | | | |
| gtg | acc | gtg | ccc | tcc | agc | agc | ttg | ggc | acc | cag | acc | tac | atc | tgc | aac | 672 |
| Val | Thr | Val | Pro | Ser | Ser | Ser | Leu | Gly | Thr | Gln | Thr | Tyr | Ile | Cys | Asn | |
| | 210 | | | | | 215 | | | | | 220 | | | | | |
| gtg | aat | cac | aag | ccc | agc | aac | acc | aag | gtg | gac | aag | aaa | gtt | gag | ccc | 720 |
| Val | Asn | His | Lys | Pro | Ser | Asn | Thr | Lys | Val | Asp | Lys | Lys | Val | Glu | Pro | |
| 225 | | | | | 230 | | | | | 235 | | | | | 240 | |
| aaa | tct | tgt | gac | aaa | act | cac | aca | tgc | cca | ccg | tgc | cca | gca | cct | gaa | 768 |
| Lys | Ser | Cys | Asp | Lys | Thr | His | Thr | Cys | Pro | Pro | Cys | Pro | Ala | Pro | Glu | |
| | | | | 245 | | | | | 250 | | | | | 255 | | |
| ctc | ctg | ggg | gga | ccg | tca | gtc | ttc | ctc | ttc | ccc | cca | aaa | ccc | aag | gac | 816 |
| Leu | Leu | Gly | Gly | Pro | Ser | Val | Phe | Leu | Phe | Pro | Pro | Lys | Pro | Lys | Asp | |
| | | | | 260 | | | | | 265 | | | | | 270 | | |

```
acc ctc atg atc tcc cgg acc cct gag gtc aca tgc gtg gtg gtg gac      864
Thr Leu Met Ile Ser Arg Thr Pro Glu Val Thr Cys Val Val Val Asp
        275                 280                 285 gtg agc cac gaa gac cct gag gtc aag ttc aac tgg tac gtg gac ggc      912
Val Ser His Glu Asp Pro Glu Val Lys Phe Asn Trp Tyr Val Asp Gly
    290                 295                 300 gtg gag gtg cat aat gcc aag aca aag ccg cgg gag gag cag tac aac      960
Val Glu Val His Asn Ala Lys Thr Lys Pro Arg Glu Glu Gln Tyr Asn
305                 310                 315                 320 agc acg tac cgt gtg gtc agc gtc ctc acc gtc ctg cac cag gac tgg     1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca     1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggg cag ccc cga gaa     1104
Ala Pro Ile Glu Lys Thr Ile Ser Lys Ala Lys Gly Gln Pro Arg Glu
        355                 360                 365 cca cag gtg tac acc ctg ccc cca tcc cgg gat gag ctg acc aag aac     1152
Pro Gln Val Tyr Thr Leu Pro Pro Ser Arg Asp Glu Leu Thr Lys Asn
    370                 375                 380 cag gtc agc ctg acc tgc ctg gtc aaa ggc ttc tat ccc agc gac atc     1200
Gln Val Ser Leu Thr Cys Leu Val Lys Gly Phe Tyr Pro Ser Asp Ile
385                 390                 395                 400 gcc gtg gag tgg gag agc aat ggg cag ccg gag aac aac tac aag acc     1248
Ala Val Glu Trp Glu Ser Asn Gly Gln Pro Glu Asn Asn Tyr Lys Thr
                405                 410                 415 acg cct ccc gtg ctg gac tcc gac ggc tcc ttc ttc ctc tac agc aag     1296
Thr Pro Pro Val Leu Asp Ser Asp Gly Ser Phe Phe Leu Tyr Ser Lys
            420                 425                 430 ctc acc gtg gac aag agc agg tgg cag cag ggg aac gtc ttc tca tgc     1344
Leu Thr Val Asp Lys Ser Arg Trp Gln Gln Gly Asn Val Phe Ser Cys
        435                 440                 445 tcc gtg atg cat gag gct ctg cac aac cac tac acg cag aag agc ctc     1392
Ser Val Met His Glu Ala Leu His Asn His Tyr Thr Gln Lys Ser Leu
    450                 455                 460 tcc ctg tct ccg ggt aaa tga                                         1413
Ser Leu Ser Pro Gly Lys
465                 470

<210> SEQ ID NO 180
<211> LENGTH: 470
<212> TYPE: PRT
<213> ORGANISM: Artificial Sequence
<220> FEATURE:
<223> OTHER INFORMATION: Synthetic Construct

<400> SEQUENCE: 180

Met Asp Ile Arg Leu Ser Leu Val Phe Leu Val Leu Phe Ile Lys Gly
1               5                   10                  15

Val Gln Cys Glu Val Gln Leu Val Glu Ser Gly Gly Gly Leu Val Gln
            20                  25                  30

Pro Gly Arg Ser Leu Lys Leu Ser Cys Val Ala Ser Gly Phe Thr Phe
        35                  40                  45

Asn Asn Tyr Trp Met Thr Trp Ile Arg Gln Ala Pro Gly Lys Gly Leu
    50                  55                  60

Glu Trp Val Ala Ser Ile Thr Asn Thr Gly Gly Ser Thr Ala Tyr Pro
65                  70                  75                  80

Asp Ser Val Lys Gly Arg Phe Thr Ile Ser Arg Asp Tyr Ala Lys Ser
```

```
                    85                  90                  95
Thr Leu Tyr Leu Gln Met Asn Ser Leu Arg Ser Glu Asp Thr Ala Thr
                100                 105                 110

Tyr Tyr Cys Thr Arg Ala Gly Tyr Ser Ser Tyr Pro Asp Tyr Phe Asp
            115                 120                 125

Tyr Trp Gly Gln Gly Val Met Leu Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 181
<211> LENGTH: 702
<212> TYPE: DNA
<213> ORGANISM: Artificial Sequence
```

<220> FEATURE:
<223> OTHER INFORMATION: Synthetic Construct
<220> FEATURE:
<221> NAME/KEY: CDS
<222> LOCATION: (1)..(702)

<400> SEQUENCE: 181

| | | | | | | | | | | | | | | | | |
|---|---|---|---|---|---|---|---|---|---|---|---|---|---|---|---|---|
| atg | atg | gct | cca | gtt | caa | ctc | tta | ggg | ctg | ctg | ctg | ctc | tgg | ctc | cca | 48 |
| Met | Met | Ala | Pro | Val | Gln | Leu | Leu | Gly | Leu | Leu | Leu | Leu | Trp | Leu | Pro | |
| 1 | | | | 5 | | | | | 10 | | | | | 15 | | |
| gcc | atg | aga | tgt | aac | atc | cag | atg | acc | cag | tct | cct | tca | cta | ctc | tct | 96 |
| Ala | Met | Arg | Cys | Asn | Ile | Gln | Met | Thr | Gln | Ser | Pro | Ser | Leu | Leu | Ser | |
| | | | 20 | | | | | 25 | | | | | 30 | | | |
| gca | tct | gtg | gga | gac | aga | gtc | act | ctc | agc | tgc | aaa | gca | ggt | cag | aat | 144 |
| Ala | Ser | Val | Gly | Asp | Arg | Val | Thr | Leu | Ser | Cys | Lys | Ala | Gly | Gln | Asn | |
| | | 35 | | | | | 40 | | | | | 45 | | | | |
| att | tac | aat | tac | tta | gcc | tgg | tat | cag | caa | aag | ctt | gga | gaa | gct | ccc | 192 |
| Ile | Tyr | Asn | Tyr | Leu | Ala | Trp | Tyr | Gln | Gln | Lys | Leu | Gly | Glu | Ala | Pro | |
| | 50 | | | | | 55 | | | | | 60 | | | | | |
| aaa | ctc | ctg | att | tat | aat | gca | aac | agt | ttg | caa | acg | ggc | atc | cca | tca | 240 |
| Lys | Leu | Leu | Ile | Tyr | Asn | Ala | Asn | Ser | Leu | Gln | Thr | Gly | Ile | Pro | Ser | |
| 65 | | | | 70 | | | | | 75 | | | | | 80 | | |
| agg | ttc | agt | ggc | agt | gga | tct | ggt | aca | gat | ttc | aca | ctc | acc | atc | agc | 288 |
| Arg | Phe | Ser | Gly | Ser | Gly | Ser | Gly | Thr | Asp | Phe | Thr | Leu | Thr | Ile | Ser | |
| | | | | 85 | | | | | 90 | | | | | 95 | | |
| agc | ctg | cag | cct | gaa | gat | gtt | gcc | aca | tat | ttc | tgc | cag | cag | tat | agc | 336 |
| Ser | Leu | Gln | Pro | Glu | Asp | Val | Ala | Thr | Tyr | Phe | Cys | Gln | Gln | Tyr | Ser | |
| | | | 100 | | | | | 105 | | | | | 110 | | | |
| agt | ggg | tgg | acg | ttc | ggt | gga | ggc | acc | aag | ctg | gaa | ttg | aaa | cgt | acg | 384 |
| Ser | Gly | Trp | Thr | Phe | Gly | Gly | Gly | Thr | Lys | Leu | Glu | Leu | Lys | Arg | Thr | |
| | | 115 | | | | | 120 | | | | | 125 | | | | |
| gtg | gct | gca | cca | tct | gtc | ttc | atc | ttc | ccg | cca | tct | gat | gag | cag | ttg | 432 |
| Val | Ala | Ala | Pro | Ser | Val | Phe | Ile | Phe | Pro | Pro | Ser | Asp | Glu | Gln | Leu | |
| | 130 | | | | | 135 | | | | | 140 | | | | | |
| aaa | tct | gga | act | gcc | tct | gtt | gtg | tgc | ctg | ctg | aat | aac | ttc | tat | ccc | 480 |
| Lys | Ser | Gly | Thr | Ala | Ser | Val | Val | Cys | Leu | Leu | Asn | Asn | Phe | Tyr | Pro | |
| 145 | | | | 150 | | | | | 155 | | | | | 160 | | |
| aga | gag | gcc | aaa | gta | cag | tgg | aag | gtg | gat | aac | gcc | ctc | caa | tcg | ggt | 528 |
| Arg | Glu | Ala | Lys | Val | Gln | Trp | Lys | Val | Asp | Asn | Ala | Leu | Gln | Ser | Gly | |
| | | | | 165 | | | | | 170 | | | | | 175 | | |
| aac | tcc | cag | gag | agt | gtc | aca | gag | cag | gac | agc | aag | gac | agc | acc | tac | 576 |
| Asn | Ser | Gln | Glu | Ser | Val | Thr | Glu | Gln | Asp | Ser | Lys | Asp | Ser | Thr | Tyr | |
| | | | 180 | | | | | 185 | | | | | 190 | | | |
| agc | ctc | agc | agc | acc | ctg | acg | ctg | agc | aaa | gca | gac | tac | gag | aaa | cac | 624 |
| Ser | Leu | Ser | Ser | Thr | Leu | Thr | Leu | Ser | Lys | Ala | Asp | Tyr | Glu | Lys | His | |
| | | | | 195 | | | | | 200 | | | | | 205 | | |
| aaa | gtc | tac | gcc | tgc | gaa | gtc | acc | cat | cag | ggc | ctg | agc | tcg | ccc | gtc | 672 |
| Lys | Val | Tyr | Ala | Cys | Glu | Val | Thr | His | Gln | Gly | Leu | Ser | Ser | Pro | Val | |
| | 210 | | | | | 215 | | | | | 220 | | | | | |
| aca | aag | agc | ttc | aac | agg | gga | gag | tgt | tag | | | | | | | 702 |
| Thr | Lys | Ser | Phe | Asn | Arg | Gly | Glu | Cys | | | | | | | | |
| 225 | | | | 230 | | | | | | | | | | | | |

<210> SEQ ID NO 182
<211> LENGTH: 233
<212> TYPE: PRT
<213> ORGANISM: Artificial Sequence
<220> FEATURE:
<223> OTHER INFORMATION: Synthetic Construct

<400> SEQUENCE: 182

Met Met Ala Pro Val Gln Leu Leu Gly Leu Leu Leu Leu Trp Leu Pro

```
1               5                   10                  15
Ala Met Arg Cys Asn Ile Gln Met Thr Gln Ser Pro Ser Leu Leu Ser
            20                  25                  30
Ala Ser Val Gly Asp Arg Val Thr Leu Ser Cys Lys Ala Gly Gln Asn
            35                  40                  45
Ile Tyr Asn Tyr Leu Ala Trp Tyr Gln Gln Lys Leu Gly Glu Ala Pro
50                      55                  60
Lys Leu Leu Ile Tyr Asn Ala Asn Ser Leu Gln Thr Gly Ile Pro Ser
65                  70                  75                  80
Arg Phe Ser Gly Ser Gly Ser Gly Thr Asp Phe Thr Leu Thr Ile Ser
                85                  90                  95
Ser Leu Gln Pro Glu Asp Val Ala Thr Tyr Phe Cys Gln Gln Tyr Ser
                100                 105                 110
Ser Gly Trp Thr Phe Gly Gly Gly Thr Lys Leu Glu Leu Lys Arg Thr
                115                 120                 125
Val Ala Ala Pro Ser Val Phe Ile Phe Pro Pro Ser Asp Glu Gln Leu
130                     135                 140
Lys Ser Gly Thr Ala Ser Val Val Cys Leu Leu Asn Asn Phe Tyr Pro
145                 150                 155                 160
Arg Glu Ala Lys Val Gln Trp Lys Val Asp Asn Ala Leu Gln Ser Gly
                165                 170                 175
Asn Ser Gln Glu Ser Val Thr Glu Gln Asp Ser Lys Asp Ser Thr Tyr
                180                 185                 190
Ser Leu Ser Ser Thr Leu Thr Leu Ser Lys Ala Asp Tyr Glu Lys His
                195                 200                 205
Lys Val Tyr Ala Cys Glu Val Thr His Gln Gly Leu Ser Ser Pro Val
210                     215                 220
Thr Lys Ser Phe Asn Arg Gly Glu Cys
225                 230

<210> SEQ ID NO 183
<211> LENGTH: 27
<212> TYPE: DNA
<213> ORGANISM: Artificial Sequence
<220> FEATURE:
<223> OTHER INFORMATION: Synthetic Construct

<400> SEQUENCE: 183
agcactgcct atccagactc tgtgaag                                        27

<210> SEQ ID NO 184
<211> LENGTH: 27
<212> TYPE: DNA
<213> ORGANISM: Artificial Sequence
<220> FEATURE:
<223> OTHER INFORMATION: Synthetic Construct

<400> SEQUENCE: 184
tggataggca gtgctaccac cagtatt                                        27

<210> SEQ ID NO 185
<211> LENGTH: 27
<212> TYPE: DNA
<213> ORGANISM: Artificial Sequence
<220> FEATURE:
<223> OTHER INFORMATION: Synthetic Construct

<400> SEQUENCE: 185
ccagacgctg tgaagggccg attcact                                        27
```

```
<210> SEQ ID NO 186
<211> LENGTH: 27
<212> TYPE: DNA
<213> ORGANISM: Artificial Sequence
<220> FEATURE:
<223> OTHER INFORMATION: Synthetic Construct

<400> SEQUENCE: 186
cttcacagcg tctggatagt aagtgct                                         27

<210> SEQ ID NO 187
<211> LENGTH: 27
<212> TYPE: DNA
<213> ORGANISM: Artificial Sequence
<220> FEATURE:
<223> OTHER INFORMATION: Synthetic Construct

<400> SEQUENCE: 187
ggaccggacg tcttcctctt cccccca                                         27

<210> SEQ ID NO 188
<211> LENGTH: 27
<212> TYPE: DNA
<213> ORGANISM: Artificial Sequence
<220> FEATURE:
<223> OTHER INFORMATION: Synthetic Construct

<400> SEQUENCE: 188
gaagacgtcc ggtcccccca ggagttc                                         27

<210> SEQ ID NO 189
<211> LENGTH: 27
<212> TYPE: DNA
<213> ORGANISM: Artificial Sequence
<220> FEATURE:
<223> OTHER INFORMATION: Synthetic Construct

<400> SEQUENCE: 189
ccactgcccg aggagaaaac catctcc                                         27

<210> SEQ ID NO 190
<211> LENGTH: 27
<212> TYPE: DNA
<213> ORGANISM: Artificial Sequence
<220> FEATURE:
<223> OTHER INFORMATION: Synthetic Construct

<400> SEQUENCE: 190
ctcctcgggc agtgggaggg ctttgtt                                         27

<210> SEQ ID NO 191
<211> LENGTH: 27
<212> TYPE: DNA
<213> ORGANISM: Artificial Sequence
<220> FEATURE:
<223> OTHER INFORMATION: Synthetic Construct

<400> SEQUENCE: 191
cccgaggcca aaccatctc caaagcc                                          27

<210> SEQ ID NO 192
<211> LENGTH: 27
<212> TYPE: DNA
<213> ORGANISM: Artificial Sequence
<220> FEATURE:
```

```
<223> OTHER INFORMATION: Synthetic Construct

<400> SEQUENCE: 192
ggttttggcc tcggggggctg ggagggc                                    27

<210> SEQ ID NO 193
<211> LENGTH: 30
<212> TYPE: DNA
<213> ORGANISM: Artificial Sequence
<220> FEATURE:
<223> OTHER INFORMATION: Synthetic Construct

<400> SEQUENCE: 193
atgtgttcct gctgtactac gtggacacct                                  30

<210> SEQ ID NO 194
<211> LENGTH: 31
<212> TYPE: DNA
<213> ORGANISM: Artificial Sequence
<220> FEATURE:
<223> OTHER INFORMATION: Synthetic Construct

<400> SEQUENCE: 194
atgtgttcct gctgtactta cgtggacacc t                                31

<210> SEQ ID NO 195
<211> LENGTH: 28
<212> TYPE: DNA
<213> ORGANISM: Artificial Sequence
<220> FEATURE:
<223> OTHER INFORMATION: Synthetic Construct

<400> SEQUENCE: 195
atgtgttcct gctgtaacct ggacacct                                    28

<210> SEQ ID NO 196
<211> LENGTH: 29
<212> TYPE: DNA
<213> ORGANISM: Artificial Sequence
<220> FEATURE:
<223> OTHER INFORMATION: Synthetic Construct

<400> SEQUENCE: 196
atgtgttcct ggacaccacg tggacacct                                   29

<210> SEQ ID NO 197
<211> LENGTH: 27
<212> TYPE: DNA
<213> ORGANISM: Artificial Sequence
<220> FEATURE:
<223> OTHER INFORMATION: Synthetic Construct

<400> SEQUENCE: 197
atgtgttcct gctgtactac gacacct                                     27

<210> SEQ ID NO 198
<211> LENGTH: 31
<212> TYPE: DNA
<213> ORGANISM: Artificial Sequence
<220> FEATURE:
<223> OTHER INFORMATION: Synthetic Construct

<400> SEQUENCE: 198
atgtgttcct gctgtactta cgtggacacc t                                31
```

```
<210> SEQ ID NO 199
<211> LENGTH: 31
<212> TYPE: DNA
<213> ORGANISM: Artificial Sequence
<220> FEATURE:
<223> OTHER INFORMATION: Synthetic Construct

<400> SEQUENCE: 199
atgtgttcct gctgtactta cgtggacacc t                                   31

<210> SEQ ID NO 200
<211> LENGTH: 29
<212> TYPE: DNA
<213> ORGANISM: Artificial Sequence
<220> FEATURE:
<223> OTHER INFORMATION: Synthetic Construct

<400> SEQUENCE: 200
atgtgttcct gctgtactcg tggacacct                                      29

<210> SEQ ID NO 201
<211> LENGTH: 31
<212> TYPE: DNA
<213> ORGANISM: Artificial Sequence
<220> FEATURE:
<223> OTHER INFORMATION: Synthetic Construct

<400> SEQUENCE: 201
atgtgttcct gctgtaccta cgtggacacc t                                   31

<210> SEQ ID NO 202
<211> LENGTH: 28
<212> TYPE: DNA
<213> ORGANISM: Artificial Sequence
<220> FEATURE:
<223> OTHER INFORMATION: Synthetic Construct

<400> SEQUENCE: 202
atgtgttcct gctgtacact ggacacct                                       28

<210> SEQ ID NO 203
<211> LENGTH: 30
<212> TYPE: DNA
<213> ORGANISM: Artificial Sequence
<220> FEATURE:
<223> OTHER INFORMATION: Synthetic Construct

<400> SEQUENCE: 203
atagctgtgg tgtacggctc gttggccctc                                     30

<210> SEQ ID NO 204
<211> LENGTH: 27
<212> TYPE: DNA
<213> ORGANISM: Artificial Sequence
<220> FEATURE:
<223> OTHER INFORMATION: Synthetic Construct

<400> SEQUENCE: 204
atagctgtgg tgtacggctc ggccctc                                        27

<210> SEQ ID NO 205
<211> LENGTH: 30
<212> TYPE: DNA
<213> ORGANISM: Artificial Sequence
<220> FEATURE:
<223> OTHER INFORMATION: Synthetic Construct
```

```
<400> SEQUENCE: 205
atagctgtgg tgtacggctt tcgttggtcc                                    30

<210> SEQ ID NO 206
<211> LENGTH: 22
<212> TYPE: DNA
<213> ORGANISM: Artificial Sequence
<220> FEATURE:
<223> OTHER INFORMATION: Synthetic Construct

<400> SEQUENCE: 206
atagctgtgg tgtacggccc tc                                            22
```

ANTI-TMEM-180 ANTIBODY, ANTICANCER DRUG AND CANCER TESTING METHOD

TECHNICAL FIELD

The present invention relates to a novel anti-TMEM-180 antibody, an anticancer drug containing an anti-TMEM-180 antibody, a cancer testing method involving measuring TMEM-180 in a sample, and the like.

BACKGROUND ART

Recently, numerous molecular targeted drugs that act specifically on a specific molecule have been developed for use as anticancer drugs. In particular, development has been proceeding on various antibody drugs having, as antigens, molecules specifically expressed in certain cancer cells or molecules exhibiting increased expression in cancer cells. In the development of such antibody drugs, a comparison is first made between expression of mRNA in cancer tissue collected at the time of surgery and expression of mRNA in normal tissue collected from a nearby site, molecules specifically expressed only in cancer tissue or molecules exhibiting increased expression in cancer tissue are identified, and antibodies are then prepared by using those molecules as antigens.

Colon cancer is manifest from cells of the intestinal mucosa. Cetuximab has previously been developed for use against colon cancer as an antibody drug that targets epidermal growth factor receptor (EGFR) (Non-Patent Documents 1 to 3). However, since EGFR is also expressed in normal tissue, Cetuximab also has the potential to act on normal tissue, thereby resulting in the desire to develop a molecular targeted drug that targets molecules more specifically expressed during colon cancer. With regard to this point, since there is only a small amount of mucosal tissue in which colon cancer occurs, there has been the problem of it being difficult to identify a target molecule by comparing cancerous mucosal cells and normal mucosal cells.

CITATION LIST

Non-Patent Documents

Non-Patent Document 1: Cunningham, D., et al., The New England Journal of Medicine, Vol. 351, No. 4, 2004, pp. 337-345
Non-Patent Document 2: Goldstein, N. I., et al., Clin. Cancer Res., Vol. 1, 1311-1318, 1995
Non-Patent Document 3: Karapetis, C. S., et al., The New Engl. J. Med., Vol. 359, 1757-1765

SUMMARY

Technical Problem

An object of the present invention is to provide an anticancer drug capable of treating cancer by finding a target molecule specifically expressed in cancer cells and by specifically acting on the target molecule, and to provide a cancer testing method comprising a step of measuring the target molecule in a sample.

Solution to Problem

In order to solve the above-mentioned problems, the inventors of the present invention compared mRNA expression between various types of colon cancer cell lines and normal mucosal cells contained in the washing liquid obtained during colonoscopy by analyzing using a DNA microarray to seek out molecules that are only expressed in colon cancer cell lines. As a result, transmembrane protein 180 (TMEM-180) was identified as a protein that is expressed in all colon cancer cell lines but which is not observed to be expressed in the cells of healthy subjects. Moreover, in addition to confirming that TMEM-180 is not expressed in normal colon tissue by quantitative PCR and in situ hybridization, TMEM-180 was also confirmed to not be expressed in prominent normal tissues, thereby confirming TMEM-180 to be an ideal molecule for use as a target of anticancer drugs and as an indicator in cancer testing.

Antibody to TMEM-180 was produced, and this antibody was confirmed to demonstrate a cytocidal effect on colon cancer cells as well as be able to detect recurrence in particular with greater sensitivity than conventional colon cancer markers, thereby leading to completion of the present invention.

Namely, the present invention is as indicated below.

[1] An anticancer drug containing, as an active ingredient thereof, an anti-transmembrane protein 180 (TMEM-180) antibody or an antigen-binding fragment thereof.

[2] An anticancer drug containing, as an active ingredient thereof, an anti-TMEM-180 antibody having a substance having anticancer activity bound thereto, or an antigen-binding fragment thereof.

[3] The anticancer drug described in [1] or [2] above, wherein the anti-TMEM-180 antibody has at least one of the six CDRs indicated below:

```
                                         (SEQ ID NO: 1)
heavy chain CDR1: GFSLTRYNVH;

(SEQ ID NO: 2)
heavy chain CDR2: VIWTGGSTD;

(SEQ ID NO: 3)
heavy chain CDR3: DLGY;

(SEQ ID NO: 4)
light chain CDR1: KSSQSLKYRDGKTYLN;

(SEQ ID NO: 5)
light chain CDR2: QVSKLDS;
and (SEQ ID NO: 6)
light chain CDR3: CQGSYSPHT.
```

[4] The anticancer drug described in [1] or [2] above, wherein the anti-TMEM-180 antibody has at least one of the six CDRs indicated below:

```
                                         (SEQ ID NO: 7)
heavy chain CDR1: GFSLTSYYMQ;

(SEQ ID NO: 8)
heavy chain CDR2: FIRSGGSTE;

(SEQ ID NO: 9)
heavy chain CDR3: AFYGGYYFDY;

(SEQ ID NO: 10)
light chain CDR1: KASQNVGSNVD;
```

```
                                          (SEQ ID NO: 11)
light chain CDR2: KASNRYT;
and (SEQ ID NO: 12)
light chain CDR3: MQSNTKYT.
```

[5] The anticancer drug described in [1] or [2] above, wherein the anti-TMEM-180 antibody has at least one of the six CDRs indicated below:

```
                                          (SEQ ID NO: 40)
heavy chain CDR1: GFTFSDYAMA;

(SEQ ID NO: 41)
heavy chain CDR2: TIIYDGSST;

(SEQ ID NO: 42)
heavy chain CDR3: HWYWYFDF;

(SEQ ID NO: 43)
light chain CDR1: LASEGISNDLA;

(SEQ ID NO: 44)
light chain CDR2: AASRLQD;
and (SEQ ID NO: 45)
light chain CDR3: QQSYKYPLT.
```

[6] The anticancer drug described in [1] or [2] above, wherein the anti-TMEM-180 antibody has at least one of the six CDRs indicated below:

```
                                          (SEQ ID NO: 48)
heavy chain CDR1: DCALN;

(SEQ ID NO: 49)
heavy chain CDR2: WINTQTGKPTYADDF;

(SEQ ID NO: 50)
heavy chain CDR3: EDYGYFDY;

(SEQ ID NO: 51)
light chain CDR1: QASQNINKFIA;

(SEQ ID NO: 52)
light chain CDR2: YTSTLVS;
and (SEQ ID NO: 53)
light chain CDR3: LQYDNLRT.
```

[7] The anticancer drug described in [1] or [2] above, wherein the anti-TMEM-180 antibody has at least one of the six CDRs indicated below:

```
                                          (SEQ ID NO: 56)
heavy chain CDR1: NYGMH;

(SEQ ID NO: 57)
heavy chain CDR2: SISPSGGSTYYRDSV;

(SEQ ID NO: 58)
heavy chain CDR3: SASITAYYYVMDA;

(SEQ ID NO: 59)
light chain CDR1: KASQNVGSNVD;
```

```
                                          (SEQ ID NO: 60)
light chain CDR2: KASNRYT;
and (SEQ ID NO: 61)
light chain CDR3: MQSNSYPPT.
```

[8] The anticancer drug described in [1] or [2] above, wherein the anti-TMEM-180 antibody has at least one of the six CDRs indicated below:

```
                                          (SEQ ID NO: 64)
heavy chain CDR1: NYWMT;

(SEQ ID NO: 65)
heavy chain CDR2: SITNTGGSTYYPDSV;

(SEQ ID NO: 66)
heavy chain CDR3: AGYSSYPDYFDY;

(SEQ ID NO: 67)
light chain CDR1: KAGQNIYNYLA;

(SEQ ID NO: 68)
light chain CDR2: NANSLQT;
and (SEQ ID NO: 69)
light chain CDR3: QQYSSGWT.
```

[9] The anticancer drug described in [1] or [2] above, wherein the anti-TMEM-180 antibody has at least one of the six CDRs indicated below:

```
                                          (SEQ ID NO: 72)
heavy chain CDR1: DYWVS;

(SEQ ID NO: 73)
heavy chain CDR2: EIYPNSGATNFNENFK;

(SEQ ID NO: 74)
heavy chain CDR3: DGTMGIAYYFDY;

(SEQ ID NO: 75)
light chain CDR1: KASQNINRYLN;

(SEQ ID NO: 76)
light chain CDR2: NANSLQT;
and (SEQ ID NO: 77)
light chain CDR3: LQHNSWPYT.
```

[10] The anticancer drug described in [1] or [2] above, wherein the anti-TMEM-180 antibody has at least one of the six CDRs indicated below:

```
                                          (SEQ ID NO: 80)
heavy chain CDR1: SYDIS;

(SEQ ID NO: 81)
heavy chain CDR2: AINPGSGGTGYNEKFKGK;

(SEQ ID NO: 82)
heavy chain CDR3: IHGGYRYWFAY;

(SEQ ID NO: 83)
light chain CDR1: RASSSVSYMH;
```

```
                                                (SEQ ID NO: 84)
    light chain CDR2: DTSKLAS;
    and (SEQ ID NO: 85)
    light chain CDR3: LQRSSYPPT.
```

[11] The anticancer drug described in [1] or [2] above, wherein the anti-TMEM-180 antibody has at least one of the six CDRs indicated below:

```
                                                (SEQ ID NO: 88)
    heavy chain CDR1: SNGVG;

(SEQ ID NO: 89)
    heavy chain CDR2: TIWTGGGTNYNSGVQS;

(SEQ ID NO: 90)
    heavy chain CDR3: EYMGFDY;

(SEQ ID NO: 91)
    light chain CDR1: KASQNVGINVG;

(SEQ ID NO: 92)
    light chain CDR2: WASNRDT;
    and (SEQ ID NO: 93)
    light chain CDR3: LQHNSYPRT.
```

[12] The anticancer drug described in [1] or [2] above, wherein the anti-TMEM-180 antibody has at least one of the six CDRs indicated below:

```
                                                (SEQ ID NO: 96)
    heavy chain CDR1: SNGVG;

(SEQ ID NO: 97)
    heavy chain CDR2: TIWSGGGTNYNSAVQS;

(SEQ ID NO: 98)
    heavy chain CDR3: EEKGFAY;

(SEQ ID NO: 99)
    light chain CDR1: KASQNVGINVG;

(SEQ ID NO: 100)
    light chain CDR2: WASNRDT;
    and (SEQ ID NO: 101)
    light chain CDR3: LQHNSYPRA.
```

[13] The anticancer drug described in any one of [3] to [12] above, wherein the anti-TMEM-180 antibody is such that
 at least one of the heavy chain CDR1 to CDR3 and light chain CDR1 to CDR3 contains one to several amino acid additions, substitutions or deletions, or
 at least one of the heavy chain CDR1 to CDR3 and light chain CDR1 to CDR3 has an amino acid sequence having identity of 80% or more with the amino acid sequences of the heavy chain CDR1 to CDR3 and light chain CDR1 to CDR3.

[14] The anticancer drug described in [1] or [2] above, wherein the anti-TMEM-180 antibody contains:
 a heavy chain containing the amino acid sequence represented by SEQ ID NO: 13;
 a heavy chain containing an amino acid sequence containing one to several amino acid additions, substitutions or deletions in the amino acid sequence represented by SEQ ID NO: 13; or
 a heavy chain containing an amino acid sequence having identity of 80% or more with the amino acid sequence represented by SEQ ID NO: 13, and/or
 a light chain containing the amino acid sequence represented by SEQ ID NO: 14;
 a light chain containing an amino acid sequence containing one to several amino acid additions, substitutions or deletions in the amino acid sequence represented by SEQ ID NO: 14; or
 a light chain containing an amino acid sequence having identity of 80% or more with the amino acid sequence represented by SEQ ID NO: 14.

[15] The anticancer drug described in [1] or [2] above, wherein the anti-TMEM-180 antibody contains:
 a heavy chain containing the amino acid sequence represented by SEQ ID NO: 15;
 a heavy chain containing an amino acid sequence containing one to several amino acid additions, substitutions or deletions in the amino acid sequence represented by SEQ ID NO: 15; or
 a heavy chain containing an amino acid sequence having identity of 80% or more with the amino acid sequence represented by SEQ ID NO: 15, and/or
 a light chain containing the amino acid sequence represented by SEQ ID NO: 16;
 a light chain containing an amino acid sequence containing one to several amino acid additions, substitutions or deletions in the amino acid sequence represented by SEQ ID NO: 16; or a light chain containing an amino acid sequence having identity of 80% or more with the amino acid sequence represented by SEQ ID NO: 16.

[16] The anticancer drug described in [1] or [2] above, wherein the anti-TMEM-180 antibody contains:
 a heavy chain containing the amino acid sequence represented by SEQ ID NO: 46;
 a heavy chain containing an amino acid sequence containing one to several amino acid additions, substitutions or deletions in the amino acid sequence represented by SEQ ID NO: 46; or
 a heavy chain containing an amino acid sequence having identity of 80% or more with the amino acid sequence represented by SEQ ID NO: 46, and/or a light chain containing the amino acid sequence represented by SEQ ID NO: 47;
 a light chain containing an amino acid sequence containing one to several amino acid additions, substitutions or deletions in the amino acid sequence represented by SEQ ID NO: 47; or
 a light chain containing an amino acid sequence having identity of 80% or more with the amino acid sequence represented by SEQ ID NO: 47.

[17] The anticancer drug described in [1] or [2] above, wherein the anti-TMEM-180 antibody contains:
 a heavy chain containing the amino acid sequence represented by SEQ ID NO: 54;
 a heavy chain containing an amino acid sequence containing one to several amino acid additions, substitutions or deletions in the amino acid sequence represented by SEQ ID NO: 54; or
 a heavy chain containing an amino acid sequence having identity of 80% or more with the amino acid sequence represented by SEQ ID NO: 54, and/or
 a light chain containing the amino acid sequence represented by SEQ ID NO: 55;

a light chain containing an amino acid sequence containing one to several amino acid additions, substitutions or deletions in the amino acid sequence represented by SEQ ID NO: 55; or a light chain containing an amino acid sequence having identity of 80% or more with the amino acid sequence represented by SEQ ID NO: 55.

[18] The anticancer drug described in [1] or [2], wherein the anti-TMEM-180 antibody contains:
  a heavy chain containing the amino acid sequence represented by SEQ ID NO: 62;
  a heavy chain containing an amino acid sequence containing one to several amino acid additions, substitutions or deletions in the amino acid sequence represented by SEQ ID NO: 62; or
  a heavy chain containing an amino acid sequence having identity of 80% or more with the amino acid sequence represented by SEQ ID NO: 62, and/or
  a light chain containing the amino acid sequence represented by SEQ ID NO: 63;
  a light chain containing an amino acid sequence containing one to several amino acid additions, substitutions or deletions in the amino acid sequence represented by SEQ ID NO: 63; or
  a light chain containing an amino acid sequence having identity of 80% or more with the amino acid sequence represented by SEQ ID NO: 63.

[19] The anticancer drug described in [1] or [2] above, wherein the anti-TMEM-180 antibody contains:
  a heavy chain containing the amino acid sequence represented by SEQ ID NO: 70;
  a heavy chain containing an amino acid sequence containing one to several amino acid additions, substitutions or deletions in the amino acid sequence represented by SEQ ID NO: 70; or
  a heavy chain containing an amino acid sequence having identity of 80% or more with the amino acid sequence represented by SEQ ID NO: 70, and/or
  a light chain containing the amino acid sequence represented by SEQ ID NO: 71;
  a light chain containing an amino acid sequence containing one to several amino acid additions, substitutions or deletions in the amino acid sequence represented by SEQ ID NO: 71; or
  a light chain containing an amino acid sequence having identity of 80% or more with the amino acid sequence represented by SEQ ID NO: 71.

[20] The anticancer drug described in [1] or [2] above, wherein the anti-TMEM-180 antibody contains:
  a heavy chain containing the amino acid sequence represented by SEQ ID NO: 78;
  a heavy chain containing an amino acid sequence containing one to several amino acid additions, substitutions or deletions in the amino acid sequence represented by SEQ ID NO: 78; or
  a heavy chain containing an amino acid sequence having identity of 80% or more with the amino acid sequence represented by SEQ ID NO: 78, and/or
  a light chain containing the amino acid sequence represented by SEQ ID NO: 79;
  a light chain containing an amino acid sequence containing one to several amino acid additions, substitutions or deletions in the amino acid sequence represented by SEQ ID NO: 79; or
  a light chain containing an amino acid sequence having identity of 80% or more with the amino acid sequence represented by SEQ ID NO: 79.

[21] The anticancer drug described in [1] or [2] above, wherein the anti-TMEM-180 antibody contains:
  a heavy chain containing the amino acid sequence represented by SEQ ID NO: 86;
  a heavy chain containing an amino acid sequence containing one to several amino acid additions, substitutions or deletions in the amino acid sequence represented by SEQ ID NO: 86; or
  a heavy chain containing an amino acid sequence having identity of 80% or more with the amino acid sequence represented by SEQ ID NO: 86, and/or
  a light chain containing the amino acid sequence represented by SEQ ID NO: 87;
  a light chain containing an amino acid sequence containing one to several amino acid additions, substitutions or deletions in the amino acid sequence represented by SEQ ID NO: 87; or
  a light chain containing an amino acid sequence having identity of 80% or more with the amino acid sequence represented by SEQ ID NO: 87.

[22] The anticancer drug described in [1] or [2] above, wherein the anti-TMEM-180 antibody contains:
  a heavy chain containing the amino acid sequence represented by SEQ ID NO: 94;
  a heavy chain containing an amino acid sequence containing one to several amino acid additions, substitutions or deletions in the amino acid sequence represented by SEQ ID NO: 94; or
  a heavy chain containing an amino acid sequence having identity of 80% or more with the amino acid sequence represented by SEQ ID NO: 94, and/or
  a light chain containing the amino acid sequence represented by SEQ ID NO: 95;
  a light chain containing an amino acid sequence containing one to several amino acid additions, substitutions or deletions in the amino acid sequence represented by SEQ ID NO: 95; or
  a light chain containing an amino acid sequence having identity of 80% or more with the amino acid sequence represented by SEQ ID NO: 95.

[23] The anticancer drug described in [1] or [2] above, wherein the anti-TMEM-180 antibody contains:
  a heavy chain containing the amino acid sequence represented by SEQ ID NO: 102;
  a heavy chain containing an amino acid sequence containing one to several amino acid additions, substitutions or deletions in the amino acid sequence represented by SEQ ID NO: 102; or
  a heavy chain containing an amino acid sequence having identity of 80% or more with the amino acid sequence represented by SEQ ID NO: 102, and/or
  a light chain containing the amino acid sequence represented by SEQ ID NO: 103;
  a light chain containing an amino acid sequence containing one to several amino acid additions, substitutions or deletions in the amino acid sequence represented by SEQ ID NO: 103; or
  a light chain containing an amino acid sequence having identity of 80% or more with the amino acid sequence represented by SEQ ID NO: 103.

[24] The anticancer drug described in any one of [1] to [23] above, wherein the anti-TMEM-180 antibody has one or more N-linked oligosaccharides bound to the Fc region and fucose is not bound to N-acetylglucosamine on the reducing end of the N-linked oligosaccharide.

[25] The anticancer drug described in any one of [1] to [24] above, which is targeted at cancer expressing TMEM-180.

[26] The anticancer drug described in any one of [1] to [24] above, which is targeted at colon cancer.

[27] The anticancer drug described in any one of [1] to [24] above, which is administered concomitantly with vaccine therapy using a composition containing at least one peptide comprising an amino acid sequence represented by SEQ ID NOs: 104 to 170.

[28] An anti-TMEM-180 antibody described in any one of [3] to [24] above or an antigen-binding fragment thereof.

[29] A nucleic acid encoding any one of the heavy chains CDR1 to CDR3 and light chains CDR1 to CDR3 described in any one of [3] to [13] above.

[30] A nucleic acid encoding any one of the heavy chains and light chains described in any one of [14] to [23] above.

[31] An expression vector containing the nucleic acid described in [29] or [30] above.

[32] A transformant containing the expression vector described in [31] above.

[33] A method for producing an anti-TMEM-180 antibody, or an antigen-binding fragment thereof, the method comprising the steps of:
  expressing an antibody in the transformant described in [32] above; and
  recovering the antibody.

[34] A cancer testing method, comprising a step of measuring the amount of TMEM-180 in a sample collected from a subject.

[35] The cancer testing method described in [34] above, wherein the amount of TMEM-180 is measured by immunoassay using an anti-TMEM-180 antibody or an antigen-binding fragment thereof.

[36] The cancer testing method described in [35] above, wherein the anti-TMEM-180 antibody or antigen-binding fragment thereof is the anti-TMEM-180 antibody or antigen-binding fragment thereof described in [28] above.

[37] The cancer testing method described in any one of [34] to [36] above, which is targeted at colon cancer.

[38] The cancer testing method described in [34] to [37], which is used to test for recurrence or metastasis following treatment.

[39] A cancer testing kit containing an anti-TMEM-180 antibody or an antigen-binding fragment thereof.

[40] The cancer testing kit described in [39] above, wherein the anti-TMEM-180 antibody or antigen-binding fragment thereof is the anti-TMEM-180 antibody or antigen-binding fragment thereof described in [28] above.

[41] The cancer testing kit described in [39] or [40] above, which is targeted at colon cancer.

Advantageous Effects of Invention

The present inventors also discovered that TMET-180 is existed and presented on the surface of the exosomes in the serum from a subject having cancer. According to this finding, the invention below is also provided.

[A17] A cancer testing method, comprising a step of detecting the amount of exosomes having TMEM-180 in a body fluid sample obtained from a subject.

[A18] The cancer testing method according to [A17], wherein the step of detecting the amount of exosomes having TMEM-180 is conducted with an antibody binding to TMEM-180 or an antigen-binding fragment thereof.

[A21] The cancer testing method according to [A18], wherein the step of detecting the amount of exosomes having TMEM-180 is conducted with the anti-TMEM-180 antibody according to any one of [3] to [24] or an antigen-binding fragment thereof.

[A22] A pharmaceutical composition for use in treating cancer in a subject having cancer, comprising an antibody binding to TMEM-180, wherein the subject is a subject whose body fluid sample is a sample from which TMEM-180 has been detected.

The present inventors further obtained a 1361-5 clone antibody, in which non-specific attachment has been reduced, from a 1361 antibody. Thus, the present invention also provides the following inventions.

[A1] An antibody binding to the transmembrane protein 180 (TMEM-180) or an antigen-binding fragment thereof,
(1) wherein the antibody comprises a heavy chain variable region having
a heavy chain CDR1: NYWMT (SEQ ID NO: 171);
a heavy chain CDR2: SITNTGGSTAYPDSV (SEQ ID NO: 172); and
a heavy chain CDR3: AGYSSYPDYFDY (SEQ ID NO: 173), and
a light chain variable region having
a light chain CDR1: KAGQNIYNYLA (SEQ ID NO: 174);
a light chain CDR2: NANSLQT (SEQ ID NO: 175); and
a light chain CDR3: QQYSSGWT (SEQ ID NO: 176); or
(2) wherein the antibody competes with the antibody according to above (1) for binding to TMEM-180.

[A2] The antibody according to above [A1] or an antigen-binding fragment thereof, wherein the antibody comprises a heavy chain variable region (SEQ ID NO: 177) and a light chain variable region (SEQ ID NO: 178).

[A3] The antibody according to above [A1] or [A2] or an antigen-binding fragment thereof, wherein the antibody has a heavy chain (SEQ ID NO: 180) and a light chain (SEQ ID NO: 182).

[A4] The antibody according to any one of above [A1] to [A3], wherein the antibody has one or more N-linked oligosaccharides bound to the Fc region and fucose is not bound to N-acetylglucosamine on the reducing end of the N-linked oligosaccharide.

[A5] A pharmaceutical composition for use in treating cancer, comprising the antibody according to any one of above [A1] to [A4].

[A6] A composition for use in diagnosing cancer, comprising the antibody according to any one of above [A1] to [A4] or an antigen-binding fragment thereof.

[A7] A diagnostic kit for use in diagnosing cancer, comprising the antibody according to any one of above [A1] to [A4] or an antigen-binding fragment thereof.

[A8] The pharmaceutical composition according to above [A5], which is targeted at cancer expressing TMEM-180.

[A9] The pharmaceutical composition according to above [A5], which is targeted at colon cancer.

[A10] A nucleic acid encoding any one of the heavy chain CDRs 1 to 3 and the light chain CDRs 1 to 3 as defined in any one of above [A1] to [A4].

[A11] A nucleic acid encoding any one of the heavy chain and the light chain according to any one of above [A1] to [A4].

[A12] A vector comprising the nucleic acid according to above [A10] or [A11].

[A13] A transformant comprising the vector according to above [A12].

[A14] A cancer testing method comprising a step of measuring the amount of TMEM-180 in the sample obtained from a subject with the antibody according to above [A1] to [A4] or an antigen-binding fragment thereof.

[A15] The cancer testing method according to above [A14], which is targeted at colon cancer.

[A16] The cancer testing method according to above [A14] or [A15], which is used for testing recurrence or metastasis after a treatment.

[A19] The method according to above [A18], wherein the step of detecting the amount of exosomes having TMEM-180 is conducted with the antibody according to any one of [A1] to [A4] or an antigen-binding fragment thereof.

[A20] A method for detecting stage 1 or stage 2 cancer, comprising a step of measuring the amount of TMEM-180 in the sample obtained from a subject.

[A23] The cancer testing method according to any one of above [A17] to [A19], for use in detecting stage 1 or stage 2 cancer.

[A24] The method according to any one of above [A17] to [A19], wherein the cancer is colon cancer.

[B1] A pharmaceutical composition for use in treating cancer, comprising an antibody-drug conjugate of the anti-TMEM-180 and a cytotoxic agent.

[B2] The pharmaceutical composition according to above [B1],
wherein the anti-TMEM-180 antibody is
(1) an antibody comprising
a heavy chain having
a heavy chain CDR1: NYWMT (SEQ ID NO: 171);
a heavy chain CDR2: SITNTGGSTAYPDSV (SEQ ID NO: 172); and
a heavy chain CDR3: AGYSSYPDYFDY (SEQ ID NO: 173); and
a light chain having
a light chain CDR1: KAGQNIYNYLA (SEQ ID NO: 174);
a light chain CDR2: NANSLQT (SEQ ID NO: 175); and
a light chain CDR3: QQYSSGWT (SEQ ID NO: 176); or
(2) an antibody which competes with the antibody according to above (1) for binding to TMEM-180.

[B3] The pharmaceutical composition according to above [B2], wherein the anti-TMEM-180 antibody has a heavy chain (SEQ ID NO: 180) and a light chain (SEQ ID NO: 182).

[B4] The pharmaceutical composition according to above [B1],
wherein the anti-TMEM-180 antibody is
(1) an antibody comprising
a heavy chain comprising
a heavy chain CDR1: DYWVS (SEQ ID NO: 72);
a heavy chain CDR2: EIYPNSGATNFNENFK (SEQ ID NO: 73); and
a heavy chain CDR3: DGTMGIAYYFDY (SEQ ID NO: 74); and
a light chain comprising
a light chain CDR1: KASQNINRYLN (SEQ ID NO: 75);
a light chain CDR2: NANSLQT (SEQ ID NO: 76); and
a light chain CDR3: LQHNSWPYT (SEQ ID NO: 77); or
(2) an antibody which competes with the antibody according to above (1) for binding to TMEM-180.

[B5] The pharmaceutical composition according to any one of above [B1] to [B4], wherein the antibody and the drug are linked via a cleavable linker.

[B6] The pharmaceutical composition according to above [B5], wherein the cleavable linker is a linker which is cleavable with peptidase in bodies, a hydrazine linker, or a linker comprising a carbamate bond or an ester bond.

[B7] The pharmaceutical composition according to above [B6], wherein the cleavable linker is a linker comprising a dipeptide of valine-citrulline or phenylalanine-lysin.

[B8] The pharmaceutical composition according to above [B7], wherein the cleavable linker is a valine-citrulline linker.

[B9] The pharmaceutical composition according to above [B8], wherein the cleavable linker comprises a polyethylene glycol block and a valine-citrulline block (for example, comprises Mal-PEG$_{12}$-Val-Cit-PABC).

[B10] The pharmaceutical composition according to any one of above [B1] to [B9], in particular [B9], wherein the cytotoxic agent is monomethylauristatin E.

[B11] The pharmaceutical composition according to above [B9] or [B10], wherein the antibody is the antibody according to any one of above [1] to [23] and [A1].

[B12] A pharmaceutical composition comprising an antibody-drug conjugate of anti-TMEM-180 antibody and a cytotoxic agent; or a pharmaceutical composition for use in treating cancer according to above [A5], wherein the anti-TMEM-180 antibody is in a form linked to a cytotoxic agent.

The anticancer drug containing an anti-TMEM-180 antibody or an antigen-binding fragment thereof according to the present invention targets TMEM-180, which is a protein specifically expressed in certain cancers but is not expressed in normal tissue, and is thought to allow the obtaining of a potent effect specific to cancer cells with few adverse side effects.

Since TMEM-180 is specifically expressed in certain cancers but not expressed in normal tissue, a cancer testing method and testing kit that uses the anti-TMEM-180 antibody or antigen-binding fragment thereof according to the present invention enables cancer testing to be carried out easily. The cancer testing method and testing kit according to the present invention are able to detect recurrence of cancer in particular with greater sensitivity in comparison with conventional colon cancer markers.

In addition, according to the anticancer drug containing an anti-TMEM-180 antibody having a substance having anticancer activity bound thereto, or an antigen-binding fragment thereof, according to the present invention, that anticancer drug can be specifically delivered to cancer cells expressing TMEM-180, thereby facilitating the use of a highly toxic substance for the substance having anticancer activity.

BRIEF DESCRIPTION OF THE DRAWINGS

FIG. 13 shows that the 1361-5 antibody does not recognize normal skin tissues.

FIG. 14 shows that the 1361-5 antibody does not recognize normal tissues besides skin.

FIG. 23 shows the electron microscope image showing that TMEM-180 is expressed on the surface of the exosomes.

FIG. 24 is a diagram showing the antibody-drug conjugate (ADC) prepared in Example C15.

FIG. 25 is a diagram showing internalization of the TMEM-180 antibody.

FIG. 27 shows positions of the guide RNAs used in preparing TMEM-180 knockout mice and disrupted sequences of the gene. The sequences in the figure are SEQ ID NOs: 193-206 as listed from the top to the bottom of the figure.

Figure 1:
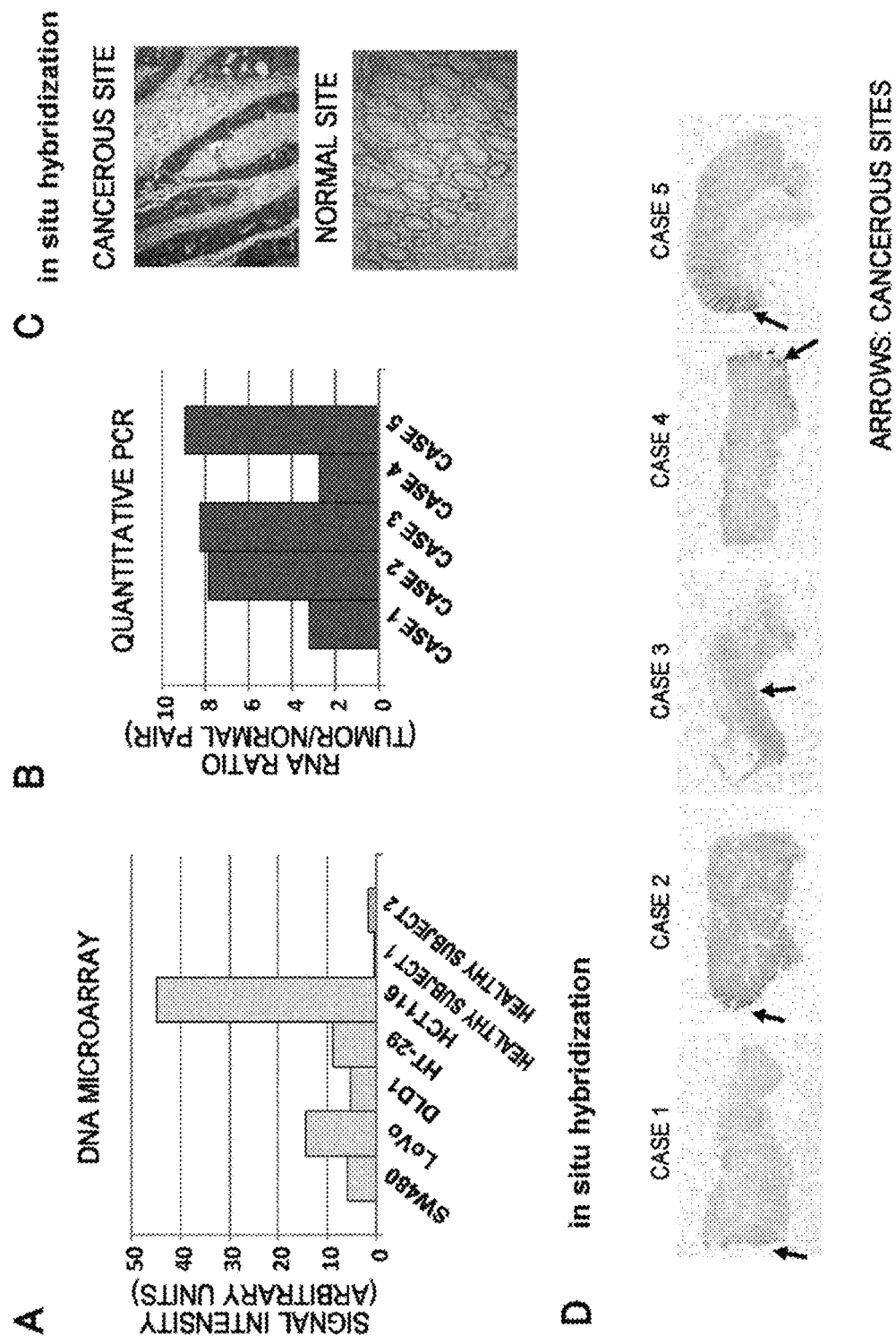
FIG. 1A indicates expression levels of TMEM-180 obtained as a result of conducting an exhaustive expression analysis on human colon cancer cell lines and colon mucosal cells obtained from healthy subjects by DNA microarray analysis.
FIG. 1B indicates the results of analyzing expression of TMEM-180 in colon cancer cells and adjacent normal colon tissue by quantitative PCR.
FIGS. 1C and 1D indicate the results of investigating expression of TMEM-180 at cancerous sites and normal sites by in situ hybridization.

DESCRIPTION OF EMBODIMENTS (Anti-TMEM-180 Antibody and Anticancer Drug)

One aspect of the anticancer drug according to the present invention contains an anti-TMEM-180 antibody, or an antigen-binding fragment thereof, as active ingredient.

In the present description, the anti-TMEM-180 antibody refers to an antibody that binds to the transmembrane protein 180 (TMEM-180), and the antibody may specifically bind to TMEM-180. In the present description, in the case of referring to TMEM-180, the TMEM-180 may be TMEM-180 derived from any animal, and may be a mutant thereof provided it serves as a target of an anticancer drug or an indicator of a cancer testing method. The amino acid sequence of human TMEM-180 is indicated in SEQ ID NO: 17 as an example of TMEM-180.

In the present description, an "antibody" refers to an immunoglobulin, that is, a protein having a structure in which two heavy chains (H chains) and two light chains (L chains) are associated as stabilized by a pair of disulfide bonds. The heavy chains are formed from a heavy chain variable region VH, heavy chain constant regions CH1, CH2 and CH3, and a hinge region between CH1 and CH2, while the light chains are formed from a light chain variable region VL and a light chain constant region CL. Among these chains, a variable region fragment (Fv) formed of VH and VL is directly involved in antigen binding and is a region that provides the antibody with diversity. In addition, an antigen-binding region formed of VL, CL, VH and CH1 is referred to as the Fab region, while the region formed of the hinge region, CH2 and CH3 is referred to as the Fc region.

Among the variable regions, the region that makes direct contact with antigen undergoes considerable change in particular, and is referred to as a complementarity-determining region (CDR). The region other than CDR that remains comparatively unchanged is referred to as the framework region (FR). Three CDRs each are present in the variable regions of the light chain and heavy chain, and are referred to as heavy chain CDR1 to CDR3 and light chain CDR1 to CDR3, respectively, in order starting from the side of the N-terminal.

The term "treatment" as used herein means therapeutic treatment and prophylactic treatment. Therefore, the phrase "a pharmaceutical composition for use in treating cancer"

means a pharmaceutical composition for use in therapeutically or prophylactically treating cancer, for example, an anti-cancer agent.

The anti-TMEM-180 antibody according to the present invention may be a monoclonal antibody or polyclonal antibody. In addition, the anti-TMEM-180 antibody of the present invention may be an isotype of any of IgG, IgM, IgA, IgD or IgE. It may also be that produced by immunizing a non-human animal such as a mouse, rat, hamster, guinea pig, rabbit or chicken, or may be a recombinant antibody, chimeric antibody, humanized antibody, fully human antibody or the like. A chimeric antibody refers to an antibody in which fragments of antibodies from different species are linked.

A "humanized antibody" refers to an antibody in which a location corresponding to human antibody has been substituted with an amino acid sequence specific to an antibody from a non-human origin, and an example thereof is an antibody that has the heavy chain CDR1 to CDR3 and light chain CDR1 to CDR3 of an antibody produced by immunizing a mouse or rat, and in which all other regions, including each of the four framework regions (FR) of the heavy chain and light chain, are derived from human antibody. This type of antibody may also be referred to as a CDR-grafted antibody. The term "humanized antibody" may also include human chimeric antibody.

The term "human chimera antibody" is an antibody derived from a non-human antibody, in which constant regions of the non-human antibody are replaced with constant regions of a human antibody. In a human chimera antibody, for example, IgG1 can be used as a subtype of the human antibody for the constant regions in light of obtaining a high ADCC activity.

In the present description, an "antigen-binding fragment" refers to a fragment of the antibody that binds to TMEM-180. More specifically, examples thereof include, but are not limited to, Fab formed of a VL, VH, CL and CH1 region, F(ab')2 obtained by linking two Fab in a hinge region with disulfide bonds, Fv formed of VL and VH, single-stranded antibody in the form of scFv, in which VL and VH are linked with an artificial polypeptide linker, as well as bispecific antibodies such as diabodies, scDb, tandem sdFv and leucine zippers.

One aspect of the anti-TMEM-180 antibody according to the present invention has at least one of the six CDRs indicated below. These CDRs are the CDR sequences of anti-TMEM-180 antibody clone 98 indicated in the examples to be subsequently described.

```
                                    (SEQ ID NO: 1)
Heavy chain CDR1: GFSLTRYNVH (SEQ ID NO: 2)
Heavy chain CDR2: VIWTGGSTD (SEQ ID NO: 3)
Heavy chain CDR3: DLGY (SEQ ID NO: 4)
Light chain CDR1: KSSQSLKYRDGKTYLN (SEQ ID NO: 5)
Light chain CDR2: QVSKLDS (SEQ ID NO: 6)
Light chain CDR3: CQGSYSPHT
```

One aspect of the anti-TMEM-180 antibody according to the present invention has at least one of the six CDRs indicated below. These CDRs are the CDR sequences of anti-TMEM-180 antibody clone 101 indicated in the examples to be subsequently described.

```
                                    (SEQ ID NO: 7)
Heavy chain CDR1: GFSLTSYYMQ (SEQ ID NO: 8)
Heavy chain CDR2: FIRSGGSTE (SEQ ID NO: 9)
Heavy chain CDR3: AFYGGYYFDY (SEQ ID NO: 10)
Light chain CDR1: KASQNVGSNVD (SEQ ID NO: 11)
Light chain CDR2: KASNRYT (SEQ ID NO: 12)
Light chain CDR3: MQSNTKYT
```

One aspect of the anti-TMEM-180 antibody according to the present invention has at least one of the six CDRs indicated below. These CDRs are the CDR sequences of anti-TMEM-180 antibody clone 212 indicated in the examples to be subsequently described.

```
                                    (SEQ ID NO: 40)
Heavy chain CDR1: GFTFSDYAMA (SEQ ID NO: 41)
Heavy chain CDR2: TIIYDGSST (SEQ ID NO: 42)
Heavy chain CDR3: HWYWYFDF (SEQ ID NO: 43)
Light chain CDR1: LASEGISNDLA (SEQ ID NO: 44)
Light chain CDR2: AASRLQD (SEQ ID NO: 45)
Light chain CDR3: QQSYKYPLT
```

One aspect of the anti-TMEM-180 antibody according to the present invention has at least one of the six CDRs indicated below. These CDRs are the CDR sequences of anti-TMEM-180 antibody clone 129 indicated in the examples to be subsequently described.

```
Heavy chain CDR1:
                                    (SEQ ID NO: 48)
DCALN

Heavy chain CDR2:
                                    (SEQ ID NO: 49)
WINTQTGKPTYADDF Heavy chain CDR3:
                                    (SEQ ID NO: 50)
EDYGYFDY Light chain CDR1:
                                    (SEQ ID NO: 51)
QASQNINKFIA Light chain CDR2:
                                    (SEQ ID NO: 52)
YTSTLVS Light chain CDR3:
                                    (SEQ ID NO: 53)
LQYDNLRT
```

One aspect of the anti-TMEM-180 antibody according to the present invention has at least one of the six CDRs indicated below. These CDRs are the CDR sequences of anti-TMEM-180 antibody clone 382 indicated in the examples to be subsequently described.

```
Heavy chain CDR1:
                                     (SEQ ID NO: 56)
NYGMH Heavy chain CDR2:
                                     (SEQ ID NO: 57)
SISPSGGSTYYRDSV Heavy chain CDR3:
                                     (SEQ ID NO: 58)
SASITAYYYVMDA Light chain CDR1:
                                     (SEQ ID NO: 59)
KASQNVGSNVD Light chain CDR2:
                                     (SEQ ID NO: 60)
KASNRYT Light chain CDR3:
                                     (SEQ ID NO: 61)
MQSNSYPPT
```

One aspect of the anti-TMEM-180 antibody according to the present invention has at least one of the six CDRs indicated below. These CDRs are the CDR sequences of anti-TMEM-180 antibody clone 1361 indicated in the examples to be subsequently described.

```
Heavy chain CDR1:
                                     (SEQ ID NO: 64)
NYWMT Heavy chain CDR2:
                                     (SEQ ID NO: 65)
SITNTGGSTYYPDSV Heavy chain CDR3:
                                     (SEQ ID NO: 66)
AGYSSYPDYFDY Light chain CDR1:
                                     (SEQ ID NO: 67)
KAGQNIYNYLA Light chain CDR2:
                                     (SEQ ID NO: 68)
NANSLQT Light chain CDR3:
                                     (SEQ ID NO: 69)
QQYSSGWT
```

One aspect of the anti-TMEM-180 antibody according to the present invention has at least one of the six CDRs indicated below. These CDRs are the CDR sequences of anti-TMEM-180 antibody clone 669 indicated in the examples to be subsequently described.

```
Heavy chain CDR1:
                                     (SEQ ID NO: 72)
DYWVS Heavy chain CDR2:
                                     (SEQ ID NO: 73)
EIYPNSGATNFNENFK Heavy chain CDR3:
                                     (SEQ ID NO: 74)
DGTMGIAYYFDY Light chain CDR1:
                                     (SEQ ID NO: 75)
KASQNINRYLN Light chain CDR2:
                                     (SEQ ID NO: 76)
NANSLQT Light chain CDR3:
                                     (SEQ ID NO: 77)
LQHNSWPYT
```

In an embodiment of the present invention, an anti-TMEM-180 antibody comprises all of the above CDRs. In an embodiment of the present invention, an anti-TMEM-180 antibody is a humanized antibody comprising all of the above CDRs.

One aspect of the anti-TMEM-180 antibody according to the present invention has at least one of the six CDRs indicated below. These CDRs are the CDR sequences of anti-TMEM-180 antibody clone 699 indicated in the examples to be subsequently described.

```
Heavy chain CDR1:
                                     (SEQ ID NO: 80)
SYDIS Heavy chain CDR2:
                                     (SEQ ID NO: 81)
AINPGSGGTGYNEKFKGK Heavy chain CDR3:
                                     (SEQ ID NO: 82)
IHGGYRYWFAY Light chain CDR1:
                                     (SEQ ID NO: 83)
RASSSVSYMH Light chain CDR2:
                                     (SEQ ID NO: 84)
DTSKLAS Light chain CDR3:
                                     (SEQ ID NO: 85)
LQRSSYPPT
```

One aspect of the anti-TMEM-180 antibody according to the present invention has at least one of the six CDRs indicated below. These CDRs are the CDR sequences of anti-TMEM-180 antibody clone 1052 indicated in the examples to be subsequently described.

```
Heavy chain CDR1:
                                     (SEQ ID NO: 88)
SNGVG Heavy chain CDR2:
                                     (SEQ ID NO: 89)
TIWTGGGTNYNSGVQS Heavy chain CDR3:
                                     (SEQ ID NO: 90)
EYMGFDY Light chain CDR1:
                                     (SEQ ID NO: 91)
KASQNVGINVG
```

-continued

```
Light chain CDR2:
                        (SEQ ID NO: 92)
WASNRDT

Light chain CDR3:
                        (SEQ ID NO: 93)
LQHNSYPRT
```

One aspect of the anti-TMEM-180 antibody according to the present invention has at least one of the six CDRs indicated below. These CDRs are the CDR sequences of anti-TMEM-180 antibody clone 1105 indicated in the examples to be subsequently described.

```
Heavy chain CDR1:
                        (SEQ ID NO: 96)
SNGVG

Heavy chain CDR2:
                        (SEQ ID NO: 97)
TIWSGGGTNYNSAVQS

Heavy chain CDR3:
                        (SEQ ID NO: 98)
EEKGFAY

Light chain CDR1:
                        (SEQ ID NO: 99)
KASQNVGINVG

Light chain CDR2:
                        (SEQ ID NO: 100)
WASNRDT

Light chain CDR3:
                        (SEQ ID NO: 101)
LQHNSYPRA
```

In an embodiment of the present invention, an anti-TMEM-180 antibody comprises at least one of the six CDRs shown below. These CDRs are CDR sequences of the 1361-5 clone antibody shown in the examples described below.

```
a heavy chain CDR1:
                        (SEQ ID NO: 171)
NYWMT a heavy chain CDR2:
                        (SEQ ID NO: 172)
SITNTGGSTAYPDSV a heavy chain CDR3:
                        (SEQ ID NO: 173)
AGYSSYPDYFDY a light chain CDR1:
                        (SEQ ID NO: 174)
KAGQNIYNYLA a light chain CDR2:
                        (SEQ ID NO: 175)
NANSLQT a light chain CDR3:
                        (SEQ ID NO: 176)
QQYSSGWT
```

In an embodiment of the present invention, an anti-TMEM-180 antibody is an antibody which compete with the antibody in this embodiment for binding to TMEM-180.

In an embodiment of the present invention, an anti-TMEM-180 antibody comprises all of the six CDRs below. These CDRs are CDR sequences of the 1361-5 clone antibody shown in the examples described below.

```
a heavy chain CDR1:
                        (SEQ ID NO: 171)
NYWMT a heavy chain CDR2:
                        (SEQ ID NO: 172)
SITNTGGSTAYPDSV a heavy chain CDR3:
                        (SEQ ID NO: 173)
AGYSSYPDYFDY a light chain CDR1:
                        (SEQ ID NO: 174)
KAGQNIYNYLA a light chain CDR2:
                        (SEQ ID NO: 175)
NANSLQT a light chain CDR3:
                        (SEQ ID NO: 176)
QQYSSGWT
```

In an embodiment of the present invention, an anti-TMEM-180 antibody is an antibody which compete with the antibody in this embodiment for binding to TMEM-180.

In an embodiment of the present invention, an anti-TMEM-180 antibody comprises a heavy chain variable region (SEQ ID NO: 177) and a light chain variable region (SEQ ID NO: 178).

In an embodiment of the present invention, an anti-TMEM-180 antibody is an antibody which compete with the antibody in this embodiment for binding to TMEM-180.

In an embodiment of the present invention, an anti-TMEM-180 antibody has a heavy chain (SEQ ID NO: 180) and a light chain (SEQ ID NO: 182). In an embodiment of the present invention, an anti-TMEM-180 antibody is an antibody which compete with the antibody in this embodiment for binding to TMEM-180.

In each of the above-mentioned aspects, although the anti-TMEM-180 antibody may contain any of the six CDRs provided the effects of the present invention are demonstrated, it can also contain, for example, two or more, three or more, four or more, five or more or all six of the six CDRs.

In each of the above-mentioned aspects, at least one of heavy chain CDR1 to CDR3 and light chain CDR1 to CDR3 may contain one to several amino acid additions, substitutions or deletions.

In the present description, an "amino acid" is used in the broadest sense, and includes artificial amino acid variants and derivatives in addition to naturally-occurring amino acids. Amino acids may be indicated using customary one-letter or three-letter codes. In the present description, examples of amino acids or derivatives thereof include natural protein L-amino acids, unnatural amino acids, and chemically synthesized compounds having properties widely known in the art to be properties of amino acids. Examples of unnatural amino acids include, but are not limited to, α,α-disubstituted amino acids (such as x-methylalanine), N-alkyl-α-amino acids, D-amino acids, β-amino acids and α-hydroxy acids having main chain structures that differ from those occurring naturally, amino acids having side chain structures that differ from those occurring naturally (such as norleucine or homohistidine), amino acids having a surplus methylene in a side chain thereof (such as homoamino acid, homophenylalanine or homohistidine), and amino acids in which a carboxylic acid functional group has been substituted with a sulfonic acid group in a side chain thereof (such as cysteic acid).

In the present description, in the case of referring to "having one to several amino acid additions, substitutions or deletions", although there are no particular limitations on the number of, for example, added, substituted or deleted amino acids provided the polypeptide obtained as a result thereof retains the function of a CDR, examples thereof include one, two, three or four amino acid additions, substitutions or deletions. The substituted or added amino acids may be unnatural amino acids or amino acid analogs in addition to natural protein amino acids. The location of an amino acid deletion, substitution or addition may be at any location of the original CDR sequence provided the function of a CDR is retained.

In each of the aspects of the above-mentioned anti-TMEM-180 antibody, at least one of the heavy chain CDR1 to CDR3 and light chain CDR1 to CDR3 may have an amino acid sequence having identity of 80% or more with the original amino acid sequences of the heavy chain CDR1 to CDR3 and light chain CDR1 to CDR3.

In the present description, "having identity of 80% or more" means that the number of common amino acid residues is 80% or more of the amino acids of the original sequence when the amino acid sequence of a polypeptide having the original sequence is aligned with the amino acid sequence of a polypeptide having a mutated sequence so that there is maximum agreement between the two.

Identity may be of any percentage of 80% or more that retains the function of a CDR, and can be, for example, 85% or more, 90% or more, 95% or more, 98% or more or 99% or more.

A CDR comprising an amino acid sequence in which an amino acid has been added, substituted or deleted in the amino acid sequences of heavy chain CDR1 to CDR3 and light chain CDR1 to CDR3, or a CDR having sequence identity of 80% or more with the amino acid sequences of heavy chain CDR1 to CDR3 and light chain CDR1 to CDR3, can be produced using a known method such as site-specific mutagenesis, random mutagenesis, chain shuffling or CDR walking. According to these methods, antibody or antigen fragments having various mutations in the CDR thereof can be presented on a phage surface by phage display, and CDRs having a higher degree of affinity maturation are well known among persons with ordinary skill in the art to be obtained by screening using antigen (see, for example, Wu, et al., PNAS, 95: 6037-6042 (1998); Schier, R., et al., J. Mol. Biol., 263, 551-567 (1996); Schier, R., et al., J. Mol. Biol., 255, 28-43 (1996); Yang, W. P., et al., J. Mol. Biol., 254, 392-403 (1995)).

Another aspect of the anti-TMEM-180 antibody according to the present invention contains:
  a heavy chain containing the amino acid sequence represented by SEQ ID NO: 13;
  a heavy chain containing an amino acid sequence containing one to several amino acid additions, substitutions or deletions in the amino acid sequence represented by SEQ ID NO: 13; or
  a heavy chain containing an amino acid sequence having identity of 80% or more with the amino acid sequence represented by SEQ ID NO: 13.

The amino acid sequence represented by SEQ ID NO: 13 is an amino acid sequence of the heavy chain variable region of anti-TMEM-180 antibody clone 98.

In the present description, in the case of one to several amino acid additions, substitutions or deletions in the amino acid sequence of the heavy chain or light chain, the number of amino acids that are added, substituted or deleted can be, for example, one, two, three, four, five, six, seven, eight, nine, or ten. Other terms are as previously described.

Another aspect of the anti-TMEM-180 antibody according to the present invention contains:
  a light chain containing the amino acid sequence represented by SEQ ID NO: 14;
  a light chain containing an amino acid sequence containing one to several amino acid additions, substitutions or deletions in the amino acid sequence represented by SEQ ID NO: 14; or
  a light chain containing an amino acid sequence having identity of 80% or more with the amino acid sequence represented by SEQ ID NO: 14.

The amino acid sequence represented by SEQ ID NO: 14 is an amino acid sequence of the light chain variable region of anti-TMEM-180 antibody clone 98.

The anti-TMEM-180 antibody according to the present invention may contain a heavy chain containing the amino acid sequence represented by SEQ ID NO: 13, a heavy chain containing an amino acid sequence containing one to several amino acid additions, substitutions or deletions in the amino acid sequence represented by SEQ ID NO: 13, or a heavy chain containing an amino acid sequence having identity of 80% or more with the amino acid sequence represented by SEQ ID NO: 13, and
  a light chain containing the amino acid sequence represented by SEQ ID NO: 14, a light chain containing an amino acid sequence containing one to several amino acid additions, substitutions or deletions in the amino acid sequence represented by SEQ ID NO: 14, or a light chain containing an amino acid sequence having identity of 80% or more with the amino acid sequence represented by SEQ ID NO: 14.

Another aspect of the anti-TMEM-180 antibody according to the present invention contains:
  a heavy chain containing the amino acid sequence represented by SEQ ID NO: 15;
  a heavy chain containing an amino acid sequence containing one to several amino acid additions, substitutions or deletions in the amino acid sequence represented by SEQ ID NO: 15; or
  a heavy chain containing an amino acid sequence having identity of 80% or more with the amino acid sequence represented by SEQ ID NO: 15.

The amino acid sequence represented by SEQ ID NO: 15 is an amino acid sequence of the heavy chain variable region of anti-TMEM-180 antibody clone 101.

Another aspect of the anti-TMEM-180 antibody according to the present invention contains:
  a light chain containing the amino acid sequence represented by SEQ ID NO: 16;
  a light chain containing an amino acid sequence containing one to several amino acid additions, substitutions or deletions in the amino acid sequence represented by SEQ ID NO: 16; or
  a light chain containing an amino acid sequence having identity of 80% or more with the amino acid sequence represented by SEQ ID NO: 16.

The amino acid sequence represented by SEQ ID NO: 16 is an amino acid sequence of the light chain variable region of anti-TMEM-180 antibody clone 101.

Another aspect of the anti-TMEM-180 antibody according to the present invention may contain a heavy chain containing the amino acid sequence represented by SEQ ID NO: 15, a heavy chain containing an amino acid sequence containing one to several amino acid additions, substitutions or deletions in the amino acid sequence represented by SEQ ID NO: 15, or a heavy chain containing an amino acid sequence having identity of 80% or more with the amino acid sequence represented by SEQ ID NO: 15, and
    a light chain containing the amino acid sequence represented by SEQ ID NO: 16, a light chain containing an amino acid sequence containing one to several amino acid additions, substitutions or deletions in the amino acid sequence represented by SEQ ID NO: 16, or a light chain containing an amino acid sequence having identity of 80% or more with the amino acid sequence represented by SEQ ID NO: 16.

Another aspect of the anti-TMEM-180 antibody according to the present invention contains:
    a heavy chain containing the amino acid sequence represented by SEQ ID NO: 46;
    a heavy chain containing an amino acid sequence containing one to several amino acid additions, substitutions or deletions in the amino acid sequence represented by SEQ ID NO: 46; or
    a heavy chain containing an amino acid sequence having identity of 80% or more with the amino acid sequence represented by SEQ ID NO: 46.

The amino acid sequence represented by SEQ ID NO: 46 is an amino acid sequence of the heavy chain variable region of anti-TMEM-180 antibody clone 212.

Another aspect of the anti-TMEM-180 antibody according to the present invention contains:
    a light chain containing the amino acid sequence represented by SEQ ID NO: 47;
    a light chain containing an amino acid sequence containing one to several amino acid additions, substitutions or deletions in the amino acid sequence represented by SEQ ID NO: 47; or
    a light chain containing an amino acid sequence having identity of 80% or more with the amino acid sequence represented by SEQ ID NO: 47.

The amino acid sequence represented by SEQ ID NO: 47 is an amino acid sequence of the light chain variable region of anti-TMEM-180 antibody clone 212.

Another aspect of the anti-TMEM-180 antibody according to the present invention may contain a heavy chain containing the amino acid sequence represented by SEQ ID NO: 46, a heavy chain containing an amino acid sequence containing one to several amino acid additions, substitutions or deletions in the amino acid sequence represented by SEQ ID NO: 46, or a heavy chain containing an amino acid sequence having identity of 80% or more with the amino acid sequence represented by SEQ ID NO: 46, and
    a light chain containing the amino acid sequence represented by SEQ ID NO: 47, a light chain containing an amino acid sequence containing one to several amino acid additions, substitutions or deletions in the amino acid sequence represented by SEQ ID NO: 47, or a light chain containing an amino acid sequence having identity of 80% or more with the amino acid sequence represented by SEQ ID NO: 47.

Another aspect of the anti-TMEM-180 antibody according to the present invention contains:
    a heavy chain containing the amino acid sequence represented by SEQ ID NO: 54;
    a heavy chain containing an amino acid sequence containing one to several amino acid additions, substitutions or deletions in the amino acid sequence represented by SEQ ID NO: 54; or
    a heavy chain containing an amino acid sequence having identity of 80% or more with the amino acid sequence represented by SEQ ID NO: 54.

The amino acid sequence represented by SEQ ID NO: 54 is an amino acid sequence of the heavy chain variable region of anti-TMEM-180 antibody clone 129.

Another aspect of the anti-TMEM-180 antibody according to the present invention contains:
    a light chain containing the amino acid sequence represented by SEQ ID NO: 55;
    a light chain containing an amino acid sequence containing one to several amino acid additions, substitutions or deletions in the amino acid sequence represented by SEQ ID NO: 55; or
    a light chain containing an amino acid sequence having identity of 80% or more with the amino acid sequence represented by SEQ ID NO: 55.

The amino acid sequence represented by SEQ ID NO: 55 is an amino acid sequence of the light chain variable region of anti-TMEM-180 antibody clone 129.

Another aspect of the anti-TMEM-180 antibody according to the present invention may contain a heavy chain containing the amino acid sequence represented by SEQ ID NO: 54, a heavy chain containing an amino acid sequence containing one to several amino acid additions, substitutions or deletions in the amino acid sequence represented by SEQ ID NO: 54, or a heavy chain containing an amino acid sequence having identity of 80% or more with the amino acid sequence represented by SEQ ID NO: 54, and
    a light chain containing the amino acid sequence represented by SEQ ID NO: 55, a light chain containing an amino acid sequence containing one to several amino acid additions, substitutions or deletions in the amino acid sequence represented by SEQ ID NO: 55, or a light chain containing an amino acid sequence having identity of 80% or more with the amino acid sequence represented by SEQ ID NO: 55.

Another aspect of the anti-TMEM-180 antibody according to the present invention contains:
    a heavy chain containing the amino acid sequence represented by SEQ ID NO: 62;
    a heavy chain containing an amino acid sequence containing one to several amino acid additions, substitutions or deletions in the amino acid sequence represented by SEQ ID NO: 62; or
    a heavy chain containing an amino acid sequence having identity of 80% or more with the amino acid sequence represented by SEQ ID NO: 62.

The amino acid sequence represented by SEQ ID NO: 62 is an amino acid sequence of the heavy chain variable region of anti-TMEM-180 antibody clone 382.

Another aspect of the anti-TMEM-180 antibody according to the present invention contains:
    a light chain containing the amino acid sequence represented by SEQ ID NO: 63;
    a light chain containing an amino acid sequence containing one to several amino acid additions, substitutions or deletions in the amino acid sequence represented by SEQ ID NO: 63; or
    a light chain containing an amino acid sequence having identity of 80% or more with the amino acid sequence represented by SEQ ID NO: 63.

The amino acid sequence represented by SEQ ID NO: 63 is an amino acid sequence of the light chain variable region of anti-TMEM-180 antibody clone 382.

Another aspect of the anti-TMEM-180 antibody according to the present invention may contain a heavy chain containing the amino acid sequence represented by SEQ ID NO: 62, a heavy chain containing an amino acid sequence containing one to several amino acid additions, substitutions or deletions in the amino acid sequence represented by SEQ ID NO: 62, or a heavy chain containing an amino acid sequence having identity of 80% or more with the amino acid sequence represented by SEQ ID NO: 62, and a light chain containing the amino acid sequence represented by SEQ ID NO: 63, a light chain containing an amino acid sequence containing one to several amino acid additions, substitutions or deletions in the amino acid sequence represented by SEQ ID NO: 63, or a light chain containing an amino acid sequence having identity of 80% or more with the amino acid sequence represented by SEQ ID NO: 63.

Another aspect of the anti-TMEM-180 antibody according to the present invention contains:

a heavy chain containing the amino acid sequence represented by SEQ ID NO: 70;

a heavy chain containing an amino acid sequence containing one to several amino acid additions, substitutions or deletions in the amino acid sequence represented by SEQ ID NO: 70; or a heavy chain containing an amino acid sequence having identity of 80% or more with the amino acid sequence represented by SEQ ID NO: 70.

The amino acid sequence represented by SEQ ID NO: 70 is an amino acid sequence of the heavy chain variable region of anti-TMEM-180 antibody clone 1361.

Another aspect of the anti-TMEM-180 antibody according to the present invention contains:

a light chain containing the amino acid sequence represented by SEQ ID NO: 71;

a light chain containing an amino acid sequence containing one to several amino acid additions, substitutions or deletions in the amino acid sequence represented by SEQ ID NO: 71; or a light chain containing an amino acid sequence having identity of 80% or more with the amino acid sequence represented by SEQ ID NO: 71.

The amino acid sequence represented by SEQ ID NO: 71 is an amino acid sequence of the light chain variable region of anti-TMEM-180 antibody clone 1361.

Another aspect of the anti-TMEM-180 antibody according to the present invention may contain a heavy chain containing the amino acid sequence represented by SEQ ID NO: 70, a heavy chain containing an amino acid sequence containing one to several amino acid additions, substitutions or deletions in the amino acid sequence represented by SEQ ID NO: 70, or a heavy chain containing an amino acid sequence having identity of 80% or more with the amino acid sequence represented by SEQ ID NO: 70, and a light chain containing the amino acid sequence represented by SEQ ID NO: 71, a light chain containing an amino acid sequence containing one to several amino acid additions, substitutions or deletions in the amino acid sequence represented by SEQ ID NO: 71, or a light chain containing an amino acid sequence having identity of 80% or more with the amino acid sequence represented by SEQ ID NO: 71.

Another aspect of the anti-TMEM-180 antibody according to the present invention contains:

a heavy chain containing the amino acid sequence represented by SEQ ID NO: 78;

a heavy chain containing an amino acid sequence containing one to several amino acid additions, substitutions or deletions in the amino acid sequence represented by SEQ ID NO: 78; or a heavy chain containing an amino acid sequence having identity of 80% or more with the amino acid sequence represented by SEQ ID NO: 78.

The amino acid sequence represented by SEQ ID NO: 78 is an amino acid sequence of the heavy chain variable region of anti-TMEM-180 antibody clone 669.

Another aspect of the anti-TMEM-180 antibody according to the present invention contains:

a light chain containing the amino acid sequence represented by SEQ ID NO: 79;

a light chain containing an amino acid sequence containing one to several amino acid additions, substitutions or deletions in the amino acid sequence represented by SEQ ID NO: 79; or a light chain containing an amino acid sequence having identity of 80% or more with the amino acid sequence represented by SEQ ID NO: 79.

The amino acid sequence represented by SEQ ID NO: 79 is an amino acid sequence of the light chain variable region of anti-TMEM-180 antibody clone 669.

Another aspect of the anti-TMEM-180 antibody according to the present invention may contain a heavy chain containing the amino acid sequence represented by SEQ ID NO: 78, a heavy chain containing an amino acid sequence containing one to several amino acid additions, substitutions or deletions in the amino acid sequence represented by SEQ ID NO: 78, or a heavy chain containing an amino acid sequence having identity of 80% or more with the amino acid sequence represented by SEQ ID NO: 78, and a light chain containing the amino acid sequence represented by SEQ ID NO: 79, a light chain containing an amino acid sequence containing one to several amino acid additions, substitutions or deletions in the amino acid sequence represented by SEQ ID NO: 79, or a light chain containing an amino acid sequence having identity of 80% or more with the amino acid sequence represented by SEQ ID NO: 79.

Another aspect of the anti-TMEM-180 antibody according to the present invention contains:

a heavy chain containing the amino acid sequence represented by SEQ ID NO: 86;

a heavy chain containing an amino acid sequence containing one to several amino acid additions, substitutions or deletions in the amino acid sequence represented by SEQ ID NO: 86; or a heavy chain containing an amino acid sequence having identity of 80% or more with the amino acid sequence represented by SEQ ID NO: 86.

The amino acid sequence represented by SEQ ID NO: 86 is an amino acid sequence of the heavy chain variable region of anti-TMEM-180 antibody clone 699.

Another aspect of the anti-TMEM-180 antibody according to the present invention contains:

a light chain containing the amino acid sequence represented by SEQ ID NO: 87;

a light chain containing an amino acid sequence containing one to several amino acid additions, substitutions or deletions in the amino acid sequence represented by SEQ ID NO: 87; or a light chain containing an amino acid sequence having identity of 80% or more with the amino acid sequence represented by SEQ ID NO: 87.

The amino acid sequence represented by SEQ ID NO: 87 is an amino acid sequence of the light chain variable region of anti-TMEM-180 antibody clone 699.

Another aspect of the anti-TMEM-180 antibody according to the present invention may contain a heavy chain containing the amino acid sequence represented by SEQ ID NO: 86, a heavy chain containing an amino acid sequence containing one to several amino acid additions, substitutions or deletions in the amino acid sequence represented by SEQ ID NO: 86, or a heavy chain containing an amino acid sequence having identity of 80% or more with the amino acid sequence represented by SEQ ID NO: 86, and
- a light chain containing the amino acid sequence represented by SEQ ID NO: 87, a light chain containing an amino acid sequence containing one to several amino acid additions, substitutions or deletions in the amino acid sequence represented by SEQ ID NO: 87, or a light chain containing an amino acid sequence having identity of 80% or more with the amino acid sequence represented by SEQ ID NO: 87.

Another aspect of the anti-TMEM-180 antibody according to the present invention contains:
- a heavy chain containing the amino acid sequence represented by SEQ ID NO: 94;
- a heavy chain containing an amino acid sequence containing one to several amino acid additions, substitutions or deletions in the amino acid sequence represented by SEQ ID NO: 94; or
- a heavy chain containing an amino acid sequence having identity of 80% or more with the amino acid sequence represented by SEQ ID NO: 94.

The amino acid sequence represented by SEQ ID NO: 94 is an amino acid sequence of the heavy chain variable region of anti-TMEM-180 antibody clone 1052.

Another aspect of the anti-TMEM-180 antibody according to the present invention contains:
- a light chain containing the amino acid sequence represented by SEQ ID NO: 95;
- a light chain containing an amino acid sequence containing one to several amino acid additions, substitutions or deletions in the amino acid sequence represented by SEQ ID NO: 95; or
- a light chain containing an amino acid sequence having identity of 80% or more with the amino acid sequence represented by SEQ ID NO: 95.

The amino acid sequence represented by SEQ ID NO: 95 is an amino acid sequence of the light chain variable region of anti-TMEM-180 antibody clone 1052.

Another aspect of the anti-TMEM-180 antibody according to the present invention may contain a heavy chain containing the amino acid sequence represented by SEQ ID NO: 94, a heavy chain containing an amino acid sequence containing one to several amino acid additions, substitutions or deletions in the amino acid sequence represented by SEQ ID NO: 94, or a heavy chain containing an amino acid sequence having identity of 80% or more with the amino acid sequence represented by SEQ ID NO: 94, and
- a light chain containing the amino acid sequence represented by SEQ ID NO: 95, a light chain containing an amino acid sequence containing one to several amino acid additions, substitutions or deletions in the amino acid sequence represented by SEQ ID NO: 95, or a light chain containing an amino acid sequence having identity of 80% or more with the amino acid sequence represented by SEQ ID NO: 95.

Another aspect of the anti-TMEM-180 antibody according to the present invention contains:
- a heavy chain containing the amino acid sequence represented by SEQ ID NO: 102;
- a heavy chain containing an amino acid sequence containing one to several amino acid additions, substitutions or deletions in the amino acid sequence represented by SEQ ID NO: 102; or
- a heavy chain containing an amino acid sequence having identity of 80% or more with the amino acid sequence represented by SEQ ID NO: 102.

The amino acid sequence represented by SEQ ID NO: 102 is an amino acid sequence of the heavy chain variable region of anti-TMEM-180 antibody clone 1105.

Another aspect of the anti-TMEM-180 antibody according to the present invention contains:
- a light chain containing the amino acid sequence represented by SEQ ID NO: 103;
- a light chain containing an amino acid sequence containing one to several amino acid additions, substitutions or deletions in the amino acid sequence represented by SEQ ID NO: 103; or
- a light chain containing an amino acid sequence having identity of 80% or more with the amino acid sequence represented by SEQ ID NO: 103.

The amino acid sequence represented by SEQ ID NO: 103 is an amino acid sequence of the light chain variable region of anti-TMEM-180 antibody clone 1105.

Another aspect of the anti-TMEM-180 antibody according to the present invention may contain a heavy chain containing the amino acid sequence represented by SEQ ID NO: 102, a heavy chain containing an amino acid sequence containing one to several amino acid additions, substitutions or deletions in the amino acid sequence represented by SEQ ID NO: 102, or a heavy chain containing an amino acid sequence having identity of 80% or more with the amino acid sequence represented by SEQ ID NO: 102, and
- a light chain containing the amino acid sequence represented by SEQ ID NO: 103, a light chain containing an amino acid sequence containing one to several amino acid additions, substitutions or deletions in the amino acid sequence represented by SEQ ID NO: 103, or a light chain containing an amino acid sequence having identity of 80% or more with the amino acid sequence represented by SEQ ID NO: 103.

In an embodiment of the present invention, an anti-TMEM-180 antibody comprises
a heavy chain containing the amino acid sequence represented by SEQ ID NO: 180; a heavy chain containing an amino acid sequence having one to several amino acid additions, substitutions or deletions in the amino acid sequence represented by SEQ ID NO: 180; or
a heavy chain containing an amino acid sequence having identity of 80% or more with the amino acid sequence represented by SEQ ID NO: 180.

The amino acid sequence represented by SEQ ID NO: 180 is the amino acid sequence of the heavy chain variable region of the 1361-5 clone anti-TMEM-180 antibody.

In an embodiment of the present invention, an anti-TMEM-180 antibody comprises
a light chain containing the amino acid sequence represented by SEQ ID NO: 182;
a light chain containing an amino acid sequence having one to several amino acid additions, substitutions or deletions in the amino acid sequence represented by SEQ ID NO: 182; or
a light chain containing an amino acid sequence having identity of 80% or more with the amino acid sequence represented by SEQ ID NO: 182.

The amino acid sequence represented by SEQ ID NO: 182 is the amino acid sequence of the light chain variable region of the 1361-5 clone anti-TMEM-180

In an embodiment of the present invention, an anti-TMEM-180 antibody may comprise
a heavy chain containing the amino acid sequence represented by SEQ ID NO: 180;
a heavy chain containing an amino acid sequence having one to several amino acid additions, substitutions or deletions in the amino acid sequence represented by SEQ ID NO: 180; or
a heavy chain containing an amino acid sequence having identity of 80% or more with the amino acid sequence represented by SEQ ID NO: 180; and
a light chain containing the amino acid sequence represented by SEQ ID NO: 182;
a light chain containing an amino acid sequence having one to several amino acid additions, substitutions or deletions in the amino acid sequence represented by SEQ ID NO: 182; or
a light chain containing an amino acid sequence having identity of 80% or more with the amino acid sequence represented by SEQ ID NO: 182.

In another embodiment of the present invention, an anti-TMEM-180 antibody may be an antibody that compete with the anti-TMEM-180 antibody of the present invention for binding to TMEM-180. In this specific embodiment, the anti-TMEM-180 antibody may not be an antibody comprising the amino acid sequences represented by SEQ ID NOs: 64 to 66 for heavy chain CDRs and the amino acid sequence represented by SEQ ID NOs: 67 to 69 for light chain CDRs.

In the antibody of the present invention or an antibody that compete with the antibody of the present invention for binding to TMEM-180, Fc region may have one or more amino acid substitutions. For example, the heavy chain may have, but not limited to, an amino acid substitution of serine to aspartic acid in the amino acid corresponding to the position 262 in SEQ ID NO: 180, an amino acid substitution of alanine to leucine in the amino acid corresponding to the position 353 of SEQ ID NO: 180, and an amino acid substitution of leucine to glutamine in the amino acid corresponding to the position 355 of SEQ ID NO: 180. For example, the heavy chain may further have, but not limited to, an amino acid substitution of serine to aspartic acid in the amino acid corresponding to the position 262 in SEQ ID NO: 180, an amino acid substitution of leucine to glutamine in the amino acid corresponding to the position 355 in SEQ ID NO: 180, and an amino acid substitution of glutamate to alanine in the amino acid corresponding to the position 356 in SEQ ID NO: 180.

The anti-TMEM-180 antibody according to the present invention may be an antibody in which one or more N-linked oligosaccharides are bound to the Fc region, and fucose is not bound to N-acetylglucosamine on the reducing end of the N-linked oligosaccharide.

For example, two N-linked oligosaccharide binding sites are present in the Fc region of IgG antibody and a complex oligosaccharide is bound to this site. N-linked oligosaccharides refer to oligosaccharides bound to Asn of the sequence Asn-X-Ser/Thr that have the common structure of Man3GlcNAc2-Asn. These are classified into high mannose types, mixed types, complex types and the like depending on the type of oligosaccharide that binds to the two mannose (Man) on the non-reducing end.

Although fucose can be bound to N-acetylglucosamine (GlcNAc) on the reducing end of N-linked oligosaccharides, ADCC activity is known to increase considerably in the case fucose is not bound to this site in comparison with the case in which it is bound thereto. This finding is described in, for example, WO 2002/031140, and the disclosure thereof is incorporated in the present description in its entirety by reference.

Since the dosage of an antibody can be reduced in the case of using as a pharmaceutical due to this considerable increase in ADCC activity, in addition to making it possible to reduce adverse side effects, medical expenses can also be reduced.

One aspect of the anticancer drug according to the present invention contains, as an active ingredient thereof, an anti-TMEM-180 antibody having a substance having anticancer activity bound thereto, or an antigen-binding fragment thereof. These substances are also referred to as antibody-drug conjugates (ADC). In this aspect, the anti-TMEM-180 antibody or antigen-binding fragment thereof may also have anticancer activity per se or may only have the ability to bind to TMEM-180 without exhibiting anticancer activity.

In the present description, a "substance having anticancer activity" refers to a substance that causes at least one of a reduction (delay or interruption) of tumor size, inhibition of tumor metastasis, inhibition (delay or interruption) of tumor growth and alleviation of one or multiple symptoms associated with cancer. More specifically, examples thereof include, but are not limited to, toxins, anticancer drugs and radioisotopes.

Examples of toxins having anticancer activity include *Pseudomonas* exotoxin (PE) and cytotoxic fragments thereof (such as PE38), diphtheria toxin and lysin A. Since these toxins having anticancer activity demonstrate toxicity only in cells recognized by the anti-TMEM-180 antibody, namely cancer cells expressing TMEM-180, they offer the advantage of allowing the obtaining of specific effects without having a detrimental effect on surrounding cells.

Examples of anticancer drugs include low molecular weight compounds such as adriamycin, daunomycin, mitomycin, cisplatin, vincristine, epirubicin, methotrexate, 5-fluorouracil, aclacinomycin, nitrogen mustard, cyclophosphamide, bleomycin, daunorubicin, doxorubicin, vincristine, vinblastine, vindesine, tamoxifen, monomethylauristatin E, SN-38, or dexamethasone, and proteins such as cytokines that activate immunocompetent cells (such as human interleukin 2, human granulocyte-macrophage colony stimulating factor, human macrophage colony stimulating factor or human interleukin 12).

Examples of radioisotopes having anticancer activity include $^{32}P$, $^{14}C$, $^{125}I$, $^{3}H$, $^{131}I$, $^{211}At$ and $^{90}Y$.

Substances having anticancer activity are able to bind to the anti-TMEM-180 antibody either directly or through a linker (for example, a cleavable linker) according to a known method or method in compliance therewith. A substance having anticancer activity may be enclosed in a carrier such as a micelle or liposome and then bind the liposome to the anti-TMEM-180 antibody or an antigen-binding fragment thereof.

In the case the above-mentioned substance having anticancer activity is a protein or polypeptide, it may also be expressed in the form of a fusion protein formed of the substance having anticancer activity and an anti-TMEM-180 antibody by linking a nucleic acid encoding the anti-TMEM-180 antibody of the present invention to be subsequently described, encoding a substance having anticancer activity using DNA, and then inserting into a suitable expression vector.

In the present description, an "anticancer drug" refers to a pharmaceutical that causes at least one of a reduction (delay or interruption) of tumor size, inhibition of tumor metastasis, inhibition (delay or interruption) of tumor growth and alleviation of one or multiple symptoms associated with cancer. The term "anticancer drug" as used herein is interchangeably used with the term "pharmaceutical composition for use in treating cancer".

The anticancer drug according to the present invention may also contain a pharmaceutically acceptable carrier or additive in addition to the active ingredient.

Examples of carriers and additives include, but are not limited to, pharmaceutically acceptable organic solvents such as water, saltwater, phosphate buffer, dextrose, glycerol and ethanol, as well as collagen, polyvinyl alcohol, polyvinylpyrrolidone, carboxyvinyl polymer, carboxymethyl cellulose sodium, sodium polyacrylate, sodium alginate, water-soluble dextran, sodium carboxymethyl starch, pectin, methyl cellulose, ethyl cellulose, xanthan gum, gum arabic, casein, agar, polyethylene glycol, diglycerin, glycerin, propylene glycol, Vaseline, paraffin, stearyl alcohol, stearic acid, human serum albumin, mannitol, sorbitol, lactose and surfactants.

The pharmaceutical composition of the present invention can adopt various forms, such as a liquid (e.g. injection preparation), dispersion, suspension, tablet, pill, powder or suppository. The pharmaceutical composition is preferably in the form of an injection preparation, and is preferably administered parenterally (such as intravenously, percutaneously, intraperitoneally or intramuscularly).

The pharmaceutical composition of the present invention is effective for treatment of cancer expressing TMEM-180. Examples of cancer expressing TMEM-180 include, but are not limited to, colon cancer and brain tumors. Examples of cancer include, but not limited to, solid cancers, for example, colon cancer, brain tumor, gastric cancer, pancreas cancer, breast cancer, prostate cancer, kidney cancer, and bladder cancer.

The pharmaceutical composition of the present invention is a pharmaceutical composition for use in treating cancer in a subject having the cancer, comprising an antibody that binds to TMEM-180. In an embodiment of the present invention, the subject to be treated may be a subject that has a cancer expressing TMEM-180. In an embodiment of the present invention, the subject to be treated may be a subject wherein TMEM-180 has been detected in the body fluid sample of the subject. In an embodiment of the present invention, the subject to be treated may be a subject wherein exosomes expressing TMEM-180 on their surface have been detected in the body fluid sample of the subject.

The present invention also includes a method for treating cancer comprising administering the anticancer drug according to the present invention. In an aspect of the present invention, provided is a method for treating cancer in a subject having the cancer, comprising administrating an antibody that binds to TMEM-180 to the subject.

The dosage of the anticancer drug of the present invention is such that, for example, the dosage of the anti-TMEM-180 antibody or antigen-binding fragment thereof is 0.025 mg/kg to 50 mg/kg, preferably 0.1 mg/kg to 0 mg/kg, more preferably 0.1 mg/kg to 25 mg/kg, and even more preferably 0.1 mg/kg to 10 mg/kg or 0.1 mg/kg to 3 mg/kg, although not limited thereto.

The anticancer drug according to the present invention may be combined with other cancer therapy. Examples of other cancer therapy include administration of the above-mentioned other anticancer drugs, radiotherapy, surgery and cancer vaccine therapy.

In the present description, "cancer vaccine therapy" refers to a method for preventing or treating cancer that involves enhancing the immunity of a patient per se against cancer cells by administering a cancer antigen to the patient or stimulating patient-derived immune cells in vitro with a cancer antigen and then returning the cells to the patient. A peptide derived from a protein specifically expressed by cancer cells (cancer antigen-derived peptide) is used as an example of a cancer antigen used in cancer vaccine therapy.

A cancer antigen-derived peptide activates cytotoxic T lymphocytes (CTL) as a result of binding to human leukocyte antigen (HLA) on the surface of antigen-presenting cells such as dendritic cells and being presented on the CTL. Activated CTL then attack and eliminate cancer cells expressing the same antigen as the peptide. HLA molecules have a high degree of genetic diversity and demonstrate different genotypes depending on the individual. The sequences of those peptides having the possibility of being derived from a certain cancer antigen protein and binding to an HLA molecule of a specific genotype can be determined with known software or the like.

For example, those peptides derived from TMEM-180 protein and having the possibility of binding to HLA type A2 or HLA type A24 commonly found among Japanese were predicted as indicated below using HLA Peptide Binding Predictions published by the Bioinformatics and Molecular Analysis Section of the U.S. National Institutes of Health (bimas.cit.nih.gov/cgi-bin/molbio/ken_parker_comboform). In the tables, "Start position" indicates the location in the amino acid sequence set forth in SEQ ID NO: 17.

According to cancer vaccine therapy using these peptides, since CTL can be activated to attack cancer cells expressing TMEM-180 protein, cancer cells can be efficiently attacked by using in combination with the anticancer drug according to the present invention that targets TMEM-180, thereby making it possible to prevent or treat cancer. Cancer vaccine compositions containing these peptides can be prepared by a person with ordinary skill in the art in accordance with known methods.

TABLE 1

HLA molecule type: A_0201
Cutoff Score: 10 (Estimate of Half Time of Disassociation of a Molecule Containing This Subsequence)

| Rank | Start Position | Sequence | SEQ ID NO |
|---|---|---|---|
| 1 | 132 | CLYDgFLTLV | 104 |
| 2 | 33 | FLLYyVDTFV | 105 |
| 3 | 266 | FLWFvSMDLV | 106 |
| 4 | 322 | FLSLcRRWGV | 107 |
| 5 | 339 | FLLKIGLSLL | 108 |
| 6 | 376 | KLLTIVVTDL | 109 |
| 7 | 401 | ALLFgMVALV | 110 |
| 8 | 23 | ALFTtILHNV | 111 |
| 9 | 9 | WLLGIPTAVV | 112 |
| 10 | 482 | QLFTwSQFTL | 113 |
| 11 | 109 | LALSfLAFWV | 114 |
| 12 | 342 | KLGLsLLMLL | 115 |

TABLE 1-continued

HLA molecule type: A_0201
Cutoff Score: 10 (Estimate of Half Time of Disassociation of a Molecule Containing This Subsequence)

| Rank | Start Position | Sequence | SEQ ID NO |
|---|---|---|---|
| 13 | 2 | GLGQpQAWLL | 116 |
| 14 | 490 | TLHGrRLHMV | 117 |
| 15 | 60 | LLWNsLNDPL | 118 |
| 16 | 64 | SLNDpLFGWL | 119 |
| 17 | 139 | TLVDIHHHAL | 120 |
| 18 | 49 | KMAFwVGETV | 121 |
| 19 | 469 | YLLVIVPITC | 122 |
| 20 | 505 | NLSQaQTLDV | 123 |
| 21 | 377 | LLTLvVTDLV | 124 |
| 22 | 294 | LLSDhISLST | 125 |
| 23 | 348 | LMLLaGPDHL | 126 |
| 24 | 258 | RQLArHRNFL | 127 |
| 25 | 130 | CLCLyDGFLT | 128 |
| 26 | 425 | LLCFyTGHDL | 129 |
| 27 | 472 | VLVPiTCALL | 130 |
| 28 | 350 | LLAGpDHLSL | 131 |
| 29 | 70 | FGWLsDRQFL | 132 |
| 30 | 324 | SLCRrWGVYA | 133 |
| 31 | 481 | LQLFtWSQFT | 134 |
| 32 | 78 | FLSSqPRSGA | 135 |
| 33 | 204 | GLGFIGATQL | 136 |
| 34 | 124 | GLQFILCLCL | 137 |
| 35 | 153 | ALSAhDRTHL | 138 |
| 36 | 212 | QLLRrRVEAA | 139 |
| 37 | 17 | VVYGsLALFT | 140 |
| 38 | 470 | LLVLvPITCA | 141 |
| 39 | 402 | LLFGmVALVT | 142 |
| 40 | 271 | SMDLvQVFHC | 143 |
| 41 | 147 | ALLAdLALSA | 144 |
| 42 | 332 | YAVVrGLFLL | 145 |
| 43 | 45 | YKINkMAFWV | 146 |
| 44 | 282 | FNSNfFPLFL | 147 |
| 45 | 471 | LVLVpITCAL | 148 |
| 46 | 88 | GLSSrAVVLA | 149 |
| 47 | 417 | FAPLIGTWLL | 150 |

TABLE 2

HLA molecule type: A24
Cutoff Score: 10 (Estimate of Half Time of Disassociation of a Molecule Containing This Subsequence)

| Rank | Start Position | Sequence | SEQ ID |
|---|---|---|---|
| 1 | 311 | SYVApHLNNL | 151 |
| 2 | 331 | VYAVvRGLFL | 152 |
| 3 | 180 | SYAFwNKEDF | 153 |
| 4 | 265 | NFLWfVSMDL | 154 |
| 5 | 286 | FFPLfLEHLL | 155 |
| 6 | 338 | LFLLkLGLSL | 156 |
| 7 | 416 | TFAPILGTWL | 157 |
| 8 | 369 | VFTEgTCKLL | 158 |
| 9 | 285 | NFFPIFLEHL | 159 |
| 10 | 51 | AFWVgETVFL | 160 |
| 11 | 281 | HFNSnFFPLF | 161 |
| 12 | 376 | KLLTIVVTDL | 162 |
| 13 | 32 | VFLLyYVDTF | 163 |
| 14 | 258 | RQLArHRNFL | 164 |
| 15 | 336 | RGLFILKLGL | 165 |
| 16 | 503 | RQNLsQAQTL | 166 |
| 17 | 24 | LFTTiLHNVF | 167 |
| 18 | 64 | SLNDpLFGWL | 168 |
| 19 | 277 | VFHChFNSNF | 169 |
| 20 | 69 | LFGWISDRQF | 170 |

(Nucleic Acid)

The present invention also includes a nucleic acid that encodes the anti-TMEM-180 antibody, or antigen-binding fragment thereof, according to the present invention. The nucleic acid may be a naturally-occurring nucleic acid or artificial nucleic acid, and examples thereof include, but are not limited to, DNA, RNA and chimeras of DNA and RNA. The base sequence of a nucleic acid encoding the anti-TMEM-180 antibody or antigen-binding fragment thereof can be determined by a person with ordinary skill in the art in accordance with a known method or method complying therewith, and can also be prepared using a known method or method complying therewith.

Examples of nucleic acids encoding the anti-TMEM-180 antibody or antigen-binding fragment thereof according to the present invention include, but are not limited to, nucleic acid containing DNA encoding a heavy chain or light chain of anti-TMEM-180 antibody clone 98, nucleic acid containing DNA encoding any of heavy chain CDR1 to CDR3 and light chain CDR1 to CDR3 of anti-TMEM-180 antibody clone 98, nucleic acid containing DNA encoding a heavy chain or light chain of anti-TMEM-180 antibody clone 101, nucleic acid containing DNA encoding any of heavy chain CDR1 to CDR3 and light chain CDR1 to CDR3 of anti-TMEM-180 antibody clone 101, nucleic acid containing DNA encoding a heavy chain or light chain of anti-TMEM- 180 antibody clone 212, and nucleic acid containing DNA encoding any of heavy chain CDR1 to CDR3 and light chain CDR1 to CDR3 of anti-TMEM-180 antibody clone 212.

Examples of the nucleic acid encoding the anti-TMEM-180 antibody of the present invention or an antigen-binding fragment thereof include a nucleic acid comprising DNA encoding the heavy chain or the light chain of the 1361-5 clone antibody, a nucleic acid comprising any one of the heavy chain CDRs 1 to 3 and the light chain CDRs 1 to 3 (in particular, the heavy chain CDR2) of the 1361-5 clone antibody.

(Expression Vector)

The expression vector according to the present invention contains nucleic acid encoding the anti-TMEM-180 antibody, or antigen-binding fragment thereof, according to the present invention. The expression vector can be suitably selected according to the host cells used, and examples thereof include plant virus vectors such as a plasmid, retrovirus vector, adenovirus vector, adeno-associated virus (AAV) vector, cauliflower mosaic virus vector or tobacco mosaic virus vector, as well as a cosmid, YAC or EBV-derived episomal vector. Nucleic acid encoding the anti-TMEM-180 antibody of the present invention can be inserted into these expression vectors using a known method (such as a method using a restriction enzyme).

The expression vector according to the present invention can further contain a promoter for regulating expression of antibody gene, a replication origin or a selection marker gene and the like. The promoter and replication origin can be suitably selected according to the types of host cells and vector.

(Transformant)

The transformant according to the present invention contains the vector according to the present invention. A transformant can be obtained by transfecting suitable host cells with the vector of the present invention. Examples of host cells that can be used include eukaryotic cells in the manner of mammalian cells (such as CHO cells, COS cells, myeloma cells, HeLa cells or Vero cells), insect cells, plant cells and fungal cells (such as cells of fungi belonging to the genii *Saccharomyces* and *Aspergillus*), and prokaryotic cells in the manner of *Escherichia coli* (*E. coli*) or *Bacillus subtilis* cells.

(Antibody Production Method)

Although there are no particular limitations on the method used to produce the anti-TMEM-180 antibody or antigen-binding fragment thereof according to the present invention, anti-TMEM-180 monoclonal antibody, for example, can be obtained by isolating antibody-producing cells from a non-human mammal immunized with TMEM-180 or a fragment thereof, fusing these cells with myeloma cells or the like to produce a hybridoma, and then purifying antibody produced by this hybridoma. In addition, anti-TMEM-180 polyclonal antibody can be obtained from the serum of an animal immunized with TMEM-180 or a fragment thereof.

Immunization can be performed by immunizing an animal with TMEM-180 protein according to a common general technique. Immunization can be performed also by using exosomes expressing TMEM-180 on their surfaces instead of TMEM-180 protein. Antibodies obtained by immunization with exosomes expressing TMEM-180 on their surfaces may be suitable, but not limited, for detecting exosomes expressing TMEM-180 on their surfaces.

In the case of producing the anti-TMEM-180 antibody according to the present invention by genetic recombination, for example, a suitable host is transformed with an expression vector containing the nucleic acid according to the present invention and this transformant is then cultured under suitable conditions to express antibody followed by isolating and purifying the antibody in accordance with known methods.

Examples of isolation and purification methods include an affinity column using Protein A or the like, other chromatography column, filter, ultrafiltration, salting out and dialysis, and these methods can also be suitably combined.

Human chimeric antibody and human CDR-grafted antibody can be produced by cloning antibody gene from mRNA of a hybridoma that produces antibody of an animal other than a human, and then linking this with a portion of a human antibody gene using genetic recombination technology.

For example, in the case of human chimeric antibody, cDNA is synthesized from the mRNA of a hybridoma producing mouse antibody using reverse transcriptase, and the heavy chain variable region (VH) and light chain variable region (LH) are cloned by PCR followed by analysis of the sequences thereof. Next, 5'-primers containing a leader sequence are produced starting with the antibody base sequence having the highest identity rate, and the region from the signal sequence to the 3'-end of the variable region is cloned by PCR from the above-mentioned cDNA by the 5'-primer and variable region 3'-primer. On the other hand, the constant regions of the heavy chain and light chain of human IgG1 are cloned, and the variable portions derived from mouse antibody and the constant regions derived from human antibody are linked for each of heavy chain and light chain by PCR using the overlapping hanging method and then amplified. The resulting DNA can then be inserted into a suitable vector followed by transformation thereof to obtain human chimeric antibody.

In the case of CDR-grafted antibody, the variable portion of mouse antibody used and the variable portion of human antibody demonstrating the highest homology are selected and cloned followed by modifying the base sequence of the CDR by site-directed mutagenesis using the megaprimer method. In cases in which antigen cannot be bound specifically following humanization of the amino acid sequence that composes the framework region, the amino acids of a portion of the framework region may be converted from human amino acids to rat amino acids.

CDRs comprising an amino acid sequence having one or two amino acid deletions, substitutions or additions in the original sequence, and CDRs comprising an amino acid sequence having identity of X % or more with the original sequence can be produced using a known method such as site-specific mutagenesis, random mutagenesis, chain shuffling or CDR walking.

According to these methods, CDRs having a higher degree of affinity maturation are well known among persons with ordinary skill in the art to be obtained by presenting antibodies or antibody fragments having various mutations in the CDR thereof on a phage surface by phage display followed by screening using antigen (see, for example, Wu, et al., PNAS, 95, 6037-6042 (1998); Schier, R., et al., J. Mol. Biol., 263, 551-567 (1996); Schier, R., et al., J. Mol. Biol., 255, 28-43 (1996); Yang, W. P., et al., J. Mol. Biol., 254, 392-403 (1995)). The present invention also includes an antibody containing the CDR subjected to affinity maturation using such methods.

Examples of other antibody production methods include the Adlib method, by which an antibody-producing line is acquired from a chicken B cell-derived DT40 cell line treated with trichostatin A (Seo, H., et al., Nat. Biotechnol., 6, 731-736, 2002), and a method involving immunizing KM mice introduced with human antibody gene following destruction of mouse antibody gene to produce human antibody (Itoh, K., et al., Jpn. J. Cancer Res., 92, 1313-1321, 2001; Koide, A., et al., J. Mol. Biol., 284, 1141-1151, 1998), and these methods can be applied to production of the antibody according to the present invention.

An antigen-binding fragment of the anti-TMEM-180 antibody according to the present invention may be expressed according to the above-mentioned methods using DNA encoding the fragment, or by fragmenting the full-length antibody by treating with an enzyme such as papain or pepsin.

Antibodies that compete with a certain antibody for binding to an antigen can be obtained by a competition assay which is well-known in the art. For example, if an antibody can block the binding of the desired antibody by at least 20%, preferably at least 20 to 50%, more preferably at least 50%, the antibody can be an antibody that compete for binding to the same antigen. A competing antibody can be confirmed by a cross-blocking assay, preferably a competitive ELISA assay. In a cross-blocking assay, for example, a microtiter plate is coated with an antigen and then a candidate competing antibody is added to the plate, which is followed by incubation to form binding between the antigen and the candidate antibody. Then, the desired antibody, which has been labeled, is further added to the plate, and the plate is washed. Whether the antibody competes or not can be determined by measuring the amount of the bound desired antibody. The amount of the labels left in the well should decrease when the antibody competes.

The anti-TMEM-180 antibody according to the present invention can vary in terms of amino acid sequence, molecular weight, isoelectric point, presence or absence of oligosaccharide or form and the like according to the production method or purification method. However, the resulting antibody is included in the present invention provided it has a function that is equivalent to that of the antibody of the present invention. For example, in the case the antibody of the present invention has been expressed in *E. coli* or other prokaryotic cells, a methionine residue is added to the N-terminal of the amino acid sequence of the original antibody. This antibody is also included in the present invention.

In the case the anti-TMEM-180 antibody according to the present invention is an antibody having an N-linked oligosaccharide in which fucose is not bound to N-acetylglucosamine of the reducing end, the antibody can be produced in accordance with a known method or method complying therewith. Methods for producing this antibody are described in, for example, WO 2002/031140 and Japanese Patent Application Publication No. 2009-225781, and the disclosure thereof is incorporated in the present description in its entirety by reference.

More specifically, the anti-TMEM-180 antibody according to the present invention can be obtained, for example, by transforming cells deficient in or lacking enzyme activity involved in synthesis of GDP-fucose or α-1,6-fucosyl transferase activity using a vector containing DNA encoding the anti-TMEM-180 antibody according to the present invention, and then culturing the resulting transformant followed by purifying the target anti-TMEM-180 antibody.

Examples of enzymes involved in synthesis of GDP-fucose include GDP-mannose 4,6-dehydratase (GMP), GDP-keto-6-deoxymannose 3,5-epimerase, 4-reductase (Fx) and GDP-beta-L-fucose pyrophosphorylase (GFPP).

Here, although there are no particular limitations thereon, the cells are preferably mammalian cells, and for example, CHO cells deficient in or lacking the above-mentioned enzyme activity can be used.

Although there are cases in which an antibody composition obtained according to the above-mentioned method may contain antibody in which fucose is bound to N-acetylglucosamine on the reducing end, the proportion of antibody in which fucose is bound in this manner is 20% by weight or less, preferably 10% by weight or less, more preferably 5% by weight or less, and most preferably 3% by weight or less of total antibody weight.

In addition, antibody having an N-linked oligosaccharide in which fucose is not bound to N-acetylglucosamine on the reducing end can be obtained by introducing a vector containing DNA encoding the anti-TMEM-180 antibody according to the present invention into insect eggs, allowing the eggs to hatch and grow into insects, and then cross-breeding the insects as necessary to produce transgenic insects followed by extracting the anti-TMEM-180 antibody from the transgenic insects or secretions thereof. Silkworms can be used as the transgenic insects and in this case, antibody can be extracted from the cocoon.

Although there are also cases in which an antibody composition obtained according to this method may contain antibody in which fucose is bound to N-acetylglucosamine of the reducing end, the proportion antibody in which fucose is bound in this manner is 20% by weight or less, preferably 10% by weight or less, more preferably 5% by weight or less, and most preferably 3% by weight or less of total antibody weight.

(Activity of Antibody of Present Invention)

The mechanism of the efficacy of an antibody drug is based on two types of biological activity associated with the antibody. The first is binding activity specific to a target antigen in which the function of a target antigen molecule is neutralized as a result of binding thereto. Neutralization of the function of a target antigen molecule is demonstrated via the Fab region.

The other type of biological activity is antibody biological activity referred to as effector activity. Effector activity is demonstrated via the antibody Fc region in the form of, for example, antibody-dependent cellular cytotoxicity (ADCC), complement-dependent cytotoxicity (CDC) or direction induction of apoptosis.

Activity of the anti-TMEM-180 antibody according to the present invention can be measured using the methods indicated below.

(1) Binding Activity

Antibody binding activity can be measured using a known method such as enzyme-linked immunosorbent assay (ELISA), enzyme immunoassay (EIA), radioimmunoassay (RIA), fluorescent antibody technique or FACS.

(2) ADCC Activity

ADCC activity refers to activity that causes damage to a target cell when the antibody of the present invention has bound to an antigen on the surface of a target cell and an Fcγ receptor-retaining cell (effector cell) binds to the Fc moiety thereof via an Fcγ receptor.

ADCC activity can be determined by mixing a target cell expressing TMEM-180, an effector cell and the antibody of the present invention and measuring the degree of ADCC. Examples of effector cells that can be used include mouse spleen cells and monocytes isolated from human peripheral blood or bone marrow. TMEM-180-positive colon cancer mucosal cells, for example, can be used as target cells. The target cells are preliminarily labeled with a label such as $^{51}$Cr and the antibody of the present invention is then added thereto and incubated, followed by adding a suitable ratio of effector cells to the target cells and incubating. Following incubation, the supernatant is collected and ADCC activity can be measured by counting the level of the above-mentioned label in the supernatant.

(3) CDC Activity

CDC activity refers to cytotoxic activity involving complement.

CDC activity can be measured by using complement instead of effector cells in a test of ADCC activity.

(4) Tumor Growth Inhibitory Activity

Tumor growth inhibitory activity can be measured using tumor model animals. For example, the antibody of the present invention is administered after having transplanted a tumor beneath the skin of a mouse. Tumor growth inhibitory effect can be measured by comparing the volume of tumor tissue between a non-dose group and dose group.

Furthermore, the tumor growth inhibitory activity of the present invention may be that occurring as a result of inhibiting the growth of individual cells or that occurring as a result of inducting cell death.

(Testing Method and Testing Kit)

Cancers to be detected by the testing method of the present invention or with the testing kit of the present invention may include, for example, solid cancers, for example, colon cancer, brain tumor, gastric cancer, pancreas cancer, breast cancer, prostate cancer, kidney cancer, and bladder cancer. As was previously described, TMEM-180 is expressed in specific cancer cells, while TMEM-180 is not expressed in normal tissues and tissues of healthy subjects. Thus, the cancer testing method according to the present invention includes a step of measuring the amount of TMEM-180 in a sample collected from a subject.

In the present description, the sample collected from a subject can be any sample suitable for cancer testing, and can be suitably determined and collected according to the type of cancer by a person with ordinary skill in the art. Examples of samples include, but are not limited to, serum, plasma, whole blood, urine, stool, coelomic fluid and tissue. In the case of testing for colon cancer, the sample may be tissue collected from the subject with a colon endoscope or the like, or mucosal cells contained in washings following colonoscopy.

Carcinoembryonic antigen (CEA) has conventionally been widely used as a marker for colon cancer. Although plasma CEA levels decrease due to treatment such as surgical excision of the cancer, since they increase again accompanying recurrence or metastasis, measurement of CEA level is used to monitor progress following treatment. In cases in which CEA level has been observed to rise again, follow-up examinations involving abdominal ultrasonography and abdominal CT are required. However, since only 45% of colon cancer patients demonstrate an increase in CEA level, patients having cancer of a type that does not exhibit an increase in CEA level must undergo several rounds of follow-up examinations in order to monitor their progress.

In contrast, plasma TMEM-180 levels increase even in patients not exhibiting increases in CEA levels and are lower after surgery than before surgery as is indicated in the examples to be subsequently described. Moreover, plasma TMEM-180 levels are also observed to temporarily decrease after surgery and then exhibit a significant increase at the time of recurrence. This increase has been shown to be observed particularly in patients who do not exhibit an increase in CEA levels at the time of recurrence. Thus, this is considered to be an extremely useful marker capable of being used in a wide range of cancer patients.

The cancer testing method according to the present invention may be used for cancer diagnosis or may be used to confirm recurrence or metastasis when monitoring progress following surgery or other treatment.

In the present description, the "step for measuring the amount of TMEM-180 in a sample" includes not only a step of quantifying the amount of TMEM-180, but also includes a step of detecting for the presence or absence of TMEM-180, a step of determining a change in the amount of TMEM-180, and a step of comparing with the amount of TMEM-180 present in another sample.

Cancers (or the existence of cancers) can be detected by detecting exosomes expressing TMEM-180 on the surface, because TMEM-180 expresses on the membranes of the exosomes contained in the body fluid sample (for example, serum, plasma, whole blood, urine, and celomic fluid) obtained from a subject. Then, when exosomes expressing TMEM-180 on the surfaces are detected, it is indicated that the existence of cancer in the body of the subject is detected. The "step of measuring the amount of TMEM-180 in a sample" of above may comprise a step of detecting the existence or absence or the amount of exosomes expressing TMEM-180 on the surface in the body fluid sample (for example, serum, plasma, whole blood, urine, or celomic fluid) and a step of determining that cancer is detected when the amount of the exosomes detected are higher than a prescribed value. The prescribed value can be determined by those skilled in the art based on a false positive rate and a false negative rate. Namely, in order to decrease the false negative rate, the prescribed value needs to be increased, and in order to decrease the false positive rate, the prescribed value needs to be decreased.

The prescribed value may include, for example, but not limited to, the amount of the exosomes in the body fluid sample from a healthy subject. The prescribed value may also include, for example, but not limited to, the average of the amounts of the exosomes in the body fluids from a plurality of healthy subjects. When comparing to the amount of the exosomes in the body fluids from a plurality of healthy subjects, the prescribed value may be the average value of the amounts, the maximum value among the amounts, the third quartile value of the amounts, or a value between two values from these values, or a value larger than the value. Further, the prescribed value may be, for example, but not limited to, a value more than the average value, the maximum value, or the third quartile value, or a value selected between two values from these values, a value more than twice of the value, a value more than triple of the value, a value more than four times of the value, or a value more than five times of the value. For example, the prescribed value may be the average value of the amounts of the exosomes in the body fluid samples from a plurality of healthy subjects. For example, the prescribed value may be the maximum value among the amounts of the exosomes in the body fluid samples from a plurality of healthy subjects. For example, the prescribed value may be a value more than the average value of the amounts of the exosomes in the body fluid samples from a plurality of healthy subjects, a value more than twice of the average value, a value more than triple of the average value, a value more than four times of the average value, or a value more than five times of the average value, or a value from twice to five times of the average value or a value from triple to five times of the average value. Cancers to be detected in the invention may include, for example, solid cancers, for example, colon cancer, brain tumor, gastric cancer, pancreas cancer, breast cancer, prostate cancer, kidney cancer, and bladder cancer. The number of the healthy subjects which should be referred in order to determine the prescribed value may be, for example, but not limited to, 5 to 100 subjects.

Detecting exosomes expressing TMEM-180 on the surface can be performed by detecting TMEM-180 after purification of exosomes, or by detecting exosomes in a purified product after purification of the substance containing TMEM-180. Namely, the present invention provides a method for detecting exosomes, comprising purifying exosomes expressing TMEM-180 on the surface from a body fluid sample, and detecting the exosomes expressing TMEM-180 on the surface, thereby determining that exosomes expressing TMEM-180 on the surface exist in the body fluid sample, provided that anti-TMEM-180 antibody is used in the purification or the detection, or both.

Purifying or detecting exosomes can be performed by well-known techniques, for example, but not limited to, using an antibody binding to exosomes (e.g., anti-CD9 antibody, anti-CD63 antibody, or anti-CD81 antibody). Detecting TMEM-180 or purifying substance containing TMEM-180 can be performed by using the anti-TMEM-180 antibody of the present invention. An antibody to be used in the detection may be an antibody which has been detectably labelled with a label such as an enzyme including peroxidase and alkaline phosphatase, a radio isotope, a fluorescent material, and a luminescent material. Detecting such an antibody can be performed by a technique well-known by those skilled in the art. The amount of exosomes and the above-mentioned prescribed value can be determined based on the measured values by these detecting methods or a standardized value therefrom. Exosomes can be purified with an anti-TMEM-180 antibody and detected with another anti-TMEM-180 antibody.

For example, exosomes expressing TMEM-180 on the surface can be immunoprecipitated from a sample with beads attaching the anti-TMEM-180 antibody of the present invention, and then can be detected with an antibody that binds to exosomes (e.g., anti-CD9 antibody, anti-CD63 antibody, or anti-CD81 antibody) in the purified TMEM-180 fraction. For example, exosomes expressing TMEM-180 on the surface can also be immunoprecipitated from a sample with beads attaching an antibody that binds to exosomes (e.g., anti-CD9 antibody, anti-CD63 antibody, or anti-CD81 antibody), and then can be detected with the anti-TMEM-180 antibody of the present invention in the purified TMEM-180 fraction.

Any anti-TMEM-180 antibody can be used as the antibody of the present invention in purifying or detecting exosomes, and, for example, the 1361 antibody or the 1361-5 antibody, or an antibody that compete with these antibodies for binding to TMEM-180 can be used.

The amount of TMEM-180 in a sample can be measured using any method used to measure the amount of a specific protein in a sample, and examples thereof include, but are not limited to, immunoassay (including agglutination and turbidimetry), western blotting and surface plasmon resonance (SPR). Among these, immunoassay using an anti-TMEM-180 antibody or an antigen-binding fragment thereof is both easy and useful.

Since TMEM-180 is a membrane protein, the amount thereof may be measured after having solubilized the membrane protein by treating with a commercially available cell lysis buffer, nonionic surfactant, membrane protein solubilizing reagent or the like.

Immunoassay uses an anti-TMEM-180 antibody labeled to allow subsequent detection and/or an antibody to the anti-TMEM-180 antibody labeled to allow subsequent detection (secondary antibody). Antibody labeling methods are classified into enzyme immunoassay (EIA or ELISA), radioimmunoassay (RIA), fluorescent immunoassay (FIA), fluorescence polarization immunoassay (FPIA), chemiluminescence immunoassay (CLIA), fluorescence enzyme immunoassay (FLEIA), chemiluminescence enzyme immunoassay (CLEIA), electrochemiluminescence immunoassay (ECLIA) and the like, and any of these methods can be used in the method of the present invention.

An antibody labeled with an enzyme such as peroxidase or alkaline phosphatase is used in the ELISA method, an antibody labeled with a radioactive substance such as $^{125}$I, $^{131}$I, $^{35}$S or $^{3}$H is used in the RIA method, an antibody labeled with a fluorescent substance such as fluorescein isocyanate, rhodamine, dansyl chloride, phycoerythrin, tetramethylrhodamine isothiocyanate or near-infrared fluorescent material is used in the FPIA method, and an antibody labeled with a luminescent substance such as luciferase, luciferin or aequorin is used in the CLIA method. Antibodies labeled with other substances in the manner of nanoparticles such as metal colloids or quantum dots can also be detected.

In addition, when using an immunoassay, the anti-TMEM-180 antibody can also be detected by labeling with biotin and then binding with avidin or streptavidin labeled with an enzyme and the like.

Among these immunoassays, the ELISA method using an enzyme label enables antigen to be measured both easily and quickly.

The ELISA method includes a competitive method and a sandwich method. In the competitive method, an anti-TMEM-180 antibody or an antigen-binding fragment thereof is immobilized on a microplate or other solid-phase support, and a sample and enzyme-labeled TMEM-180 are added thereto followed by allowing an antigen-antibody reaction to occur. After having washed the support, the antigen-antibody complex is allowed to react with the enzyme substrate resulting in the generation of color followed by measurement of optical absorbance. Since coloring is lighter if a large amount of TMEM-180 is contained in the sample and darker if only a small amount thereof is contained in the sample, the amount of TMEM-180 can be determined using a calibration curve.

In the sandwich method, an anti-TMEM-180 antibody or an antigen-binding fragment thereof is immobilized on a solid-phase support, and after adding a sample and allowing to react, an enzyme-labeled anti-TMEM-180 antibody that recognizes a different epitope is further added and allowed to react. After washing, the resulting complex is allowed to react with the enzyme substrate to generate color followed by measurement of optical absorbance to determine the amount of TMEM-180. In the sandwich method, after having reacted TMEM-180 in a sample with antibody immobilized on a solid-phase support, an unlabeled antibody (primary antibody) may be added followed by enzyme-labeling an antibody to this unlabeled antibody (secondary antibody) and further adding thereto.

Examples of enzyme substrates that can be used in the case the enzyme is peroxidase include 3,3'-diaminobenzidine (DAB), 3,3',5,5'-tetramethylbenzidine (TMB) and o-phenylenediamine (OPD), while examples of substrates in the case the enzyme is alkaline phosphatase include p-nitropheny phosphate (NPP).

Alternatively, TMEM-180 antigen in a sample may be immobilized directly on a microtiter plate or other solid-phase support, and after carrying out the required blocking, an unlabeled antibody (primary antibody) is added followed by enzyme-labeling and further adding an antibody to this unlabeled antibody (secondary antibody).

In the present description, there are no particular limitations on the "solid-phase support" provided it is a support that is capable of immobilizing antibody thereon, and examples thereof include microtiter plates made of glass, metal, resin or the like, substrates, beads, nitrocellulose membranes, nylon membranes and PVDF membranes, and a target substance can be immobilized on these solid-phase supports in accordance with known methods.

In addition, among these immunoassays, agglutination methods are preferable since they enable a trace amount of protein to be detected easily. Examples of agglutination methods include latex agglutination that uses latex particles bound to antibody.

When the anti-TMEM-180 antibody is allowed to bind to the latex particles and then mixed with a suitably treated sample, antibody-bound latex particles end up agglutinating if TMEM-180 is present. Therefore, antigen concentration can be determined by quantifying the amount of agglomerate by irradiating the sample with near-infrared light and measuring optical absorbance (turbidimetry) or measuring scattered light (nephelometry).

The previously described anti-TMEM-180 antibody, or antigen-binding fragment thereof, having the previously listed CDR sequences may be used for the anti-TMEM-180 antibody or antigen-binding fragment thereof.

The cancer testing kit according to the present invention is a kit for testing for cancer using the above-mentioned testing method, and contains an anti-TMEM-180 antibody or antigen-binding fragment thereof. In addition to the anti-TMEM-180 antibody or antigen-binding fragment thereof, the cancer testing kit according to the present invention may also contain reagents and apparatuses required to measure the amount of TMEM-180 in a sample by immunoassay.

One aspect of a testing kit is that for measuring TMEM-180 according to the sandwich method, and contains a microtiter plate, anti-TMEM-180 capture antibody or antigen-binding fragment thereof, an anti-TMEM-180 antibody or antigen-binding fragment thereof labeled with alkaline phosphatase or peroxidase, and alkaline phosphatase substrate (such as NPP) or peroxidase substrate (such as DAB, TMB or OPD).

The capture antibody and labeled antibody recognize different epitopes.

In this type of kit, the capture antibody is first immobilized on a microtiter plate followed by suitably diluting a sample and adding thereto, incubating, removing the sample and washing. Next, the labeled antibody is added followed by incubating and adding substrate to develop color. The amount of TMEM-180 can be determined by measuring the degree of coloring using a microtiter plate reader and the like.

Another aspect of the testing kit is for measuring TMEM-180 according to the sandwich method using secondary antibody, and contains a microtiter plate, anti-TMEM-180 capture antibody, primary antibody in the form of anti-TMEM-180 antibody, secondary antibody in the form of alkaline phosphatase- or peroxidase-labeled anti-TMEM-180 antibody, and alkaline phosphatase substrate (such as NPP) or peroxidase substrate (such as DAB, TMB or OPD).

The capture antibody and primary antibody recognize different epitopes.

In this type of kit, the capture antibody is first immobilized on a microtiter plate followed by suitably diluting a sample and adding thereto, incubating, removing the sample and washing. Continuing, the primary antibody is added followed by incubating and washing, after which the enzyme-labeled secondary antibody is added and incubated followed by adding the substrate to develop color. The amount of TMEM-180 can be determined by measuring the degree of coloring using a microtiter plate reader and the like. The use of secondary antibody makes it possible to amplify the reaction and enhance detection sensitivity.

The testing kit may further contain a required buffer solution, enzyme reaction stopping solution or microplate reader and the like.

The labeled antibody is not limited to an enzyme-labeled antibody, but rather may also be an antibody labeled with a radioactive substance (such as $^{25}I$, $^{131}I$, $^{35}S$ or $^{3}H$), fluorescent substance (such as fluorescein isocyanate, rhodamine, dansyl chloride, phycoerythrin, tetramethylrhodamine isothiocyanate or near-infrared fluorescent material), luminescent substance (such as luciferase, luciferin or aequorin), nanoparticles (such as metal colloids or quantum dots) or the like. In addition, biotinated antibody can be used for the labeled antibody and labeled avidin or streptavidin can be added to the kit.

Still another aspect of the testing kit is a testing kit used to measure the amount of TMEM-180 by latex agglutination. This kit contains anti-TMEM-180 antibody-sensitized latex, and agglomerates are quantified by an optical method after mixing with a sample and an anti-TMEM-180 antibody. An agglutination reaction plate for visualizing the agglutination reaction is also preferably contained in the kit.

Disclosures of all patent documents and non-patent documents cited in the present description are incorporated in the present description in their entirety by reference.

EXAMPLES

Although the following provides a detailed explanation of the present invention based on examples thereof, the present invention is not limited thereto. A person with ordinary skill in the art would be able to modify the present invention in various forms without deviating from the significance of the present invention, and all such modifications are included within the scope of the present invention.

1. Identification of TMEM-180 Molecule

1) DNA Microarray Analysis

10 µg aliquots of mRNA were used that were respectively derived from five types of human colon cancer cell lines (HT29, SW480, LOVO, HCT116 and DLD-1) and two types of free colon cells derived from healthy human subjects. Biotin-labeled cRNA was synthesized after obtaining double-stranded cDNA from RNA in accordance with the instructions of the manufacturer (Affymetrix, Inc.). Following fragmentation, the fragments were hybridized with the GeneChip Human Genome U133 Plus 2.0 Array (Affymetrix, Inc.). The hybrids were scanned using the GeneChip Scanner 3000 7G (Affymetrix, Inc.). CEL data was acquired and then subjected to statistical processing to calculate the signal value of each sample. TMEM-180 was selected as a colon cancer cell-specific surface marker for which expression was observed in the five types of human colon cancer cell lines but not observed in the two types of healthy subject colon cells (FIG. 1A).

2) Quantitative PCR

Colon cancer cell tissue sample cDNA (Clontech Laboratories, Inc.) was analyzed with the ABI 7500Fast analyzer (Applied Biosystems) using adjacent normal colon tissue as a negative control for the colon cancer surgical specimens of five patients. 10 μL of 2×TaqMan Fast Universal PCR Master Mix (Applied Biosystems) and 1 μL of 20×TaqMan Gene Expression Assay (Applied Biosystems) were used in 20 μL of reaction solution. In addition, quantitative PCR was carried out with a fast run under conditions of 40 cycles of AMPLITAQ GOLD™ (DNA polymerase) enzyme activation at 95° C. and 20 seconds per cycle, denaturation at 95° C. for 3 seconds, and annealing/extending for 30 seconds at 62° C. The results were analyzed with 7500 Fast System SDS Software Version 1.3. The results of calculating the ratio of the amount of RNA in colon cancer tissue to the amount of RNA in normal tissue are shown in FIG. 1B for each case. In each of the cases, TMEM-180 was confirmed to be strongly expressed in colon cancer tissue as compared with normal colon tissue.

3) In Situ Hybridization

A colon cancer tissue paraffin section (Genostaff Co., Ltd.) was subjected to dewaxing treatment with xylene and then hydrated with ethanol and PBS. The section was then fixed for 15 minutes with 4% para-formaldehyde in PBS. After treating with PBS containing 7 μg/mL of Proteinase K (F. Hoffmann-La Roche Ltd.), the section was again fixed with 4% para-formaldehyde in PBS. The section was acetylated with 0.1 M Tris-HCl (pH 8.0) containing 0.25% acetic anhydride. After washing with PBS, the section was dehydrated with ethanol. The section was then subjected to a hybridization reaction with 300 ng/mL of an RNA probe of digoxigenin-labeled TMEM-180 (475 bp sequence from the 1314th nucleotide to the 1789th nucleotide of GeneBank Accession No. NM_024789, Genostaff Co., Ltd.) for 16 hours at 60° C. After washing, the section was treated with 50 μg/mL of RNaseA, 10 mM Tris-HCl (pH 8.0), 0.1 M NaCl and 1 mM EDTA. After washing again, the section was allowed to react using 0.5% blocking reaction solution (F. Hoffmann-La Roche Ltd.) followed by reacting for 1 hour in blocking reaction solution containing 20% heat-treated sheep serum (Sigma-Aldrich Co. LLC.). AP-labeled anti-DIG antibody (F. Hoffmann-La Roche Ltd.) was then added and allowed to react for 2 hours at room temperature. After washing, color was developed in NBT/NCIP solution (F. Hoffmann-La Roche Ltd.). The results of enclosure and microscopic observation are shown in FIGS. 1C and 1D. TMEM-180 was confirmed to be positive in all five types of the colon cancer tissue and negative in normal colon mucosa.

2. Expression Analysis of TMEM-180 in Normal Tissue

A search was made for TMEM-180 using the public database, PaxDB, in the form of a comprehensive absolute protein abundance database (pax-db.org/#!home, which measures the expression level of each protein by analyzing unique peptides by LC/MS/MS) to investigate measured values in each type of normal tissue. Other than TMEM-180, expression of the following molecules was also investigated as controls.

β-actin (βACT) (housekeeping molecule)

Glyceraldehyde 3-phosphate dehydrogenase (GAPDH) (housekeeping molecule)

Epidermal growth factor receptor (EGFR) (target molecule of antibody drug)

HER2 (target molecule of antibody drug)

Carcinoembryonic antigen (CEA) (typical tumor marker molecule)

Figure 2:
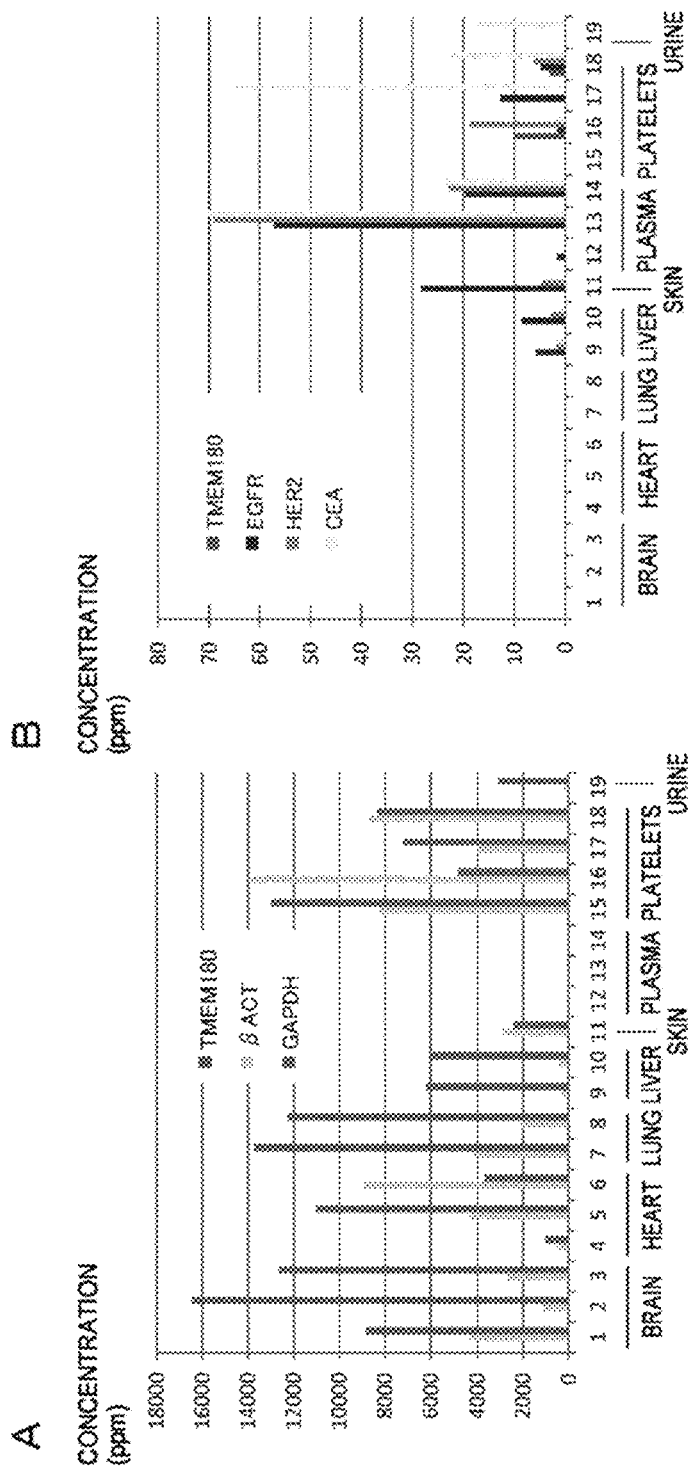
FIG. 2A indicates the results of investigating expression of TMEM-180 in various normal tissues using a database.
FIG. 2B indicates the results of investigating expression of trace amounts of TMEM-180 for molecules targeted by TMEM-180 and conventional anticancer drugs using the same method as in FIG. 2A.

The results of entering the data into an Excel (2010, Microsoft Corporation) file and generating graphs are shown in FIG. 2. Although TMEM-180 is rarely expressed normally (FIG. 2A) and was observed to be only slightly expressed in platelets when sensitivity was increased, expression was much lower than the conventional antibody drug target molecules of EGFR and HER2 (FIG. 2B), thereby confirming that TMEM-180 is specifically expressed in cancer tissue.

3. Antibody Production and FACS on Various Types of Cancer Cells

1) Antigen Production

[PCR Reaction]

PCT amplification was carried out on a tag sequence incorporated in pET21 b using the primers indicated below.

PCR enzyme used: PRIMESTAR@ HS DNA polymerase (Takara Bio Inc., R010A)

```
Primer sequences for producing immunizing
antigen 1:
(i)
                                      (SEQ ID NO: 18)
cagacctgcacctgaacgtggttgagagctgaggaattgacggtcactga gggactgtaatgctgcacttcgc (ii)
                                      (SEQ ID NO: 19)
caaccacgttcaggtgcaggtctgtcttcacgtgctgttgtactggctcg tgttcaagagttcaaactggaggacctg (iii)
                                      (SEQ ID NO: 20)
gagatatacatatgtcggaggtgactcgtagtc (iv)
                                      (SEQ ID NO: 21)
tggtgctcgagaataggctgaacatcaaatg Primer sequences for producing immunizing
antigen 2:
(i)
                                      (SEQ ID NO: 22)
gcgaagtgcagcattacagtccgatcatctgagtctgctgtgcctcttca ttgc (ii)
                                      (SEQ ID NO: 23)
caggtcctccagtttgaactcagaagctgcttgcttacgatgattcagca ccaggtcctcgtctac (iii)
                                      (SEQ ID NO: 24)
gagatatacatatgtcggaggtgactcgtagtc (iv)
                                      (SEQ ID NO: 25)
tggtgctcgagaataggctgaacatcaaatg
```

[Restriction Enzyme Treatment]

NdeI (Takara Bio Inc.) and XhoI (Takara Bio Inc.) were reacted for 2 hours with expression vector pET21 b and the PCR products in accordance with the manufacturer's protocol, and carrying out 1% agarose gel electrophoresis, the products were purified using the Promega Wizard SV Gal and PCR Clean-up System kit.

[Ligation Reaction]

A vector and insert were reacted for 30 minutes using Ligation High (Toyobo Co., Ltd.).

[Transformation]

Transformation was carried out using Competent High DH5a (Toyobo Co., Ltd.) followed by culturing in plates containing LB medium (50 μg/mL).

[Gene Confirmation]

The plasmid was extracted from the transformed *E. coli* and the sequence was analyzed to confirm the target sequence.

[Transformation (*E. coli*)]

BL21(DE3) was transformed with the plasmid inserted with the target sequence.

[Culturing]

The transformed *E. coli* was inoculated into 10 mL of LB medium and cultured for 16 hours at 37° C. followed by transferring the medium to 1 L of LB medium and culturing at 37° C. IPTG was added to a final concentration of 1 mM when the OD value at 600 nm reached 0.6 followed by additionally culturing for 4 hours.

[Purification]

Sediment of the disrupted *E. coli* was suspended in 50 mM Tris-HCl, 500 mM NaCl and 6 M GdnHCl followed by recovering supernatant from the sample after shaking for 16 hours and purifying with a nickel column.

[Refolding]

Since the target antigen had been denatured as a result of dissolving with 6 M GdnHCl, refolding (protein unwinding) was carried out by dialysis.

Refolding was carried out according to the following steps under the conditions indicated below.
(1) 50 mM Tris-HCl, pH 8.5, 500 mM NaCl, 1 mM EDTA, 1 mM DTT, 3 M GdnHCl, 6 hours
(2) 50 mM Tris-HCl, pH 8.5, 500 mM NaCl, 1 mM EDTA, 1 mM DTT, 2 M GdnHCl, 6 hours
(3) 50 mM Tris-HCl, pH 8.5, 500 mM NaCl, 1 mM EDTA, 1 mM DTT, 1 M GdnHCl, 12 hours
(4) 50 mM Tris-HCl, pH 8.5, 500 mM NaCl, 1 mM EDTA, 1 mM DTT, 0.5 M GdnHCl, 12 hours
(5) 50 mM Tris-HCl, pH 8.5, 150 mM NaCl, 50 mM L-Arg, 6 hours
(6) 50 mM Tris-HCl, pH 8.5, 150 mM NaCl, 50 mM L-Arg, 6 hours The dialysis solution of the above-mentioned sample was replaced with 50 mM phosphate buffer (pH 8.0) and 500 mM NaCl using an ultrafiltration membrane (Amicon-Ultra 10K).

[Measurement of CD]

Helix content was confirmed to approach the theoretical value using a circular dichroic disperser (JASCO Corporation, J-725) in order to confirm whether the refolded immunizing antigen retained its steric structure.

2) Antibody Production

An emulsion prepared by mixing immunizing antigen 1 or immunizing antigen 2, diluted to 100 Ig/mL with PBS, with Freund's Complete Adjuvant in a 1:1 ratio was administered in 100 µL aliquots at both sides of the base of the caudal vein in rats (Japan SLC, Inc., Wistar, females, age 6 to 8 weeks). Blood was collected from the caudal vein at 12 to 13 days after immunization and serum antibody titers were evaluated by ELISA using the prepared antiserum and immunizing antigen for the solid phase or by flow cytometry using DLD-1 cells and K562 cells to select individuals for use in cell fusion. Iliac lymph nodes, inguinal lymph nodes, axillary lymph nodes and popliteal lymph nodes were dissected from individuals selected at 14 days after immunization, and lymph node cells and mouse myeloma cells p3X63 were fused according to the PEG method. Culture supernatant was recovered 10 to 14 days after fusion and antibody-producing hybridoma cells that were positive for DLD-1 cells and negative for K562 cells were selected by flow cytometry. The selected antibody-producing hybridoma cells were single-cloned and established by limiting dilution. Antibody isotypes were identified by isotype-specific ELISA (Bethyl Laboratories).

The single-cloned clones were clone 98, clone 101, clone 212 (which are IgM antibodies), clone 129, clone 382, clone 1361 (which are IgG antibodies), clone 669, clone 699, clone 1052 and clone 1105 (which are IgM antibodies). An antibody obtainable from the clone having the clone number x may be referred to as "x antibody".

3) Flow Cytometry

Cancer cells targeted for measurement were cultured in medium and then added to a V-bottom 96-well plate (Corning Incorporated) to a concentration of $1 \times 10^5$ cells/well. The plate was centrifuged for 3 minutes at 440×g and 4° C. followed by removing the supernatant, adding antibody-producing hybridoma culture supernatant or antibody solution to the cell pellet at 50 µL/well and suspending therein. After allowing to react for 45 minutes on ice, the plate was washed three times with a mixture of 0.1% BSA, 2 mM EDTA and PBS at 200 µL/well. The supernatant was removed and secondary antibody was added to the cell pellet at 50 µL/well followed by suspending the cells therein. ALEXAFLUOR 647@ (fluorescent compound) goat anti-rat IgG (H-L) (Life Technologies Corporation) was used for the secondary antibody after diluting 400-fold with a mixture of 0.1% BSA, 2 mM EDTA and PBS. After allowing to react for 45 minutes on ice, the plate was washed three times with a mixture of 0.1% BSA, 2 mM EDTA and PBS at 200 µL/well. After removing the supernatant, 50 ng/mL of propidium iodide, 0.1% BSA, 2 mM EDTA and PBS were added to the cell pellet at 250 L/well followed by suspending therein. The cells stained in this manner were measured using a flow cytometer such as the Guava easyCyte 8HT (Merck Millipore Corporation) followed by analysis of the resulting data using FlowJO (Tomy Digital Biology Co., Ltd.). FACS analysis was carried out using colon cancer, brain tumor and hematologic cancer.

Figure 3:
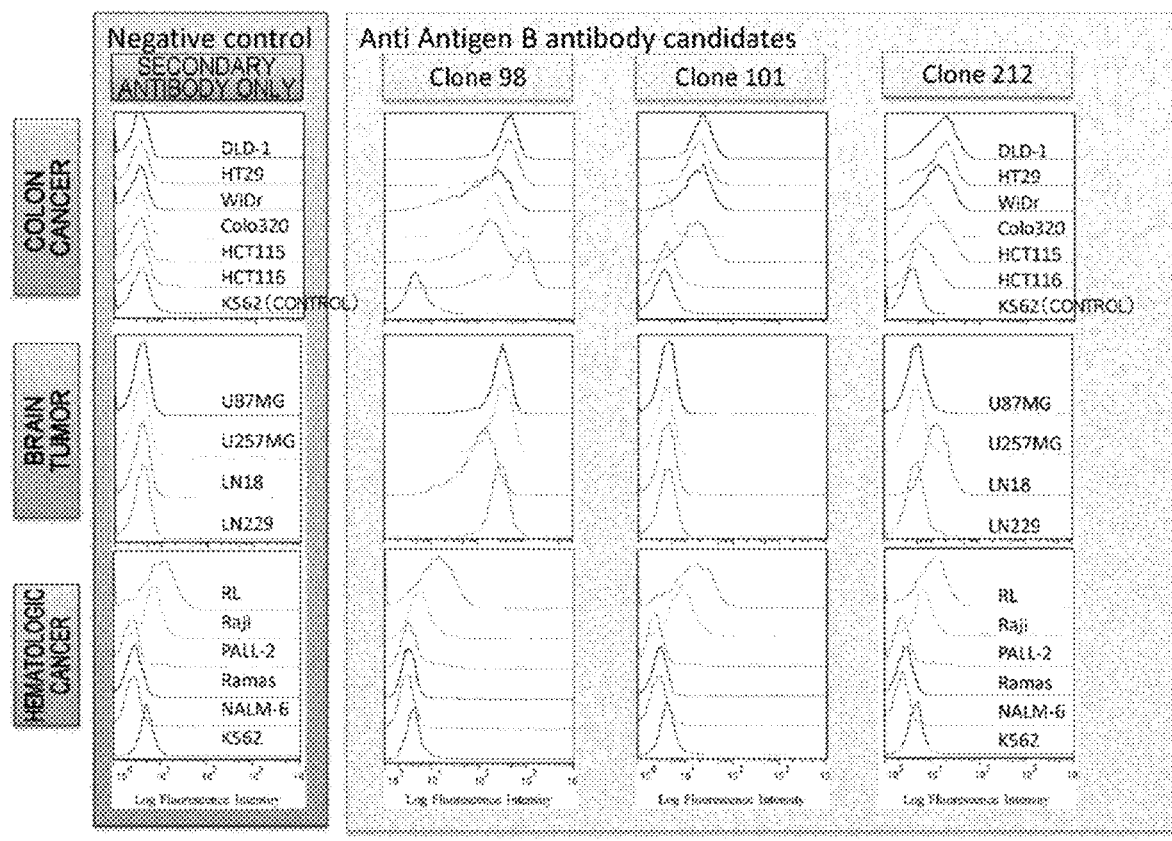
FIG. 3 indicates the results of a flow cytometry analysis of various colon cancer, brain tumor and hematologic cancer cell lines using anti-TMEM-180 antibody clones 98, 101 and 212.

The results of FACS analysis using the acquired anti-TMEM-180 IgM antibody are shown in FIG. 3. Clone 98 was positive for all six types of colon cancers and all four types of brain tumors while clone 101 was positive for four types of colon cancers and negative for all of the brain tumors. Clone 212 was positive for all six types of colon cancers and was positive for only one type of brain tumor. All of the clones were negative for hematologic tumors.

4. Fluorescent Immunostaining of DLD-1 Colon Cancer Cells

DLD-1 cells were added to a 96-well plate (Corning Incorporated, CellBIND) to a concentration of $5 \times 10^3$ cells/well and subjected to cell staining after culturing for 2 days. The cells were subjected to fixation and permeation treatment in the manner indicated below. After washing the cell culturing plate twice with PBS at 200 µL/well, the washings were removed followed by the addition of 4% para-formaldehyde-phosphate buffer (Wako Pure Chemical Industries, Ltd.) containing 0.1% TRITON™ (surfactant) X-100 (Wako Pure Chemical Industries, Ltd.) at 100 L/well while cooling with ice and fixing the cells for 10 minutes. After removing the fixation solution, the plate was washed once with PBS at 200 µL/well and once with a mixture of 1% FBS in PBS at 200 µL/well to obtain a cell-immobilized plate. The cells were stained in the manner indicated below. Namely, after removing medium from the non-immobilized cell culturing plate and removing washings from the cell-immobilized plate, cell-producing hybridoma culture supernatant or diluted antibody solution was added at 50 µL/well. After allowing to react for 1 hour on ice, the plate was washed once with PBS at 200 µL/well and twice with a mixture of 1% FBS in PBS at 200 μL/well. After removing the washings, a mixture of 5 μg/mL ALEXAFLUOR 647@ (fluorescent compound) goat anti-rat IgG (H-L), 2 μg/mL Hoechst 33342 and 1% FBS/PBS was added at 50 μL/well. After allowing to react for 1 hour on ice, the plate was washed twice with PBS at 200 μL/well. PBS was then added at 50 μL/well followed by measuring with ArrayScan (Thermo Fisher Scientific Inc.).

Figure 4:
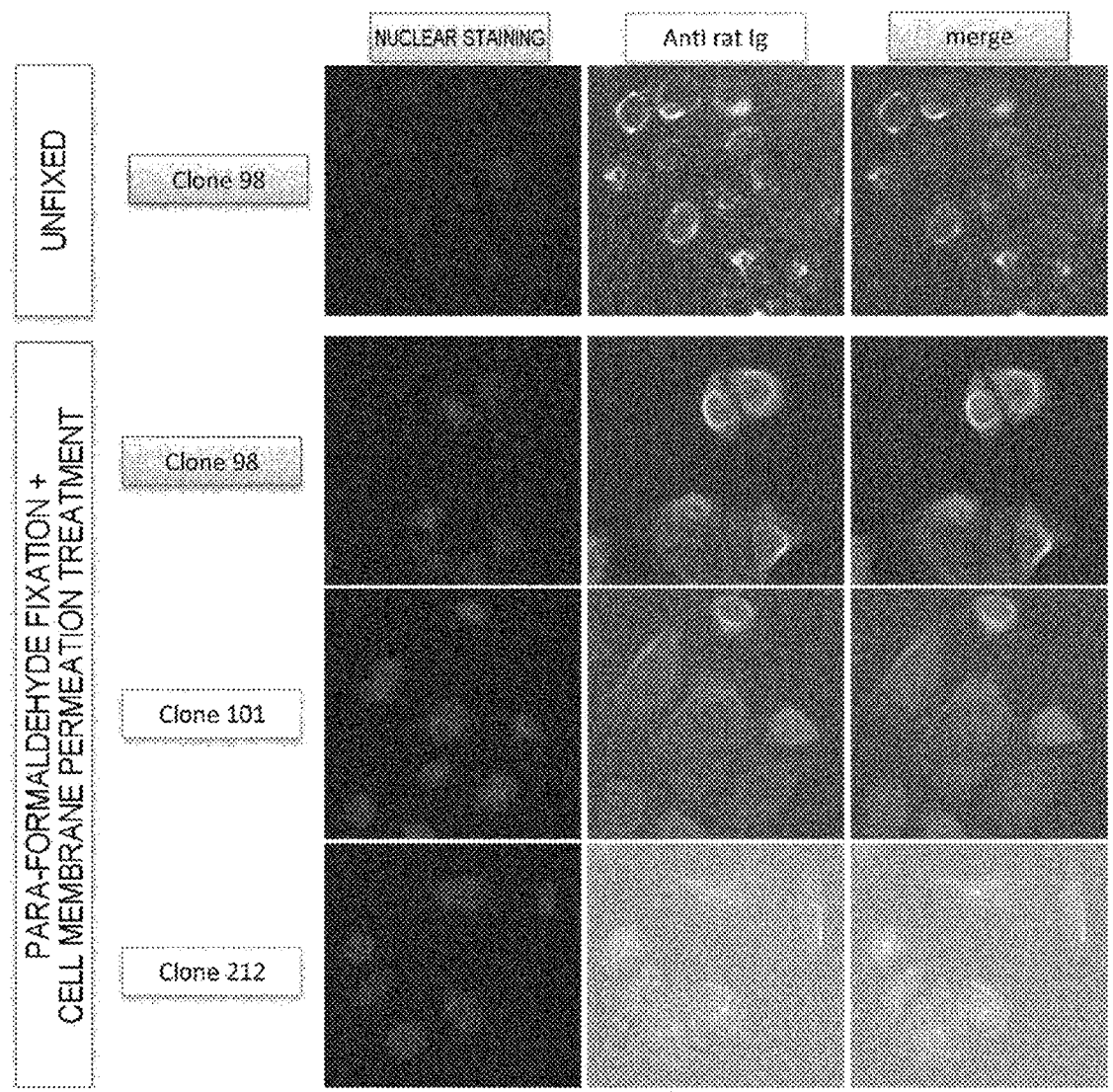
FIG. 4 indicates the results of immunofluorescent staining of colon cancer cells by anti-TMEM-180 antibody clones 98, 101 and 212. Furthermore, the antibody concentrations of each clone are not aligned.

The results of fluorescent immunostaining using clones 98, 101 and 212 of anti-TMEM-180 IgM antibody are shown in FIG. 4. Clone 98 was stained primarily in the membrane. Clones 101 and 212 exhibited weaker fluorescence intensity than clone 98 and the cytoplasm was also stained.

5. FACS of DLD-1 Parent Line and TMEM-180 Knockout Line using Anti-TMEM-180 Antibody 1) Production of Knockout Cells

[Transfection]

2.5 μg of Sigma CRISPR/Cas9 System (HS0000468201) plasmid were diluted with 0.5 mL of Opti-MEM (Invitrogen Corporation) followed by the addition of 11 μL of Lipofectionamine LTX. After allowing to stand undisturbed for 30 minutes at room temperature, DLD-1 cells ($6.26 \times 10^5$ cells/well, 6-well plate (Corning Incorporated)) were added to the DNA-Lipofection preparation.

[Selection of GFP-Expressing Cells]

Cells cultured for 2 days after transfection were subjected to cell sorting using the FACSAria Cell Sorter (BD) to acquire only cells that express GFP.

[Cloning]

After culturing the GFP-expressing cells and confirming that GFP was no longer expressed, the cells were subjected to limiting dilution in a 96-well plate. Genome purification was carried out on those wells containing only a single cell colony using the PureLink Genomic DNA Mini Kit (Invitrogen Corporation) followed by determining knockout cells by confirming the target sequence.

2) Flow Cytometry

Flow cytometry was carried out in accordance with the procedure described in the above-mentioned section 3. Rat IgM antibody clone 98 used as primary antibody was used after diluting antibody-producing hybridoma culture supernatant to 1 μg/mL. The supernatant of a culture of hybridoma producing rat IgM antibody clone 365 was used as a negative control after similarly diluting to 1 μg/mL. Rat-human chimeric antibody clone 98 was used after diluting the culture supernatant of chimeric antibody constantly-expressing cells two-fold. Human tissue factor antibody clone hTF1849, rat anti-human EpCAM antibody clone B8-4, mouse anti-human CD44v6 antibody clone 2F10 (Medical & Biological Laboratories Co., Ltd.) and mouse-human chimeric anti-EGFR antibody (trade name: Erbitux) were respectively used as positive controls after diluting to 1 μg/mL. A mixture of RPMI and 10% FBS was used to dilute each of the antibodies. Furthermore, antibody concentration in the hybridoma culture supernatant was measured by rat IgM-specific ELISA (Bethyl Laboratories). In addition, secondary antibody formed of any of ALEXAFLUOR 647@ (fluorescent compound) goat anti-rat IgG (H+L), ALEXAFLUOR 647@ (fluorescent compound) goat anti-human IgG (H+L) or ALEXAFLUOR 647@ (fluorescent compound) goat anti-mouse IgG (H+L) (Life Technologies Corporation) was used corresponding to the origin of the primary antibody after diluting 400-fold with a mixture of 0.1% BSA, 2 mM EDTA and PBS.

3) Production of Human Chimeric Antibody

Total RNA was extracted from the hybridoma cell lines and cDNA of variable regions of antibody H chain and variable regions of antibody L chain was synthesized with the SMARTER@ (cDNA synthesis kit) RACE cDNA Amplification Kit (Takara Bio Inc.) using the 5-end rapid amplification of cDNA ends (RACE) method.

The synthesized cDNA was subjected to amplification by PCR and cloned to pUC19 (Invitrogen Corporation). The variable regions of the H chain and variable regions of the L chain are shown in subsequently indicated Tables 3 to 22.

After amplifying the variable regions of the H chain and L chain by PCR, the variable region of the H chain was inserted into pQCxIP incorporating a constant region (Clontech Laboratories, Inc.) while the variable region of the L chain was inserted into pQCxIH incorporating a constant region (Clontech Laboratories, Inc.) to complete the expression vector. The expression vector was then transfected into 293T cells using LIPOFECTAMINE™ (transfection reagent) 2000 (Invitrogen Corporation). Human anti-TMEM-180 antibody constantly expressing cell line was subjected to drug selection using puromycin (Sigma-Aldrich Co. LLC.) at 10 μg/mL and hygromycin B (Invitrogen Corporation) at 1 mg/mL and established by acquiring a cell line resistant to both drugs. The established cell line was subjected to maintenance culturing in DMEM (sigma) with 10% FBS, 1% penicillin-streptomycin (Invitrogen Corporation), 10 μg/mL of puromycin and 1 mg/mL of hygromycin B.

Figure 5:
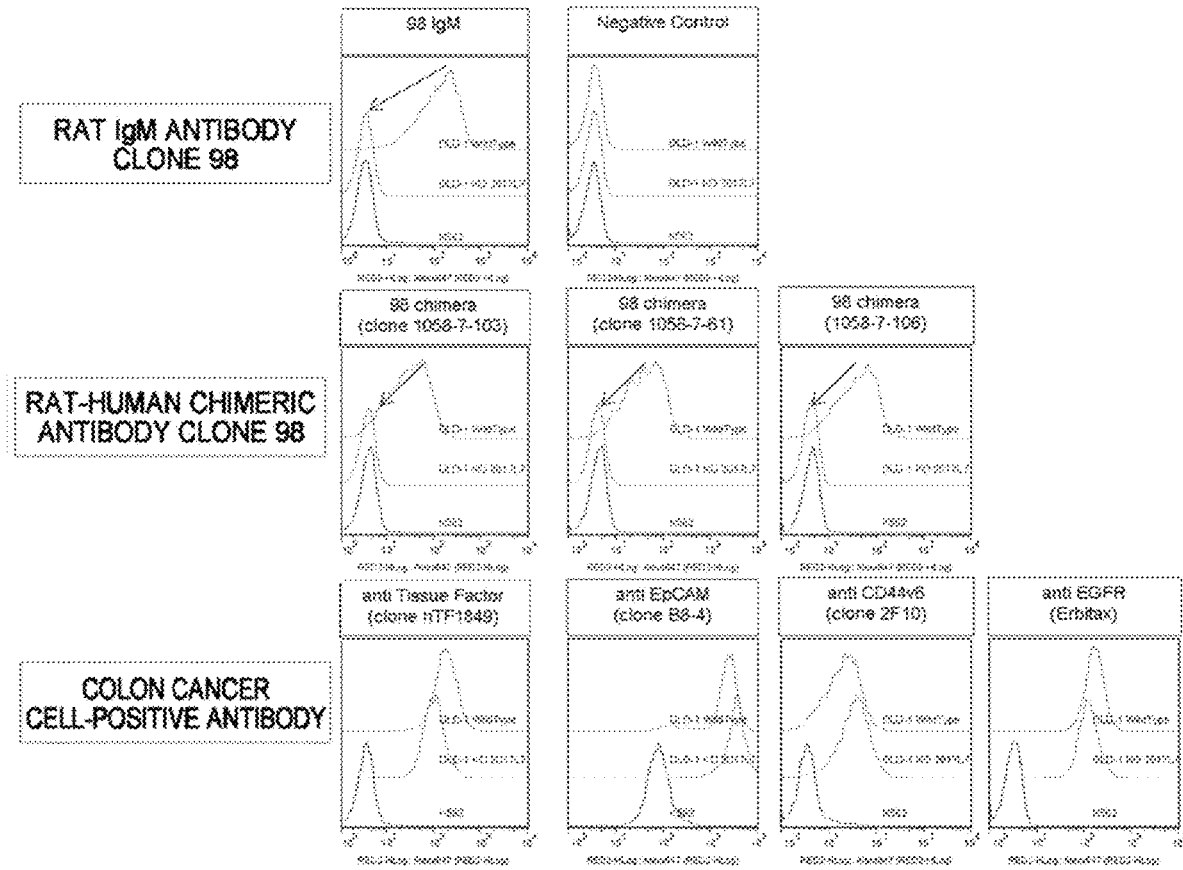
FIG. 5 indicates the results of investigating the reactivity of rat IgM antibody clone 98 and rat-human chimeric antibody clone 98 with colon cancer cell line DLD-1 and a TMEM-180 knockout line thereof by flow cytometry.

FACS was carried out on the colon cancer DLD-1 parent line and the TMEM-180 knockout line using rat IgM antibody clone 98 and human chimeric IgG1 antibody. The results are shown in FIG. 5. The rat IgM antibody clone 98 and human chimeric IgG antibody both demonstrated a considerable left shift. There were no differences between the parent line and knockout line in FACS using anti-tissue factor antibody, anti-EpCAM antibody, anti-CD44v6 antibody and anti-EGFR antibody as controls. This indicates that both rat IgM antibody clone 98 and human chimeric IgG1 antibody specifically recognize TMEM-180.

Figure 6:
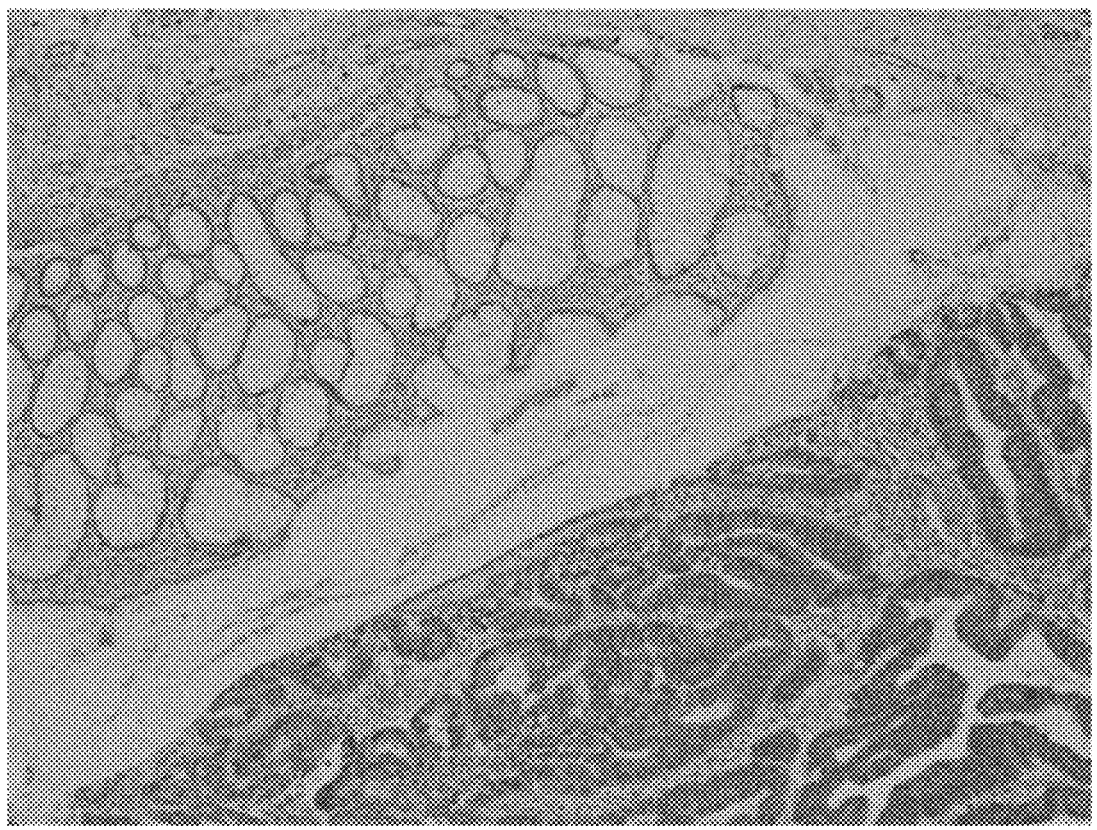
FIG. 6 indicates the results of staining human colon cancer and nearby normal tissue using rat IgM antibody clone 98.

6. Immunostaining of Formalin-Fixed Section of Human Colon Cancer Surgical Specimens by Anti-TMEM-180 Antibody Anti-TMEM-180 IgM rat antibody (clone 98) was reacted with a colon cancer formalin-fixed section at 1 μg/mL. HRP-labeled anti-rat antibody was used as secondary antibody and the section was stained with DAB followed by post-staining with hematoxylin. The result is shown in FIG. 6. Colon cancer was shown to be stained specifically. Both the cell membrane and cytoplasm of the colon cancer cells were stained.

7. Cytocidal Effect of Anti-TMEM-180 IgM Antibody

Figure 7:
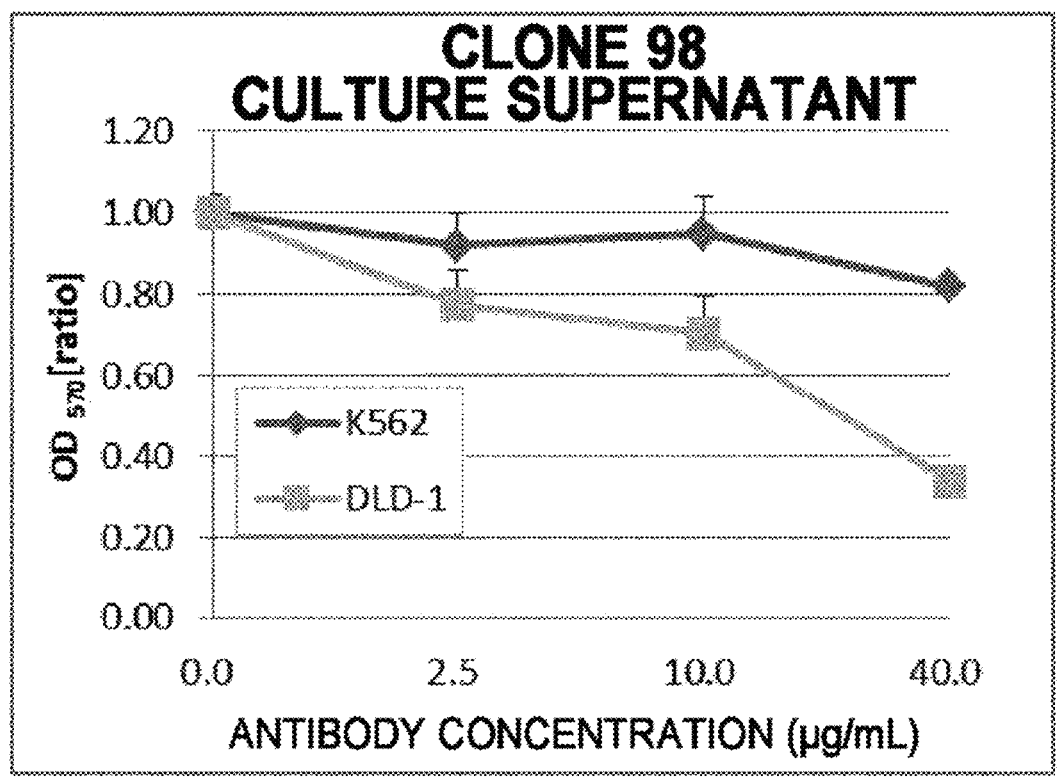
FIG. 7 indicates the results of a cytotoxicity test using culture supernatant of a hybridoma producing rat IgM antibody clone 98. Antibody concentration in the hybridoma culture supernatant was measured by ELISA using IgM-specific antibody.
Figure 8:
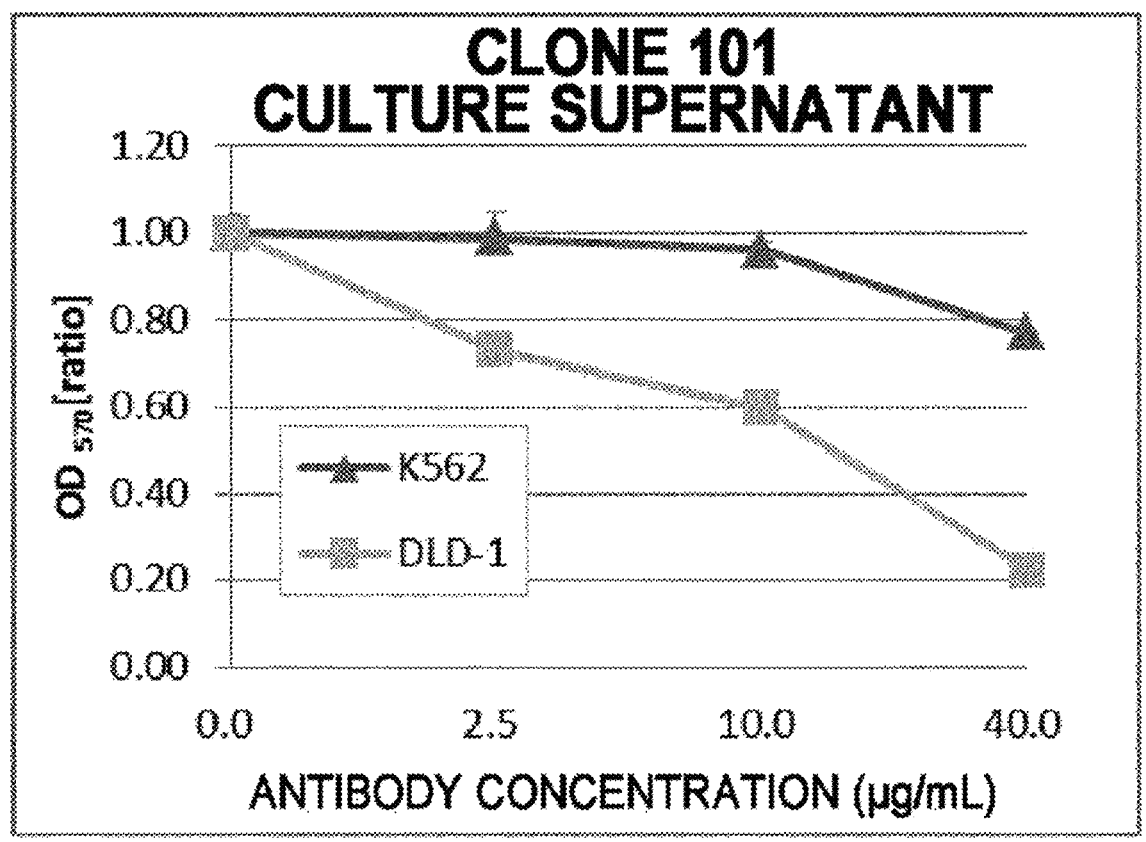
FIG. 8 indicates the results of a cytotoxicity test using culture supernatant of a hybridoma producing rat IgM antibody clone 101. Antibody concentration in the hybridoma culture supernatant was measured by ELISA using IgM-specific antibody.

DLD-1 cells and K562 cells were added to a 96-well plate at $1 \times 10^3$ cells/100 μL/well followed by culturing for 24 hours. 50 μL of medium were removed from each well of the 96-well plate followed by the addition of rat IgM antibody clone 98-producing hybridoma culture supernatant or rat IgM antibody clone 101-producing hybridoma culture supernatant, in which antibody concentration had been adjusted to 80 μg/mL, 20 μg/mL or 5 μg/mL, at 50 μL/well. Here, n number in each culture condition was 3, and wells containing medium only were prepared as controls. is added After culturing for 96 hours, WST-8 (Dojindo Laboratories, Cell Counting Kit-8) was added at 10 μL/well followed by measuring absorbance at 450 nm with a microplate reader after culturing for 3 hours. The relative values of absorbance at each antibody concentration were plotted by plotting antibody concentration on the horizontal axis and assigning a value of 1 to the optical absorbance of the well containing medium only. The results are shown in FIGS. 7 and 8. Both clone 98 and clone 101 only demonstrated cytocidal effects against colon cancer DLD-1 cells and did not demonstrate cytocidal effects against hematologic tumor K562 cells. Cytocidal effects were also observed for other colon cancer cells Difi, Carl, SW480 and Colo201. In addition, similar effects were observed for brain tumor LN229 cells and breast cancer MCF7 cells. Cytocidal effects are therefore predicted to be demonstrated against a wide range of cancers other than hematologic tumors.

8. Determination of the Base Sequences and CDR of the Variable Portion of Each Clone 1) Extraction of Total RNA Total RNA was extracted from each antibody-producing hybridoma using the RNEASY® (RNA isolation kit) Mini Kit (Qiagen).

2) Production of cDNA cDNA was synthesized with the SMARTER® (cDNA synthesis kit) RACE cDNA Amplification Kit (Takara Bio Inc.) according to the 5-end rapid amplification of cDNA ends (RACE) method using the total RNA obtained in the manner described above.

3) Cloning of Anti-TMEM-180 Antibody Gene The target gene was amplified by using PrimeStar HS DNA Polymerase (Takara Bio Inc.) on the above-mentioned cDNA. Amplification was carried out by touchdown PCR under amplification condition of 5 cycles of denaturing for 10 seconds at 98° C. and annealing/extending for 90 seconds at 72° C., 5 cycles of denaturing for 10 seconds at 98° C., annealing for 5 seconds at 67° C. and extending for 90 seconds at 72° C., and 25 cycles of denaturing for 10 seconds at 98° C., annealing for 5 seconds at 62° C. and extending for 90 seconds at 72° C.

PCR device: Takara PCR Thermal Cycler Dice Gradient
Primer sequences used:
H chain primer:

```
Forward primer:
                                        (SEQ ID NO: 26)
CTAATACGACTCACTATAGGGCAAGCAGTGGTATCAACGCAGAGT Forward primer:
                                        (SEQ ID NO: 27)
CTAATACGACTCACTATAGGGC Reverse primer:
                                        (SEQ ID NO: 28)
CCCATGGCCACCARATTCTYATCAGACAG
```

L chain primer:

```
Forward primer:
                                        (SEQ ID NO: 29)
CTAATACGACTCACTATAGGGCAAGCAGTGGTATCAACGCAGAGT Forward primer:
                                        (SEQ ID NO: 30)
CTAATACGACTCACTATAGGGC Reverse primer:
                                        (SEQ ID NO: 31)
GTTGTTCAWGARGCACACGACTGAGGCA
```

The amplified PCR products of the H chain and L chain were phosphorylated using T4 Polynucleotide Kinase (Takara Bio Inc.). The phosphorylated PCR products were inserted into pUC19 (Invitrogen Corporation) cleaved at the SmaI site using Ligation High reagent (Toyobo Co., Ltd.). Following insertion, the PCR products were transformed to DH5a (Toyobo Co., Ltd.) and plasmids were extracted from single colonies using the Plasmid Mini Kit (Qiagen).

4) Gene Analysis

Genes of each of the cloned H chains and L chains were analyzed for gene base sequence using the ABI Prism 3100 Genetic Analyzer. The sequences of the H chain variable region and L chain variable region of each clone are shown in Tables 3 to 22.

Clone 98 H Chain (SEQ ID NO: 13)

TABLE 3

| 1 | ATG | GCT | GTC | CTG | GTG | CTG | TTG | CTC | TGC | CTG | GTG | ACA | TTT | CCA | ACC | TGT | GTC | CTG | TCC | CAG | 60 |
|---|-----|-----|-----|-----|-----|-----|-----|-----|-----|-----|-----|-----|-----|-----|-----|-----|-----|-----|-----|-----|-----|
|   | M | A | V | L | V | L | L | L | C | L | V | T | F | P | T | C | V | L | S | Q | |
| 61 | GTG | CAG | CTG | AAG | GAG | TCA | GGA | CCT | GGT | CTG | GTG | CAG | CCC | TCA | CAG | ACC | CTG | TCC | CTC | ACC | 120 |
|   | V | Q | L | K | E | S | G | P | G | L | V | Q | P | S | Q | T | L | S | L | T | |
| 121 | | | | | CDR1 | | | | | | | | | | | | | | | | 180 |
| | TGC | ACT | GTC | TCT | GGG | TTC | TCA | CTA | ACC | AGG | TAC | AAT | GTG | CAC | TGG | GTT | CGA | CAG | CCT | ACA | |
| | C | T | V | S | G | F | S | L | T | R | Y | N | V | H | W | V | R | Q | P | T | |
| 181 | | | | | | | CDR2 | | | | | | | | | | | | | | 240 |
| | GGA | AAA | GGT | CTG | GAG | TGG | ATG | GGA | GTA | ATA | TGG | ACT | GGT | GGA | AGC | ACA | GAT | TAC | AAT | TCA | |
| | G | K | G | L | E | W | M | G | V | I | W | T | G | G | S | T | D | Y | N | S | |
| 241 | GCT | CTC | AAA | TCC | CGA | CTG | AGC | ATC | AGC | AGG | GAC | ACC | TCC | AAG | AGC | CAA | GTT | TTC | TTA | AAA | 300 |
| | A | L | K | S | R | L | S | I | S | R | D | T | S | K | S | Q | V | F | L | K | |
| 301 | | | | | | | | | | | | | | | | | | CDR3 | | | 360 |
| | ATG | AAC | AGT | CTG | CAA | ACT | GAA | GAC | ATA | GCC | ACT | TAC | TAC | TGT | GCC | AGA | GAT | CTG | GGT | TAC | |
| | M | N | S | L | Q | T | E | D | I | A | T | Y | Y | C | A | R | D | L | G | Y | |
| 361 | TGG | GGC | CAA | GGA | GTC | ATG | GTC | ACA | GTC | TCC | TCA | | | | | | | | | | 393 |
| | W | G | Q | G | V | M | V | T | V | S | S | | | | | | | | | | |

Clone 98 L Chain (SEQ ID NO: 14)

TABLE 4

| | | | | | | | | | | | | | | | | | | | | |
|---|---|---|---|---|---|---|---|---|---|---|---|---|---|---|---|---|---|---|---|---|
| 1 | ATG | ATG | AGT | CCT | GCC | CAG | TTC | CTG | TTT | CTG | CTA | ATG | CTC | TGG | ATC | CAG | GAA | ACC | CAC | AGT | 60 |
| | M | M | S | P | A | Q | F | L | F | L | L | M | L | W | I | Q | E | T | H | S | |
| 61 | GAT | ATT | GTG | ATG | ACA | CAG | ACT | CCA | CTC | TCT | TTG | TCA | GTT | GCC | ATT | GGA | CAA | TCA | GCC | TCC | 120 |
| | D | T | V | M | T | Q | T | P | L | S | L | S | V | A | I | G | Q | S | A | S | |
| 121 | | | | *CDR1* | | | | | | | | | | | | | | | | | 180 |
| | ATC | TCT | TGC | AAA | TCG | AGT | CAG | AGC | CTC | AAA | TAT | CGT | GAT | GGA | AAG | ACA | TAT | TTG | AAT | TGG | |
| | I | S | C | K | S | S | Q | S | L | K | Y | R | D | G | K | T | Y | L | N | W | |
| 181 | | | | | | | | | | | | | | | | *CDR2* | | | | | 240 |
| | GTA | TTT | CAG | AGT | CCT | GGC | CAG | TCT | CCA | AAG | CGC | CTA | ATC | TAT | CAG | GTG | TCT | AAA | CTG | GAC | |
| | V | F | Q | S | P | G | Q | S | P | K | R | L | I | Y | Q | V | S | K | L | D | |
| 241 | TCT | GGA | GTT | CCT | GAC | AGG | TTC | AGT | GGC | ACT | GGA | TCA | GAG | ACA | GAT | TTT | ACA | CTT | AAA | ATC | 300 |
| | S | G | V | P | D | R | F | S | G | T | G | S | E | T | D | F | T | L | K | I | |
| 301 | | | | | | | | | | | | | | | *CDR3* | | | | | | 360 |
| | AGC | AGA | GTG | GAG | GCA | GAG | GAT | TTG | CGA | GTT | TAT | TAC | TGC | TGT | CAA | GGT | TCA | TAT | TCT | CCT | |
| | S | R | V | E | A | E | D | L | G | V | Y | Y | C | C | Q | G | S | Y | S | P | |
| 361 | CAC | ACG | TTT | GGA | GCT | GGG | ACC | AAG | CTG | GAA | CTG | AAA | | | | | | | | | 396 |
| | H | T | F | G | A | G | T | K | L | E | L | K | | | | | | | | | |

TABLE 5

| | | | | | | | | | | | | | | | | | | | | |
|---|---|---|---|---|---|---|---|---|---|---|---|---|---|---|---|---|---|---|---|---|
| 1 | ATG | GCT | ATC | CTG | GTG | CTG | CTT | CTC | TGC | CTG | GTG | ACC | ATT | CCA | CAC | TCT | GTC | TTG | TCC | CAG | 60 |
| | M | A | I | L | V | L | L | L | C | L | V | T | I | P | H | S | V | L | S | Q | |
| 61 | GTG | CAG | CTG | AAG | GAG | ACA | GGA | CCT | GGC | CTG | GTG | CAA | CCA | ACA | CAG | ACC | CTG | TCC | ATC | ACA | 120 |
| | V | Q | L | K | E | T | G | P | G | L | V | Q | P | T | Q | T | L | S | I | T | |
| 121 | | | | | *CDR1* | | | | | | | | | | | | | | | | 180 |
| | TGT | ACT | GTT | TCT | GGG | TTC | TCA | TTA | ACC | AGC | TAT | TAT | ATG | CAG | TGG | GTT | CGC | CAG | ACT | CCA | |
| | C | T | V | S | G | F | S | L | T | S | Y | Y | M | Q | W | V | R | Q | T | P | |
| 181 | | | | | | | *CDR2* | | | | | | | | | | | | | | 240 |
| | GGA | AAG | GGA | CTA | GAA | TGG | ATG | GGA | TTT | ATA | CGG | AGT | GGT | GGA | AGC | ACA | GAG | TAT | AAT | TCA | |
| | G | K | G | L | E | W | M | G | F | I | R | S | G | G | S | T | E | Y | N | S | |
| 241 | GAG | TTC | AAA | TCC | CGA | CTT | AGC | ATC | AGC | AGG | GAC | ACC | TCC | AAG | AAC | CAA | GTT | TTC | TTA | AAA | 300 |
| | E | F | K | S | R | L | S | I | S | R | D | T | S | K | N | Q | V | F | L | K | |
| 301 | | | | | | | | | | | | | | | | | *CDR3* | | | | 360 |
| | ATG | AAC | AGT | CTG | AAA | ACA | GAG | GAC | ACA | GGC | GTG | TAC | TAC | TGT | GCC | AGA | GCC | TTC | TAC | GGA | |
| | M | N | S | L | K | T | E | D | T | G | V | Y | Y | C | A | R | A | F | Y | G | |
| 361 | GGG | TAC | TAC | TTT | GAT | TAC | TGG | GGC | CAA | GGA | GTC | ATG | GTC | ACA | GTC | TCC | TCA | | | | 411 |
| | G | Y | Y | F | D | Y | W | G | Q | G | V | M | V | T | V | S | S | | | | |

Clone 101 L Chain (SEQ ID NO: 16)

TABLE 6

| | | | | | | | | | | | | | | | | | | | | |
|---|---|---|---|---|---|---|---|---|---|---|---|---|---|---|---|---|---|---|---|---|
| 1 | ATG | GGC | ATC | AGG | ATG | GAG | TCA | CAT | ACT | AGG | GTC | TTC | ATA | TTC | CTG | CTG | CTC | TGG | TTG | TCT | 60 |
| | M | G | I | R | M | E | S | H | T | R | V | F | I | F | L | L | L | W | L | S | |
| 61 | GGT | GCT | GAT | GGG | GAC | ATT | GTG | ATG | ACT | CAG | TCT | CCC | ACA | TCC | ATT | TCC | ATA | TCA | GTA | GGA | 120 |
| | G | A | D | G | D | I | V | M | T | Q | S | P | T | S | I | S | I | S | V | G | |
| 121 | | | | | | | *CDR1* | | | | | | | | | | | | | | 180 |
| | GAG | AGG | GTC | ACC | ATG | AAC | TGC | AAG | GCC | AGT | CAG | AAT | GTG | GGT | TCT | AAT | GTA | GAC | TGG | TAC | |
| | E | R | V | T | M | N | C | K | A | S | Q | N | V | G | S | N | V | D | W | Y | |
| 181 | | | | | | | | | | | | | | | *CDR2* | | | | | | 240 |
| | CAA | CAG | AAA | ACA | GGG | CAG | TCT | CCT | AAA | CTG | CTT | ATC | TAC | AAG | GCA | TCC | AAC | CGG | TAC | ACT | |
| | Q | Q | K | T | G | Q | S | P | K | L | L | I | Y | K | A | S | N | R | Y | T | |

TABLE 6-continued

| | | | | | | | | | | | | | | | | | | | | |
|---|---|---|---|---|---|---|---|---|---|---|---|---|---|---|---|---|---|---|---|---|
| 241 | GGC | GTC | CCT | GAT | CGC | TTC | ACA | GGC | AGT | GGA | TCT | GGA | ACA | GAT | TTC | ACT | TTC | ACC | ATC | AGC | 300 |
| | G | V | P | D | R | F | T | G | S | G | S | G | T | D | F | T | F | T | I | S | |
| 300 | AAC | ATG | CAG | GCT | GAA | GAC | CTG | GCT | GTT | TAT | TAC | TGT | ATG | CAG | TCT | AAC | ACC | AAG | TAC | ACG | 360 |
| | | | | | | | | | | | | | | | | | | | CDR3 | | |
| | N | M | Q | A | E | D | L | A | V | Y | Y | C | M | Q | S | N | T | K | Y | T | |
| 361 | TTT | GGA | GCT | GGG | ACC | AAG | CTG | GAA | CTG | AAA | | | | | | | | | | | 390 |
| | P | G | A | G | T | K | L | E | L | K | | | | | | | | | | | |

Clone 212 H Chain (SEQ ID NO: 46)

TABLE 7

| | | | | | | | | | | | | | | | | | | | | |
|---|---|---|---|---|---|---|---|---|---|---|---|---|---|---|---|---|---|---|---|---|
| 1 | ATG | GAC | ATC | AGG | CTC | AGC | TTG | GCT | TTC | CTT | GTC | CTT | TTC | ATA | AAA | GGT | GTC | CAG | TGT | GAG | 60 |
| | M | D | I | R | L | S | L | A | F | L | V | L | F | I | K | G | V | Q | C | E | |
| 61 | GTG | CAG | CTG | GTG | GAG | TCT | GGC | GGA | GGA | TTG | GTA | CAG | CCT | GGA | AAC | TCC | CTG | AAA | CTC | TCC | 120 |
| | V | Q | L | V | E | S | G | G | G | L | V | Q | P | G | N | S | L | K | L | S | |
| 121 | | | | | CDR1 | | | | | | | | | | | | | | | | 180 |
| | TGT | GCA | GCC | TCA | GGA | TTC | ACT | TTC | AGT | GAC | TAT | GCC | ATG | GCC | TGG | GTC | CGC | CAG | TCT | CCA | |
| | C | A | A | S | G | F | T | F | S | D | Y | A | M | A | W | V | R | Q | S | P | |
| 181 | | | | | | | CDR2 | | | | | | | | | | | | | | 240 |
| | AAG | AAG | GGT | CTG | GAG | TGG | GTC | GCA | ACC | ATT | ATT | TAT | GAT | GGT | AGT | AGC | ACT | TAC | TAT | CGA | |
| | K | K | G | L | E | W | V | A | T | I | I | Y | D | G | S | S | T | Y | Y | R | |
| 241 | GAC | TCC | GTG | AAG | GGC | CGA | TTC | ACT | ATC | TCC | AGA | GAT | AAT | GCA | AAA | AGC | ACC | CTA | TAC | CTG | 300 |
| | D | S | V | K | G | R | F | T | I | S | R | D | N | A | K | S | T | L | Y | L | |
| 301 | | | | | | | | | | | | | | | | | | | CDR3 | | 360 |
| | CAA | ATG | GAC | AGT | CTG | AGG | TCT | GAG | GAC | ACG | GCC | ACT | TAT | TAC | TGT | GCA | ACA | CAT | TGG | TAC | |
| | Q | M | D | S | L | R | S | E | D | T | A | T | Y | Y | C | A | T | H | W | Y | |
| 361 | TGG | TAC | TTT | GAC | TTC | TGG | GGC | CCA | GGA | ACC | ATG | GTC | ACC | GTG | TCC | TCA | | | | | 408 |
| | W | Y | F | D | F | W | G | P | G | T | M | V | T | V | S | S | | | | | |

Clone 212 L Chain (SEQ ID NO: 47)

TABLE 8

| | | | | | | | | | | | | | | | | | | | | |
|---|---|---|---|---|---|---|---|---|---|---|---|---|---|---|---|---|---|---|---|---|
| 1 | ATG | GGT | GTG | CCC | ACT | CAG | CTC | CTG | GGG | TTG | TTG | CTG | CTC | TGG | ATT | ACA | GAT | GCC | ATA | TGT | 61 |
| | M | G | V | P | T | Q | L | L | G | L | L | L | L | W | I | T | D | A | T | C | |
| 61 | GAC | ATC | CAG | ATG | ACA | CAG | TCT | CCA | GCT | TCC | CTG | TCT | GCA | TCT | CTT | GGA | GAA | ACT | GTC | TCC | 120 |
| | D | I | Q | M | T | Q | S | P | A | S | L | S | A | S | L | G | E | T | V | S | |
| | | | | CDR1 | | | | | | | | | | | | | | | | | |
| 121 | ATC | GAA | TGT | CTA | GCA | AGT | GAG | GGC | ATT | TCC | AAT | GAT | TTA | GCG | TGG | TAT | CAG | CAG | AAG | TCA | 180 |
| | I | E | C | L | A | S | E | G | I | S | N | D | L | A | W | Y | Q | Q | K | S | |
| | | | | | | | | | | CDR2 | | | | | | | | | | | |
| 181 | GGG | AAA | TCT | CCT | CAG | CTC | CTG | ATC | TAT | GCT | GCA | AGT | AGG | TTG | CAA | GAC | GGG | GTC | CCA | TCA | 240 |
| | G | K | S | P | Q | L | L | I | Y | A | A | S | R | L | Q | D | G | V | P | S | |
| 241 | CGG | TTC | AGT | GGC | AGT | GGA | TCT | GGC | ACA | CGG | TAT | TCT | CTC | AAG | ATC | AGC | GGC | ATG | CAA | CCT | 300 |
| | R | F | S | G | S | G | S | G | T | R | Y | S | L | K | I | S | G | M | Q | P | |
| | | | | | | | CDR3 | | | | | | | | | | | | | | |
| 301 | GAA | GAT | GAA | GCA | GAT | TAT | TTC | TGT | CAA | CAG | AGT | TAC | AAG | TAT | CCT | CTC | ACG | TTC | GGT | TCT | 360 |
| | E | D | E | A | D | Y | F | C | Q | Q | S | Y | K | Y | P | L | T | F | G | S | |
| 361 | GGG | ACC | AAG | CTG | GAG | ATC | AAA | | | | | | | | | | | | | | 381 |
| | G | T | K | L | E | I | K | | | | | | | | | | | | | | |

Clone 129 H Chain (SEQ ID NO: 54)

TABLE 9

| ATG | GAT | TGG | TTG | TGG | AAC | TTG | CTA | TTC | CTG | ATG | GTA | GTT | GCC | CAA | AGT | GCT | CAA | GCA | CAG |
|---|---|---|---|---|---|---|---|---|---|---|---|---|---|---|---|---|---|---|---|
| M | D | W | L | W | N | L | L | F | L | M | V | V | A | Q | S | A | Q | A | Q |

| ATC | CAG | TTG | GTA | CAG | TCT | GGT | CCT | GAA | CTG | AAG | AAG | CCT | GGA | GAG | TCA | GTG | AAG | ATC | TCC |
|---|---|---|---|---|---|---|---|---|---|---|---|---|---|---|---|---|---|---|---|
| I | Q | L | V | Q | S | G | P | E | L | K | K | P | G | E | S | V | K | I | S |

*CDR1*

| TGC | AAG | GCT | TCT | GGG | TAT | ACC | TTC | ACA | GAC | TGT | GCA | CTG | AAC | TGG | GTG | AAA | CAG | GCT | CCA |
|---|---|---|---|---|---|---|---|---|---|---|---|---|---|---|---|---|---|---|---|
| C | K | A | S | G | Y | T | F | T | D | C | A | L | N | W | V | K | Q | A | P |

*CDR2*

| GGA | AAT | GGC | ITG | AAG | TGG | ATG | GGC | TGG | ATC | AAC | ACC | CAA | ACT | GGA | AAG | CCA | ACA | TAT | GCG |
|---|---|---|---|---|---|---|---|---|---|---|---|---|---|---|---|---|---|---|---|
| G | N | G | L | K | W | M | G | W | I | N | T | Q | T | G | K | P | T | Y | A |

| GAT | GAT | TTC | AAA | CAA | CGG | TTT | GTC | TTC | TCC | TTG | GAA | ACT | TCT | GCC | AGC | ACT | GCA | TAC | TTG |
|---|---|---|---|---|---|---|---|---|---|---|---|---|---|---|---|---|---|---|---|
| D | D | F | K | Q | R | F | V | F | S | L | E | T | S | A | S | T | A | Y | L |

*CDR3*

| CAG | ATC | AAC | AAC | CTC | AAT | ATT | GAG | GAC | ACA | GCT | ACA | TAT | TTC | TGT | ACA | AGA | GAG | GAC | TAC |
|---|---|---|---|---|---|---|---|---|---|---|---|---|---|---|---|---|---|---|---|
| Q | I | N | N | L | N | I | E | D | T | A | T | Y | F | C | T | R | E | D | Y |

| GGG | TAT | TIT | GAT | TAC | TGG | GGC | CAA | GGA | GTC | ATG | GTC | ACA | GTC | TCC | TCA |
|---|---|---|---|---|---|---|---|---|---|---|---|---|---|---|---|
| G | Y | F | D | Y | W | G | Q | G | V | M | V | T | V | S | S |

Clone 129 L Chain (SEQ ID NO: 55)

TABLE 10

| ATG | AGG | ACT | TCA | ATT | CAA | CTC | CTG | GGG | CTC | TTG | CTG | TTG | CTC | TGG | CTT | CAT | GAT | GCT | TGT |
|---|---|---|---|---|---|---|---|---|---|---|---|---|---|---|---|---|---|---|---|
| M | R | T | S | I | Q | L | L | G | L | L | L | L | L | W | L | H | D | A | Q | C |

| GAC | ATC | CAA | ATG | ACA | CAG | TCT | CCT | CCC | TCC | CTG | TCT | GCA | TCT | CTG | GGA | GAC | AAA | GIC | ACC |
|---|---|---|---|---|---|---|---|---|---|---|---|---|---|---|---|---|---|---|---|
| D | I | Q | M | T | Q | S | P | P | S | L | S | A | S | L | G | D | K | V | T |

*CDR1*

| ATC | ACT | TGC | CAG | GCA | AGT | CAA | AAC | ATT | AAC | AAA | TTT | ATA | GCT | TGG | TAT | CAG | CAA | AAG | CCT |
|---|---|---|---|---|---|---|---|---|---|---|---|---|---|---|---|---|---|---|---|
| I | T | C | Q | A | S | Q | N | I | N | K | F | I | A | W | Y | Q | Q | K | P |

*CDR2*

| GGA | AAA | GCT | CCT | AGG | CAT | CTC | GTA | CAT | TAC | ACT | TCT | ACA | CTA | GTG | TCA | GGC | ACC | CCA | TCG |
|---|---|---|---|---|---|---|---|---|---|---|---|---|---|---|---|---|---|---|---|
| G | K | A | P | R | H | L | V | H | Y | T | S | T | L | V | S | G | T | P | S |

| AGG | TTC | AGT | GGC | AGT | GGA | TCT | GGG | AGA | GAT | TAT | TCA | TTC | AGC | ATC | AGC | AAC | GTG | GAG | TCT |
|---|---|---|---|---|---|---|---|---|---|---|---|---|---|---|---|---|---|---|---|
| R | F | S | G | S | G | S | G | R | D | Y | S | F | S | I | S | N | V | E | S |

*CDR3*

| GAA | GAT | ATT | GCA | AGT | TAT | TAC | TGT | CTA | CAG | TAC | GAT | AAC | CIT | CGG | ACG | TTC | GGT | GGA | GGC |
|---|---|---|---|---|---|---|---|---|---|---|---|---|---|---|---|---|---|---|---|
| E | D | I | A | S | V | Y | C | L | Q | Y | D | N | L | R | T | F | G | G | G |

| ACC | AAG | CTG | GAA | TTG | AAA |
|---|---|---|---|---|---|
| T | K | L | E | L | K |

Clone 382 H Chain (SEQ ID NO: 62)

TABLE 11

| ATG | GAC | ATC | AGG | CTC | AGC | TTG | GTT | TTC | CTT | GTC | CTT | TTC | ATA | AAA | GGT | GTC | CAA | TGT | GAG |
|---|---|---|---|---|---|---|---|---|---|---|---|---|---|---|---|---|---|---|---|
| M | D | I | R | L | S | L | G | F | L | V | L | F | I | K | G | V | Q | C | E |

| GTG | CAG | CTG | GTG | GAG | TCT | GGG | GGA | GGC | TTG | GTG | CAG | CCT | GGA | AGG | TCC | CTG | AAA | CTC | TCC |
|---|---|---|---|---|---|---|---|---|---|---|---|---|---|---|---|---|---|---|---|
| V | Q | L | V | E | S | G | G | G | L | V | Q | P | G | R | S | L | K | L | S |

*CDR1*

| TGT | GCA | GCC | TCA | GGA | TTC | ACT | TTC | AGT | AAC | TAT | GGC | ATG | CAG | TGG | ATC | CGC | CAG | GCT | CCA |
|---|---|---|---|---|---|---|---|---|---|---|---|---|---|---|---|---|---|---|---|
| C | A | A | S | G | F | T | F | S | N | Y | G | M | H | W | I | R | Q | A | P |

*CDR2*

| ACG | AAG | GGT | CTG | GAG | TGG | GTC | GCA | TCC | ATT | AGT | CCT | AGT | GGT | GGT | AGC | ACT | TAC | TAT | CGA |
|---|---|---|---|---|---|---|---|---|---|---|---|---|---|---|---|---|---|---|---|
| T | K | G | L | E | W | V | A | S | I | S | P | S | G | G | S | T | Y | Y | R |

TABLE 11-continued

| GAC | TCC | GTG | AAG | GGC | CGA | TTC | ACT | ATC | TCC | AGG | GAT | AAT | GCA | AAA | AGC | ACC | CTA | TAC | CTG |
|---|---|---|---|---|---|---|---|---|---|---|---|---|---|---|---|---|---|---|---|
| D | S | V | K | G | R | F | T | I | S | R | D | N | A | K | S | T | L | Y | L |

(CDR3)

| CAA | ATG | GAC | AGT | CTG | AGG | TCT | GAG | GAC | ACG | GCC | ACT | TAT | TAC | TGT | GCA | ACC | AGC | GCG | TCT |
|---|---|---|---|---|---|---|---|---|---|---|---|---|---|---|---|---|---|---|---|
| Q | M | D | S | L | R | S | E | D | T | A | T | Y | Y | C | A | T | S | A | S |

| ATA | ACA | GCA | TAT | TAC | TAT | GTT | ATG | GAT | GCC | TGG | GGT | CAA | GGA | GCT | TCA | GTC | ACT | GTC | TCC |
|---|---|---|---|---|---|---|---|---|---|---|---|---|---|---|---|---|---|---|---|
| I | T | A | Y | Y | Y | V | M | D | A | W | G | Q | G | A | S | V | T | V | S |

| TCA |
|---|
| S |

Clone 382 L Chain (SEQ ID NO: 63)

TABLE 12

| ATG | GAG | TCA | CAT | ACT | AGG | GTC | TTC | ATA | TTC | CTG | CTG | CTG | TGG | TTG | TCT | GGT | GCT | GAT | GGG |
|---|---|---|---|---|---|---|---|---|---|---|---|---|---|---|---|---|---|---|---|
| M | E | S | H | T | R | V | F | I | F | L | L | L | W | L | S | G | A | D | G |

| GAC | ATT | GTG | ATG | ACT | CAG | TCT | CCC | ACA | TCC | ATG | TCC | ATA | TCA | GTA | GGA | GAC | AGG | GTC | ACC |
|---|---|---|---|---|---|---|---|---|---|---|---|---|---|---|---|---|---|---|---|
| D | I | V | M | T | Q | S | P | T | S | M | S | I | S | V | G | D | R | V | T |

(CDR1)

| ATG | AAC | TGC | AAG | GCC | AGT | CAA | AAT | GTG | GGT | TCT | AAT | GTA | GAC | TGG | TAC | CAA | CAG | AAA | ACA |
|---|---|---|---|---|---|---|---|---|---|---|---|---|---|---|---|---|---|---|---|
| M | N | C | K | A | S | Q | N | V | G | S | N | V | D | W | Y | Q | Q | K | T |

(CDR2)

| GGG | CAG | TCT | CCT | AAA | CTG | CTT | ATC | TAC | AAA | GCA | TCC | AAG | CGG | TAC | ACG | GGA | GTC | CCT | GAT |
|---|---|---|---|---|---|---|---|---|---|---|---|---|---|---|---|---|---|---|---|
| G | Q | S | P | K | L | L | I | Y | K | A | S | N | R | Y | T | G | V | P | G |

| CGC | TTC | ACA | GGC | AGT | GGA | TCT | GGA | ACA | GAT | TTC | ACT | TTC | ACC | ATC | AGG | AAC | ATG | CAG | GCT |
|---|---|---|---|---|---|---|---|---|---|---|---|---|---|---|---|---|---|---|---|
| R | F | T | G | S | G | S | G | T | D | F | T | F | T | I | S | N | M | Q | A |

(CDR3)

| GAA | GAC | CTG | GCT | GTT | TAT | TAC | TGT | ATG | CAG | TCT | AAC | TCC | TAT | CCT | CCG | ACG | TTC | GGT | GGA |
|---|---|---|---|---|---|---|---|---|---|---|---|---|---|---|---|---|---|---|---|
| E | D | L | A | V | Y | Y | C | M | Q | S | N | S | Y | P | P | T | F | G | G |

| GGC | ACC | AAG | CTG | GAA | TTG | AGA |
|---|---|---|---|---|---|---|
| G | T | K | L | E | L | R |

Clone 1361 H Chain (SEQ ID NO: 70)

TABLE 13

| ATG | GAC | ATC | AGG | CTC | AGC | TTG | GTT | TTC | CTT | GTC | CTT | TTC | ATA | AAA | GGT | GTC | CAG | TGT | GAG |
|---|---|---|---|---|---|---|---|---|---|---|---|---|---|---|---|---|---|---|---|
| M | D | I | R | L | S | L | V | F | L | V | L | F | I | K | G | V | Q | C | E |

| GTG | CAG | CTG | GTG | GAG | TCT | GGG | GGA | GGC | CTA | GTG | CAG | CCT | GGA | AGG | TCT | CTG | AAA | CTA | TCC |
|---|---|---|---|---|---|---|---|---|---|---|---|---|---|---|---|---|---|---|---|
| V | Q | L | V | E | S | G | G | G | L | V | Q | P | G | R | S | L | K | L | S |

(CDR1)

| TGT | GTA | GCC | TCT | GGA | TTC | ACA | TTC | AAT | AAC | TAC | TGG | ATG | ACC | TGG | ATC | CGC | CAG | GCT | CCA |
|---|---|---|---|---|---|---|---|---|---|---|---|---|---|---|---|---|---|---|---|
| C | V | A | S | G | F | T | F | N | N | Y | W | M | T | W | I | R | Q | A | P |

(CDR2)

| GGG | AAG | GGG | CTG | GAG | TGG | GTT | GCA | TCC | ATT | ACT | AAT | ACT | GGT | GGT | AGC | ACT | TAC | TAT | CCA |
|---|---|---|---|---|---|---|---|---|---|---|---|---|---|---|---|---|---|---|---|
| G | K | G | L | E | W | V | A | S | I | T | N | T | G | G | S | T | Y | Y | P |

| GAC | TCT | GTG | AAG | GGC | CGA | TTC | ACT | ATC | TCC | AGA | GAT | TAT | GCA | AAA | AGC | ACC | CTA | TAC | CTG |
|---|---|---|---|---|---|---|---|---|---|---|---|---|---|---|---|---|---|---|---|
| D | S | V | K | G | R | F | T | I | S | R | D | Y | A | K | S | T | L | Y | L |

(CDR3)

| CAA | ATG | AAC | AGT | CTG | AGG | TCT | GAG | GAC | ACG | GCC | ACT | TAT | TAC | TGT | ACA | AGA | GCT | GGC | TAT |
|---|---|---|---|---|---|---|---|---|---|---|---|---|---|---|---|---|---|---|---|
| Q | M | N | S | L | R | S | E | D | T | A | T | Y | Y | C | T | R | A | G | Y |

| AGC | AGC | TAT | CCC | GAC | TAC | TTT | GAT | TAC | TGG | GGC | CAA | GGA | GTC | ATG | CTC | ACA | GTC | TCC | TCA |
|---|---|---|---|---|---|---|---|---|---|---|---|---|---|---|---|---|---|---|---|
| S | S | Y | P | D | Y | F | D | Y | W | G | Q | G | V | M | L | T | V | S | S |

Clone 1361 L Chain (SEQ ID NO: 71)

TABLE 14

```
ATG ATG CCT CCA GTT CAA CTC TTA GGG CTG CTG CTG CTC TGG CTC CCA GCC ATG AGA TGT
 M   M   P   P   V   Q   L   L   G   L   L   L   L   W   L   P   A   M   R   C
AAC ATC CAG ATG ACC CAG TCT CCT TCA CTA CTC TCT GCA TCT GTG GGA GAC AGA GTC ACT
 N   I   Q   M   T   Q   S   P   S   L   L   S   A   S   V   G   D   R   V   T
                        CDR1
CTC AGC TGC |AAA GCA GGT CAG AAT ATT TAC AAT TAC TTA GCC| TGG TAT CAG CAA AAG CTT
 L   S   C  | K   A   G   Q   N   I   Y   N   Y   L   A | W   Y   Q   Q   K   L
                                                   CDR2
GGA GAA GCT CCC AAA CTC CTG ATT TAT |AAT GCA AAC AGT TTG CAA ACG| GGC ATC CCA TGA
 G   E   A   P   K   L   L   I   Y  | N   A   N   S   L   Q   T | G   I   P   S
AGG TTC AGT GGC ACT GGA TCT GGT ACA GAT TTC ACA CTC ACC ATC AGC AGC CTG CAG CCT
 R   F   S   G   S   G   S   G   T   D   F   T   L   T   I   S   S   L   Q   P
                                            CDR3
GAA GAT GTT GCC ACA TAT TTC TGC CAG |CAG TAT AGC AGT GGG TGG| ACG TTC GGT GGT GGC
 E   D   V   A   T   Y   F   C   Q  | Q   Y   S   S   G   W | T   F   G   G   G
ACC AAG CTG GAA TTG AAA
 T   K   L   E   L   K
```

Clone 669 H Chain (SEQ ID NO: 78)

TABLE 15

```
  1 ATG GGA TGG ATC TGT ATC ATC TTT CTT GTG GCA ACA GCT ACA GGT GTC CAC TCC CAG GTC  60
     M   G   W   I   C   I   I   F   L   V   A   T   A   T   G   V   H   S   Q   V
 61 AAG CTG CTG CAG TCT GGG GCT GCA CTG GTG AAG CCT GGA GCC TCT GTG AAG ATG TCT TGC 120
     K   L   L   Q   S   G   A   A   L   V   K   P   G   A   S   V   K   M   S   C
                                                 CDR1
121 AAA GCT TCT GGT TAT ACA TTC ACT |GAC TAC TGG GTG AGC| TGG GTG AAG CAG AGT CAT GGA 180
     K   A   S   G   Y   T   F   T  | D   Y   W   V   S | W   V   K   Q   S   H   G
                                                   CDR2
181 AAG AGC CTT GAG TGG ATT GGG |GAA ATT TAT CCT AAC AGT GGT GCT ACT AAC TTC AAT GAA 240
     K   S   L   E   W   I   G  | E   I   V   P   N   S   G   A   T   N   F   N   E
241 AAC TTC AAG| GGC AAG GCC ACA TTG ACT GTA GAC AAA TCC ACC AGC ACA GCC TAT ATG GAG 300
     N   F   K | G   K   A   T   L   T   V   D   K   S   T   S   T   A   Y   M   E
                                                                           CDR3
301 CTC AGC AGA TTG ACA TCT GAG GAC TCT GCA ATC TAT TAC TGT ACA AGA |GAC GGG ACT ATG 360
     L   S   R   L   T   S   E   D   S   A   I   Y   Y   C   T   R  | D   G   T   M
361 GGT ATA GCC TAC TAC TTT GAT TAC| TGG GGC CAA GGA GTC ATG GTC ACA GTC TCC TCA    420
     G   I   A   Y   Y   F   D   Y | W   G   Q   G   V   M   V   T   V   S   S
```

50

Clone 669 L Chain (SEQ ID NO: 79)

TABLE 16

```
  1 ATG ATG GCT GCA GTT CAA CTC TTA GGG CTG CTG CTG CTT TGG GTC CCA GCC ATG AGA TGT  60
     M   M   A   A   V   Q   L   L   G   L   L   L   L   W   V   P   A   M   R   C
 61 GAC ATC CAG ATG ACC CAG TCT CCT TCA TTC CTG TCT GCA TCT GTG GGA GAC AGA GTC ACT 120
     D   I   Q   M   T   Q   S   P   S   F   L   S   A   S   V   G   D   R   V   T
                        CDR1
121 ATC AAC TGC |AAA GCA AGT CAG AAT ATT AAC AGG TAC TTA AAC| TGG TAC CAG CAA AAG CTT 180
     I   N   C  | K   A   S   Q   N   I   N   R   Y   L   N | W   Y   Q   Q   K   L
                                                   CDR2
181 GGA GAA GCT CCC AAA CTC CTG ATA TAT |AAT GCA AAC AGT TTG CAA ACG| GGC ATC CCA TCA 240
     G   E   A   P   K   L   L   I   Y  | N   A   N   S   L   Q   T | G   I   P   S
```

TABLE 16-continued

```
241 CGG TTC AGT GGC AGT GGA TCT GGT ACT GAT TTC ACA CTC ACC ATC AGC AGC CTG CAG CCT 300
     R   F   S   G   S   G   S   G   T   D   F   T   L   T   I   S   S   L   Q   P
                                                                          CDR3
301 GAA GAT GTT GCC ACA TAT TTC TGC |TTG CAG CAT AAT AGT TGG CCG TAC ACG| TTT GGA GCT 360
     E   D   V   A   T   Y   F   C  | L   Q   H   N   S   W   P   Y   T | F   G   A

361 GGG ACC AAG CTG GAA CTG AAA                                                     420
     G   T   K   L   E   L   K
```

Clone 699 H Chain (SEQ ID NO: 86)

TABLE 17

```
  1 ATG GAA TGG AAC TGG GTC TTT CTC TTC CTC CTG TCA GTA ACT GCA GGA GTC CAC TCC CAG  60
     M   E   W   N   W   V   F   L   F   L   L   S   V   T   A   G   V   H   S   Q

61 GTC CAG CTG CAG CAG TCT GGA GCT GAG CTG ACA AAG CCT GGC TCT TCA GTG AAG ATT TCC 120
     V   Q   L   Q   Q   S   G   A   E   L   T   K   P   G   S   S   V   K   I   S
                                                     CDR1
121 TGC AAG GCT TCT GGC TAC ACC TTT ACC |AGC TAC GAT ATA| AGC TGG ATA AAG CAG AGG CCT 180
     C   K   A   S   G   Y   T   F   T  | S   Y   D   I | S   W   I   K   Q   R   P
                                         CDR2
181 GGA CAG GCC CTT GAG TGG ATT GGA |GCT ATT AAT CCA GGA AGT GGA GGT ACA GGC TAC AAT|240
     G   Q   A   L   E   W   I   G  | A   I   N   P   G   S   G   G   T   G   Y   N |

241 |GAG AAG TTC AAG GGC AAG| GCC ACA TTG ACT GTA GAC AAA TCC TCC AGC ACA GCC TTC ATG 300
    | E   K   F   K   G   K | A   T   L   T   V   D   K   S   S   S   T   A   F   M
                                                                            CDR3
301 CAA CTC AGC AGC CTG ACA CCT GAG GAC ACT GCG GTC TAT TAC TGT GCA AGA |ATC CAC GGA 360
     Q   L   S   S   L   T   P   E   D   T   A   V   Y   Y   C   A   R  | I   H   G

361 |GGG TAT AGA TAT TGG TTT GCT TAC| TGG GGC CAA GGC ACT CTG GTC ACT GTC TCT TCA    420
    | G   Y   R   Y   W   F   A   Y | W   G   Q   G   T   L   V   T   V   S   S
```

Clone 699 L Chain (SEQ ID NO: 87)

TABLE 18

```
  1 ATG GAT TTT CAG GTG CAC ACT TTC AGC CTC CTG CTA ATC AGT ATC ACA GTC ATA GTG TCC 120
     M   D   F   Q   V   Q   S   F   S   L   L   L   I   S   I   T   V   I   V   S

61 AGT GGA GAA ATT GTG CTC ACC CAG TCT CCA ACA ACC ATG GCT GCA TCT CCA GGA GAG AAG 180
     S   G   E   I   V   L   T   Q   S   P   T   T   M   A   A   S   P   G   E   K
                                      CDR1
121 GTC ACC ATC ACC TGC |CGT GCC AGC TCA AGT GTA AGT TAC ATG CAC| TGG TTC CAG CAG AAG 210
     V   T   I   T   C  | R   A   S   S   S   V   S   Y   M   H | W   F   Q   Q   K
                                                   CDR2
181 TCA GGC ACC TCC CCC AAA CCC TGG ATT TAT |GAC ACA TCC AAG CTG GCT TCT| GGA GTC CCA 300
     S   G   T   S   P   K   P   W   I   Y  | D   T   S   K   L   A   S | G   V   P

241 GAT CGC TTC AGT GGC AGT GGG TCT GGG ACC TCT TAT TCT CTC ACA ATC AGC TCC ATG GAG 360
     D   R   F   S   G   S   G   S   G   T   S   Y   S   L   T   I   S   S   M   E
                                                    CDR3
301 GCT GAA GAT GCT GCT ACT TAT TAC TGT |CTG CAG AGG AGT AGT TAC CCA CCA ACG| TTT GGA 420
     A   E   D   A   A   T   Y   Y   C  | L   Q   R   S   S   Y   P   P   T | F   G

361 GCT GGG ACC AAG CTG GAA CTG AAA                                                 480
     A   G   T   K   L   E   L   K
```

Clone 1052 H Chain (SEQ ID NO: 94)

TABLE 19

| 1 | ATG | GCT | GTC | CTG | GTG | CTA | TTG | CTC | TGC | CTG | GTG | ACA | TTT | CCA | AGC | TGT | GTC | CTG | TCC | CAG | 60 |
|---|---|---|---|---|---|---|---|---|---|---|---|---|---|---|---|---|---|---|---|---|---|
|  | M | A | V | L | V | L | L | C | L | V | T | F | P | S | C | V | L | S | Q |  |
| 61 | GTG | CAG | CTG | AAG | GAG | TCA | GGA | CCT | GGC | TTG | ATG | CAG | CCC | TCA | GAG | ACC | CTG | TCC | CTC | ACC | 120 |
|  | V | Q | L | K | E | S | G | P | G | L | M | Q | P | S | E | T | L | S | L | T |  |

CDR1

| 121 | TGC | ACT | GTC | TCT | GGC | TTC | TCA | CTC | ACC | AGC | AAT | GGT | GTA | GGC | TGG | GTT | CGA | CAA | CCT | CTA | 180 |
|---|---|---|---|---|---|---|---|---|---|---|---|---|---|---|---|---|---|---|---|---|---|
|  | C | T | V | S | G | F | S | L | T | S | N | G | V | G | W | V | R | Q | P | L |  |

CDR2

| 181 | GGA | AAG | GGT | TTG | GTG | TGG | ATG | GGA | ACA | ATA | TGG | ACT | GGT | GGA | GGT | ACA | AAT | TAT | AAT | TCA | 240 |
|---|---|---|---|---|---|---|---|---|---|---|---|---|---|---|---|---|---|---|---|---|---|
|  | G | K | G | L | V | W | M | G | T | I | W | T | G | G | G | T | N | Y | N | S |  |
| 241 | GGT | GTC | CAA | TCC | CGA | CTG | AGC | ATC | AGC | AGG | GAC | ACC | TCC | AAG | AGC | CAA | GTG | TTC | TTA | AAA | 300 |
|  | G | V | Q | S | R | L | S | I | S | R | D | T | S | K | S | Q | V | F | L | K |  |

CDR3

| 301 | ATG | AAC | AGT | CTG | CAA | CCT | GAA | GAC | ACA | GGC | ACT | TAC | TAC | TGT | GCC | AGA | CAG | TAT | ATG | GGT | 360 |
|---|---|---|---|---|---|---|---|---|---|---|---|---|---|---|---|---|---|---|---|---|---|
|  | M | N | S | L | Q | P | E | D | T | G | T | Y | Y | C | A | R | E | Y | M | G |  |
| 361 | TTT | GAT | TAC | TGG | GGC | CAA | GGA | GTC | ATG | GTC | ACA | GTC | TCC | TCA |  |  |  |  |  |  | 420 |
|  | F | D | Y | W | G | Q | G | V | M | V | T | V | S | S |  |  |  |  |  |  |  |

Clone 1052 L Chain (SEQ ID NO: 95)

TABLE 20

| 1 | ATG | GAG | TTA | ATC | AGT | CAG | GTC | TTC | GTA | TTT | CTG | CTG | CTC | TGG | TTG | TCT | GGG | GTT | TAT | GGG | 120 |
|---|---|---|---|---|---|---|---|---|---|---|---|---|---|---|---|---|---|---|---|---|---|
|  | M | E | L | I | S | Q | V | F | V | F | L | L | L | W | L | S | G | V | Y | G |  |
| 61 | AAT | ACT | GTG | ATG | ACC | CAG | TCT | CCC | ACA | TCT | ATG | TTC | ACA | TCA | GTA | GGA | GAC | AGG | GTT | ACC | 180 |
|  | N | T | V | M | T | Q | S | P | T | S | M | F | T | S | V | G | D | R | V | T |  |

CDR1

| 121 | ATG | AGC | TGC | AAG | GCC | AGT | CAG | AAT | GTA | GGT | ATT | AAT | GTA | GGC | TGG | TAC | CAA | CAG | AAA | ACA | 210 |
|---|---|---|---|---|---|---|---|---|---|---|---|---|---|---|---|---|---|---|---|---|---|
|  | M | S | C | K | A | S | Q | N | V | G | I | N | V | G | W | Y | Q | Q | K | T |  |

CDR2

| 181 | GGG | CAG | TCT | CCT | AAA | CGG | CTT | ATC | TAC | TGG | GCA | TCC | AAC | CGG | GAC | ACT | GGG | GTC | CCT | GAT | 300 |
|---|---|---|---|---|---|---|---|---|---|---|---|---|---|---|---|---|---|---|---|---|---|
|  | G | Q | S | P | K | R | L | I | Y | W | A | S | N | R | D | T | G | V | P | D |  |
| 241 | GCG | TTC | ACA | GGC | AGT | GGA | TCT | GGG | ACA | GAT | TTC | ACT | CTC | ACC | ATC | AGC | AAC | ATG | CAG | GCT | 360 |
|  | R | F | T | G | S | G | S | G | T | D | F | T | L | T | I | S | N | M | Q | A |  |

CDR3

| 301 | GAA | GAC | CCA | GCT | ATT | TAT | TAC | TGT | CTG | CAG | CAT | AAC | TCC | TAT | CCT | CGG | ACG | TTC | GGT | GGA | 420 |
|---|---|---|---|---|---|---|---|---|---|---|---|---|---|---|---|---|---|---|---|---|---|
|  | E | D | P | A | I | Y | Y | C | L | Q | H | N | S | Y | P | R | T | F | G | G |  |
| 361 | GGC | ACC | AAG | CTG | GAA | TTG | AAA |  |  |  |  |  |  |  |  |  |  |  |  |  | 480 |
|  | G | T | K | L | E | L | K |  |  |  |  |  |  |  |  |  |  |  |  |  |  |

50

Clone 1105 H Chain (SEQ ID NO: 102)

TABLE 21

| 1 | ATG | GCT | GTC | CTG | GTG | CTA | TTG | CTC | TGC | CTG | CTG | ACA | TTT | CCA | AGC | TGT | CTG | CTG | TCC | CAG | 60 |
|---|---|---|---|---|---|---|---|---|---|---|---|---|---|---|---|---|---|---|---|---|---|
|  | M | A | V | L | V | L | L | L | C | L | V | T | F | P | S | C | L | L | S | Q |  |
| 61 | GTG | CAG | CTG | AAG | GAG | TCA | GGA | CCT | GGC | TTG | ATG | CAG | CCC | TCA | GAG | ACC | CTG | TCC | CTC | ACC | 120 |
|  | V | Q | L | K | E | S | G | P | G | L | M | Q | P | S | F | T | L | S | L | T |  |

CDR1

| 121 | TGC | ACT | GTC | TCT | GGC | TTC | TCA | CTA | ACC | AGC | AAT | GGT | GTA | GGC | TGG | GTT | CGA | CAA | CCT | CTA | 180 |
|---|---|---|---|---|---|---|---|---|---|---|---|---|---|---|---|---|---|---|---|---|---|
|  | C | T | V | S | G | F | S | L | T | S | N | G | V | G | W | V | R | Q | P | L |  |

CDR2

| 181 | GGA | AAG | GGT | TTG | GTG | TGG | ATG | GGA | ACA | ATA | TGG | TCT | CGT | GGA | GGT | ACA | AAC | TAT | AAT | TCA | 240 |
|---|---|---|---|---|---|---|---|---|---|---|---|---|---|---|---|---|---|---|---|---|---|
|  | G | K | G | L | V | W | M | G | T | I | W | S | G | G | G | T | N | Y | N | S |  |

TABLE 21-continued

| 241 | GCT GTC CAA TCC | CGA CTG AGC ATC ACC ACG GAC ACC TCC AAG AGC CAA GTT TTC TTA AAA | 300 |
|---|---|---|---|
| | A V Q S | R L S I T R D T S K S Q V F L K | |

CDR3

| 301 | ATG AAC AGT CTG CAA CCT GAA GAC ACA GGC ACT TAC TAC TGT GCC AGA | GAG GAA AAG GGG | 360 |
|---|---|---|---|
| | M N S L Q P E D T G T Y Y C A R | E E K G | |

| 361 | TTT GCT TAC | TGG GGC CAA GGC ACT CTG GTC ACT GTC TCT TCA | 402 |
|---|---|---|---|
| | F A Y | W G Q G T L V T V S S | |

Clone 1052 L Chain (SEQ ID NO: 103)

TABLE 22

| 1 | ATG GAG TTA ATC AGT CAG GTC TTC GTA TTT CTG CTG CTC TGG TTG TCT GGG GTT TAT GGG | 60 |
|---|---|---|
| | M E L I S Q V F V F L L L W L S G V Y G | |

| 61 | AAC ATT GTG ATG ACC CAG TCT CCC ACA TCT ATG TCC ACA TCA GTA GGA GAC AGG GTT ACC | 120 |
|---|---|---|
| | N T V M T Q S P T S M S T S V G D R V T | |

CDR1

| 121 | ATG AGC TGC | AAG GCC AGT CAG AAT GTA GGT ATT AAT GTA GGC | TGG TAC CAA CAG AAA ACA | 180 |
|---|---|---|---|---|
| | M S C | K A S Q N V G I N V G | W Y Q Q K T | |

CDR2

| 181 | GGG CAG TCT CCT AAA CGG CTT ATC TAC | TGG GCA TCC AAC CGG GAC ACT | GGG GTC CCT GAT | 240 |
|---|---|---|---|---|
| | G Q S P K R L J Y | W A S N R D T | G V P D | |

| 241 | CGC TTC ACA GGC AGT GGA TCT GGG ACA GAT TTC ACT CTC ACC ATC AGC AAC ATG CAG GCT | 300 |
|---|---|---|
| | R F T G S G S G T D F T L T I S N M Q A | |

CDR3

| 301 | GAA GAC CCA GCT ATT TAT TAC TGT | CTG CAG CAT AAC TCC TAT CCT CGG GCG | TTC GGT GGA | 360 |
|---|---|---|---|
| | E D P A I Y Y C | L Q H N S Y P R A | F G G | |

| 361 | GGC ACC AAG CTG GAA TTG AGA | 381 |
|---|---|---|
| | G T K L E L R | |

9. Cancer Testing Method Involving Measurement of Amount of TMEM-180

1) ELISA Protocol

First, the following indicates the protocol for the ELISA method used in the following examples.

(Reagents)

The following reagents were used.

96-well plate: C8 Maxi Breakapart (Nunc Co., Ltd. #473768)

Plate washing solution: PBS/0.05% TWEEN® 20 (polysorbate 20)

Blocking solution: PBS/1% BSA

Antibody diluent: PBS/0.05% TWEEN® 20 (polysorbate 20)/1% BSA

Primary antibody: IgM 98 (hybridoma culture supernatant)

Secondary antibody: Polyclonal rabbit anti-rat immunoglobulins/HRP (Dako #P0450)

Color developing solution: 1-Step Slow TMB-ELISA Substrate (Thermo Fisher Scientific Inc. #34024)

Stopping solution: 2N H2SO4

(Procedure)

Testing was carried out according to the procedure indicated below.

(i) Antigen Immobilization

Antibody culture supernatant or human serum (diluted 1/10 and 1/50) was added to a 96-well plate at 50 μL/well followed by incubating overnight at 4° C.

(ii) Blocking

The antigen-immobilized plate was repeatedly washed five times with plate washing solution at 200 μL/well. Blocking was then carried out with blocking solution at 200 μL/well followed by incubating for 1 hour at room temperature.

(iii) Primary Antibody Reaction

The antigen-immobilized plate was repeatedly washed five times with plate washing solution at 200 μL/well. IgM 98 antibody solution was then added at 100 μL/well and 10 μg/mL followed by incubating for 1 hour at room temperature.

(iv) Secondary Antibody Reaction

The antigen-immobilized plate was repeatedly washed five times with plate washing solution at 200 μL/well. Secondary antibody diluted 4000-fold was added at 100 L/well followed by incubating for 1 hour at room temperature.

(v) Color Development and Stopping of the Reaction

The antigen-immobilized plate was repeated washed five times with plate washing solution at 200 μL/well. Color developing solution was then added at 100 μL/well followed by incubating for 15 minutes at room temperature. Stopping solution was then added at 100 L/well.

(vi) Measurement

Absorbance at 450 nm was measured after stopping the reaction.

2) Measurement of Amount of TMEM-180 Protein in Cancer Cell Culture Supernatant (Preparation of TMEM-180-Forcibly Expressed Line)

Plasmid RC219636 (Origen) comprising human TMEM180 cDNA (NM 024789.2) were transfected into DLD-1 cells with LIPOFECTAMINE® (transfection reagent) LTX (Invitrogen). Human TMEM-180 expressing lines were subjected to drug selection using Geneticin (Invitrogen) to obtain a resistant line. The obtained resistant line was subjected to limited dilution to confirm the reactivity of the antibody with FACS for each single clone. The obtained line was further subjected to maintenance culture in DMEM (Wako), 10% FBS, 1% penicillin, streptomycin, amphoterin B (Wako), 600 µg/mL of Geneticin (Invitrogen).

(Preparation of TMEM-180 Knockdown Line)

The TMEM-180 knockdown line was generated by using MISSION™ shRNA Lentiviral Transduction Particles (Sigma-Aldrich Corporation, St. Louis, Mo.) according to the manufacturer's manual for each of the colon cancer cell lines DLD-1, HCT116, HCT15 and Colo320 purchased from American Type Culture Collection (ATCC, Manassas, Va.). Knockdown of TMEM-180 gene expression was confirmed by a quantitative PCR using TaqMan@ Gene Expression Assays (Life Technologies Corporation, Carlsbad, Calif.).

(Measurement of the Amount of TMEM-180 Protein in the Culture Supernatant from Cancer Cells)

Colon cancer cell line DLD-1 that forcibly expresses TMEM-180, the parent line and the TMEM-180 knockdown line were cultured and washed with PBS after nearly reaching confluency. The medium was replaced with serum-free DMEM medium followed by culturing overnight and recovering the supernatant on the following day. This supernatant was used as sample antigen and immobilized on a 96-well plate followed by carrying out ELISA according to the method described in section 1). In addition, a similar experiment was conducted on brain tumor cell line LN229.

Figure 9:
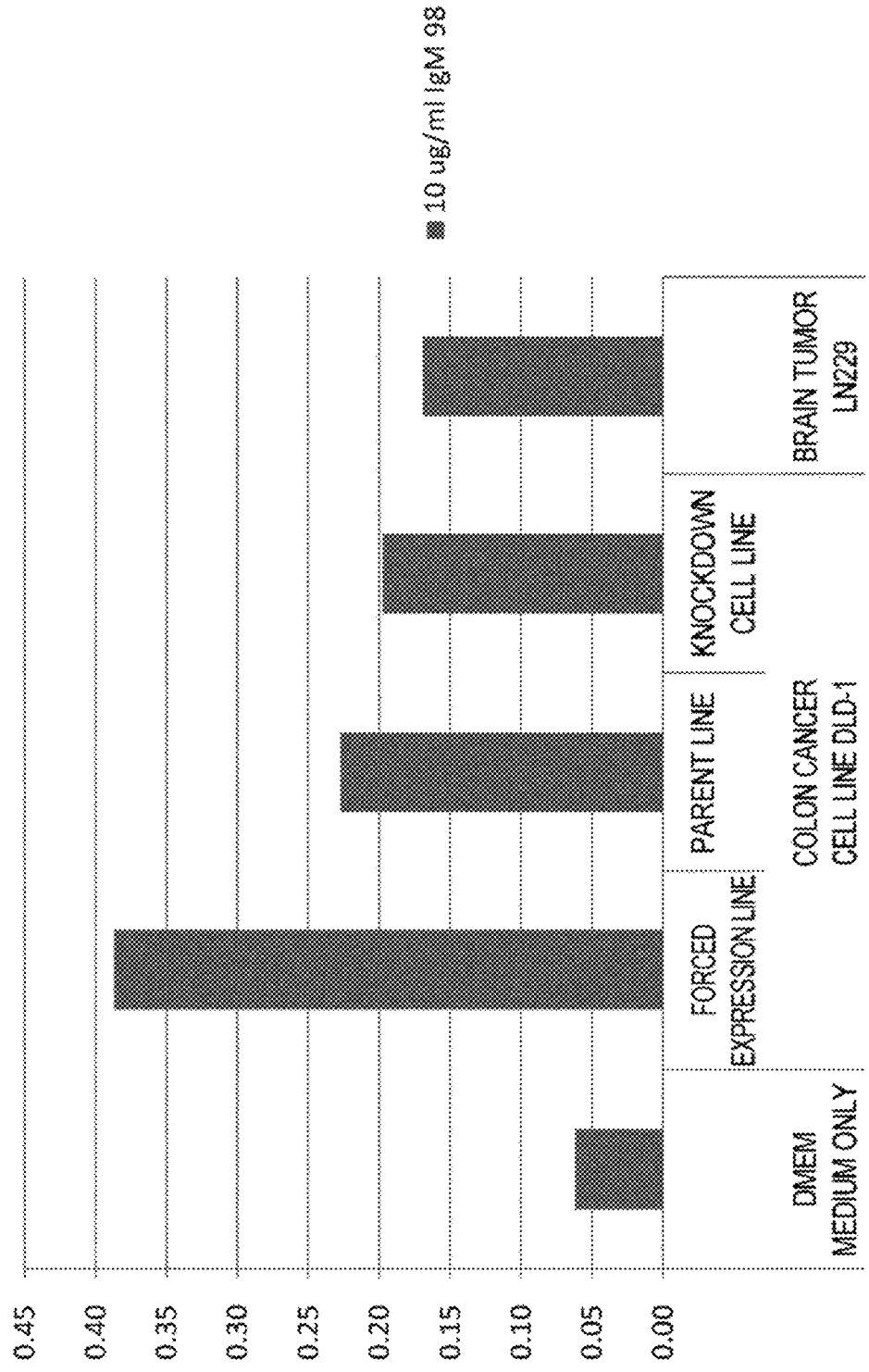
FIG. 9 indicates the results of measuring TMEM-180 protein concentration in culture supernatants of cancer cells.

The results are shown in FIG. 9. In comparison with the normal control (medium only), TMEM-180 exhibited high levels in all of the samples. The forced expression cell line, parent cell line and knockdown cell line demonstrated high levels in that order in colon cancer DLD-1. High levels were also demonstrated in brain tumor cells.

3) Measurement of Amount of TMEM-180 Protein in Plasma of Stage IV Colon Cancer Patients After diluting human plasma collected in EDTA (formed of four samples from stage IV patients and normal subjects) at dilution factors of 1/10 and 1/50, the plasma was used as sample antigen and immobilized on a 96-well plate followed by carrying out ELISA according to the method described in section 1).

Figure 10:
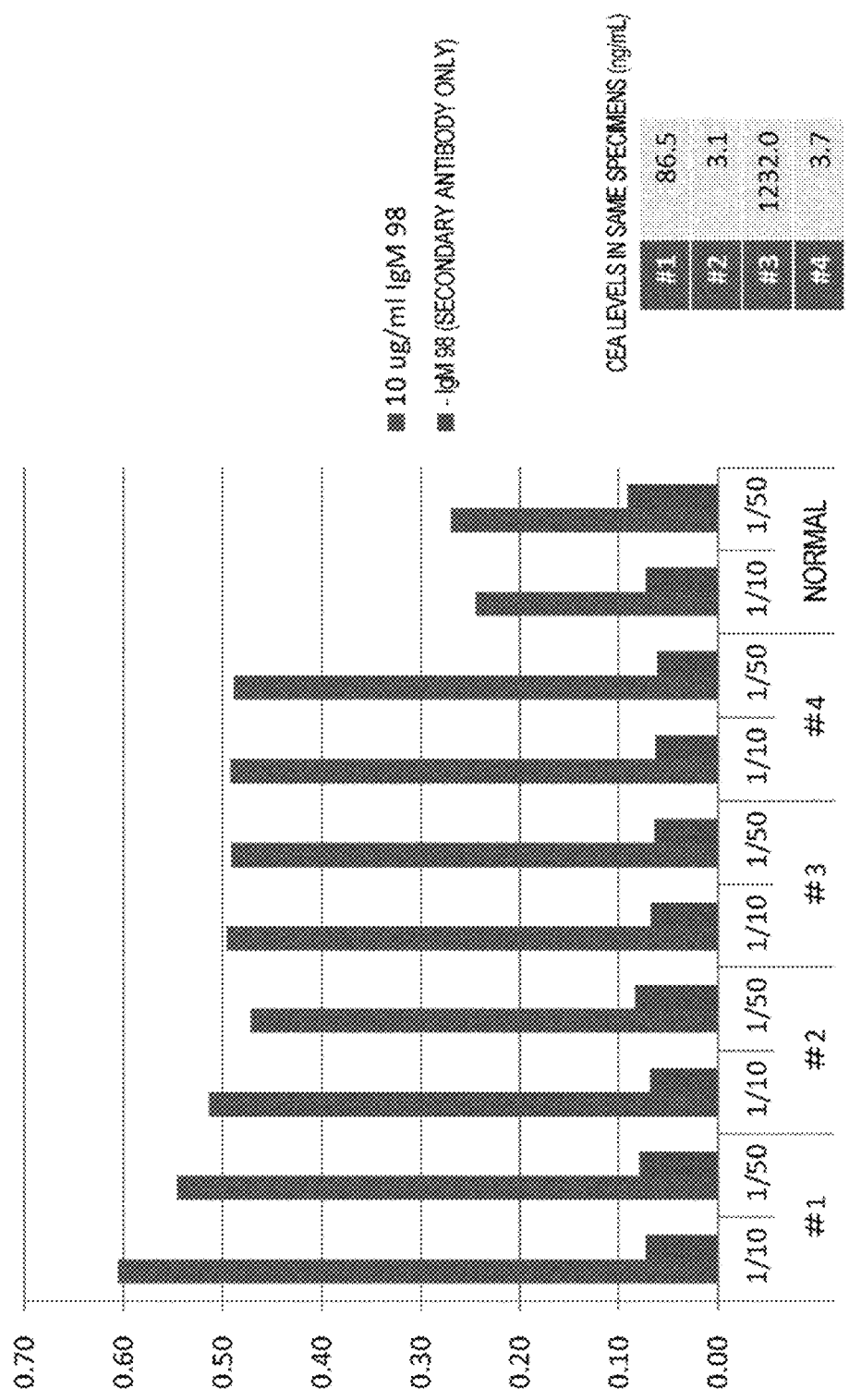
FIG. 10 indicates the results of measuring plasma TMEM-180 protein concentrations in four stage IV colon cancer patients. In addition, the table shown to the right of the graph indicates the results of measuring CEA levels in specimens collected from the same patients.

The results are shown in FIG. 10. In comparison with normal plasma, high levels were demonstrated in all of the patient samples. In addition, plasma TMEM-180 levels were positive (higher than normal) even in patients #2 and #4 who were negative for CEA.

4) Measurement of Amount of TMEM-180 Protein in Plasma of Stage III Colon Cancer Patients Before and After Surgery The amount of TMEM-180 protein in the plasma of stage III colon cancer patients before and after surgery was measured using the same method as section 3).

Figure 11:
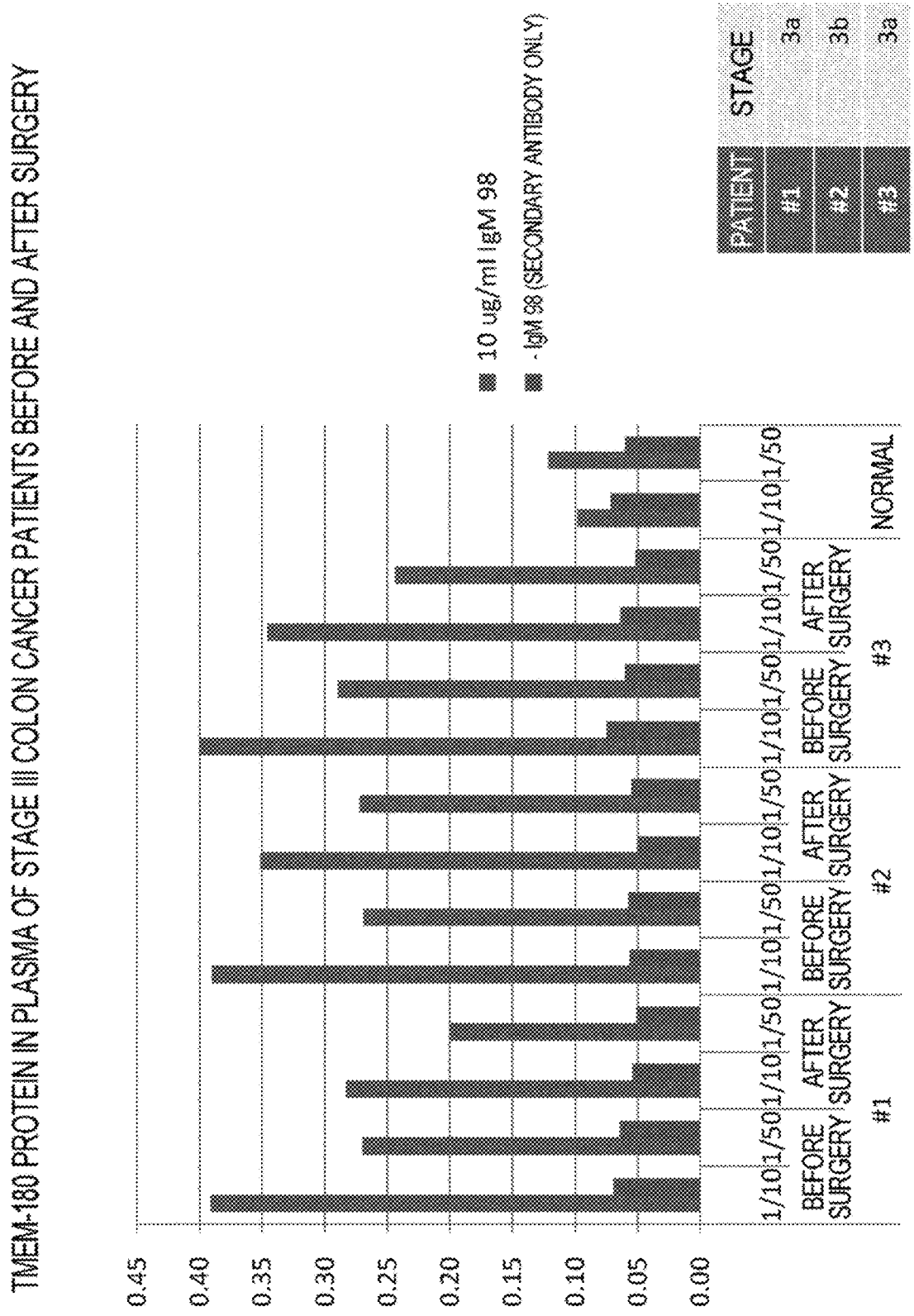
FIG. 11 indicates the results of measuring plasma TMEM-180 protein concentrations before and after surgery in three stage Ill colon cancer patients.

The results are shown in FIG. 11. TMEM-180 levels decreased after surgery in comparison with before surgery in all of the patients.

5) The amount of TMEM-180 protein and the colon cancer tumor marker, CEA, were measured in the plasma of stage III, II, IV and IIIa colon cancer patients before and after surgery and at the time of recurrence. Measurement of TMEM-180 was carried out by sandwich ELISA using clone 669 and clone 1361. The average of the levels of TMEM-180 in the normal plasma of 8 subjects as measured by ELISA in the same manner as in the case of the patient samples was used for the TMEM-180 cutoff value. The normal value used at the National Cancer Center Japan was used for the CEA cutoff value.

Figure 12:
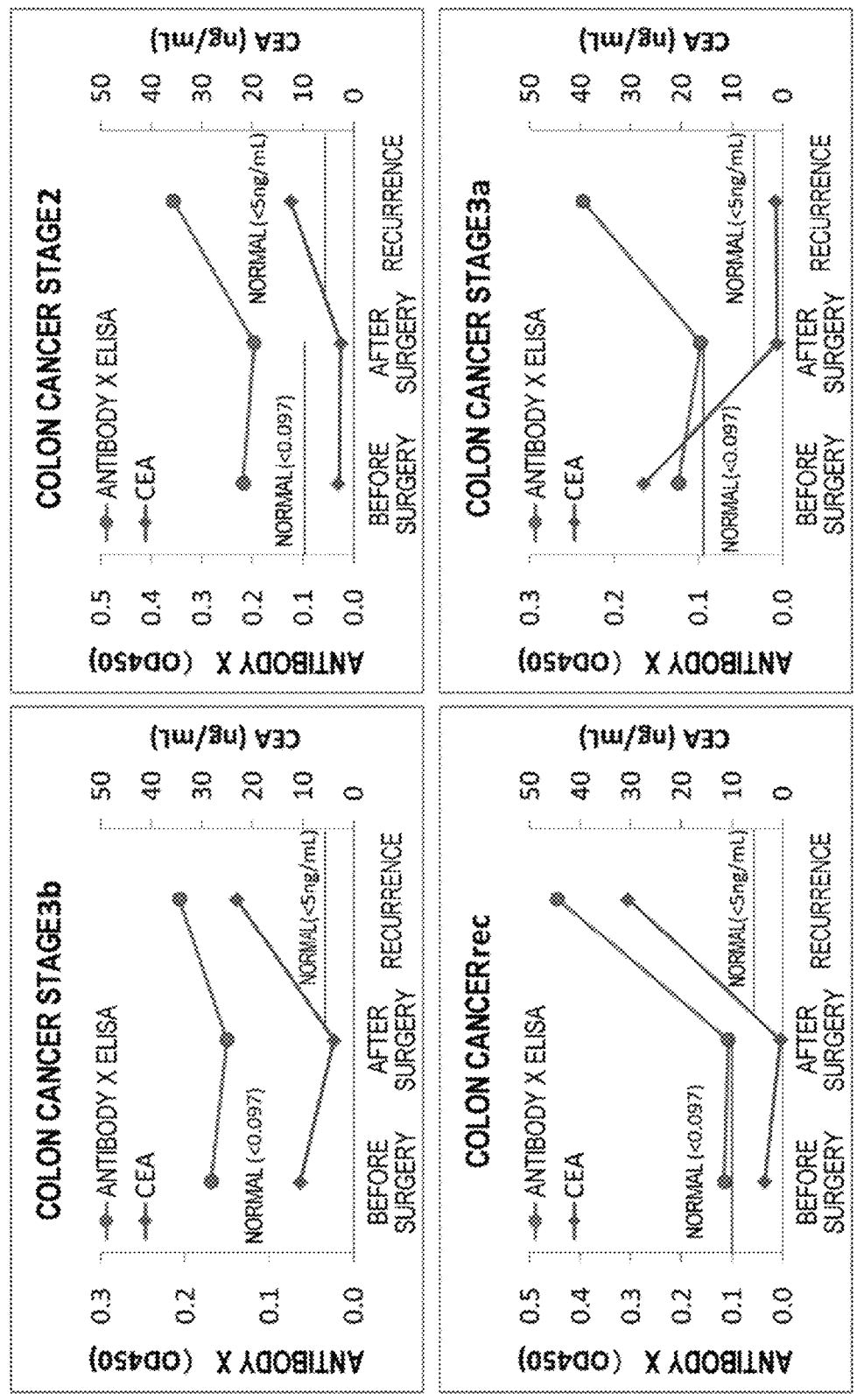
FIG. 12 indicates the results of measuring plasma TMEM-180 protein concentrations and CEA concentrations before surgery, after surgery and at the time of recurrence in colon cancer patients at various stages.

The results are shown in FIG. 12. Stage II patients were positive for TMEM-180 despite being negative for CEA level prior to surgery. In addition, although stage IIIa patients remained negative for CEA even after confirmation of recurrence by CT, TMEM-180 levels increased again.

Example 10A. Comparison in Cancer-Detection Frequency Using Each Clone

Cancer-detection rates were tested using monoclonal antibodies (the 669 antibody, 1052 antibody, 1105 antibody, and 1361 antibody).

In this Example, the reactivity of the antibodies to the cell lines derived from cancers which were obtained from ATCC and JCRB was analyzed by FACS. The results are shown in Table 23 below.

TABLE 23

Detection Sensitivity of Cancers with antibodies

| Cancer Type | Antibody Clone | | | | | | | |
|---|---|---|---|---|---|---|---|---|
| | 1361 | | 669 | | 1052 | | 1105 | |
| | Percentage (%) | P/N* | Percentage (%) | P/N* | Percentag (%) | P/N* | Percentage (%) | P/N* |
| Colon | 70 | (7/10) | 30 | (3/10) | 30 | (3/10) | 30 | (3/10) |
| Gastric | 63 | (5/8) | ND | | 25 | (2/8) | 25 | (2/8) |
| Pancreas | 100 | (9/9) | 33 | (3/9) | 44 | (4/9) | 44 | (4/9) |
| Brest | 33 | (2/6) | ND | | 50 | (3/6) | 50 | (3/6) |
| Prostate | 67 | (2/3) | ND | | ND | | ND | |
| Kidney | 100 | (3/3) | ND | | ND | | ND | |
| Bladder | 75 | (3/4) | ND | | 50 | (2/4) | 50 | (2¥4) |
| Brain | 100 | (7/7) | ND | | ND | | ND | |

*"P" indicates the number of positive clones and "N" indicates the number of negative clones.
*ND indicates that no data was obtained in the Example.

As shown in Table 23, it was found that any one of the antibodies produced by the clones was able to definitely recognize the cancers in the tissue specimens. It was also found that the 1361 antibody can detect several cancers with the highest sensitivity.

Next, the cancer-detection frequency by the antibodies was examined using various human tissue specimens which were obtained from those who had been diagnosed to have cancer. The paraffin sections were prepared from the tissue specimens in the same way as shown in Example 6 according to a routine procedure. The prepared sections were subjected to reactions with 1 µg/mL of one of the above antibodies. An HRP-labelled anti rat antibody was used as a secondary antibody, which emitted light with DAB. The observation was performed after hematoxylin staining. 1361 antibody-staining was negative in immune histochemistry of normal tissues from skin, brain, small intestine, liver, heart, lung and kidney. On the contrary, cetuximab, which is an EGFR blocker, showed a strong positive reaction to normal skin tissues. FIG. 13 shows the difference of the reactivities to skin tissue between the 1361 antibody and cetuximab. FIG. 14 shows the results of the immune histochemistry of other tissues besides skin.

Cetuximab exhibits strong reactivity to normal skin, which was consistent with the fact that skin disorders were reported as adverse effects. On the contrary, the 1361 antibody is expected to reduce such adverse effects due to the low reactivity to skin tissues.

Example A11. Preparation and Evaluation of the Variants of 1361 Clone

Site specific mutations were introduced in the heavy chain and the light chain by an inverse PCR method to obtain variants of the 1361 clone.

(1) Preparation of variants of 1361 clone

One amino acid substitution Y78A, where tyrosine located in heavy chain CDR2 in the 1361 clone was replaced with alanine, was introduced using the forward primer (SEQ ID NO: 183), the reverse primer (SEQ ID NO: 184), and PrimeSTAR Max DNA polymerase (takara, R045A) by an inverse PCR method (e.g., Ochman, H. et al., Genetics, 120(3): 621-623, 1988). Additional twenty-two variants of the 1361 clone into which an amino acid mutation was introduced were prepared in a similar way. For example, the variant 1361-7 was a variant having an amino acid substitution S82A where serine at position 82 was replaced with alanine in the 1361 antibody, using the forward primer (SEQ ID NO: 185) and the reverse primer (SEQ ID NO: 186) as PCR primers for the modification. After the introduction, the antibody gene sequences and the introduction of the mutations were confirmed with ABI PRISM 3100 Genetic Analyzer. Human chimera antibodies were prepared from the obtained variants according to the method described in 3) of Example 5 above. The Human chimera clone into which one amino acid substitution Y78A substituting tyrosine located at the heavy chain CDR2 with alanine was introduced is referred to as "1361-5 clone", and the antibody produced from the clone is referred to as "1361-5 antibody". The 1361-5 antibody is an IgG1 antibody.

(2) Evaluation of the binding properties of the antibodies by flowcytometry

TMEM-180-forcibly expressed line of the colon cancer cell DLD-1 line, the parent line thereof, and the TMEM-180 knockdown line were cultured. Then, the binding properties of the obtained 1361-5 antibody to these cancer cell lines were analyzed below. K562 cells were used as a negative control.

The cancer cell lines to be subjected to the measurement were suspended in the medium, and then were added to a V-bottom, 96 well plate (corning) at $1\times10^5$ cells/well. After the plate was centrifuged at 440×g for 3 minutes at 4° C., the supernatant was removed and the antibody solution was added at 50 µL/well to the cell pellet, which was then suspended. The final concentration of the primary antibody was 1 µg/mL or 0.1 µg/mL. After reaction for 45 minutes on ice, the pellet was washed three times with 200 µg/well of 0.1% BSA/2 mM EDTA/PBS. After the supernatant was discarded, the secondary antibody was added at 50 µL/well to the cell pellet, which was then suspended. The ALEXAFLUOR 647@(fluorescent compound) Goat anti-Human IgG (H-L) (Life Technologies) diluted with 0.1% BSA/2 mM EDTA/PBS 400 times was used as a secondary antibody. After reaction for 45 minutes on ice, the cell pellet was washed three times with 0.1% BSA/2 mM EDTA/PBS 200 µL/well. After the supernatant was discarded, 50 ng/mL Propidium Iodide/0.1% BSA/2 mM EDTA/PBS was added at 200 µg/well to the cell pellet to be suspended. The cells thus stained were measured with a flow cytometer such as Guava easyCyte 8HT (Merck Millipore). The obtained data were analyzed with FlowJO (TOMY Digital Biology). The results are shown in FIGS. 15 and 16.

Figure 15:
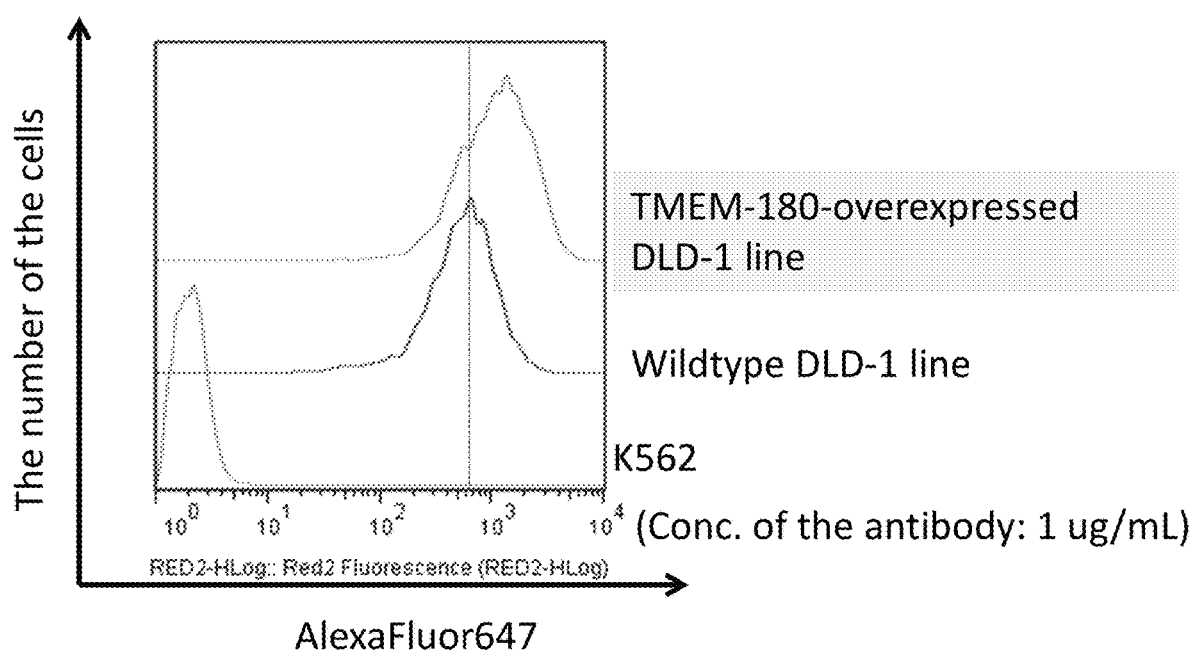
FIG. 15 shows that the 1361-5 antibody binds to the surface of a colon cancer cell line DLD-1.
Figure 16:
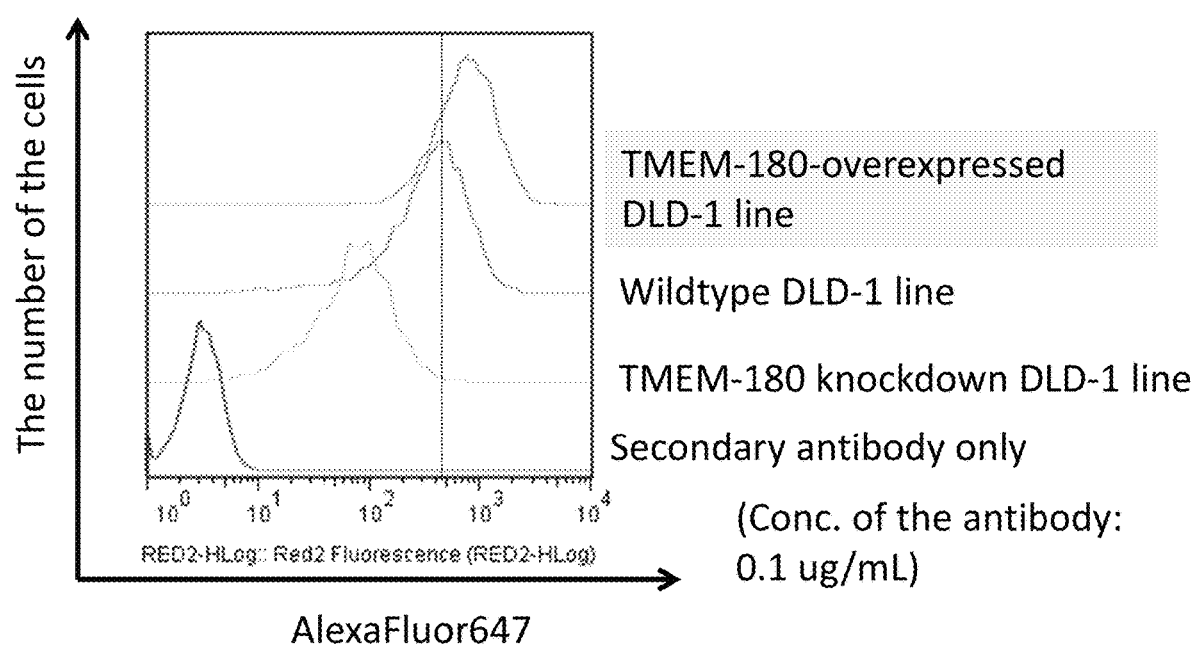
FIG. 16 shows that the 1361-5 antibody binds to the surface of a colon cancer cell line DLD-1.

As shown in FIGS. 15 and 16, the 1361-5 antibody recognized DLD-1 cell line in a TMEM-180 dependent manner, while the 1361-5 antibody did not recognize K562 cells.

As for the other twenty-two clones prepared, four clones among fourteen clones where a mutation was introduced in the heavy chain CDRs showed reduced binding properties to the antigen, and three clones among eight clones where a mutation was introduced in the light chain CDRs showed reduced binding properties to the antigen, and the other clones showed comparable binding properties to TMEM-180 to that of the 1361-5 antibody. Further, in the variants which maintain their binding properties to TMEM-180 (e.g., 1361-7 clone), the reactivity to normal stroma is almost the same as that of the 1361 antibody. On the contrary, the 1361-5 antibody showed reduced reactivity to normal stroma compared with the 1361 antibody or the other variants, while no difference was observed between the 1361-5 antibody and 1361 antibody for a binding property to TMEM-180 and recognition of cancer. It was shown that the 1361-5 antibody is more preferable in view of a binding property and specificity to cancers.

Example B11-2. Study on ADCC Activity of the Antibody

It was considered that the 1361-5 antibody would have a high ADCC activity due to its IgG subclass. In this Example, ADCC activity of the 1361-5 antibody was studied. In this Example, Fc variants were prepared and the ADCC activity of the variants was studied. The detail will be described below.

Site specific mutations were introduced in the Fc region of the heavy chain by an inverse PCR method to obtain Fc variants of the 1361-5 clone.

1) Preparation of FcDLE, a Fc-modified clone of 1361-5

Specifically, the triple amino acid substitutions S239D/A330L/I332E located at the Fc region of 1361-5 clone were introduced according to an inverse PCR method (e.g., Ochman, H. et al., Genetics, 120(3): 621-623, 1988) using the forward primers (SEQ ID NOS: A1, B1) and the reverse primers (SEQ ID NOS: A2, B2) and PrimeSTAR Max DNA polymerase (takara, R045A).

The obtained variant is hereinafter referred to as Variant 1.

2) Preparation of FcDEA, a Fc-Modified Clone of 1361-5

Specifically, the triple amino acid substitutions S239D/I332E/E333A located at the Fc region of 1361-5 clone was introduced according to an inverse PCR method (e.g., Ochman, H. et al., Genetics, 120(3): 621-623, 1988) using the forward primers (SEQ ID NOS: 187, 189 or 191) and the reverse primers (SEQ ID NOS: 188, 190, or 192) and PrimeSTAR Max DNA polymerase (takara, R045A).

The obtained variant is hereinafter referred to as Variant 2.

```
(Fc_S239D_Fw)
                           SEQ ID NO: 187
GGACCGGACGTCTTCCTCTTCCCCCCA (Fc_S239D_Rv)
                           SEQ ID NO: 188
GAAGACGTCCGGTCCCCCCAGGAGTTC (Fc_A330L_I332E_Fw)
                           SEQ ID NO: 189
CCACTGCCCGAGGAGAAAACCATCTCC (Fc_A330L_I332E_Rv)
                           SEQ ID NO: 190
CTCCTCGGGCAGTGGGAGGGCTTTGTT (Fc_I332E_E333A_Fw)
                           SEQ ID NO: 191
CCCGAGGCCAAAACCATCTCCAAAGCC (Fc_I332E_E333A_Rv)
                           SEQ ID NO: 192
GGTTTTGGCCTCGGGGGCTGGGAGGGC
```

3) Study on ADCC Activity

The ADCC activities of 1361-5, Variants 1 and 2 were studied by using cetuximab as a positive control.

Specifically, TK176V (a natural killer cell line stably expressing FcγRIII) was used as an effector cell, which was obtained from Chemicals Evaluation and Research Institute, Japan. The wild type DLD-1 cell line was used as a target cell.

T176V was cultured in RPM11640 containing 10 ng/mL IL-2 and 10% FBS. For passages, the medium was diluted with a fresh medium every 2 to 3 days. In the passage, the cells were detached by a trypsin treatment and then suspended in a fresh medium to be plated on a dish every 2 to 3 days.

The measurement of the ADCC activity was performed as described below.

First, the amount of 51Cr release was measured when only the target cells were cultured in medium as a negative control, which is referred to as "Spontaneous release measurement". The amount of 51 Cr release was measured when the all target cells were damaged by adding 0.1% TRITON™ (surfactant) X-100, which is referred to as "Max release measurement."

1) Adding DLD-1 WT labelled with 50 µCi of $^{51}$Cr to a U-bottom, 96 well plate at 5,000 cells/50 µL/well.
2) Adding TK176V at 200,000 cells/50 µL/well (ET ratio: 40): A medium was added at 50 µL/well to the well for Spontaneous release measurement and the well for Max release measurement.
3) Adding seven dilution series of an antibody at 100 µL/well, wherein the antibody was diluted with a common ratio of 5 and the maximum concentration of 2,000 ng/mL (i.e., the final concentrations of the antibody during the reaction: 0, 0.064, 0.32, 1.6, 8, 40, 200, and 1,000 ng/mL).
4) Adding 100 µL/well of 0.2% TRITON™ (surfactant)×100 to the well for Max release measurement, while adding 100 µL/well of the culture medium to the well for Spontaneous release measurement.
5) Centrifuging the plate at 250×g for 4 minutes followed by culturing it at 37° C. for 4 hours.
6) Centrifuging the plate at 250×g for 4 minutes.
7) Transferring 50 µL/well of the supernatant to a test tube.
8) Measuring the radiation unit (CPM) in each test tube with a gamma counter.
9) Calculating the cytotoxicity and ADCC activity using the following formula:

Cytotoxicity (%)=(CPM for each test tube–the average of Spontaneous release CPMs)/(the average of Max release CPMs–Spontaneouse release CPMs)   Formula 1

ADCC activity (%)=Cytotoxicity when the antibody is added–Cytotoxicity when no antibody is added   Formula 2

10) Calculating 50% Effective Concentration (EC50) with an analytical software Prism.

Figure 20A:
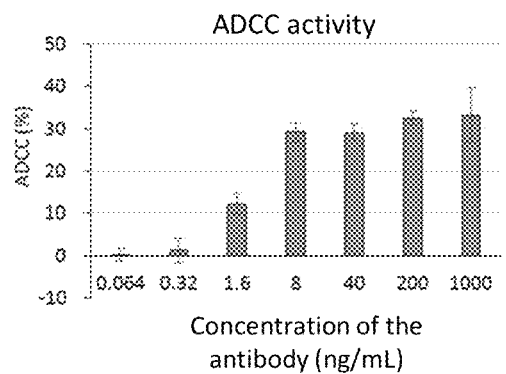
FIG. 20A shows the results of evaluating the ADCC activity of cetuximab on a colon cancer cell line DLD-1.
Figure 20B:
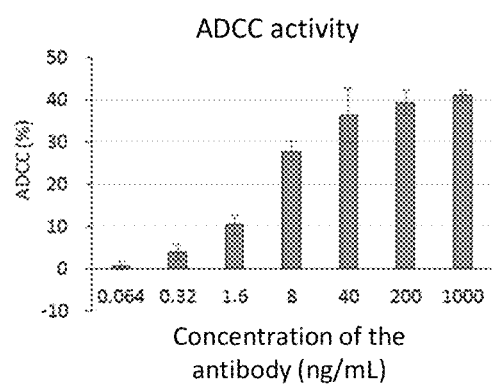
FIG. 20B shows the results of evaluating the ADCC activity of the 1361-5 antibody on a colon cancer cell line DLD-1.
Figure 20C:
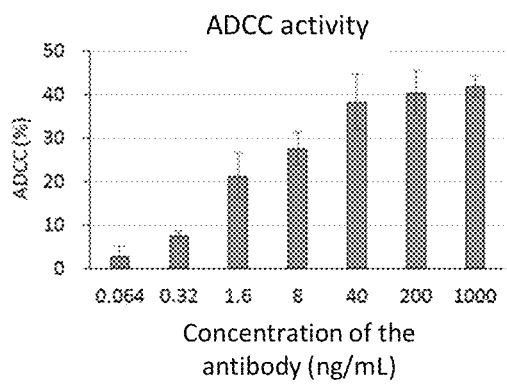
FIG. 20C shows the results of evaluating the ADCC activity of a Fc variant of the 1361-5 antibody (Variant 1) on a colon cancer cell line DLD-1.
Figure 20D:
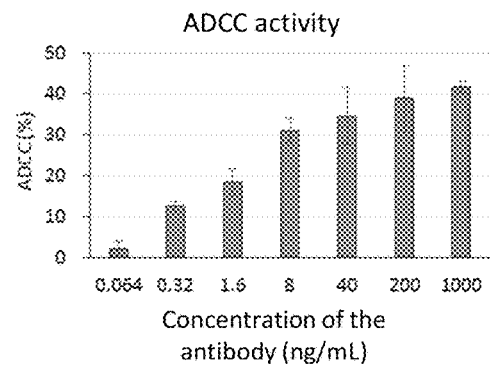
FIG. 20D shows the results of evaluating the ADCC activity of a Fc variant of the 1361-5 antibody (Variant 2) on a colon cancer cell line DLD-1.

The results are shown in FIGS. 20A to 20D. As shown in FIG. 20A, cetuximab showed the strong ADCC activity against wild type DLD-1 cells. On the contrary, as shown in FIG. 20B, the 1361-5 antibody showed an ADCC activity against wild type DLD-1 cells stronger than that of cetuximab. As shown in FIGS. 20C and 20D, Variants 1 and 2 showed an ADCC activity which is equal to or stronger than that of the 1361-5 antibody. Further, no ADCC activity was observed against TMEM-180 negative cells.

From these results, it was confirmed that the 1361-5 antibody and the variants therefrom have an ADCC activity.

Example B11-3. Effect of Anti-TMEM-180 Antibody in In Vivo Tumor Models

In this Example, the anti-tumor effect of humanized 669 IgG antibody was tested by using mouse xenograft models having human colon cancer cell lines DLD-1.

The humanized 669 IgG antibody was prepared by substituting CDRs of human IgG1 with those of the 669 antibody.

DLD-1 cells were subcutaneously injected at 5×10$^6$ cells/100 µL PBS to the left abdominal sites of ICR nude mice (female, 5 to 6 weeks old, Charles River Laboratories Japan, INC.). Mice having a tumor volume of 100 to 200 mm$^3$ were grouped into five groups, and 500 µL of PBS, 500 µL of PBS containing 500 µg of humanized 669 IgG antibody, 500 µL of PBS containing 100 µg of humanized 669 IgG antibody, 500 µL of PBS containing 500 µg of anti-EGFR antibody Erbitux, or 500 µL of PBS containing 100 µg of Erbitux was administered to each of the groups three times per week. Each group consists of 4 to 5 mice. The tumor diameter and the weight were recorded for each of the mice upon administration. Tumor volume was calculated as [tumor major diameter×tumor minor diamiter$^2$]. The results are shown in FIG. 21.

Figure 21:
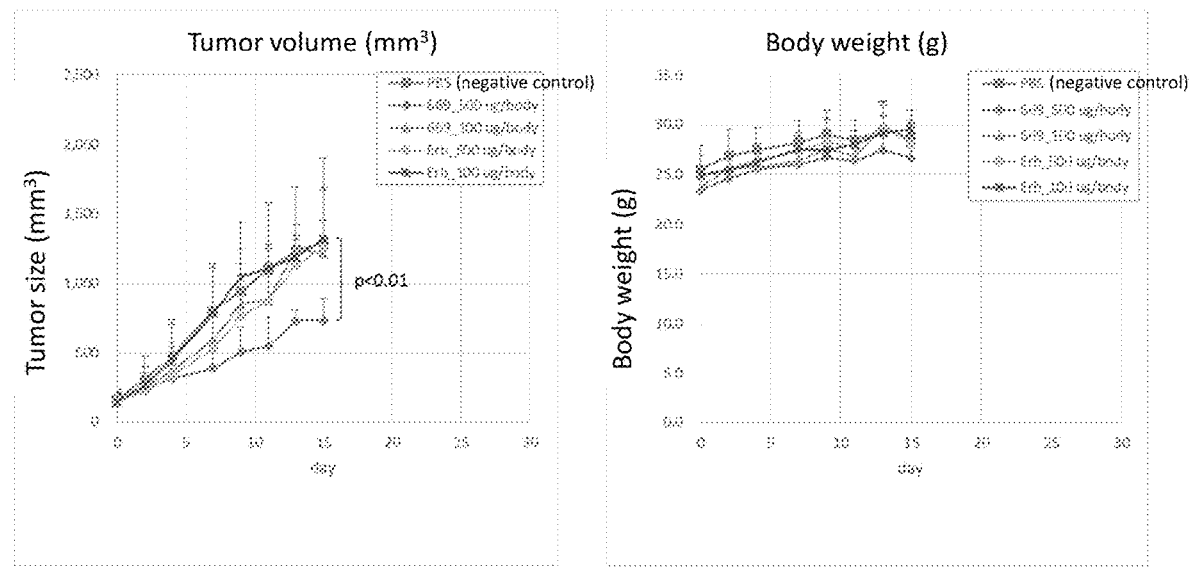
FIG. 21 shows that a humanized 669 IgG antibody has a strong anti-cancer effect in mouse models transplanted with human colon cancer cells. In the figure, "Erb" indicates the results in the Erbitux-administrated group.

As shown in FIG. 21, the humanized 669 IgG antibody significantly inhibited the increase of tumor size, compared to the negative control injected with PBS. It was clear that the humanized 669 IgG antibody has an anti-tumor activity stronger than that of Erbitux. No significant change was observed in weight of mice between before and after administrations.

Example A12. Staining of Colon Cancer Tissue Array Using the 1361-5 Antibody In this Example, colon cancers were stained by immunohistochemistry using the 1361-5 antibody obtained in Example A11.

Figure 17:
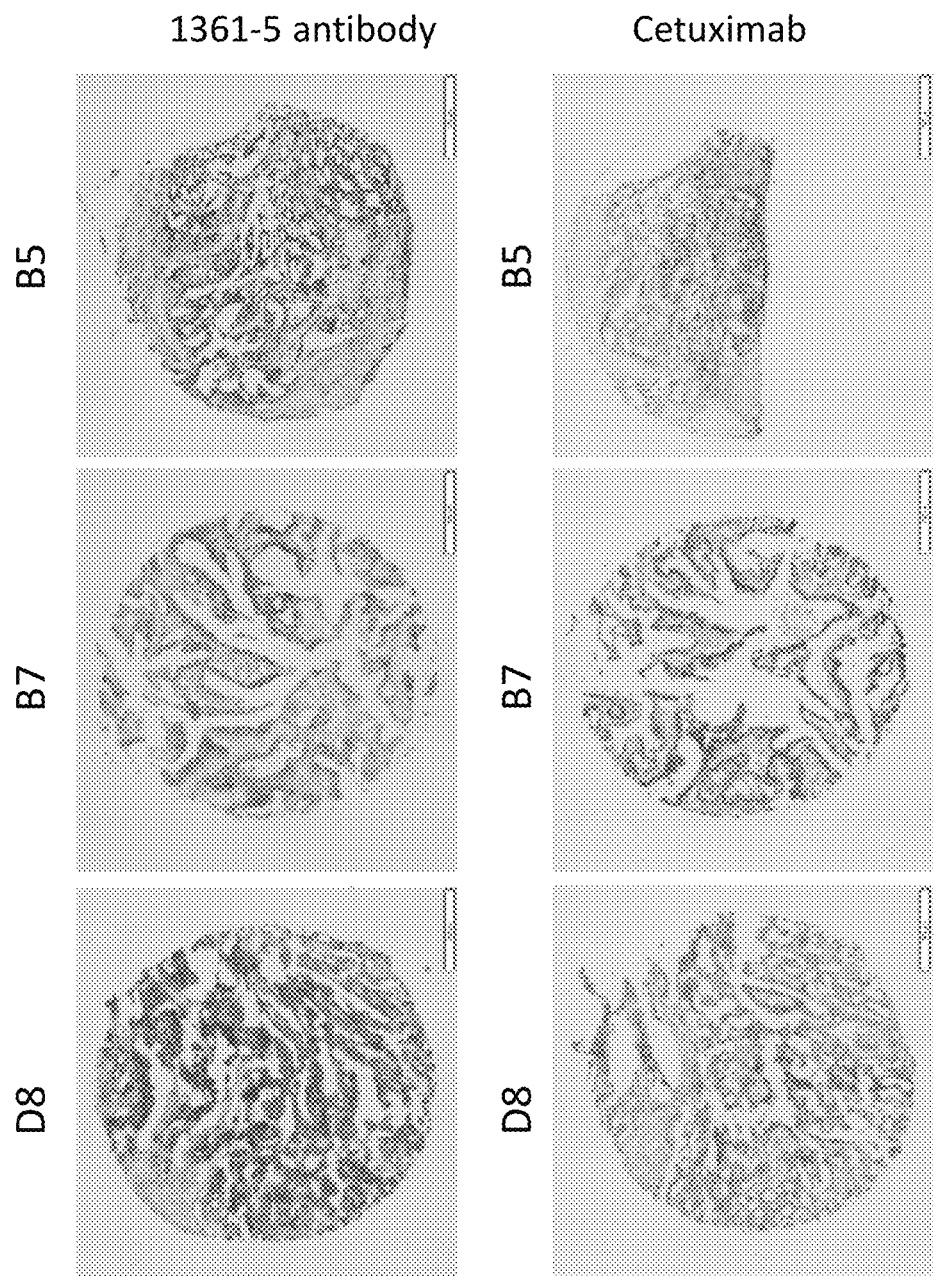
FIG. 17 shows that the 1361-5 antibody well stains the tissues on a colon cancer tissue array.

The colon cancer tissue arrays were purchased from BioChain Institute Inc. (Newark, Calif.) and used in the experiment. Each tissue array was stained according to the manufacturer's manual. The results are shown in FIG. 17. As shown in FIG. 17, colon cancer tissues (D8, B7 and B5) were well stained with the 1361-5 antibody (see top three panels). On the contrary, all tissues in the arrays were negative in staining with cetuximab (see bottom three panels in FIG. 17).

Example A13. Analysis of Exosomes

In this Example, it was discovered that TMEM-180, which is a transmembrane protein, is released into exosomes from cancer cells and presented as a transmembrane protein on the surfaces of exosomes.

Figure 19:
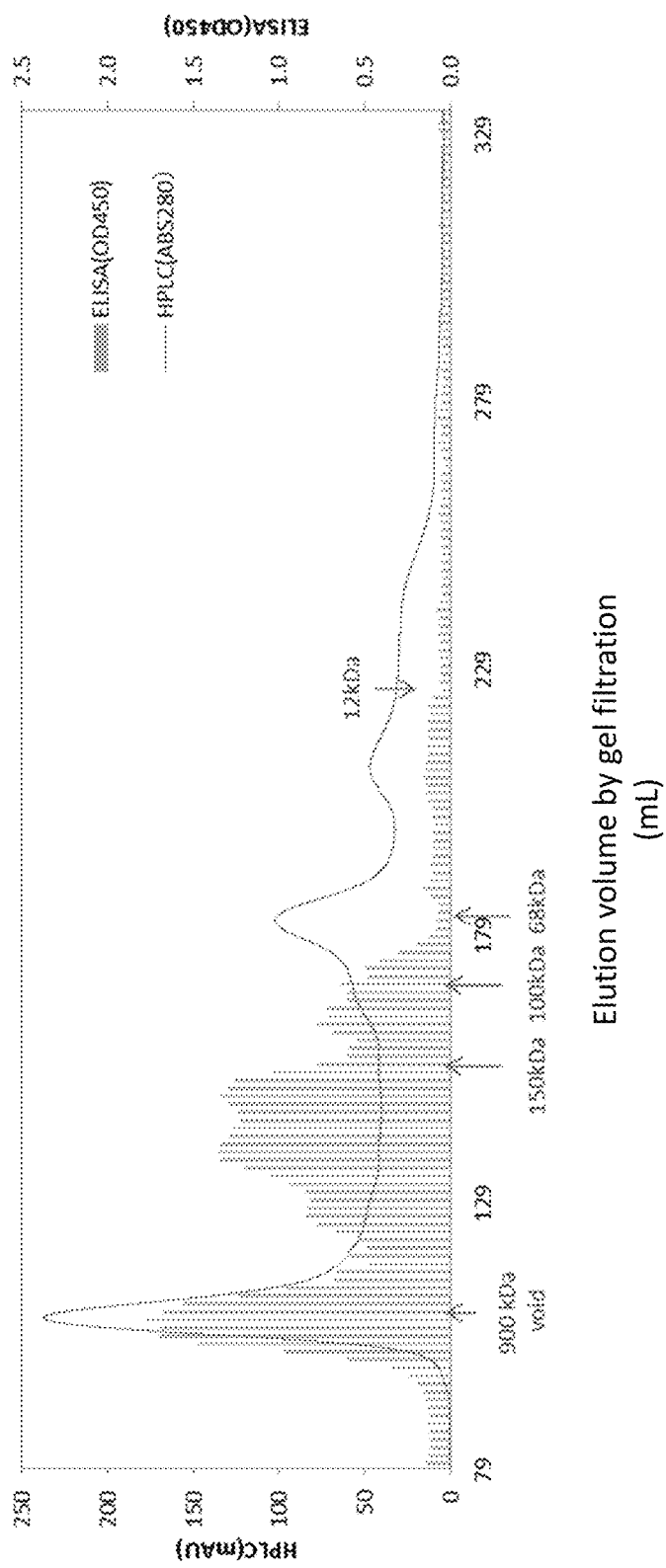
FIG. 19 shows the amount of 98 antibody positive components in the fraction obtained by a gel-filtration of the culture supernatant of a TMEM-180-forcibly expressed line of a colon cancer cell line DLD-1.

Specifically, the colon cancer cell line DLD-1 was cultured and the supernatant of the culture was obtained. After gel filtration, each fraction was checked by using the 98 antibody to find that 98 antibody positive fractions exist in large molecular weight fractions, in which the molecular weight was much larger than the molecular weight of the protein. This result suggests that TMEM-180 would form a large complex (see e.g., FIG. 19).

Thus, the inventors constructed a system for detecting exosomes in the culture supernatant. In this system, an anti-TMEM-180 antibody was immobilized on the surface of the plate, and exosomes containing TMEM-180 which were bound to the immobilized antibody were detected with an anti-CD9 antibody which CD9 is an exosome maker. The DLD-1 cell line (also referred to as "wild type DLD-1 cell line") was used as cells. The TMEM-180 knockdown DLD-1 cell line and K562 cell line were used as negative controls.

Specifically, an anti-TMEM-180 antibody was diluted with phosphate buffer such that the concentration will be 5 µg/mL, and then added to a 96 well plate (Maxisorp #442404, Thermo Fisher Co., Ltd.) at 50 µL/well. The immobilization reaction was performed by incubation for 2 hours at room temperature or for overnight at 4° C. The plate after the immobilization was washed three times with 300 µL/well of a plate washing solution. The plate was blocked with 200 µL/well of a blocking agent (1% BSA/TBS-T), and allowed to stand for 1 hour at room temperature or for overnight at 4° C. After removing the blocking agent, each of the culture supernatants of wild type DLD-1 cell line, TMEM-180 knockdown DLD-1 cell line, and K562 cell line cultured in serum-free medium was added to the plate at 50 µL/well, and allowed to stand for 1 hour at room temperature. Fresh serum-free medium was used as a negative control. After the plate was washed three times with the plate washing solution, a biotin-labeled anti-CD9 antibody (156-030, Ancell co., LTD.) diluted with 1% BSA/TBS-T to have 5 µg/mL was added to the plate at 50 µL/well. After allowing the plate to stand for 1 hour at room temperature, the plate was washed three times with the plate washing solution. Streptavidin-HRP conjugated (SA-5004, Vector Laboratories) diluted with 1% BSA/TBS-T 5,000 times was added to the plate at 50 µL/well. After allowing the plate to stand for 30 minutes at room temperature, the plate was washed three times with the plate washing solution. Then, 100 µL/well of a color development solution was added to the plate and the plate was allowed to stand for 30 minutes at room temperature. The color reaction was stopped with 30 µL/well of a stop solution. Then, the optical density at 450 nm was measured with a plate reader. The results are shown in FIG. 18.

Figure 18:
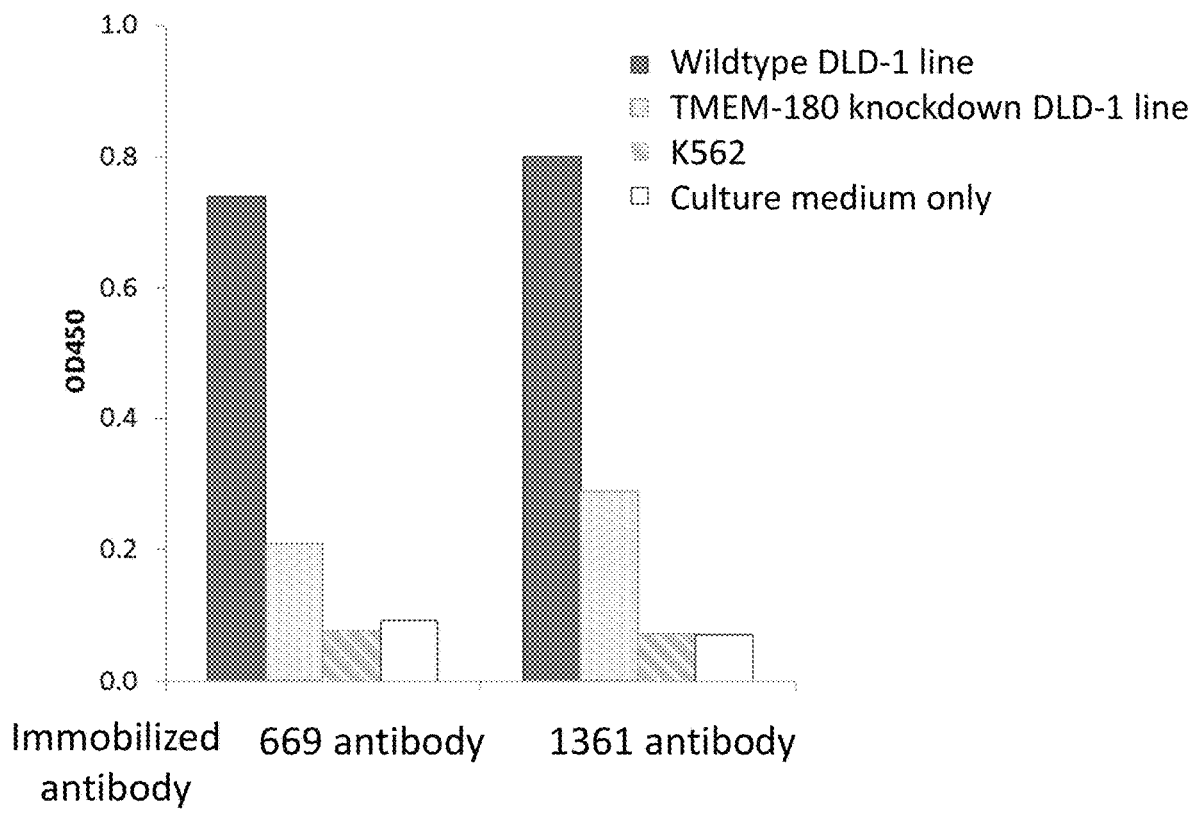
FIG. 18 shows that the exosomes existing in the culture supernatant of a colon cancer cell line DLD-1 contains TMEM-180 protein. In the figure, an immobilized antibody means the antibody which is immobilized on the plate surface. The detection of the exosomes was performed with an anti-CD9 antibody.

As shown in FIG. 18, the DLD-1 cell line releases exosomes to the culture supernatant, which exosomes presented TMEM-180 protein on the surfaces and were successfully detected with the 669 antibody and 1361 antibody and an anti-CD9 antibody. The amount of exosomes presenting TMEM-180 on their surfaces were reduced in the TMEM-180 knockdown cell line. The similar results were observed in the K562 cell line expressing no TMEM-180, which were comparable to the result of the medium used as a negative control.

From the above, it was discovered that exosomes presenting TMEM-180 on their surfaces are released from cancer cells and can be detected with an anti-TMEM-180 antibody and anti-exosome antibody. The inventors have found that exosomes presenting TMEM-180 on their surfaces are released in the serum obtained from human colon cancer patients. From these results, it was shown that cancers can be diagnosed by determining whether exosomes presenting TMEM-180 on their surfaces are detected or not in a body fluid sample as an index for testing cancer.

Example B13-2. Diagnosis of Colon Cancer Using Exosomes

In this Example, it was shown that exosomes contained in the serum from colon cancer patients can be used in order to diagnose cancer.

In this Example, the components reacting with the 1361 antibody were purified from the serums from colon cancer patients (51 cases) by using 1361 antibody immobilized beads. Then, the exosomes contained in the components were detected by using an anti-CD9 antibody, in which CD9 is an exosome marker. The detail will be provided below.

1) Preparation of Antibody-Bound Magnetic Beads

The 1361 antibody was diluted with 25 mM MES-NaOH to have 1 mg/mL. NHS-FG beads (Tamagawa seiki co., ltd., Cat. No.: TAS8848N1141) were suspended in 50 µL of 25 mM MES-NaOH per 100 µg beads and then were mixed with the equal volume of the antibody solution followed by agitation for 30 minutes at 4° C. to allow the antibody bound to the beads. After removing the supernatant, 250 µL of 1 M ethanolamine (pH8.0) was added and the blocking was performed for overnight at 4° C. The beads were washed three times with 200 µL of 10 mM HEPES-NaOH (pH7.9)/50 mM KCl/1 mM EDTA/10% glycerol. The obtained antibody-bound magnetic beads were suspended in 200 µL of 10 mM HEPES-NaOH (pH7.9)/50 mM KCl/1 mM EDTA/10% glycerol in order to be used in the experiment.

2) Preparation of Positive Specimens

The DLD-1 cells were cultured overnight at $6.85 \times 10^6$ cells per 15 cm dish. After removal of the culture supernatant, 7 mL of PBS was added to remove the culture components. After washing with PBS was performed twice, 30 mL of a serum-free medium was added and then the cells were cultured for 24 hours. The obtained supernatant of the serum-free medium was filtrated with a 0.22 µm filter and was subjected to the measurement.

3) Detection of Exosomes Containing TMEM-180
The following materials were used:
96 well plate (Corning Co., Ltd, Cat. No. 3600)
Plate washing solution 10 mM TBS (pH7.2)/0.1% TWEEN® (polysorbate 20)/140 mM NaCl
Dilution solution 10 mM TBS (pH7.2)/0.05% TWEEN@ 20 (polysorbate 20)/140 mM NaCl/1% BSA
Dilution solution for specimen 10 mM TBS (pH7.2)/0.1% TWEEN® 20 (polysorbate 20)/140 mM NaCi/1% BSA/20 μg/mL TRU Block (Meridian Life Science, Inc., Cat. No. A66800H-0.1)
Biotinylated anti-CD9 antibody (Ancell corporation, Cat. No. 156-030)
Streptavidin ALP (R&D systems, Inc., Cat. No. AR001)
Light-emitting substrate Lumipulse® substrate solution (Fujirebio Inc.)
Plate reader Spectra Max Paradigm (MolecuLar Devices, LLC.)

(Procedures)
The experiment was performed according to the following.

(i) Preparation of Antibody-Bound Magnetic Beads
The 1361 antibody-bound magnetic beads were suspended in Dilution solution such that the concentration will be 0.001 mg/50 μL.

(ii) Preparation of Specimens
A positive specimen and serum specimens were diluted to 10 times.

(iii) Primary Reaction
The 1361 antibody-bound magnetic beads and a specimen were mixed in 96 well plate at 50 μL/well each, and were stirred with a plate mixer for 30 minutes to react.

(iv) Labelled Antibody Reaction
The plate was washed three times with 300 μL/well of a plate washing solution. A biotin-labelled antibody was prepared with Dilution solution at 0.3 μg/mL. The antibody was added at 50 μL/well. The plate was stirred on a plate mixer for 30 minutes for the reaction.

(v) Streptavidin ALP Reaction
The plate was washed three times with 300 μL/well of a plate washing solution. Streptavidin ALP solution was diluted with Dilution solution to 2,000 times. The solution was added at 50 μL/well. The plate was stirred on a plate mixer for 30 minutes for the reaction.

(vi) Measurement
The plate was washed three times with 300 μL/well of a plate washing solution. Light-emitting substrate solution was added at 50 μL/well and then incubated for 10 minutes at room temperature. The amount of light emission was measured with a plate reader.

Figure 22:
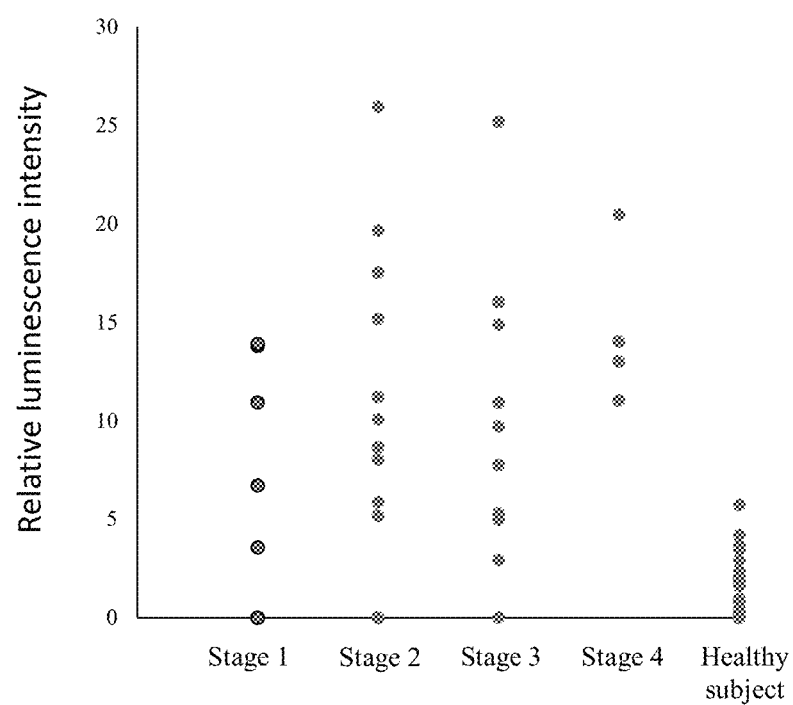
FIG. 22 shows that the exosomes contained in serums from colon cancer patients (51 cases from stage 1 to stage 4) are TMEM-180 positive.

The results are shown in FIG. 22. As shown in FIG. 22, it was clear that the serums from colon cancer patients contained more TMEM-180 positive exosomes than those contained in healthy subjects.

Next, the cutoff values (thresholds) were determined by using the data shown in FIG. 22 to evaluate the sensitivity and the specificity of the diagnosis. Specifically, the average (N) of the relative luminescence intensities in the healthy subjects (50 cases) was used as a reference value, and a cutoff value (threshold) was set as a value three times (S/N=3), four times (S/N=4), or five times (S/N=5) larger than the reference value. When the relative luminescence intensity exceeds the cutoff value, the sample was determined as colon cancer and thereby verifying the specificity of this diagnosis. The results are shown in Table 24.

TABLE 24

An example of serological diagnosis using serums from colon cancer patients (51 cases)

|  | Stage 1 | Stage 2 | Stage 3 | Stage 4 | Specificity |
|---|---|---|---|---|---|
| S/N = 3 | 62.5% (5/8) | 76.9% (10/13) | 90.0% (9/10) | 100% (4/4) | 88% |
| S/N = 4 | 62.5% (5/8) | 76.9% (10/13) | 80.0% (8/10) | 100% (4/4) | 92% |
| S/N = 5 | 50.0% (4/8) | 76.9% (10/13) | 80.0% (8/10) | 100% (4/4) | 98% |

As shown in Table 24, it was found that colon cancers at every stage can be detected with a very high sensitivity according to the present invention. In particular, the stage 2 cancers were detected at the high sensitivities of over 75% by using any one of the cutoff values. Further, the stage 1 cancers were detected also at the high sensitivities of over 50%. The detection specificity was over 85% in all cases.

In the examples of above, S/N is 3 or more. However, from the results shown in FIG. 22, it is clear that cancers can be detected even when S/N is set to be 1. Generally, the sensitivity will drop while the specificity will rise, when the cutoff value is high; the sensitivity will rise while the specificity will drop, when the cutoff value is low. It can be recognized that those skilled in the art would determine the cutoff value, depending on whether the purpose is to decrease false negatives or false positive.

Example B13-3 Observation of the Expression of TMEM-180 on Surfaces of Exosomes

In the Example, the expression of TMEM-180 on surfaces of exosomes was checked by using an electron microscope.

Harvesting Exosomes from Culture Supernatant
Each of DLD-1 cells and TMEM-180-forcibly expressed DLD-1 cells were plated on plastic dishes and were incubated overnight. After removing the culture supernatant, the cells were washed twice with PBS such that the cells were not detached from the dishes, and then the medium was exchanged with a serum-free D-MEM medium. After culturing the cells for 24 hours, the culture supernatant was harvested. The supernatant filtrated with a 0.22 μm filter was used as a serum-free culture supernatant containing exosomes. The K562 cells which were washed three times with PBS were cultured in a serum-free RPMI-1640 medium for 24 hours. The culture supernatant was harvested and filtrated with a 0.22 μm filter for use. The obtained serum-free culture supernatant containing exosomes were centrifuged at 100,000×g, 4° C. for 24 hours. The obtained pellet was suspended in PBS as an exosome concentrate.

Immunological Staining of the Exosomes
The exosome concentrate was dispersed and then attached on a Ni grid with a stretched supporting membrane. The 669 antibody, which is an anti-TMEM-180 antibody clone, or an anti-human CD9 antibody (Cosmo bio) was added to the Ni grid and reacted at room temperature. The Ni grid was washed with 1% BSA/PBS, followed by addition of an anti-mouse Ig antibody labelled with gold colloid or an anti-rat Ig antibody labelled with gold colloid. The reaction was performed at room temperature. After washing with PBS, fixation with glutaraldehyde was performed for 3 minutes. Negative staining was performed with a 2% phosphotungstic acid solution (pH7.0). The fixed Ni grid was dried, and the binding of exosomes and the antibody was checked with a transmission electron microscope. Gold colloid was detected as a black dot under transmission electron microscopy. The results are shown in FIG. 23.

As shown in FIG. 23, the exosomes associated with a plurality of black dots in the staining with an anti-CD9 antibody, which indicates that the exosomes were stained with the anti-CD9 antibody (see Panel A in FIG. 23). Further, the exosomes, which were stained with an anti-TMEM-180 antibody, also associated with a plurality of black dots (see Panel B in FIG. 23) in the staining with the anti-TMEM-180 antibody. Those from K562 cells expressing no TMEM-180 did not reacted with the anti-TMEM-180 antibody. From these results, it was shown that the exosomes released from colon cancer cells into body fluids express TMEM-180. These results support that a cancer diagnosis is possible by using exosomes and an anti-TMEM-180 antibody.

Example A14. Preparation of an Anti-TMEM-180 Antibody by Using Exosomes as an Antigen After it was shown that TMEM-180 protein was detected on the exosomes, an anti-TMEM-180 antibody was prepared by using the exosomes of above as an antigen instead of the antigen used in Example 3.
Preparation of Immunogen
1) Preparation of Serum-Free Culture Supernatant A TMEM-180-overexpressed DLD-1 cell line was cultured in a 15 cm dish (#430599, Corning Co., Ltd.) containing 30 mL of DMEM low glucose medium (Wako) containing 10% FBS at $6.75 \times 10^6$ cells per dish, at 37° C. under the conditions of 5% $CO_2$ for 24 hours. The culture medium was removed from the culture dish and the dish was gently washed with PBS. Then, 30 mL/dish of D-MEM low glucose medium was added and then the cells were cultured for 24 hours. The harvested serum-free culture supernatant was filtrated with a 0.22 μm filter flask. After the cell debris was removed, Protease Inhibitor (Wako) was added to the supernatant at the ratio of 1/1000. The supernatant was stored at 4° C.
2) Preparation of exosome fraction A column filled with CHT ceramic hydroxyapatite type II (Bio-Rad) was equilibrated with 30 mM HEPES, 100 mM NaCl, pH6.7. The serum-free culture supernatant was loaded to the column, then washed with the same buffer, and then eluted with 500 mM KPB, pH6.7. The eluent was concentrated to a volume of less than 10 mL by using ultrafiltration, and was fractionated with a gel filtration column, Superdex 200 μg (GE). Each of the fractions was subjected to the measurement of TMEM-180 positive fractions. Then, the peak of the positive fractions detected at the void volume was collected and used as TMEM-180 containing exosomes.
3) Measurement of TMEM-180 Positive Fractions The samples for the measurement were diluted with the stock solution or a phosphate buffer, and were added to a 96-well plate (Maxisorp #442404, Thermo Fisher co., Ltd.) at 50 μL/well. The immobilization reaction was conducted at room temperature for 2 hours. The immobilized plate was washed three times with 300 μL/well of the plate washing solution. The plate was blocked with 200 μL/well of 1% BSA/TBS-T and left at room temperature for 1 hour. After the removal of the blocking agent, clone 98 antibody diluted with 1% BSA/TBS-T at 5 μg/mL was added to the plate at 50 μL/well. The plate was allowed to stand at room temperature for 1 hour. Then, the plate was washed three times with the plate washing solution. Goat anti rat IgM antibody HRP conjugated (A110-100P, Bethyl laboratories, Inc.) which has been diluted 10,000 times with 1% BSA/TBS-T was added to the plate at 50 μL/well. The plate was left standing at room temperature for 30 minutes, and was washed three times with the plate washing solution. The color development solution was added at 100 μL/well, and then the plate was left standing at room temperature for 20 minutes. 30 μL/well of the stop solution was added to stop the color reaction, and then the plate was subjected to the measurement of 450 nm absorbance with the plate reader.
4) Preparation of Antibody TMEM-180-containing exosomes and Freund complete adjuvant were mixed at 1:1 ratio to obtain emulsion, 100 μL of which was administered to each rat (Japan SLC, Inc., Wister, female, 6-8 weeks old) at the both sides of the root of the tail. The liac lymph node, the inguinal lymph node, the axillary lymph node, and popliteal lymph node were isolated 14 days after the immunization. The obtained lymph node cells and mouse myeloma cells p3X63 were fused by a PEG method. Ten to fourteen days after the fusion, the culture supernatant was harvested. Then, the hybridomas which produced antibodies positively reacted to DLD-1 cells and negatively reacted to K562 cells were selected by flow cytometry, and then were further screened by using the reactivity to the TMEM-180-overexpressing DLD-1 cell line, the TMEM-180 knockdown DLD-1 cell line, and the TMEM-180 knockout DLD-1 cell line. The selected antibody-producing hybridoma cells were cloned to be established by a limiting dilution method. The isotype of the antibody was determined with an isotype-specific ELISA (Bethyl).

One IgG antibody and three IgM antibodies were obtained as a result of the above method. These antibodies well recognized TMEM-180 protein on the exosomes and well stained the cancer tissues, which was similar to the results in the above Example. No wonder that the antibodies obtained by immunizations with exosomes are useful for the cancer diagnoses using the exosomes. It is thought that TMET-180 has the native conformation on the exosomes and presents the same part as that presented on the cell membrane. Further, immunohistological staining and FACS showed that the antibodies, which were obtained by immunizations with exosomes, bound to TMEM-180 on cell membranes. Thus, it is thought that a method of obtaining an antibody by immunization with exosomes is useful as a method of obtaining an anti-membrane protein antibody, in particular, an anti-TMEM-180 antibody.

Example C15. Construction of Antibody-Drug Conjugate (ADC) and Physiological Examination Thereof In this Example, ADC was constructed, and the effects thereof on colon cancer cell lines were examined.

The 669 antibody or 372 antibody was used as an anti-TMEM-180 antibody and monomethyl auristatin E (MMAE) was used as a drug in ADC. The antibody and MMAE were linked via a linker. The valine-citrulline linker (Val-Cit linker), which can be cleaved with cathepsin, was used as a liker. The specific structure of the ADC is shown in FIG. 24.

Example C15-1. Preparation of the ADC (1) Synthesis of the Linker

An N,N-dimethylformamide (DMF) solution (18 mL) containing Fmoc-Val-OSu (2.80 g, 6.42 mmol) was added to an aqueous solution (18 mL) containing H-Cit-OH (1.18 g, 6.74 mmol) and NaHCO (566 mg, 6.74 mmol), and then tetrahydrofuran (THF) (9 mL) was added to the solution. After overnight stirring, the reaction was stopped with a 15% citric acid solution (40 mL). The aqueous layer was extracted with the mixture solutions of AcOEt/i-PrOH (9/1) (100 mL, and 20 mL×2). A combined organic layer was washed with water (70 mL) and then was subjected to vacuum concentration. The residual solid was washed with diethyl ether and then dipeptide Fmoc-Val-Cit-OH (3.11 g, 97%) was obtained as a white solid.

To a solution containing Fmoc-Val-Cit-OH (3.00 g, 6.04 mmol) and p-aminobenzyl alcohol (PAB) (1.49 g, 12.1 mmol)-methanol (30 mL), 1-ethoxycarbonyl-2-ethoxy-1,2-dihydroquinoline (EEDQ) (2.99 g, 12.1 mmol) was added. One day later, EEDQ (1.50 g, 6.04 mmol) was further added to the solution, followed by overnight stirring. The reaction solution was concentrated and then diethyl ether was added to the residue and was washed by sonication. Thus, Fmoc-Val-Cit-PAB-OH (2.51 g, 69%) was obtained.

(2) Connection of the Linker and MMAE and Preparation of the ADC

MMAE (1.00 g, 1.39 mmol) was added to a solution of dimethyl formamide (3.4 mL) and pyridine (0.85 mL) containing p-nitrophenyl carbonate body (1.28 g, 1.67 mmol) and 1-hydroxybenzotriazol (HOBt) (376 mg, 2.78 mmol). After 24 hours, the reaction solution was purified with Sephadex LH20 (solvents: CHCla:MeOH 1:1) to obtain Fmoc-Val-Cit-PABC-MMAE (1.44 g, 77%).

Et$_2$NH (5 mL) was added to a dimethylformamide solution (20 mL) containing Fmoc-Val-Cit-PABC-MMAE (1.44 g, 1.07 mmol). After overnight stirring, the reaction solution was subjected to vacuum concentration. The residue was washed with ethyl acetate and diethyl ether to obtain a light-yellow solid (960 mg, 80%).

Maleimide-polyethylene glycol 12-succinimidyl ester (Mal-PEG$_{12}$-Osu) (814 mg, 0.94 mmol) and diisopropylethylamine (0.45 mmol, 2.57 mmol) were added to a dichloromethane solution (20 mL) containing H-Val-Cit-PABC-MMAE (960 mg, 0.855 mmol). After overnight stirring, the reaction solution was purified with Sephadex LH20 (CHCla:MeOH 1:1) and by size exclusion high performance liquid chromatography to obtain Mal-PEG$_{12}$-Val-Cit-PABC-MMAE (769 mg, 48%) as a colorless oil.

Then, according to the general common technique, the antibody was reduced with mercaptoethylamine. The maleimide group of Mal-PEG$_{12}$-Val-Cit-PABC-MMAE and the thiol group of the antibody were linked by Michel addition reaction to obtain the ADC. The 669 antibody and a control antibody were used as antibodies.

Example C15-2. Checkinq of Internalization of the Antibody

Wildtype DLD-1 cells were plated on a 96-well plate at 5,000 cells/well. The plate was incubated at 37° C. for 18 hours. After washing, a 488-labelled 669 antibody was added to the wells at 2 µL/well and was incubated at 37° C. for certain hours (1 hour, 3 hours, or 6 hours). After the wells were washed three times, a rabbit anti 488 antibody was added at 2 µL/well to stand still at 4° C. for 30 minutes to quench the fluorescence derived from the antibodies binding to the cell surface. After the wells were washed three times, 4% PFA was added at 100 µL/well to stand still at room temperature for 10 minutes. After the wells were washed three times, DAPI (1/500 dilution) was added to the wells at 100 µL/well to stand still at room temperature for 5 minutes. After the wells were washed three times, the wells were subjected to photographing or Array Scan analysis. An anti-EGFR antibody, Cetuximab (Erbitux) was used as a control. The results are shown in FIG. 25.

As shown in FIG. 25, it was observed that the 669 antibody was concentrated at a high concentration in the cells. On the contrary, the amount of internalized cetuximab was limited.

Example C15-3. Cytotoxicity of the ADC

SW480 cells were plated on a 96-well plate at 2×10$^3$ cells/well. On the next day, dilution series of MMAE (single agent), the ADC of 669 antibody, or the ADC of the control antibody (control ADC) were prepared with the concentrations in terms of MMAE. Three days later, WST-8, which is a cytotoxicity measuring agent, was added. After three hours, the cell viability (%) was checked. The results are shown in FIG. 26.

Figure 26:
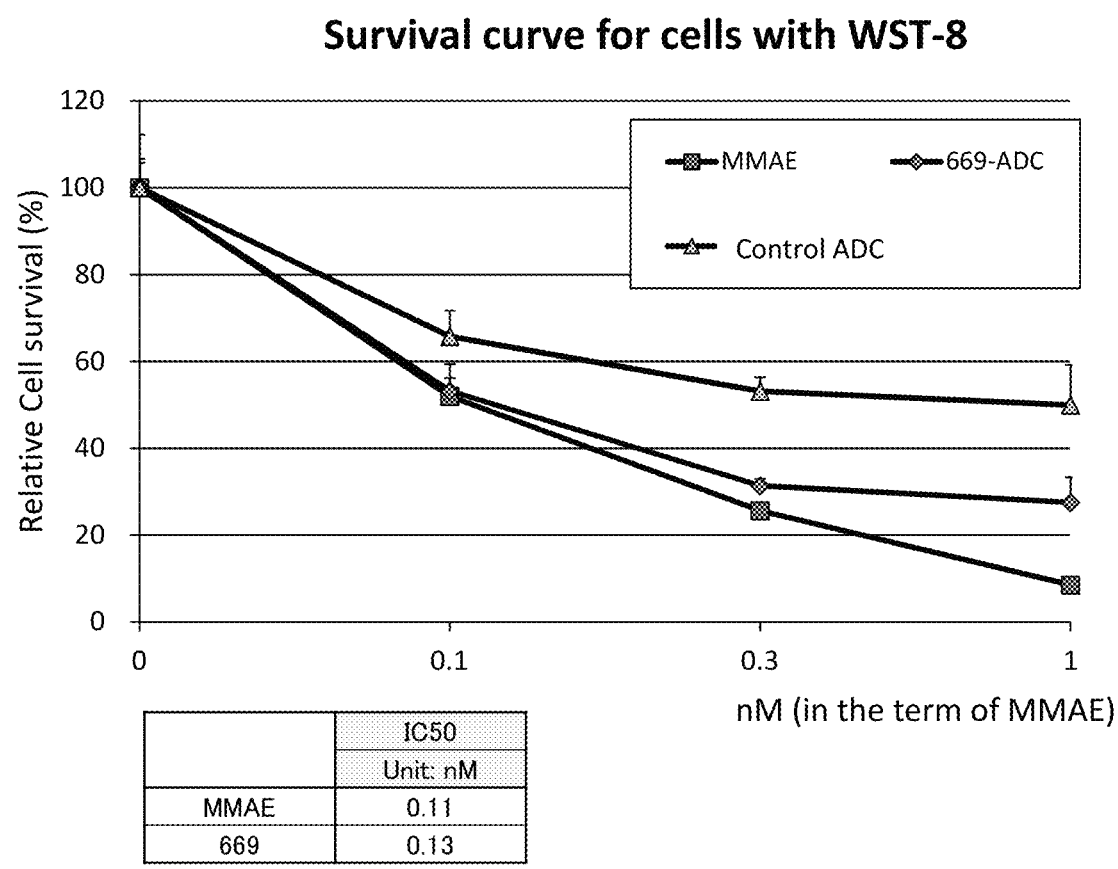
FIG. 26 shows a diagram showing cytotoxicity of the ADC prepared in Example 15C.

As shown in FIG. 26, it was shown that the ADC of 669 antibody exhibited the cytotoxicity to the cells as well as MMAE. Further, the ADC of 669 antibody exhibited a stronger cytotoxicity than the control ADC.

Example C15-4. TMEM-180 Knockout Mice

TMEM-180 knockout mice were generated, and the phenotype thereof were checked.

The TMEM-180 homo knockout mice were obtained by preparing a guide RNA at exon 2 in TMEM-180 by using CRISPR/Cas9 system and mating the obtained mice (see FIG. 27). It was confirmed that they are not embryonic lethal. This result suggests that the lack of the function of TMEM-180 will show little effect on normal tissues.

SEQ ID NOs: 1 to 3 respectively indicate the amino acid sequences of clone 98 heavy chain CDR1 to CDR3.

SEQ ID NOs: 4 to 6 respectively indicate the amino acid sequences of clone 98 light chain CDR1 to CDR3.

SEQ ID NOs: 7 to 9 respectively indicate the amino acid sequences of clone 101 heavy chain CDR1 to CDR3.

SEQ ID NOs: 10 to 12 respectively indicate the amino acid sequences of clone 101 light chain CDR1 to CDR3.

SEQ ID NOs: 13 and 14 respectively indicate the amino acid sequences of the heavy chain variable region and light chain variable region of clone 98.

SEQ ID NOs: 15 and 16 respectively indicate the amino acid sequences of the heavy chain variable region and light chain variable region of clone 101.

SEQ ID NO: 17 indicates the amino acid sequence of human TMEM-180 protein.

SEQ ID NOs: 18 to 21 respectively indicate primers (i) to (iv) for producing immunizing antigen 1.

SEQ ID NOs: 22 to 25 respectively indicate primers (i) to (iv) for producing immunizing antigen 2.

SEQ ID NOs: 26 to 31 indicate primers used for cloning an anti-TMEM-180 antibody.

SEQ ID NOs: 40 to 42 respectively indicate the amino acid sequences of clone 212 heavy chain CDR1 to CDR3.

SEQ ID NOs: 43 to 45 respectively indicate the amino acid sequences of clone 212 light chain CDR1 to CDR3.

SEQ ID NOs: 46 and 47 respectively indicate the amino acid sequences of the heavy chain variable region and light chain variable region of clone 212.

SEQ ID NOs: 48 to 50 respectively indicate the amino acid sequences of clone 129 heavy chain CDR1 to CDR3.

SEQ ID NOs: 51 to 53 respectively indicate the amino acid sequences of clone 129 light chain CDR1 to CDR3.

SEQ ID NOs: 54 and 55 respectively indicate the amino acid sequences of the heavy chain variable region and light chain variable region of clone 129.

SEQ ID NOs: 56 to 58 respectively indicate the amino acid sequences of clone 382 heavy chain CDR1 to CDR3.

SEQ ID NOs: 59 to 61 respectively indicate the amino acid sequences of clone 382 light chain CDR1 to CDR3.

SEQ ID NOs: 62 and 63 respectively indicate the amino acid sequences of the heavy chain variable region and light chain variable region of clone 382.

SEQ ID NOs: 64 to 66 respectively indicate the amino acid sequences of clone 1361 heavy chain CDR1 to CDR3.

SEQ ID NOs: 67 to 69 respectively indicate the amino acid sequences of clone 1361 light chain CDR1 to CDR3.

SEQ ID NOs: 70 and 71 respectively indicate the amino acid sequences of the heavy chain variable region and light chain variable region of clone 1361.

SEQ ID NOs: 72 to 74 respectively indicate the amino acid sequences of clone 669 heavy chain CDR1 to CDR3.

SEQ ID NOs: 75 to 77 respectively indicate the amino acid sequences of clone 669 light chain CDR1 to CDR3.

SEQ ID NOs: 78 and 79 respectively indicate the amino acid sequences of the heavy chain variable region and light chain variable region of clone 669.

SEQ ID NOs: 80 to 82 respectively indicate the amino acid sequences of clone 699 heavy chain CDR1 to CDR3.

SEQ ID NOs: 83 to 85 respectively indicate the amino acid sequences of clone 699 light chain CDR1 to CDR3.

SEQ ID NOs: 86 and 87 respectively indicate the amino acid sequences of the heavy chain variable region and light chain variable region of clone 699.

SEQ ID NOs: 88 to 90 respectively indicate the amino acid sequences of clone 1052 heavy chain CDR1 to CDR3.

SEQ ID NOs: 91 to 93 respectively indicate the amino acid sequences of clone 1052 light chain CDR1 to CDR3.

SEQ ID NOs: 94 and 95 respectively indicate the amino acid sequences of the heavy chain variable region and light chain variable region of clone 1052.

SEQ ID NOs: 96 to 98 respectively indicate the amino acid sequences of clone 1105 heavy chain CDR1 to CDR3.

SEQ ID NOs: 99 to 101 respectively indicate the amino acid sequences of clone 1105 light chain CDR1 to CDR3.

SEQ ID NOs: 102 and 103 respectively indicate the amino acid sequences of the heavy chain variable region and light chain variable region of clone 1105.

SEQ ID NOs: 104 to 150 indicate the amino acid sequences of TMEM-180-derived peptides binding to HLA type A2 as predicted by HLA Peptide Binding Predictions.

SEQ ID NOs: 151 to 170 indicate the amino acid sequences of TMEM-180-derived peptides binding to HLA type A24 as predicted by HLA Peptide Binding Predictions.

SEQ ID Nos: 171 to 173 indicate the amino acid sequences of clone 1361-5 heavy chain CDR 1 to 3, respectively.

SEQ ID Nos: 174 to 176 indicate the amino acid sequences of clone 1361-5 light chain CDR 1 to 3, respectively.

SEQ ID NOs: 177 and 178 indicate the amino acid sequences of the heavy chain variable region and light chain variable region of clone 1361-5, respectively SEQ ID Nos: 179 and 180 indicate the nucleic acid sequence and amino acid sequence of clone 1361-5 heavy chain, respectively.

SEQ ID Nos: 181 and 182 indicate the nucleic acid sequence and amino acid sequence of clone 1361-5 light chain, respectively.

SEQ ID Nos: 183 and 184 indicate the nucleic acid sequences of the forward primer and reverse primer used for the introduction of Y79A mutation in 1361-5 clone.

SEQ ID Nos: 185 and 186 indicate the nucleic acid sequences of the forward primer and reverse primer used for the introduction of S82A mutation in 1361-5 clone.

SEQ ID Nos: 187 to 192 indicate the nucleic acid sequences of the forward primers and reverse primers used for the introduction of site specific mutations into the Fc region of 1361-5 antibody as described in Example B11-2.

What is claimed is:

1. A method of diagnosing colon cancer in a human subject, comprising a step of detecting the existence or amount of exosomes having TMEM-180 or the existence or amount of TMEM-180 expression on exosomes in a body fluid sample obtained from the human subject by using an antibody binding to transmembrane protein 180 (TMEM-180) or an antigen-binding fragment thereof,
wherein the body fluid is a blood sample, wherein the existence of exosomes having TMEM-180 and the existence of TMEM-180 expression on exosomes indicate that the human subject has a colon cancer secreting exosomes presenting TMEM-180 to the body fluid, and
wherein the antibody and the fragment thereof each comprise:
a heavy chain variable region having
a heavy chain CDR1 having DYWVS (SEQ ID NO: 72);
a heavy chain CDR2 having EIYPNSGATNFNENFK (SEQ ID NO: 73); and
a heavy chain CDR3 having DGTMGIAYYFDY (SEQ ID NO: 74); and
a light chain variable region having
a light chain CDR1 having KASQNINRYLN (SEQ ID NO: 75);
a light chain CDR2 having NANSLQT (SEQ ID NO: 76); and
a light chain CDR3 having LQHNSWPYT (SEQ ID NO: 77).

2. The method according to claim 1, wherein the antibody or antigen-binding fragment thereof comprises a heavy chain variable region comprising the sequence of SEQ ID NO: 78 and a light chain variable region comprising the sequence of SEQ ID NO: 79.

* * * * *